US012275772B2

(12) United States Patent
Shah et al.

(10) Patent No.: US 12,275,772 B2
(45) Date of Patent: Apr. 15, 2025

(54) ROR-1 SPECIFIC CHIMERIC ANTIGEN RECEPTORS AND USES THEREOF

(71) Applicant: Precigen, Inc., Blacksburg, VA (US)

(72) Inventors: Rutul R. Shah, Blacksburg, VA (US); ChangHung Chen, Blacksburg, VA (US); Cheryl G. Bolinger, Blacksburg, VA (US); Vinodhbabu Kurella, Blacksburg, VA (US); Amy Wesa, Blacksburg, VA (US)

(73) Assignee: PRECIGEN, INC., Germantown, MD (US)

( * ) Notice: Subject to any disclaimer, the term of this patent is extended or adjusted under 35 U.S.C. 154(b) by 1124 days.

(21) Appl. No.: 17/143,386

(22) Filed: Jan. 7, 2021

(65) Prior Publication Data

US 2021/0177902 A1 Jun. 17, 2021

Related U.S. Application Data

(63) Continuation of application No. PCT/US2019/041213, filed on Jul. 10, 2019.

(60) Provisional application No. 62/696,075, filed on Jul. 10, 2018.

(51) Int. Cl.

| | |
|---|---|
| ***C07K 14/725*** | (2006.01) |
| ***A61K 39/00*** | (2006.01) |
| ***A61P 35/00*** | (2006.01) |
| ***C07K 14/54*** | (2006.01) |
| ***C07K 14/705*** | (2006.01) |
| ***C07K 14/71*** | (2006.01) |
| ***C07K 16/28*** | (2006.01) |
| ***C12N 5/0783*** | (2010.01) |

(52) U.S. Cl.

CPC ...... *C07K 14/7051* (2013.01); *A61K 39/4611* (2023.05); *A61K 39/4631* (2023.05); *A61K 39/464402* (2023.05); *A61P 35/00* (2018.01); *C07K 14/5443* (2013.01); *C07K 14/70521* (2013.01); *C07K 14/70578* (2013.01); *C07K 14/71* (2013.01); *C07K 16/2803* (2013.01); *C12N 5/0636* (2013.01)

(58) Field of Classification Search

CPC ..... A61K 35/17; A61P 35/00; C07K 14/5443; C07K 14/7051; C07K 14/70521; C07K 14/70578; C07K 14/71; C07K 16/2803

See application file for complete search history.

(56) References Cited

U.S. PATENT DOCUMENTS 5,283,173 A 2/1994 Fields et al.
9,217,040 B2 * 12/2015 Kipps .................... C07K 16/40
9,228,023 B2 * 1/2016 Rohlff ...................... A61P 35/00
11,692,194 B2 * 7/2023 Shah .................. C12N 15/1055 435/69.1
11,771,718 B2 * 10/2023 Shah .................. C07K 16/2815 514/883
2013/0101607 A1 4/2013 Kipps et al.
2015/0225482 A1 * 8/2015 Song .................. C07K 16/2887 536/23.4
2016/0158285 A1 6/2016 Cooper et al.
2016/0317678 A1 11/2016 Roeth et al.
2017/0226183 A1 8/2017 Schiffer-Mannioui
2017/0283497 A1 10/2017 Schiffer-Mannioui
2018/0147271 A1 * 5/2018 Morgan ......... A61K 39/001102
2019/0048343 A1 2/2019 Gao et al.
2019/0111080 A1 4/2019 Shah et al.

FOREIGN PATENT DOCUMENTS

WO WO-9738117 A1 10/1997
WO WO-9902683 A1 1/1999
WO WO-9958155 A1 11/1999
WO 2013/154760 A1 10/2013
WO 2014/144622 A2 9/2014
WO WO-2016048903 A1 3/2016
WO 2016115559 A1 7/2016
WO WO-2015095249 A8 8/2016
WO WO-2017062953 A1 4/2017
WO WO-2017172981 A2 10/2017
WO WO-2017214333 A1 * 12/2017 ......... A61K 39/4611
WO WO-2018102606 A1 6/2018
WO WO-2018111763 A1 * 6/2018 ......... A61K 39/4611
WO 2018/226897 A1 10/2019
WO 2019/186274 A2 10/2019
WO 2020/014366 A1 1/2020

OTHER PUBLICATIONS

Sela-Culang et al. 2013. Frontiers in Immunology 4: 302. (Year: 2013).*
Deniger et al. 2015. PLOS One 10(6):e0128151. (Year: 2015).*
Wu et al. 2016. Expert Opinion on Biological Therapy 16(12): 1469-1478. (Year: 2016).*
U.S. Appl. No. 18/426,680. (Pending). Modulating Expression of Polypeptides via New Gene Switch Expression Systems. (Year: 2024).*
Harris and Kranz. 2016. Trends in Pharmacological Sciences 37(3): 220-230. (Year: 2016).*
U.S. Appl. No. 17/572,618. (Pending). Chimeric Receptor Therapy. (Year: 2022).*
Dotti et al., Immunological Reviews (2014), 257:107-126.
Hudecek et al., Clinical Cancer Research (2013), 19:3153-3164.
GenBank Accession No. AY866202.

(Continued)

*Primary Examiner* — Brad Duffy
*Assistant Examiner* — Elizabeth A Shupe
(74) *Attorney, Agent, or Firm* — Barnes & Thornburg LLP; Gene J. Yao

(57) ABSTRACT

Provided herein are chimeric antigen receptors (CARs) for cancer therapy, and more particularly, CARs containing a scFv from an anti-ROR-1 monoclonal antibody. Provided are immune effector cells containing such CARs, and methods of treating proliferative disorders.

58 Claims, 14 Drawing Sheets

Specification includes a Sequence Listing.

(56) References Cited

OTHER PUBLICATIONS

Hurton et al., "Tethered IL-15 augments antitumor activity and promotes a stem-cell memory subset in tumor-specific T cells," PNAS 2016, pp. 1-30.
International Search Report and Written Opinion for corresponding PCT Application No. PCT/US20149/041213 issued Aug. 11, 2019.

* cited by examiner

| Signal peptide | mIgVH | hGMCSFR | GM-CSFRsp | IGHV3-23 | IGHV3-23 sp |
|---|---|---|---|---|---|
| Stalk | FcM | FcM | CD8α 3x | CD8α 3x | CD8α 3x |
| ICD | CD28-Z | CD28-Z | CD28-Z | CD28-Z | CD28-Z |
| scFv | murine(VL-VH) | murine (VL-VH) | murine(VH-whitlow-VL) | murine(VL-VH) | murine(VH-whitlow-VL) |

SEQUENCE LISTING

<160> NUMBER OF SEQ ID NOS: 294

<210> SEQ ID NO 1
<211> LENGTH: 926
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Pro Leu Leu Ala Leu Leu Ala Ala Leu Leu Leu Ala Ala Arg Gly Ala
1               5                   10                  15

Ala Ala Gln Glu Thr Glu Leu Ser Val Ser Ala Glu Leu Val Pro Thr
            20                  25                  30
```

-continued

```
Ser Ser Trp Asn Ile Ser Ser Glu Leu Asn Lys Asp Ser Tyr Leu Thr
        35                  40                  45

Leu Asp Glu Pro Met Asn Asn Ile Thr Thr Ser Leu Gly Gln Thr Ala
    50                  55                  60

Glu Leu His Cys Lys Val Ser Gly Asn Pro Pro Pro Thr Ile Arg Trp
65                  70                  75                  80

Phe Lys Asn Asp Ala Pro Val Val Gln Glu Pro Arg Arg Leu Ser Phe
                85                  90                  95

Arg Ser Thr Ile Tyr Gly Ser Arg Leu Arg Ile Arg Asn Leu Asp Thr
            100                 105                 110

Thr Asp Thr Gly Tyr Phe Gln Cys Val Ala Thr Asn Gly Lys Glu Val
        115                 120                 125

Val Ser Ser Thr Gly Val Leu Phe Val Lys Phe Gly Pro Pro Pro Thr
    130                 135                 140

Ala Ser Pro Gly Tyr Ser Asp Glu Tyr Glu Glu Asp Gly Phe Cys Gln
145                 150                 155                 160

Pro Tyr Arg Gly Ile Ala Cys Ala Arg Phe Ile Gly Asn Arg Thr Val
                165                 170                 175

Tyr Met Glu Ser Leu His Met Gln Gly Glu Ile Glu Asn Gln Ile Thr
            180                 185                 190

Ala Ala Phe Thr Met Ile Gly Thr Ser Ser His Leu Ser Asp Lys Cys
        195                 200                 205

Ser Gln Phe Ala Ile Pro Ser Leu Cys His Tyr Ala Phe Pro Tyr Cys
    210                 215                 220

Asp Glu Thr Ser Ser Val Pro Lys Pro Arg Asp Leu Cys Arg Asp Glu
225                 230                 235                 240

Cys Glu Ile Leu Glu Asn Val Leu Cys Gln Thr Glu Tyr Ile Phe Ala
                245                 250                 255

Arg Ser Asn Pro Met Ile Leu Met Arg Leu Lys Leu Pro Asn Cys Glu
            260                 265                 270

Asp Leu Pro Gln Pro Glu Ser Pro Glu Ala Ala Asn Cys Ile Arg Ile
        275                 280                 285

Gly Ile Pro Met Ala Asp Pro Ile Asn Lys Asn His Lys Cys Tyr Asn
    290                 295                 300

Ser Thr Gly Val Asp Tyr Arg Gly Thr Val Ser Val Thr Lys Ser Gly
305                 310                 315                 320

Arg Gln Cys Gln Pro Trp Asn Ser Gln Tyr Pro His Thr His Thr Phe
                325                 330                 335

Thr Ala Leu Arg Phe Pro Glu Leu Asn Gly Gly His Ser Tyr Cys Arg
            340                 345                 350

Asn Pro Gly Asn Gln Lys Glu Ala Pro Trp Cys Phe Thr Leu Asp Glu
        355                 360                 365

Asn Phe Lys Ser Asp Leu Cys Asp Ile Pro Ala Cys Asp Ser Lys Asp
    370                 375                 380

Ser Lys Glu Lys Asn Lys Met Glu Ile Leu Tyr Ile Leu Val Pro Ser
385                 390                 395                 400

Val Ala Ile Pro Leu Ala Ile Ala Leu Leu Phe Phe Phe Ile Cys Val
                405                 410                 415

Cys Arg Asn Asn Gln Lys Ser Ser Ser Ala Pro Val Gln Arg Gln Pro
            420                 425                 430

Lys His Val Arg Gly Gln Asn Val Glu Met Ser Met Leu Asn Ala Tyr
        435                 440                 445

Lys Pro Lys Ser Lys Ala Lys Glu Leu Pro Leu Ser Ala Val Arg Phe
```

```
    450                 455                 460

Met Glu Glu Leu Gly Glu Cys Ala Phe Gly Lys Ile Tyr Lys Gly His
465                 470                 475                 480

Leu Tyr Leu Pro Gly Met Asp His Ala Gln Leu Val Ala Ile Lys Thr
                485                 490                 495

Leu Lys Asp Tyr Asn Asn Pro Gln Gln Trp Thr Glu Phe Gln Gln Glu
            500                 505                 510

Ala Ser Leu Met Ala Glu Leu His His Pro Asn Ile Val Cys Leu Leu
        515                 520                 525

Gly Ala Val Thr Gln Glu Gln Pro Val Cys Met Leu Phe Glu Tyr Ile
    530                 535                 540

Asn Gln Gly Asp Leu His Glu Phe Leu Ile Met Arg Ser Pro His Ser
545                 550                 555                 560

Asp Val Gly Cys Ser Ser Asp Glu Asp Gly Thr Val Lys Ser Ser Leu
                565                 570                 575

Asp His Gly Asp Phe Leu His Ile Ala Ile Gln Ile Ala Ala Gly Met
            580                 585                 590

Glu Tyr Leu Ser Ser His Phe Phe Val His Lys Asp Leu Ala Ala Arg
        595                 600                 605

Asn Ile Leu Ile Gly Glu Gln Leu His Val Lys Ile Ser Asp Leu Gly
    610                 615                 620

Leu Ser Arg Glu Ile Tyr Ser Ala Asp Tyr Tyr Arg Val Gln Ser Lys
625                 630                 635                 640

Ser Leu Leu Pro Ile Arg Trp Met Pro Pro Glu Ala Ile Met Tyr Gly
                645                 650                 655

Lys Phe Ser Ser Asp Ser Asp Ile Trp Ser Phe Gly Val Val Leu Trp
            660                 665                 670

Glu Ile Phe Ser Phe Gly Leu Gln Pro Tyr Tyr Gly Phe Ser Asn Gln
        675                 680                 685

Glu Val Ile Glu Met Val Arg Lys Arg Gln Leu Leu Pro Cys Ser Glu
    690                 695                 700

Asp Cys Pro Pro Arg Met Tyr Ser Leu Met Thr Glu Cys Trp Asn Glu
705                 710                 715                 720

Ile Pro Ser Arg Arg Pro Arg Phe Lys Asp Ile His Val Arg Leu Arg
                725                 730                 735

Ser Trp Glu Gly Leu Ser Ser His Thr Ser Ser Thr Thr Pro Ser Gly
            740                 745                 750

Gly Asn Ala Thr Thr Gln Thr Thr Ser Leu Ser Ala Ser Pro Val Ser
        755                 760                 765

Asn Leu Ser Asn Pro Arg Tyr Pro Asn Tyr Met Phe Pro Ser Gln Gly
    770                 775                 780

Ile Thr Pro Gln Gly Gln Ile Ala Gly Phe Ile Gly Pro Pro Ile Pro
785                 790                 795                 800

Gln Asn Gln Arg Phe Ile Pro Ile Asn Gly Tyr Pro Ile Pro Pro Gly
                805                 810                 815

Tyr Ala Ala Phe Pro Ala Ala His Tyr Gln Pro Thr Gly Pro Pro Arg
            820                 825                 830

Val Ile Gln His Cys Pro Pro Pro Lys Ser Arg Ser Pro Ser Ser Ala
        835                 840                 845

Ser Gly Ser Thr Ser Thr Gly His Val Thr Ser Leu Pro Ser Ser Gly
    850                 855                 860

Ser Asn Gln Glu Ala Asn Ile Pro Leu Leu Pro His Met Ser Ile Pro
865                 870                 875                 880
```

```
Asn His Pro Gly Gly Met Gly Ile Thr Val Phe Gly Asn Lys Ser Gln
                885                 890                 895

Lys Pro Tyr Lys Ile Asp Ser Lys Gln Ala Ser Leu Leu Gly Asp Ala
            900                 905                 910

Asn Ile His Gly His Thr Glu Ser Met Ile Ser Ala Glu Leu
        915                 920                 925


<210> SEQ ID NO 2
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
```

```
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala
        435


<210> SEQ ID NO 3
<211> LENGTH: 654
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220
```

-continued

```
Tyr Asp Gly Tyr Tyr Ala Met Asp Tyr Trp Gly Gln Gly Thr Ser Val
225                 230                 235                 240

Thr Val Ser Ser Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
    450                 455                 460

Lys Ser Leu Ser Leu Ser Leu Gly Lys Met Phe Trp Val Leu Val Val
465                 470                 475                 480

Val Gly Gly Val Leu Ala Cys Tyr Ser Leu Leu Val Thr Val Ala Phe
                485                 490                 495

Ile Ile Phe Trp Val Arg Ser Lys Arg Ser Arg Gly Gly His Ser Asp
            500                 505                 510

Tyr Met Asn Met Thr Pro Arg Arg Pro Gly Pro Thr Arg Lys His Tyr
        515                 520                 525

Gln Pro Tyr Ala Pro Pro Arg Asp Phe Ala Ala Tyr Arg Ser Arg Val
    530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
                565                 570                 575

Leu Asp Lys Arg Arg Gly Arg Asp Pro Glu Met Gly Gly Lys Pro Arg
            580                 585                 590

Arg Lys Asn Pro Gln Glu Gly Leu Tyr Asn Glu Leu Gln Lys Asp Lys
        595                 600                 605

Met Ala Glu Ala Tyr Ser Glu Ile Gly Met Lys Gly Glu Arg Arg Arg
    610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
```

645 650

<210> SEQ ID NO 4
<211> LENGTH: 663
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

Asp Ile Lys Met Thr Gln Ser Pro Ser Ser Met Tyr Ala Ser Leu Gly
1 5 10 15

Glu Arg Val Thr Ile Thr Cys Lys Ala Ser Pro Asp Ile Asn Ser Tyr
20 25 30

Leu Ser Trp Phe Gln Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Gly Gly Ser Gly Gln Asp Tyr Ser Leu Thr Ile Asn Ser Leu Glu Tyr
65 70 75 80

Glu Asp Met Gly Ile Tyr Tyr Cys Leu Gln Tyr Asp Glu Phe Pro Tyr
85 90 95

Thr Phe Gly Gly Gly Thr Lys Leu Glu Met Lys Gly Ser Thr Ser Gly
100 105 110

Ser Gly Lys Pro Gly Ser Gly Glu Gly Ser Thr Lys Gly Glu Val Lys
115 120 125

Leu Val Glu Ser Gly Gly Gly Leu Val Lys Pro Gly Gly Ser Leu Lys
130 135 140

Leu Ser Cys Ala Ala Ser Gly Phe Thr Phe Ser Ser Tyr Ala Met Ser
145 150 155 160

Trp Val Arg Gln Ile Pro Glu Lys Arg Leu Glu Trp Val Ala Ser Ile
165 170 175

Ser Arg Gly Gly Thr Thr Tyr Tyr Pro Asp Ser Val Lys Gly Arg Phe
180 185 190

Thr Ile Ser Arg Asp Asn Val Arg Asn Ile Leu Tyr Leu Gln Met Ser
195 200 205

Ser Leu Arg Ser Glu Asp Thr Ala Met Tyr Tyr Cys Gly Arg Tyr Asp
210 215 220

Tyr Asp Gly Tyr Tyr Ala Met Asp Tyr Trp Gly Gln Gly Thr Ser Val
225 230 235 240

Thr Val Ser Ser Gln Gly Thr Ser Val Thr Val Ser Ser Glu Ser Lys
245 250 255

Tyr Gly Pro Pro Cys Pro Pro Cys Pro Ala Pro Glu Phe Leu Gly Gly
260 265 270

Pro Ser Val Phe Leu Phe Pro Pro Lys Pro Lys Asp Thr Leu Met Ile
275 280 285

Ser Arg Thr Pro Glu Val Thr Cys Val Val Val Asp Val Ser Gln Glu
290 295 300

Asp Pro Glu Val Gln Phe Asn Trp Tyr Val Asp Gly Val Glu Val His
305 310 315 320

Asn Ala Lys Thr Lys Pro Arg Glu Glu Gln Phe Asn Ser Thr Tyr Arg
325 330 335

Val Val Ser Val Leu Thr Val Leu His Gln Asp Trp Leu Asn Gly Lys
340 345 350

-continued

```
Glu Tyr Lys Cys Lys Val Ser Asn Lys Gly Leu Pro Ser Ser Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Gln Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Arg Leu Thr Val Asp
        435                 440                 445

Lys Ser Arg Trp Gln Glu Gly Asn Val Phe Ser Cys Ser Val Met His
    450                 455                 460

Glu Ala Leu His Asn His Tyr Thr Gln Lys Ser Leu Ser Leu Ser Leu
465                 470                 475                 480

Gly Lys Met Phe Trp Val Leu Val Val Val Gly Gly Val Leu Ala Cys
                485                 490                 495

Tyr Ser Leu Leu Val Thr Val Ala Phe Ile Ile Phe Trp Val Arg Ser
            500                 505                 510

Lys Arg Ser Arg Gly Gly His Ser Asp Tyr Met Asn Met Thr Pro Arg
        515                 520                 525

Arg Pro Gly Pro Thr Arg Lys His Tyr Gln Pro Tyr Ala Pro Pro Arg
    530                 535                 540

Asp Phe Ala Ala Tyr Arg Ser Arg Val Lys Phe Ser Arg Ser Ala Asp
545                 550                 555                 560

Ala Pro Ala Tyr Gln Gln Gly Gln Asn Gln Leu Tyr Asn Glu Leu Asn
                565                 570                 575

Leu Gly Arg Arg Glu Glu Tyr Asp Val Leu Asp Lys Arg Arg Gly Arg
            580                 585                 590

Asp Pro Glu Met Gly Gly Lys Pro Arg Arg Lys Asn Pro Gln Glu Gly
        595                 600                 605

Leu Tyr Asn Glu Leu Gln Lys Asp Lys Met Ala Glu Ala Tyr Ser Glu
    610                 615                 620

Ile Gly Met Lys Gly Glu Arg Arg Arg Gly Lys Gly His Asp Gly Leu
625                 630                 635                 640

Tyr Gln Gly Leu Ser Thr Ala Thr Lys Asp Thr Tyr Asp Ala Leu His
                645                 650                 655

Met Gln Ala Leu Pro Pro Arg
                660


<210> SEQ ID NO 5
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45
```

```
Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Asn His Arg Asn Arg
305                 310                 315                 320

Ser Lys Arg Ser Arg Gly Gly His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460
```

His Met Gln Ala Leu Pro Pro Arg
465 470

<210> SEQ ID NO 6
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Asp Ile Lys Met Thr Gln Ser Pro Ser Ser Met Tyr Ala Ser Leu Gly
1 5 10 15

Glu Arg Val Thr Ile Thr Cys Lys Ala Ser Pro Asp Ile Asn Ser Tyr
20 25 30

Leu Ser Trp Phe Gln Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Gly Gly Ser Gly Gln Asp Tyr Ser Leu Thr Ile Asn Ser Leu Glu Tyr
65 70 75 80

Glu Asp Met Gly Ile Tyr Tyr Cys Leu Gln Tyr Asp Glu Phe Pro Tyr
85 90 95

Thr Phe Gly Gly Gly Thr Lys Leu Glu Met Lys Gly Ser Thr Ser Gly
100 105 110

Ser Gly Lys Pro Gly Ser Gly Glu Gly Ser Thr Lys Gly Glu Val Lys
115 120 125

Leu Val Glu Ser Gly Gly Gly Leu Val Lys Pro Gly Gly Ser Leu Lys
130 135 140

Leu Ser Cys Ala Ala Ser Gly Phe Thr Phe Ser Ser Tyr Ala Met Ser
145 150 155 160

Trp Val Arg Gln Ile Pro Glu Lys Arg Leu Glu Trp Val Ala Ser Ile
165 170 175

Ser Arg Gly Gly Thr Thr Tyr Tyr Pro Asp Ser Val Lys Gly Arg Phe
180 185 190

Thr Ile Ser Arg Asp Asn Val Arg Asn Ile Leu Tyr Leu Gln Met Ser
195 200 205

Ser Leu Arg Ser Glu Asp Thr Ala Met Tyr Tyr Cys Gly Arg Tyr Asp
210 215 220

Tyr Asp Gly Tyr Tyr Ala Met Asp Tyr Trp Gly Gln Gly Thr Ser Val
225 230 235 240

Thr Val Ser Ser Lys Pro Thr Thr Thr Pro Ala Pro Arg Pro Pro Thr
245 250 255

Pro Ala Pro Thr Ile Ala Ser Gln Pro Leu Ser Leu Arg Pro Glu Ala
260 265 270

Ser Arg Pro Ala Ala Gly Gly Ala Val His Thr Arg Gly Leu Asp Phe
275 280 285

Ala Ser Asp Lys Pro Thr Thr Thr Pro Ala Pro Arg Pro Pro Thr Pro
290 295 300

Ala Pro Thr Ile Ala Ser Gln Pro Leu Ser Leu Arg Pro Glu Ala Cys
305 310 315 320

Arg Pro Ala Ala Gly Gly Ala Val His Thr Arg Gly Leu Asp Phe Ala
325 330 335

Cys Asp Ile Tyr Ile Trp Ala Pro Leu Ala Gly Thr Cys Gly Val Leu
340 345 350

Leu Leu Ser Leu Val Ile Thr Leu Tyr Cys Asn His Arg Asn Arg Ser
        355                 360                 365

Lys Arg Ser Arg Gly Gly His Ser Asp Tyr Met Asn Met Thr Pro Arg
    370                 375                 380

Arg Pro Gly Pro Thr Arg Lys His Tyr Gln Pro Tyr Ala Pro Pro Arg
385                 390                 395                 400

Asp Phe Ala Ala Tyr Arg Ser Arg Val Lys Phe Ser Arg Ser Ala Asp
                405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
        435                 440                 445

Asp Pro Glu Met Gly Gly Lys Pro Arg Arg Lys Asn Pro Gln Glu Gly
    450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
                485                 490                 495

Tyr Gln Gly Leu Ser Thr Ala Thr Lys Asp Thr Tyr Asp Ala Leu His
            500                 505                 510

Met Gln Ala Leu Pro Pro Arg
        515

<210> SEQ ID NO 7
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe

```
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Phe Ala
                325                 330                 335

Ser Asp Lys Pro Thr Thr Thr Pro Ala Pro Arg Pro Pro Thr Pro Ala
            340                 345                 350

Pro Thr Ile Ala Ser Gln Pro Leu Ser Leu Arg Pro Glu Ala Cys Arg
        355                 360                 365

Pro Ala Ala Gly Gly Ala Val His Thr Arg Gly Leu Asp Phe Ala Cys
    370                 375                 380

Asp Ile Tyr Ile Trp Ala Pro Leu Ala Gly Thr Cys Gly Val Leu Leu
385                 390                 395                 400

Leu Ser Leu Val Ile Thr Leu Tyr Cys Asn His Arg Asn Arg Ser Lys
                405                 410                 415

Arg Ser Arg Gly Gly His Ser Asp Tyr Met Asn Met Thr Pro Arg Arg
            420                 425                 430

Pro Gly Pro Thr Arg Lys His Tyr Gln Pro Tyr Ala Pro Pro Arg Asp
        435                 440                 445

Phe Ala Ala Tyr Arg Ser Arg Val Lys Phe Ser Arg Ser Ala Asp Ala
    450                 455                 460

Pro Ala Tyr Gln Gln Gly Gln Asn Gln Leu Tyr Asn Glu Leu Asn Leu
465                 470                 475                 480

Gly Arg Arg Glu Glu Tyr Asp Val Leu Asp Lys Arg Arg Gly Arg Asp
                485                 490                 495

Pro Glu Met Gly Gly Lys Pro Arg Arg Lys Asn Pro Gln Glu Gly Leu
            500                 505                 510

Tyr Asn Glu Leu Gln Lys Asp Lys Met Ala Glu Ala Tyr Ser Glu Ile
        515                 520                 525

Gly Met Lys Gly Glu Arg Arg Arg Gly Lys Gly His Asp Gly Leu Tyr
    530                 535                 540

Gln Gly Leu Ser Thr Ala Thr Lys Asp Thr Tyr Asp Ala Leu His Met
545                 550                 555                 560

Gln Ala Leu Pro Pro Arg
                565
```

<210> SEQ ID NO 8
<211> LENGTH: 613
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Phe Ala
                325                 330                 335

Ser Asp Lys Pro Thr Thr Thr Pro Ala Pro Arg Pro Pro Thr Pro Ala
            340                 345                 350

Pro Thr Ile Ala Ser Gln Pro Leu Ser Leu Arg Pro Glu Ala Ser Arg
        355                 360                 365

Pro Ala Ala Gly Gly Ala Val His Thr Arg Gly Leu Asp Phe Ala Ser
    370                 375                 380

Asp Lys Pro Thr Thr Thr Pro Ala Pro Arg Pro Pro Thr Pro Ala Pro
```

```
385                 390                 395                 400

Thr Ile Ala Ser Gln Pro Leu Ser Leu Arg Pro Glu Ala Cys Arg Pro
                405                 410                 415

Ala Ala Gly Gly Ala Val His Thr Arg Gly Leu Asp Phe Ala Cys Asp
            420                 425                 430

Ile Tyr Ile Trp Ala Pro Leu Ala Gly Thr Cys Gly Val Leu Leu Leu
        435                 440                 445

Ser Leu Val Ile Thr Leu Tyr Cys Asn His Arg Asn Arg Ser Lys Arg
    450                 455                 460

Ser Arg Gly Gly His Ser Asp Tyr Met Asn Met Thr Pro Arg Arg Pro
465                 470                 475                 480

Gly Pro Thr Arg Lys His Tyr Gln Pro Tyr Ala Pro Pro Arg Asp Phe
                485                 490                 495

Ala Ala Tyr Arg Ser Arg Val Lys Phe Ser Arg Ser Ala Asp Ala Pro
            500                 505                 510

Ala Tyr Gln Gln Gly Gln Asn Gln Leu Tyr Asn Glu Leu Asn Leu Gly
        515                 520                 525

Arg Arg Glu Glu Tyr Asp Val Leu Asp Lys Arg Arg Gly Arg Asp Pro
    530                 535                 540

Glu Met Gly Gly Lys Pro Arg Arg Lys Asn Pro Gln Glu Gly Leu Tyr
545                 550                 555                 560

Asn Glu Leu Gln Lys Asp Lys Met Ala Glu Ala Tyr Ser Glu Ile Gly
                565                 570                 575

Met Lys Gly Glu Arg Arg Arg Gly Lys Gly His Asp Gly Leu Tyr Gln
            580                 585                 590

Gly Leu Ser Thr Ala Thr Lys Asp Thr Tyr Asp Ala Leu His Met Gln
        595                 600                 605

Ala Leu Pro Pro Arg
    610


<210> SEQ ID NO 9
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125
```

```
Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Glu Ala Cys Pro Thr Gly Leu Tyr Thr His Ser
                245                 250                 255

Gly Glu Cys Cys Lys Ala Cys Asn Leu Gly Glu Gly Val Ala Gln Pro
            260                 265                 270

Cys Gly Ala Asn Gln Thr Val Cys Glu Pro Cys Leu Asp Ser Val Thr
        275                 280                 285

Phe Ser Asp Val Val Ser Ala Thr Glu Pro Cys Lys Pro Cys Thr Glu
    290                 295                 300

Cys Val Gly Leu Gln Ser Met Ser Ala Pro Cys Val Glu Ala Asp Asp
305                 310                 315                 320

Ala Val Cys Arg Cys Ala Tyr Gly Tyr Tyr Gln Asp Glu Thr Thr Gly
                325                 330                 335

Arg Cys Glu Ala Cys Arg Val Cys Glu Ala Gly Ser Gly Leu Val Phe
            340                 345                 350

Ser Cys Gln Asp Lys Gln Asn Thr Val Cys Glu Glu Cys Pro Asp Gly
        355                 360                 365

Thr Tyr Ser Asp Glu Ala Asn His Val Asp Pro Cys Leu Pro Cys Thr
    370                 375                 380

Val Cys Glu Asp Thr Glu Arg Gln Leu Arg Glu Cys Thr Arg Trp Ala
385                 390                 395                 400

Asp Ala Glu Cys Glu Glu Ile Pro Gly Arg Trp Ile Thr Arg Ser Thr
                405                 410                 415

Pro Pro Glu Gly Ser Asp Ser Thr Ala Pro Ser Thr Gln Glu Pro Glu
            420                 425                 430

Ala Pro Pro Glu Gln Asp Leu Ile Ala Ser Thr Val Ala Gly Val Val
        435                 440                 445

Thr Thr Val Met Gly Ser Ser Gln Pro Val Val Thr Arg Gly Thr Thr
    450                 455                 460

Asp Asn Ile Tyr Ile Trp Ala Pro Leu Ala Gly Thr Cys Gly Val Leu
465                 470                 475                 480

Leu Leu Ser Leu Val Ile Thr Leu Tyr Cys Asn His Arg Asn Arg Ser
                485                 490                 495

Lys Arg Ser Arg Gly Gly His Ser Asp Tyr Met Asn Met Thr Pro Arg
            500                 505                 510

Arg Pro Gly Pro Thr Arg Lys His Tyr Gln Pro Tyr Ala Pro Pro Arg
        515                 520                 525

Asp Phe Ala Ala Tyr Arg Ser Arg Val Lys Phe Ser Arg Ser Ala Asp
    530                 535                 540

Ala Pro Ala Tyr Gln Gln Gly Gln Asn Gln Leu Tyr Asn Glu Leu Asn
```

545 550 555 560

Leu Gly Arg Arg Glu Glu Tyr Asp Val Leu Asp Lys Arg Arg Gly Arg
565 570 575

Asp Pro Glu Met Gly Gly Lys Pro Arg Arg Lys Asn Pro Gln Glu Gly
580 585 590

Leu Tyr Asn Glu Leu Gln Lys Asp Lys Met Ala Glu Ala Tyr Ser Glu
595 600 605

Ile Gly Met Lys Gly Glu Arg Arg Arg Gly Lys Gly His Asp Gly Leu
610 615 620

Tyr Gln Gly Leu Ser Thr Ala Thr Lys Asp Thr Tyr Asp Ala Leu His
625 630 635 640

Met Gln Ala Leu Pro Pro Arg
645

<210> SEQ ID NO 10
<211> LENGTH: 567
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Ile Pro Glu Lys Arg Leu Glu Trp Val
35 40 45

Ala Ser Ile Ser Arg Gly Gly Thr Thr Tyr Tyr Pro Asp Ser Val Lys
50 55 60

Gly Arg Phe Thr Ile Ser Arg Asp Asn Val Arg Asn Ile Leu Tyr Leu
65 70 75 80

Gln Met Ser Ser Leu Arg Ser Glu Asp Thr Ala Met Tyr Tyr Cys Gly
85 90 95

Arg Tyr Asp Tyr Asp Gly Tyr Tyr Ala Met Asp Tyr Trp Gly Gln Gly
100 105 110

Thr Ser Val Thr Val Ser Ser Gly Ser Thr Ser Gly Ser Gly Lys Pro
115 120 125

Gly Ser Gly Glu Gly Ser Thr Lys Gly Asp Ile Lys Met Thr Gln Ser
130 135 140

Pro Ser Ser Met Tyr Ala Ser Leu Gly Glu Arg Val Thr Ile Thr Cys
145 150 155 160

Lys Ala Ser Pro Asp Ile Asn Ser Tyr Leu Ser Trp Phe Gln Gln Lys
165 170 175

Pro Gly Lys Ser Pro Lys Thr Leu Ile Tyr Arg Ala Asn Arg Leu Val
180 185 190

Asp Gly Val Pro Ser Arg Phe Ser Gly Gly Gly Ser Gly Gln Asp Tyr
195 200 205

Ser Leu Thr Ile Asn Ser Leu Glu Tyr Glu Asp Met Gly Ile Tyr Tyr
210 215 220

Cys Leu Gln Tyr Asp Glu Phe Pro Tyr Thr Phe Gly Gly Gly Thr Lys
225 230 235 240

Leu Glu Met Lys Lys Pro Thr Thr Thr Pro Ala Pro Arg Pro Pro Thr
245 250 255

Pro Ala Pro Thr Ile Ala Ser Gln Pro Leu Ser Leu Arg Pro Glu Ala
260 265 270

Ser Arg Pro Ala Ala Gly Gly Ala Val His Thr Arg Gly Leu Asp Phe
275 280 285

Ala Ser Asp Lys Pro Thr Thr Thr Pro Ala Pro Arg Pro Pro Thr Pro
290 295 300

Ala Pro Thr Ile Ala Ser Gln Pro Leu Ser Leu Arg Pro Glu Ala Ser
305 310 315 320

Arg Pro Ala Ala Gly Gly Ala Val His Thr Arg Gly Leu Asp Phe Ala
325 330 335

Ser Asp Lys Pro Thr Thr Thr Pro Ala Pro Arg Pro Pro Thr Pro Ala
340 345 350

Pro Thr Ile Ala Ser Gln Pro Leu Ser Leu Arg Pro Glu Ala Cys Arg
355 360 365

Pro Ala Ala Gly Gly Ala Val His Thr Arg Gly Leu Asp Phe Ala Cys
370 375 380

Asp Ile Tyr Ile Trp Ala Pro Leu Ala Gly Thr Cys Gly Val Leu Leu
385 390 395 400

Leu Ser Leu Val Ile Thr Leu Tyr Cys Asn His Arg Asn Lys Arg Gly
405 410 415

Arg Lys Lys Leu Leu Tyr Ile Phe Lys Gln Pro Phe Met Arg Pro Val
420 425 430

Gln Thr Thr Gln Glu Glu Asp Gly Cys Ser Cys Arg Phe Pro Glu Glu
435 440 445

Glu Glu Gly Gly Cys Glu Leu Arg Val Lys Phe Ser Arg Ser Ala Asp
450 455 460

Ala Pro Ala Tyr Gln Gln Gly Gln Asn Gln Leu Tyr Asn Glu Leu Asn
465 470 475 480

Leu Gly Arg Arg Glu Glu Tyr Asp Val Leu Asp Lys Arg Arg Gly Arg
485 490 495

Asp Pro Glu Met Gly Gly Lys Pro Arg Arg Lys Asn Pro Gln Glu Gly
500 505 510

Leu Tyr Asn Glu Leu Gln Lys Asp Lys Met Ala Glu Ala Tyr Ser Glu
515 520 525

Ile Gly Met Lys Gly Glu Arg Arg Arg Gly Lys Gly His Asp Gly Leu
530 535 540

Tyr Gln Gly Leu Ser Thr Ala Thr Lys Asp Thr Tyr Asp Ala Leu His
545 550 555 560

Met Gln Ala Leu Pro Pro Arg
565

<210> SEQ ID NO 11
<211> LENGTH: 656
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Ile Pro Glu Lys Arg Leu Glu Trp Val
35 40 45

-continued

```
Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Ser Thr Ser Gly Ser Gly Lys Pro
        115                 120                 125

Gly Ser Gly Glu Gly Ser Thr Lys Gly Asp Ile Lys Met Thr Gln Ser
    130                 135                 140

Pro Ser Ser Met Tyr Ala Ser Leu Gly Glu Arg Val Thr Ile Thr Cys
145                 150                 155                 160

Lys Ala Ser Pro Asp Ile Asn Ser Tyr Leu Ser Trp Phe Gln Gln Lys
                165                 170                 175

Pro Gly Lys Ser Pro Lys Thr Leu Ile Tyr Arg Ala Asn Arg Leu Val
            180                 185                 190

Asp Gly Val Pro Ser Arg Phe Ser Gly Gly Gly Ser Gly Gln Asp Tyr
        195                 200                 205

Ser Leu Thr Ile Asn Ser Leu Glu Tyr Glu Asp Met Gly Ile Tyr Tyr
    210                 215                 220

Cys Leu Gln Tyr Asp Glu Phe Pro Tyr Thr Phe Gly Gly Gly Thr Lys
225                 230                 235                 240

Leu Glu Met Lys Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
    450                 455                 460
```

-continued

Lys Ser Leu Ser Leu Ser Leu Gly Lys Met Ile Tyr Ile Trp Ala Pro
465 470 475 480

Leu Ala Gly Thr Cys Gly Val Leu Leu Leu Ser Leu Val Ile Thr Leu
485 490 495

Tyr Cys Asn His Arg Asn Lys Arg Gly Arg Lys Lys Leu Leu Tyr Ile
500 505 510

Phe Lys Gln Pro Phe Met Arg Pro Val Gln Thr Thr Gln Glu Glu Asp
515 520 525

Gly Cys Ser Cys Arg Phe Pro Glu Glu Glu Glu Gly Gly Cys Glu Leu
530 535 540

Arg Val Lys Phe Ser Arg Ser Ala Asp Ala Pro Ala Tyr Gln Gln Gly
545 550 555 560

Gln Asn Gln Leu Tyr Asn Glu Leu Asn Leu Gly Arg Arg Glu Glu Tyr
565 570 575

Asp Val Leu Asp Lys Arg Arg Gly Arg Asp Pro Glu Met Gly Gly Lys
580 585 590

Pro Arg Arg Lys Asn Pro Gln Glu Gly Leu Tyr Asn Glu Leu Gln Lys
595 600 605

Asp Lys Met Ala Glu Ala Tyr Ser Glu Ile Gly Met Lys Gly Glu Arg
610 615 620

Arg Arg Gly Lys Gly His Asp Gly Leu Tyr Gln Gly Leu Ser Thr Ala
625 630 635 640

Thr Lys Asp Thr Tyr Asp Ala Leu His Met Gln Ala Leu Pro Pro Arg
645 650 655

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Asp Val Gln Ile Thr Gln Ser Pro Ser Ser Leu Tyr Ala Ser Leu Gly
1 5 10 15

Glu Arg Val Thr Ile Thr Cys Lys Ala Ser Pro Asp Ile Asn Ser Tyr
20 25 30

Leu Ser Trp Phe Gln Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Gly Gly Ser Gly Gln Asp Tyr Ser Leu Thr Ile Asn Ser Leu Glu Tyr
65 70 75 80

Glu Asp Met Gly Ile Tyr Tyr Cys Leu Gln Tyr Asp Glu Phe Pro Tyr
85 90 95

Thr Phe Gly Gly Gly Thr Lys Leu Glu Met Lys
100 105

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115
```

<210> SEQ ID NO 14
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Asp Val Gln Ile Thr Gln Ser Pro Ser Ser Leu Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240
```

Thr Val Ser Ser Lys Pro Thr Thr Thr Pro Ala Pro Arg Pro Pro Thr
245 250 255

Pro Ala Pro Thr Ile Ala Ser Gln Pro Leu Ser Leu Arg Pro Glu Ala
260 265 270

Ser Arg Pro Ala Ala Gly Gly Ala Val His Thr Arg Gly Leu Asp Phe
275 280 285

Ala Ser Asp Lys Pro Thr Thr Thr Pro Ala Pro Arg Pro Pro Thr Pro
290 295 300

Ala Pro Thr Ile Ala Ser Gln Pro Leu Ser Leu Arg Pro Glu Ala Ser
305 310 315 320

Arg Pro Ala Ala Gly Gly Ala Val His Thr Arg Gly Leu Asp Phe Ala
325 330 335

Ser Asp Lys Pro Thr Thr Thr Pro Ala Pro Arg Pro Pro Thr Pro Ala
340 345 350

Pro Thr Ile Ala Ser Gln Pro Leu Ser Leu Arg Pro Glu Ala Cys Arg
355 360 365

Pro Ala Ala Gly Gly Ala Val His Thr Arg Gly Leu Asp Phe Ala Cys
370 375 380

Asp Ile Tyr Ile Trp Ala Pro Leu Ala Gly Thr Cys Gly Val Leu Leu
385 390 395 400

Leu Ser Leu Val Ile Thr Leu Tyr Cys Asn His Arg Asn Arg Ser Lys
405 410 415

Arg Ser Arg Gly Gly His Ser Asp Tyr Met Asn Met Thr Pro Arg Arg
420 425 430

Pro Gly Pro Thr Arg Lys His Tyr Gln Pro Tyr Ala Pro Pro Arg Asp
435 440 445

Phe Ala Ala Tyr Arg Ser Arg Val Lys Phe Ser Arg Ser Ala Asp Ala
450 455 460

Pro Ala Tyr Gln Gln Gly Gln Asn Gln Leu Tyr Asn Glu Leu Asn Leu
465 470 475 480

Gly Arg Arg Glu Glu Tyr Asp Val Leu Asp Lys Arg Arg Gly Arg Asp
485 490 495

Pro Glu Met Gly Gly Lys Pro Arg Arg Lys Asn Pro Gln Glu Gly Leu
500 505 510

Tyr Asn Glu Leu Gln Lys Asp Lys Met Ala Glu Ala Tyr Ser Glu Ile
515 520 525

Gly Met Lys Gly Glu Arg Arg Arg Gly Lys Gly His Asp Gly Leu Tyr
530 535 540

Gln Gly Leu Ser Thr Ala Thr Lys Asp Thr Tyr Asp Ala Leu His Met
545 550 555 560

Gln Ala Leu Pro Pro Arg
565

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

```
            20                  25                  30

Ala Met Ser Trp Val Arg Gln Ala Pro Gly Lys Gly Leu Glu Trp Val
        35                  40                  45

Ser Ala Ile Ser Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Pro Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Asn Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
```

```
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ile Trp Val Arg Gln Ala Pro Gly Lys Gly Leu Glu Trp Val
        35                  40                  45

Ala Arg Ile Ser Arg Gly Gly Thr Thr Arg Tyr Ala Asp Ser Val Lys
    50                  55                  60

Gly Arg Phe Thr Ile Ser Ala Asp Thr Ser Lys Glu Thr Ala Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 20
<211> LENGTH: 107
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 20

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Ile Ile Trp Val Arg Gln Ala Pro Gly Lys Gly Leu Glu Trp Val
35 40 45

Ala Arg Ile Ser Arg Gly Gly Thr Thr Arg Tyr Ala Asp Ser Val Lys
50 55 60

Gly Arg Phe Thr Ile Ser Ala Asp Thr Ser Lys Glu Thr Ala Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Asp Ile Gln Met Thr Gln Ser Pro Ser Ser Leu Ser Ala Ser Val Gly
1 5 10 15

Asp Arg Val Thr Ile Thr Cys Arg Ala Ser Pro Asp Ile Asn Ser Tyr
20 25 30

```
Val Ala Trp Tyr Gln Gln Lys Pro Gly Lys Ala Pro Lys Leu Leu Ile
        35                  40                  45

Tyr Arg Ala Asn Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ile Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60

Gly Arg Phe Thr Ile Ser Arg Asp Asn Val Lys Asn Thr Leu Tyr Leu
65                  70                  75                  80

Gln Met Ser Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Met Val Thr Val Ser Ser
        115


<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Lys Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Tyr
65                  70                  75                  80

Glu Asp Met Ala Ile Tyr Tyr Cys Leu Gln Tyr Asp Glu Phe Pro Tyr
                85                  90                  95
```

Thr Phe Gly Asp Gly Thr Lys Val Glu Ile Lys
100 105

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Gln Val Ser Leu Arg Glu Ser Gly Gly Gly Leu Val Gln Pro Gly Arg
1 5 10 15

Ser Leu Arg Leu Ser Cys Thr Ala Ser Gly Phe Thr Phe Ser Ser Tyr
20 25 30

Ala Met Thr Trp Val Arg Gln Ala Pro Gly Lys Gly Leu Glu Trp Val
35 40 45

Ala Ser Ile Ser Arg Gly Gly Thr Thr His Phe Ala Asp Ser Val Lys
50 55 60

Gly Arg Phe Thr Ile Ser Arg Asp Asn Ser Asn Asn Thr Leu Tyr Leu
65 70 75 80

Gln Met Asp Asn Val Arg Asp Glu Asp Thr Ala Ile Tyr Tyr Cys Gly
85 90 95

Arg Tyr Asp Tyr Asp Gly Tyr Tyr Ala Met Asp Tyr Trp Gly Arg Gly
100 105 110

Thr Leu Val Thr Val Ser Ser
115

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Asp Ile Val Met Thr Gln Ser Pro Ser Ser Leu Ser Ala Ser Val Gly
1 5 10 15

Asp Arg Val Thr Ile Thr Cys Arg Ala Ser Pro Asp Ile Asn Ser Tyr
20 25 30

Leu Ala Trp Tyr Gln Gln Lys Pro Gly Lys Ala Pro Lys Leu Leu Ile
35 40 45

Tyr Arg Ala Asn Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Met Lys
100 105

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Ala Lys Gly Leu Glu Trp Val
35 40 45

Ala Ile Ile Ser Arg Gly Gly Thr Gln Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Gly Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

Glu Ile Val Leu Thr Gln Ser Pro Asp Phe Gln Ser Val Thr Pro Lys
1 5 10 15

Glu Lys Val Thr Ile Thr Cys Arg Ala Ser Pro Asp Ile Asn Ser Tyr
20 25 30

Leu Ser Trp Tyr Gln Gln Lys Pro Asp Gln Ser Pro Lys Leu Leu Ile
35 40 45

Lys Arg Ala Asn Gln Ser Phe Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Ala Tyr Tyr Cys Leu Gln Tyr Asp Glu Phe Pro Tyr
85 90 95

Thr Phe Gly Pro Gly Thr Lys Val Asp Ile Lys
100 105

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 29

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Phe Ser Ser Tyr
20 25 30

Ala Met His Trp Val Arg Gln Ala Pro Gly Gln Gly Leu Glu Trp Met
35 40 45

```
Gly Asn Ile Ser Arg Gly Gly Thr Thr Asn Tyr Ala Glu Lys Phe Lys
    50                  55                  60

Asn Arg Val Thr Met Thr Arg Asp Thr Ser Ile Ser Thr Ala Tyr Met
65                  70                  75                  80

Glu Leu Ser Arg Leu Arg Ser Asp Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Pro Asp Ile Asn Ser Tyr
            20                  25                  30

Leu Glu Trp Tyr Leu Gln Lys Pro Gly Gln Ser Pro Gln Leu Leu Ile
        35                  40                  45

Tyr Arg Ala Asn Asp Arg Phe Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Thr Gly Ser Gly Phe Thr Phe Ser Ser Tyr
            20                  25                  30

Ala Met His Trp Leu Arg Gln Val Pro Gly Glu Gly Leu Glu Trp Val
        35                  40                  45

Ser Gly Ile Ser Arg Gly Gly Thr Ile Asp Tyr Ala Asp Ser Val Lys
    50                  55                  60

Gly Arg Phe Thr Ile Ser Arg Asp Asp Ala Lys Lys Thr Leu Ser Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110
```

Thr Met Val Thr Val Ser Ser
115

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Glu Ile Val Leu Thr Gln Ser Pro Ala Thr Leu Ser Val Ser Pro Gly
1 5 10 15

Glu Arg Ala Thr Leu Ser Cys Arg Ala Ser Pro Asp Ile Asn Ser Tyr
20 25 30

Leu Ala Trp Tyr Gln Gln Lys Pro Gly Gln Ala Pro Arg Leu Leu Phe
35 40 45

Ser Arg Ala Asn Asn Arg Ala Thr Gly Ile Pro Ala Arg Phe Thr Gly
50 55 60

Ser Gly Ser Gly Thr Asp Phe Thr Leu Thr Ile Ser Ser Leu Glu Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Ser Ile Ser Arg Gly Gly Thr Gln Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Gly Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Glu Ile Val Leu Thr Gln Ser Pro Asp Phe Gln Ser Val Thr Pro Lys
1               5                   10                  15

Glu Lys Val Thr Ile Thr Cys Arg Ala Ser Pro Asp Ile Asn Ser Tyr
            20                  25                  30

Leu Pro Trp Tyr Gln Gln Lys Pro Asp Gln Ser Pro Lys Leu Leu Ile
        35                  40                  45

Lys Arg Ala Asn Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Tyr Asp Glu Phe Pro Tyr
                85                  90                  95

Thr Phe Gly Pro Gly Thr Lys Val Asp Ile Lys
            100                 105

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Met Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Val Asp Lys Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly

```
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Ala Gly Thr Lys Val Glu Ile Lys
            100                 105


<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ser Ser Gly Phe Thr Phe Ser Ser Tyr
            20                  25                  30

Ala Met Ser Trp Arg Arg Gln Ala Pro Gly Lys Gly Leu Glu Trp Val
        35                  40                  45

Ala Gly Ile Ser Arg Gly Gly Thr Thr Ser Tyr Ala Asp Ser Val Lys
    50                  55                  60

Gly Arg Phe Thr Ile Ser Ser Asp Asp Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Ile Glu Ile Lys
            100                 105
```

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ser Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Gly Ile Ser Arg Gly Gly Thr Thr Ser Tyr Ala Asp Ser Val Lys
    50                  55                  60

Gly Arg Phe Thr Ile Ser Ala Asp Thr Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Thr Gly Thr Lys Leu Glu Ile Lys
            100                 105
```

<210> SEQ ID NO 41
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105


<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80
```

```
Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Ala Gly Thr Lys Val Glu Ile Lys
            100                 105


<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Met Arg Lys Ala Pro Gly Lys Gly Leu Glu Tyr Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Val Asp Lys Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 46
```

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Asn Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Ala Gly Thr Lys Val Glu Ile Lys
100 105

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Glu Val Gln Leu Val Glu Ser Gly Gly Gly Leu Val Gln Pro Gly Gly
1 5 10 15

Ser Leu Arg Leu Ser Cys Val Thr Ser Gly Phe Thr Phe Ser Ser Tyr
20 25 30

Ala Met Ser Trp Val Arg Gln Ala Pro Gly Lys Gly Leu Glu Trp Val
35 40 45

Ala Ser Ile Ser Arg Gly Gly Thr Thr Tyr Tyr Ser Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Asp Ile Val Leu Thr Gln Ser Pro Ala Thr Leu Ser Leu Ser Pro Gly
1 5 10 15

-continued

```
Glu Arg Ala Thr Leu Ser Cys Lys Ala Ser Pro Asp Ile Asn Ser Tyr
            20                  25                  30

Met Asn Trp Tyr Gln Gln Lys Pro Gly Gln Ala Pro Arg Leu Leu Ile
        35                  40                  45

Ser Arg Ala Asn Arg Leu Val Asp Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Asp Pro Lys Phe Gln
    50                  55                  60

Asp Arg Ala Thr Ile Ser Ala Asp Asn Ser Lys Asn Thr Ala Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Asn Trp Tyr Gln Gln Lys Pro Gly Lys Ala Pro Lys Val Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

Glu Asp Phe Ala Thr Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Glu Val Gln Leu Val Glu Ser Gly Gly Gly Leu Val Gln Pro Gly Gly
1 5 10 15

Ser Leu Arg Leu Ser Cys Thr Gly Ser Gly Phe Thr Phe Ser Ser Tyr
20 25 30

Ala Met Ser Trp Leu Arg Gln Val Pro Gly Glu Gly Leu Glu Trp Val
35 40 45

Ser Ser Ile Ser Arg Gly Gly Thr Thr Asp Tyr Ala Asp Ser Val Lys
50 55 60

Gly Arg Phe Thr Ile Ser Arg Asp Asp Ala Lys Lys Thr Leu Ser Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Met Val Thr Val Ser Ser
115

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Glu Ile Val Leu Thr Gln Ser Pro Ala Thr Leu Ser Val Ser Pro Gly
1 5 10 15

Glu Arg Ala Thr Leu Ser Cys Lys Ala Ser Pro Asp Ile Asn Ser Tyr
20 25 30

Leu Ala Trp Tyr Gln Gln Lys Pro Gly Gln Ala Pro Arg Leu Leu Phe
35 40 45

Ser Arg Ala Asn Arg Leu Val Asp Gly Ile Pro Ala Arg Phe Thr Gly
50 55 60

Ser Gly Ser Gly Thr Asp Phe Thr Leu Thr Ile Ser Ser Leu Glu Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 53
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met Ser Trp Val Arg Gln Val Pro Gly Lys Gly Leu Val Trp Ile
        35                  40                  45

Ser Ser Ile Ser Arg Gly Gly Thr Thr Tyr Tyr Ala Asp Ser Val Arg
    50                  55                  60

Gly Arg Phe Ile Ile Ser Arg Asp Asn Ala Lys Asn Thr Leu Tyr Leu
65                  70                  75                  80

Glu Met Asn Asn Leu Arg Gly Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Leu Thr Gln Ser Pro Asp Ser Leu Ala Val Ser Leu Gly
1               5                   10                  15

Glu Arg Ala Thr Ile Asn Cys Lys Ala Ser Pro Asp Ile Asn Ser Tyr
            20                  25                  30

Leu Ser Trp Tyr Gln Gln Arg Pro Gly Gln Pro Pro Arg Leu Leu Ile
        35                  40                  45

His Arg Ala Asn Arg Leu Val Asp Gly Val Pro Asp Arg Phe Ser Gly
    50                  55                  60

Ser Gly Phe Gly Thr Asp Phe Thr Leu Thr Ile Thr Ser Leu Gln Ala
65                  70                  75                  80

Glu Asp Val Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105

<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
        35                  40                  45

Ala Ser Ile Ser Arg Gly Gly Thr Thr Tyr Tyr Ala Asp Ser Val Lys
    50                  55                  60

Gly Arg Phe Thr Ile Ser Ala Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
```

```
            100                 105                 110

Thr Leu Val Thr Val Ser Ser
        115


<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Glu Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Leu Glu Thr Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Ser Ile Ser Arg Gly Gly Thr Thr Tyr Tyr Gly Asp Ser Val Lys
    50                  55                  60

Gly Arg Phe Thr Ile Ser Arg Asp His Ala Lys Asn Ser Leu Tyr Leu
65                  70                  75                  80

Gln Met Asn Ser Leu Arg Val Glu Asp Thr Ala Val Tyr Tyr Cys Val
                85                  90                  95

Arg Tyr Asp Tyr Asp Gly Tyr Tyr Ala Met Asp Tyr Trp Gly Leu Gly
            100                 105                 110

Thr Leu Val Thr Val Ser Ser
        115


<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 60

Ala Ile Arg Met Thr Gln Ser Pro Ser Phe Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Arg Pro Gly Lys Ala Pro Lys Leu Leu Ile
35 40 45

Tyr Arg Ala Asn Arg Leu Val Asp Gly Val Pro Ser Arg Phe Ser Gly
50 55 60

Gly Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Ser Ile Ser Arg Gly Gly Thr Thr Tyr Tyr Ala Glu Ser Leu Glu
50 55 60

Gly Arg Phe Thr Ile Ser Arg Asp Asp Ser Lys Asn Ser Leu Tyr Leu
65 70 75 80

Gln Met Asn Ser Leu Lys Thr Glu Asp Thr Ala Val Tyr Tyr Cys Ala
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Lys Pro Gly Lys Ala Pro Lys Thr Leu Ile
35 40 45

```
Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

```
Gln Val Thr Leu Arg Glu Ser Gly Pro Ala Leu Val Lys Pro Thr Gln
1               5                   10                  15

Thr Leu Thr Leu Thr Cys Ala Ala Ser Gly Phe Thr Phe Ser Ser Tyr
            20                  25                  30

Ala Met Ser Trp Ile Arg Gln Pro Pro Gly Lys Ala Leu Glu Trp Leu
        35                  40                  45

Ala Ser Ile Ser Arg Gly Gly Thr Thr Tyr Tyr Asn Pro Ser Leu Lys
    50                  55                  60

Asp Arg Leu Thr Ile Ser Lys Asp Thr Ser Ala Asn Gln Val Val Leu
65                  70                  75                  80

Lys Val Thr Asn Met Asp Pro Ala Asp Thr Ala Thr Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Thr Val Thr Val Ser Ser
        115
```

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Asp Ile Gln Met Thr Gln Ser Pro Ser Thr Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Ala Phe Thr Leu Thr Ile Ser Ser Leu Gln Pro
65                  70                  75                  80

Asp Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Arg Gly Gly Thr Thr Tyr Tyr Ala Asp Ser Val Lys
50 55 60

Gly Arg Phe Thr Ile Ser Ala Asp Thr Ser Lys Glu Thr Ala Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Arg Gly Gly Thr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Arg Gly Gly Thr Thr Tyr Tyr Ala Asp Ser Val Lys
50 55 60

Gly Arg Phe Thr Ile Ser Ala Asp Thr Ser Lys Glu Thr Ala Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Asp Ile Gln Met Thr Gln Ser Pro Ser Ser Leu Ser Ala Ser Val Gly
1 5 10 15

Asp Arg Val Thr Ile Thr Cys Gln Ala Ser Pro Asp Ile Asn Ser Tyr
20 25 30

Leu Asn Trp Tyr Gln Gln Lys Pro Gly Lys Ala Pro Lys Leu Leu Ile
35 40 45

Tyr Arg Ala Asn Asn Leu Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 71
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Arg Gly Gly Thr Thr Tyr Tyr Ala Asp Ser Val Lys
50 55 60

Gly Arg Phe Thr Ile Ser Ala Asp Thr Ser Lys Glu Thr Ala Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
            20                  25                  30

Val Ala Trp Tyr Gln Gln Lys Pro Gly Lys Ala Pro Lys Leu Leu Ile
        35                  40                  45

Tyr Arg Ala Asn Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Gln Ile Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Ser Tyr
            20                  25                  30

Ala Met Ser Trp Val Arg Gln Ala Pro Gly Lys Ser Phe Lys Trp Met
        35                  40                  45

Gly Ser Ile Ser Arg Gly Gly Thr Thr Tyr Tyr Ser Ala Asp Phe Lys
    50                  55                  60

Gly Arg Phe Ala Ile Thr Lys Asp Thr Ser Ala Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Asp Ile Val Met Thr Gln Ser Pro Asp Ser Leu Ala Val Ser Leu Gly
```

```
1               5                   10                  15

Glu Arg Ala Thr Ile Ser Cys Lys Ala Ser Pro Asp Ile Asn Ser Tyr
            20                  25                  30

Leu Ser Trp Tyr Gln Gln Lys Pro Gly Gln Pro Pro Lys Leu Leu Ile
        35                  40                  45

Tyr Arg Ala Asn Arg Leu Val Asp Gly Val Pro Asp Arg Phe Ser Gly
    50                  55                  60

Ser Gly Ser Arg Thr Asp Phe Thr Leu Thr Ile Ser Ser Leu Gln Ala
65                  70                  75                  80

Glu Asp Val Ala Val Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 75
<211> LENGTH: 563
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Met Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Val Asp Lys Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Ala Gly Thr Lys Val Glu Ile
225                 230                 235                 240

Lys Lys Pro Thr Thr Thr Pro Ala Pro Arg Pro Pro Thr Pro Ala Pro
                245                 250                 255
```

-continued

```
Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 76
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45
```

-continued

```
Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ser Ile Ser Arg Gly
                165                 170                 175

Gly Thr Thr Tyr Tyr Pro Asp Ser Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Gly Arg Tyr Asp Tyr Asp Gly
    210                 215                 220

Tyr Tyr Ala Met Asp Tyr Trp Gly Gln Gly Thr Leu Val Thr Val Ser
225                 230                 235                 240

Ser Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
```

```
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 77
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Ile Ala Thr Tyr Tyr Cys Leu Gln
    210                 215                 220

Tyr Asp Glu Phe Pro Tyr Thr Phe Gly Gly Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
```

260 265 270

Ala Ala Gly Gly Ala Val His Thr Arg Gly Leu Asp Phe Ala Ser Asp
275 280 285

Lys Pro Thr Thr Thr Pro Ala Pro Arg Pro Pro Thr Pro Ala Pro Thr
290 295 300

Ile Ala Ser Gln Pro Leu Ser Leu Arg Pro Glu Ala Ser Arg Pro Ala
305 310 315 320

Ala Gly Gly Ala Val His Thr Arg Gly Leu Asp Phe Ala Ser Asp Lys
325 330 335

Pro Thr Thr Thr Pro Ala Pro Arg Pro Pro Thr Pro Ala Pro Thr Ile
340 345 350

Ala Ser Gln Pro Leu Ser Leu Arg Pro Glu Ala Cys Arg Pro Ala Ala
355 360 365

Gly Gly Ala Val His Thr Arg Gly Leu Asp Phe Ala Cys Asp Ile Tyr
370 375 380

Ile Trp Ala Pro Leu Ala Gly Thr Cys Gly Val Leu Leu Leu Ser Leu
385 390 395 400

Val Ile Thr Leu Tyr Cys Asn His Arg Asn Arg Ser Lys Arg Ser Arg
405 410 415

Gly Gly His Ser Asp Tyr Met Asn Met Thr Pro Arg Arg Pro Gly Pro
420 425 430

Thr Arg Lys His Tyr Gln Pro Tyr Ala Pro Pro Arg Asp Phe Ala Ala
435 440 445

Tyr Arg Ser Arg Val Lys Phe Ser Arg Ser Ala Asp Ala Pro Ala Tyr
450 455 460

Gln Gln Gly Gln Asn Gln Leu Tyr Asn Glu Leu Asn Leu Gly Arg Arg
465 470 475 480

Glu Glu Tyr Asp Val Leu Asp Lys Arg Arg Gly Arg Asp Pro Glu Met
485 490 495

Gly Gly Lys Pro Arg Arg Lys Asn Pro Gln Glu Gly Leu Tyr Asn Glu
500 505 510

Leu Gln Lys Asp Lys Met Ala Glu Ala Tyr Ser Glu Ile Gly Met Lys
515 520 525

Gly Glu Arg Arg Arg Gly Lys Gly His Asp Gly Leu Tyr Gln Gly Leu
530 535 540

Ser Thr Ala Thr Lys Asp Thr Tyr Asp Ala Leu His Met Gln Ala Leu
545 550 555 560

Pro Pro Arg

<210> SEQ ID NO 78
<211> LENGTH: 563
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Ser Ile Ser Arg Gly Gly Thr Thr Tyr Tyr Pro Asp Ser Val Lys

```
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Ala Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480
```

Glu Glu Tyr Asp Val Leu Asp Lys Arg Arg Gly Arg Asp Pro Glu Met
485 490 495

Gly Gly Lys Pro Arg Arg Lys Asn Pro Gln Glu Gly Leu Tyr Asn Glu
500 505 510

Leu Gln Lys Asp Lys Met Ala Glu Ala Tyr Ser Glu Ile Gly Met Lys
515 520 525

Gly Glu Arg Arg Arg Gly Lys Gly His Asp Gly Leu Tyr Gln Gly Leu
530 535 540

Ser Thr Ala Thr Lys Asp Thr Tyr Asp Ala Leu His Met Gln Ala Leu
545 550 555 560

Pro Pro Arg

<210> SEQ ID NO 79
<211> LENGTH: 563
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Ser Arg Gly Gly Thr Thr Tyr Tyr Pro Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Asp Ile Gln Met Thr Gln Ser Pro Ser Ser
130 135 140

Leu Ser Ala Ser Val Gly Asp Arg Val Thr Ile Thr Cys Lys Ala Ser
145 150 155 160

Pro Asp Ile Asn Ser Tyr Leu Asn Trp Tyr Gln Gln Lys Pro Gly Lys
165 170 175

Ala Pro Lys Leu Leu Ile Tyr Arg Ala Asn Arg Leu Val Asp Gly Val
180 185 190

Pro Ser Arg Phe Ser Gly Ser Gly Ser Gly Thr Asp Tyr Thr Leu Thr
195 200 205

Ile Ser Ser Leu Gln Pro Glu Asp Phe Ala Thr Tyr Tyr Cys Leu Gln
210 215 220

Tyr Asp Glu Phe Pro Tyr Thr Phe Gly Ala Gly Thr Lys Val Glu Ile
225 230 235 240

Lys Lys Pro Thr Thr Thr Pro Ala Pro Arg Pro Pro Thr Pro Ala Pro
245 250 255

Thr Ile Ala Ser Gln Pro Leu Ser Leu Arg Pro Glu Ala Ser Arg Pro
260 265 270

```
Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 80
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60
```

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Val Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Gln Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480
```

```
Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 81
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met Ser Trp Val Arg Gln Val Pro Gly Lys Gly Leu Val Trp Ile
        35                  40                  45

Ser Ser Ile Ser Arg Gly Gly Thr Thr Tyr Tyr Ala Asp Ser Val Arg
    50                  55                  60

Gly Arg Phe Ile Ile Ser Arg Asp Asn Ala Lys Asn Thr Leu Tyr Leu
65                  70                  75                  80

Glu Met Asn Asn Leu Arg Gly Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Gln Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Asn Leu Glu Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Ile Ala Thr Tyr Tyr Cys Leu Gln
    210                 215                 220

Tyr Asp Glu Phe Pro Tyr Thr Phe Gly Gln Gly Thr Lys Leu Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270
```

Ala Ala Gly Gly Ala Val His Thr Arg Gly Leu Asp Phe Ala Ser Asp
275 280 285

Lys Pro Thr Thr Thr Pro Ala Pro Arg Pro Pro Thr Pro Ala Pro Thr
290 295 300

Ile Ala Ser Gln Pro Leu Ser Leu Arg Pro Glu Ala Ser Arg Pro Ala
305 310 315 320

Ala Gly Gly Ala Val His Thr Arg Gly Leu Asp Phe Ala Ser Asp Lys
325 330 335

Pro Thr Thr Thr Pro Ala Pro Arg Pro Pro Thr Pro Ala Pro Thr Ile
340 345 350

Ala Ser Gln Pro Leu Ser Leu Arg Pro Glu Ala Cys Arg Pro Ala Ala
355 360 365

Gly Gly Ala Val His Thr Arg Gly Leu Asp Phe Ala Cys Asp Ile Tyr
370 375 380

Ile Trp Ala Pro Leu Ala Gly Thr Cys Gly Val Leu Leu Leu Ser Leu
385 390 395 400

Val Ile Thr Leu Tyr Cys Asn His Arg Asn Arg Ser Lys Arg Ser Arg
405 410 415

Gly Gly His Ser Asp Tyr Met Asn Met Thr Pro Arg Arg Pro Gly Pro
420 425 430

Thr Arg Lys His Tyr Gln Pro Tyr Ala Pro Pro Arg Asp Phe Ala Ala
435 440 445

Tyr Arg Ser Arg Val Lys Phe Ser Arg Ser Ala Asp Ala Pro Ala Tyr
450 455 460

Gln Gln Gly Gln Asn Gln Leu Tyr Asn Glu Leu Asn Leu Gly Arg Arg
465 470 475 480

Glu Glu Tyr Asp Val Leu Asp Lys Arg Arg Gly Arg Asp Pro Glu Met
485 490 495

Gly Gly Lys Pro Arg Arg Lys Asn Pro Gln Glu Gly Leu Tyr Asn Glu
500 505 510

Leu Gln Lys Asp Lys Met Ala Glu Ala Tyr Ser Glu Ile Gly Met Lys
515 520 525

Gly Glu Arg Arg Arg Gly Lys Gly His Asp Gly Leu Tyr Gln Gly Leu
530 535 540

Ser Thr Ala Thr Lys Asp Thr Tyr Asp Ala Leu His Met Gln Ala Leu
545 550 555 560

Pro Pro Arg

<210> SEQ ID NO 82
<211> LENGTH: 563
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Glu Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met Ser Trp Val Arg Gln Val Pro Gly Lys Gly Leu Val Trp Ile
35 40 45

Ser Ser Ile Ser Arg Gly Gly Thr Thr Tyr Tyr Ala Asp Ser Val Arg
50 55 60

-continued

```
Gly Arg Phe Ile Ile Ser Arg Asp Asn Ala Lys Asn Thr Leu Tyr Leu
65                  70                  75                  80

Glu Met Asn Asn Leu Arg Gly Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Ala Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
```

```
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 83
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45


<210> SEQ ID NO 84
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Cys Arg Pro Ala Ala
65                  70                  75                  80

Gly Gly Ala Val His Thr Arg Gly Leu Asp Phe Ala Cys Asp
                85                  90


<210> SEQ ID NO 85
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Lys Pro Thr Thr Thr Pro Ala Pro Arg Pro Pro Thr Pro Ala Pro Thr
1               5                   10                  15
```

```
Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
                85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Cys Arg Pro Ala Ala Gly
        115                 120                 125

Gly Ala Val His Thr Arg Gly Leu Asp Phe Ala Cys Asp
    130                 135                 140
```

<210> SEQ ID NO 86
<211> LENGTH: 185
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Thr Thr Pro Ala Pro Arg Pro Pro Thr Pro Ala Pro Thr Ile Ala Ser
1               5                   10                  15

Gln Pro Leu Ser Leu Arg Pro Glu Ala Ser Arg Pro Ala Ala Gly Gly
            20                  25                  30

Ala Val His Thr Arg Gly Leu Asp Phe Ala Ser Asp Lys Pro Thr Thr
        35                  40                  45

Thr Pro Ala Pro Arg Pro Pro Thr Pro Ala Pro Thr Ile Ala Ser Gln
    50                  55                  60

Pro Leu Ser Leu Arg Pro Glu Ala Ser Arg Pro Ala Ala Gly Gly Ala
65                  70                  75                  80

Val His Thr Arg Gly Leu Asp Phe Ala Ser Asp Lys Pro Thr Thr Thr
                85                  90                  95

Pro Ala Pro Arg Pro Pro Thr Pro Ala Pro Thr Ile Ala Ser Gln Pro
            100                 105                 110

Leu Ser Leu Arg Pro Glu Ala Ser Arg Pro Ala Ala Gly Gly Ala Val
        115                 120                 125

His Thr Arg Gly Leu Asp Phe Ala Ser Asp Lys Pro Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp
            180                 185
```

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Ile Tyr Ile Trp Ala Pro Leu Ala Gly Thr Cys Gly Val Leu Leu Leu
1 5 10 15

Ser Leu Val Ile Thr Leu Tyr Cys Asn His Arg Asn
20 25

<210> SEQ ID NO 88
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 89
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 90
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

Arg Ser Lys Arg Ser Arg Gly Gly His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 91
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Leu Cys Ala Arg Pro Arg Arg Ser Pro Ala Gln Glu Asp Gly Lys Val
1 5 10 15

```
Tyr Ile Asn Met Pro Gly Arg Gly
            20


<210> SEQ ID NO 92
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50


<210> SEQ ID NO 93
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 95
<211> LENGTH: 20
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Met Arg Leu Pro Ala Gln Leu Leu Gly Leu Leu Met Leu Trp Val Pro
1               5                   10                  15

Gly Ser Ser Gly
            20

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met Asp Trp Thr Trp Ile Leu Phe Leu Val Ala Ala Ala Thr Arg Val
1               5                   10                  15

His Ser

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met Ala Leu Pro Val Thr Ala Leu Leu Leu Pro Leu Ala Leu Leu Leu
1               5                   10                  15

His Ala Ala Arg Pro
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met Gly Thr Ser Leu Leu Cys Trp Met Ala Leu Cys Leu Leu Gly Ala
1               5                   10                  15

Asp His Ala Asp Ala
            20

<210> SEQ ID NO 99
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Met Lys Arg Phe Leu Phe Leu Leu Leu Thr Ile Ser Leu Leu Val Met
1               5                   10                  15

Val Gln Ile Gln Thr Gly Leu Ser

20

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Met Gly Ala Gly Ala Thr Gly Arg Ala Met Asp Gly Pro Arg Leu Leu
1 5 10 15

Leu Leu Leu Leu Leu Gly Val Ser Leu Gly Gly Ala
20 25

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Met Gly Trp Ser Cys Ile Ile Leu Phe Leu Val Ala Thr Ala Thr Gly
1 5 10 15

Val His Ser

<210> SEQ ID NO 102
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Met Ser Arg Ser Val Ala Leu Ala Val Leu Ala Leu Leu Ser Leu Ser
1 5 10 15

Gly Leu Glu Ala
20

<210> SEQ ID NO 103
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Met Thr Arg Leu Thr Val Leu Ala Leu Leu Ala Gly Leu Leu Ala Ser
1 5 10 15

Ser Arg Ala

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

```
Met Lys Trp Val Thr Phe Ile Ser Leu Leu Phe Leu Phe Ser Ser Ala
1               5                   10                  15

Tyr Ser


<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Gly Lys Asn Lys Leu Leu His Pro Ser Leu Val Leu Leu Leu Leu
1               5                   10                  15

Val Leu Leu Pro Thr Asp Ala
            20


<210> SEQ ID NO 106
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Glu Phe Gly Leu Ser Trp Leu Phe Leu Val Ala Ile Leu Lys Gly
1               5                   10                  15

Val Gln Cys


<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Met Asp Met Arg Val Pro Ala Gln Leu Leu Gly Leu Leu Leu Leu Trp
1               5                   10                  15

Leu Ser Gly Ala Arg Cys
            20


<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Met Glu Phe Gly Leu Ser Trp Val Phe Leu Val Ala Leu Phe Arg Gly
1               5                   10                  15

Val Gln Cys


<210> SEQ ID NO 109
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 109

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Cys His
275 280 285

Pro Asn Cys Thr Tyr Gly Cys Thr Gly Pro Gly Leu Glu Gly Cys Pro
290 295 300

Thr Asn Gly Pro Lys Ile Pro Ser Ile Ala Thr Gly Met Val Gly Ala
305 310 315 320

Leu Leu Leu Leu Leu Val Val Ala Leu Gly Ile Gly Leu Phe Met
325 330 335

<210> SEQ ID NO 110
<211> LENGTH: 243
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 110

Arg Lys Val Cys Asn Gly Ile Gly Ile Gly Glu Phe Lys Asp Ser Leu
1 5 10 15

```
Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Ser Gly Gly Gly Gly Ser Gly Gly
        195                 200                 205

Gly Gly Ser Phe Trp Val Leu Val Val Val Gly Gly Val Leu Ala Cys
    210                 215                 220

Tyr Ser Leu Leu Val Thr Val Ala Phe Ile Ile Phe Trp Val Arg Ser
225                 230                 235                 240

Lys Arg Ser
```

<210> SEQ ID NO 111
<211> LENGTH: 297
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125
```

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 112
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly

-continued

```
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu
            260


<210> SEQ ID NO 113
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Asp Trp Thr Trp Ile Leu Phe Leu Val Ala Ala Ala Thr Arg Val
1               5                   10                  15

His Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Gly Gly Ser Gly Gly Gly Gly Ser Gly Gly
    130                 135                 140

Gly Gly Ser Gly Gly Gly Gly Ser Gly Gly Gly Ser Leu Gln Ile Thr
145                 150                 155                 160

Cys Pro Pro Pro Met Ser Val Glu His Ala Asp Ile Trp Val Lys Ser
                165                 170                 175

Tyr Ser Leu Tyr Ser Arg Glu Arg Tyr Ile Cys Asn Ser Gly Phe Lys
            180                 185                 190

Arg Lys Ala Gly Thr Ser Ser Leu Thr Glu Cys Val Leu Asn Lys Ala
        195                 200                 205

Thr Asn Val Ala His Trp Thr Thr Pro Ser Leu Lys Cys Ile Arg Asp
    210                 215                 220

Pro Ala Leu Val His Gln Arg Pro Ala Pro Pro Ser Thr Val Thr Thr
225                 230                 235                 240

Ala Gly Val Thr Pro Gln Pro Glu Ser Leu Ser Pro Ser Gly Lys Glu
                245                 250                 255

Pro Ala Ala Ser Ser Pro Ser Ser Asn Asn Thr Ala Ala Thr Thr Ala
            260                 265                 270
```

```
Ala Ile Val Pro Gly Ser Gln Leu Met Pro Ser Lys Ser Pro Ser Thr
        275                 280                 285

Gly Thr Thr Glu Ile Ser Ser His Glu Ser Ser His Gly Thr Pro Ser
    290                 295                 300

Gln Thr Thr Ala Lys Asn Trp Glu Leu Thr Ala Ser Ala Ser His Gln
305                 310                 315                 320

Pro Pro Gly Val Tyr Pro Gln Gly His Ser Asp Thr Thr Val Ala Ile
                325                 330                 335

Ser Thr Ser Thr Val Leu Leu Cys Gly Leu Ser Ala Val Ser Leu Leu
            340                 345                 350

Ala Cys Tyr Leu Lys Ser Arg Gln Thr Pro Pro Leu Ala Ser Val Glu
        355                 360                 365

Met Glu Ala Met Glu Ala Leu Pro Val Thr Trp Gly Thr Ser Ser Arg
    370                 375                 380

Asp Glu Asp Leu Glu Asn Cys Ser His His Leu
385                 390                 395


<210> SEQ ID NO 114
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 115
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
```

-continued

```
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235


<210> SEQ ID NO 116
<211> LENGTH: 18
<212> TYPE: PRT
<213> ORGANISM: Thosea asigna virus

<400> SEQUENCE: 116

Glu Gly Arg Gly Ser Leu Leu Thr Cys Gly Asp Val Glu Glu Asn Pro
1               5                   10                  15

Gly Pro


<210> SEQ ID NO 117
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25


<210> SEQ ID NO 118
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ala Lys Arg Ser Gly Ser Gly Glu Gly Arg Gly Ser Leu Leu Thr
1               5                   10                  15
```

Cys Gly Asp Val Glu Glu Asn Pro Gly Pro
20 25

<210> SEQ ID NO 119
<211> LENGTH: 19
<212> TYPE: PRT
<213> ORGANISM: Porcine teschovirus 1

<400> SEQUENCE: 119

Ala Thr Asn Phe Ser Leu Leu Lys Gln Ala Gly Asp Val Glu Glu Asn
1 5 10 15

Pro Gly Pro

<210> SEQ ID NO 120
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 121
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Arg Ala Lys Arg Ala Pro Val Lys Gln Gly Ser Gly Ala Thr Asn Phe
1 5 10 15

Ser Leu Leu Lys Gln Ala Gly Asp Val Glu Glu Asn Pro Gly Pro
20 25 30

<210> SEQ ID NO 122
<211> LENGTH: 20
<212> TYPE: PRT
<213> ORGANISM: Equine rhinitis A virus

<400> SEQUENCE: 122

Gln Cys Thr Asn Tyr Ala Leu Leu Lys Leu Ala Gly Asp Val Glu Ser
1 5 10 15

Asn Pro Gly Pro
20

<210> SEQ ID NO 123
<211> LENGTH: 22
<212> TYPE: PRT
<213> ORGANISM: Foot-and-mouth disease virus

<400> SEQUENCE: 123

Val Lys Gln Thr Leu Asn Phe Asp Leu Leu Lys Leu Ala Gly Asp Val
1 5 10 15

Glu Ser Asn Pro Gly Pro
20

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Ala Pro Val Lys Gln Gly Ser Gly
1               5

<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Arg Ala Lys Arg
1

<210> SEQ ID NO 126
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Arg Ala Lys Arg Ala Pro Val Lys Gln Thr Leu Asn Phe Asp Leu Leu
1               5                   10                  15

Lys Leu Ala Gly Asp Val Glu Ser Asn Pro Gly Pro
            20                  25

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Gly Gly Gly Gly Ser Gly Gly Gly Gly Ser Gly Gly Gly Gly Ser
1               5                   10                  15

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Gly Ser Thr Ser Gly Ser Gly Lys Pro Gly Ser Gly Glu Gly Ser Thr
1               5                   10                  15

Lys Gly

<210> SEQ ID NO 129
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Gly Ser Gly
1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Ser Gly Ser Gly
1

<210> SEQ ID NO 131
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
            20                  25                  30

Asp Ala Leu Asp Asp Phe Asp Leu Asp Met Leu Gly Asp Gly Asp Ser
        35                  40                  45

Pro Gly Pro Gly Phe Thr Pro His Asp Ser Ala Pro Tyr Gly Ala Leu
    50                  55                  60

Asp Met Ala Asp Phe Glu Phe Glu Gln Met Phe Thr Asp Ala Leu Gly
65                  70                  75                  80

Ile Asp Glu Tyr Gly Gly
                85
```

<210> SEQ ID NO 132
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

```
Glu Met Pro Val Asp Arg Ile Leu Glu Ala Glu Leu Ala Val Glu Gln
1               5                   10                  15

Lys Ser Asp Gln Gly Val Glu Gly Pro Gly Gly Thr Gly Gly Ser Gly
            20                  25                  30

Ser Ser Pro Asn Asp Pro Val Thr Asn Ile Cys Gln Ala Ala Asp Lys
        35                  40                  45

Gln Leu Phe Thr Leu Val Glu Trp Ala Lys Arg Ile Pro His Phe Ser
    50                  55                  60

Ser Leu Pro Leu Asp Asp Gln Val Ile Leu Leu Arg Ala Gly Trp Asn
65                  70                  75                  80

Glu Leu Leu Ile Ala Ser Phe Ser His Arg Ser Ile Asp Val Arg Asp
```

```
                85                  90                  95

Gly Ile Leu Leu Ala Thr Gly Leu His Val His Arg Asn Ser Ala His
            100                 105                 110

Ser Ala Gly Val Gly Ala Ile Phe Asp Arg Val Leu Thr Glu Leu Val
        115                 120                 125

Ser Lys Met Arg Asp Met Arg Met Asp Lys Thr Glu Leu Gly Cys Leu
    130                 135                 140

Arg Ala Ile Ile Leu Phe Asn Pro Glu Val Arg Gly Leu Lys Ser Ala
145                 150                 155                 160

Gln Glu Val Glu Leu Leu Arg Glu Lys Val Tyr Ala Ala Leu Glu Glu
                165                 170                 175

Tyr Thr Arg Thr Thr His Pro Asp Glu Pro Gly Arg Phe Ala Lys Leu
            180                 185                 190

Leu Leu Arg Leu Pro Ser Leu Arg Ser Ile Gly Leu Lys Cys Leu Glu
        195                 200                 205

His Leu Phe Phe Phe Arg Leu Ile Gly Asp Val Pro Ile Asp Thr Phe
    210                 215                 220

Leu Met Glu Met Leu Glu Ser Pro Ser Asp Ser
225                 230                 235


<210> SEQ ID NO 133
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
            20                  25                  30

Asp Ala Leu Asp Asp Phe Asp Leu Asp Met Leu Gly Asp Gly Asp Ser
        35                  40                  45

Pro Gly Pro Gly Phe Thr Pro His Asp Ser Ala Pro Tyr Gly Ala Leu
    50                  55                  60

Asp Met Ala Asp Phe Glu Phe Glu Gln Met Phe Thr Asp Ala Leu Gly
65                  70                  75                  80

Ile Asp Glu Tyr Gly Gly Glu Phe Glu Met Pro Val Asp Arg Ile Leu
                85                  90                  95

Glu Ala Glu Leu Ala Val Glu Gln Lys Ser Asp Gln Gly Val Glu Gly
            100                 105                 110

Pro Gly Gly Thr Gly Gly Ser Gly Ser Ser Pro Asn Asp Pro Val Thr
        115                 120                 125

Asn Ile Cys Gln Ala Ala Asp Lys Gln Leu Phe Thr Leu Val Glu Trp
    130                 135                 140

Ala Lys Arg Ile Pro His Phe Ser Ser Leu Pro Leu Asp Asp Gln Val
145                 150                 155                 160

Ile Leu Leu Arg Ala Gly Trp Asn Glu Leu Leu Ile Ala Ser Phe Ser
                165                 170                 175

His Arg Ser Ile Asp Val Arg Asp Gly Ile Leu Leu Ala Thr Gly Leu
            180                 185                 190

His Val His Arg Asn Ser Ala His Ser Ala Gly Val Gly Ala Ile Phe
        195                 200                 205
```

```
Asp Arg Val Leu Thr Glu Leu Val Ser Lys Met Arg Asp Met Arg Met
    210                 215                 220

Asp Lys Thr Glu Leu Gly Cys Leu Arg Ala Ile Ile Leu Phe Asn Pro
225                 230                 235                 240

Glu Val Arg Gly Leu Lys Ser Ala Gln Glu Val Glu Leu Leu Arg Glu
                245                 250                 255

Lys Val Tyr Ala Ala Leu Glu Glu Tyr Thr Arg Thr Thr His Pro Asp
            260                 265                 270

Glu Pro Gly Arg Phe Ala Lys Leu Leu Leu Arg Leu Pro Ser Leu Arg
        275                 280                 285

Ser Ile Gly Leu Lys Cys Leu Glu His Leu Phe Phe Phe Arg Leu Ile
    290                 295                 300

Gly Asp Val Pro Ile Asp Thr Phe Leu Met Glu Met Leu Glu Ser Pro
305                 310                 315                 320

Ser Asp Ser
```

<210> SEQ ID NO 134
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe
145                 150
```

<210> SEQ ID NO 135
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

```
Ile Arg Pro Glu Cys Val Val Pro Glu Thr Gln Cys Ala Met Lys Arg
1               5                   10                  15

Lys Glu Lys Lys Ala Gln Lys Glu Lys Asp Lys Leu Pro Val Ser Thr
```

```
            20                  25                  30

Thr Thr Val Asp Asp His Met Pro Pro Ile Met Gln Cys Glu Pro Pro
        35                  40                  45

Pro Pro Glu Ala Ala Arg Ile His Glu Val Val Pro Arg Phe Leu Ser
    50                  55                  60

Asp Lys Leu Leu Val Thr Asn Arg Gln Lys Asn Ile Pro Gln Leu Thr
65                  70                  75                  80

Ala Asn Gln Gln Phe Leu Ile Ala Arg Leu Ile Trp Tyr Gln Asp Gly
                85                  90                  95

Tyr Glu Gln Pro Ser Asp Glu Asp Leu Lys Arg Ile Thr Gln Thr Trp
            100                 105                 110

Gln Gln Ala Asp Asp Glu Asn Glu Glu Ser Asp Thr Pro Phe Arg Gln
        115                 120                 125

Ile Thr Glu Met Thr Ile Leu Thr Val Gln Leu Ile Val Glu Phe Ala
    130                 135                 140

Lys Gly Leu Pro Gly Phe Ala Lys Ile Ser Gln Pro Asp Gln Ile Thr
145                 150                 155                 160

Leu Leu Lys Ala Cys Ser Ser Glu Val Met Met Leu Arg Val Ala Arg
                165                 170                 175

Arg Tyr Asp Ala Ala Ser Asp Ser Ile Leu Phe Ala Asn Asn Gln Ala
            180                 185                 190

Tyr Thr Arg Asp Asn Tyr Arg Lys Ala Gly Met Ala Glu Val Ile Glu
        195                 200                 205

Asp Leu Leu His Phe Cys Arg Cys Met Tyr Ser Met Ala Leu Asp Asn
    210                 215                 220

Ile His Tyr Ala Leu Leu Thr Ala Val Val Ile Phe Ser Asp Arg Pro
225                 230                 235                 240

Gly Leu Glu Gln Pro Gln Leu Val Glu Glu Ile Gln Arg Tyr Tyr Leu
                245                 250                 255

Asn Thr Leu Arg Ile Tyr Ile Leu Asn Gln Leu Ser Gly Ser Ala Arg
            260                 265                 270

Ser Ser Val Ile Tyr Gly Lys Ile Leu Ser Ile Leu Ser Glu Leu Arg
        275                 280                 285

Thr Leu Gly Met Gln Asn Ser Asn Met Cys Ile Ser Leu Lys Leu Lys
    290                 295                 300

Asn Arg Lys Leu Pro Pro Phe Leu Glu Glu Ile Trp Asp Val Ala Asp
305                 310                 315                 320

Met Ser His Thr Gln Pro Pro Pro Ile Leu Glu Ser Pro Thr Asn Leu
                325                 330                 335


<210> SEQ ID NO 136
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Arg Pro Glu Cys Val Val Pro Glu Thr Gln Cys Ala Met Lys Arg Lys
1               5                   10                  15

Glu Lys Lys Ala Gln Lys Glu Lys Asp Lys Leu Pro Val Ser Thr Thr
            20                  25                  30

Thr Val Asp Asp His Met Pro Pro Ile Met Gln Cys Glu Pro Pro Pro
        35                  40                  45
```

```
Pro Glu Ala Ala Arg Ile His Glu Val Val Pro Arg Phe Leu Ser Asp
    50                  55                  60

Lys Leu Leu Val Thr Asn Arg Gln Lys Asn Ile Pro Gln Leu Thr Ala
65                  70                  75                  80

Asn Gln Gln Phe Leu Ile Ala Arg Leu Ile Trp Tyr Gln Asp Gly Tyr
                85                  90                  95

Glu Gln Pro Ser Asp Glu Asp Leu Lys Arg Ile Thr Gln Thr Trp Gln
            100                 105                 110

Gln Ala Asp Asp Glu Asn Glu Glu Ser Asp Thr Pro Phe Arg Gln Ile
        115                 120                 125

Thr Glu Met Thr Ile Leu Thr Val Gln Leu Ile Val Glu Phe Ala Lys
    130                 135                 140

Gly Leu Pro Gly Phe Ala Lys Ile Ser Gln Pro Asp Gln Ile Thr Leu
145                 150                 155                 160

Leu Lys Ala Cys Ser Ser Glu Val Met Met Leu Arg Val Ala Arg Arg
                165                 170                 175

Tyr Asp Ala Ala Ser Asp Ser Ile Leu Phe Ala Asn Asn Gln Ala Tyr
            180                 185                 190

Thr Arg Asp Asn Tyr Arg Lys Ala Gly Met Ala Glu Val Ile Glu Asp
        195                 200                 205

Leu Leu His Phe Cys Arg Cys Met Tyr Ser Met Ala Leu Asp Asn Ile
    210                 215                 220

His Tyr Ala Leu Leu Thr Ala Val Val Ile Phe Ser Asp Arg Pro Gly
225                 230                 235                 240

Leu Glu Gln Pro Gln Leu Val Glu Glu Ile Gln Arg Tyr Tyr Leu Asn
                245                 250                 255

Thr Leu Arg Ile Tyr Ile Leu Asn Gln Leu Ser Gly Ser Ala Arg Ser
            260                 265                 270

Ser Val Ile Tyr Gly Lys Ile Leu Ser Ile Leu Ser Glu Leu Arg Thr
        275                 280                 285

Leu Gly Met Gln Asn Ser Asn Met Cys Ile Ser Leu Lys Leu Lys Asn
    290                 295                 300

Arg Lys Leu Pro Pro Phe Leu Glu Glu Ile Trp Asp Val Ala Asp Met
305                 310                 315                 320

Ser His Thr Gln Pro Pro Pro Ile Leu Glu Ser Pro Thr Asn Leu
                325                 330                 335


<210> SEQ ID NO 137
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80
```

```
Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Pro Glu Cys Val Val Pro
145                 150                 155                 160

Glu Thr Gln Cys Ala Met Lys Arg Lys Glu Lys Lys Ala Gln Lys Glu
                165                 170                 175

Lys Asp Lys Leu Pro Val Ser Thr Thr Thr Val Asp Asp His Met Pro
            180                 185                 190

Pro Ile Met Gln Cys Glu Pro Pro Pro Pro Glu Ala Ala Arg Ile His
        195                 200                 205

Glu Val Val Pro Arg Phe Leu Ser Asp Lys Leu Leu Val Thr Asn Arg
    210                 215                 220

Gln Lys Asn Ile Pro Gln Leu Thr Ala Asn Gln Gln Phe Leu Ile Ala
225                 230                 235                 240

Arg Leu Ile Trp Tyr Gln Asp Gly Tyr Glu Gln Pro Ser Asp Glu Asp
                245                 250                 255

Leu Lys Arg Ile Thr Gln Thr Trp Gln Gln Ala Asp Asp Glu Asn Glu
            260                 265                 270

Glu Ser Asp Thr Pro Phe Arg Gln Ile Thr Glu Met Thr Ile Leu Thr
        275                 280                 285

Val Gln Leu Ile Val Glu Phe Ala Lys Gly Leu Pro Gly Phe Ala Lys
    290                 295                 300

Ile Ser Gln Pro Asp Gln Ile Thr Leu Leu Lys Ala Cys Ser Ser Glu
305                 310                 315                 320

Val Met Met Leu Arg Val Ala Arg Arg Tyr Asp Ala Ala Ser Asp Ser
                325                 330                 335

Ile Leu Phe Ala Asn Asn Gln Ala Tyr Thr Arg Asp Asn Tyr Arg Lys
            340                 345                 350

Ala Gly Met Ala Glu Val Ile Glu Asp Leu Leu His Phe Cys Arg Cys
        355                 360                 365

Met Tyr Ser Met Ala Leu Asp Asn Ile His Tyr Ala Leu Leu Thr Ala
    370                 375                 380

Val Val Ile Phe Ser Asp Arg Pro Gly Leu Glu Gln Pro Gln Leu Val
385                 390                 395                 400

Glu Glu Ile Gln Arg Tyr Tyr Leu Asn Thr Leu Arg Ile Tyr Ile Leu
                405                 410                 415

Asn Gln Leu Ser Gly Ser Ala Arg Ser Ser Val Ile Tyr Gly Lys Ile
            420                 425                 430

Leu Ser Ile Leu Ser Glu Leu Arg Thr Leu Gly Met Gln Asn Ser Asn
        435                 440                 445

Met Cys Ile Ser Leu Lys Leu Lys Asn Arg Lys Leu Pro Pro Phe Leu
    450                 455                 460

Glu Glu Ile Trp Asp Val Ala Asp Met Ser His Thr Gln Pro Pro Pro
465                 470                 475                 480

Ile Leu Glu Ser Pro Thr Asn Leu
                485
```

<210> SEQ ID NO 138
<211> LENGTH: 487
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 138

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Arg Pro Glu Cys Val Val Pro Glu
145                 150                 155                 160

Thr Gln Cys Ala Met Lys Arg Lys Glu Lys Lys Ala Gln Lys Glu Lys
                165                 170                 175

Asp Lys Leu Pro Val Ser Thr Thr Thr Val Asp Asp His Met Pro Pro
            180                 185                 190

Ile Met Gln Cys Glu Pro Pro Pro Pro Glu Ala Ala Arg Ile His Glu
        195                 200                 205

Val Val Pro Arg Phe Leu Ser Asp Lys Leu Leu Val Thr Asn Arg Gln
    210                 215                 220

Lys Asn Ile Pro Gln Leu Thr Ala Asn Gln Gln Phe Leu Ile Ala Arg
225                 230                 235                 240

Leu Ile Trp Tyr Gln Asp Gly Tyr Glu Gln Pro Ser Asp Glu Asp Leu
                245                 250                 255

Lys Arg Ile Thr Gln Thr Trp Gln Gln Ala Asp Asp Glu Asn Glu Glu
            260                 265                 270

Ser Asp Thr Pro Phe Arg Gln Ile Thr Glu Met Thr Ile Leu Thr Val
        275                 280                 285

Gln Leu Ile Val Glu Phe Ala Lys Gly Leu Pro Gly Phe Ala Lys Ile
    290                 295                 300

Ser Gln Pro Asp Gln Ile Thr Leu Leu Lys Ala Cys Ser Ser Glu Val
305                 310                 315                 320

Met Met Leu Arg Val Ala Arg Arg Tyr Asp Ala Ala Ser Asp Ser Ile
                325                 330                 335

Leu Phe Ala Asn Asn Gln Ala Tyr Thr Arg Asp Asn Tyr Arg Lys Ala
            340                 345                 350

Gly Met Ala Glu Val Ile Glu Asp Leu Leu His Phe Cys Arg Cys Met
        355                 360                 365
```

Tyr Ser Met Ala Leu Asp Asn Ile His Tyr Ala Leu Leu Thr Ala Val
370 375 380

Val Ile Phe Ser Asp Arg Pro Gly Leu Glu Gln Pro Gln Leu Val Glu
385 390 395 400

Glu Ile Gln Arg Tyr Tyr Leu Asn Thr Leu Arg Ile Tyr Ile Leu Asn
405 410 415

Gln Leu Ser Gly Ser Ala Arg Ser Ser Val Ile Tyr Gly Lys Ile Leu
420 425 430

Ser Ile Leu Ser Glu Leu Arg Thr Leu Gly Met Gln Asn Ser Asn Met
435 440 445

Cys Ile Ser Leu Lys Leu Lys Asn Arg Lys Leu Pro Pro Phe Leu Glu
450 455 460

Glu Ile Trp Asp Val Ala Asp Met Ser His Thr Gln Pro Pro Pro Ile
465 470 475 480

Leu Glu Ser Pro Thr Asn Leu
485

<210> SEQ ID NO 139
<211> LENGTH: 244
<212> TYPE: DNA
<213> ORGANISM: Homo sapiens

<400> SEQUENCE: 139
gagcgtgcgt gaggctccgg tgcccgtcag tgggcagagc gcacatcgcc cacagtcccc 60
gagaagttgg ggggaggggg tcggcgattg aaccggtgcc tagagaaggt ggcgcggggt 120
aaactgggaa agtgatgtcg tgtactggct ccgccttttt cccgagggtg ggggagaacc 180
gtatataagt gcagtagtcg ccgtgaacgt tctttttcgc aacgggtttg ccgccagaac 240
acag 244

<210> SEQ ID NO 140
<211> LENGTH: 571
<212> TYPE: DNA
<213> ORGANISM: Unknown
<220> FEATURE:
<223> OTHER INFORMATION: Description of Unknown:
UBC promoter sequence

<400> SEQUENCE: 140
ggcctccgcg ccgggttttg gcgcctcccg cgggcgcccc cctcctcacg gcgagcgctg 60
ccacgtcaga cgaagggcgc agcgagcgtc ctgatccttc cgcccggacg ctcaggacag 120
cggcccgctg ctcataagac tcggccttag aaccccagta tcagcagaag gacattttag 180
gacgggactt gggtgactct agggcactgg ttttctttcc agagagcgga acaggcgagg 240
aaaagtagtc ccttctcggc gattctgcgg agggatctcc gtggggcggt gaacgccgat 300
gattatataa ggacgcgccg ggtgtggcac agctagttcc gtcgcagccg ggatttgggt 360
cgcggttctt gtttgtggat cgctgtgatc gtcacttggt gagtagcggg ctgctgggct 420
gggtacgtgc gctcggggtt ggcgagtgtg ttttgtgaag ttttttaggc accttttgaa 480
atgtaatcat ttgggtcaat atgtaatttt cagtgttaga ctagtaaatt gtccgctaaa 540
ttctggccgt ttttggcttt tttgttagac g 571

<210> SEQ ID NO 141
<211> LENGTH: 148
<212> TYPE: DNA
<213> ORGANISM: Unknown

```
<220> FEATURE:
<223> OTHER INFORMATION: Description of Unknown:
      6 site GAL4-inducible proximal factor binding element
      (PFB) sequence

<400> SEQUENCE: 141

attgttcgga gcagtgcggc gcgtttagcg gagtactgtc ctccgatatt aatcggggca     60

gactattccg gggtttaccg gcgcactctc gcccgaactt caccggcggt ctttcgtccg    120

tgctttatcg gggcggatca ctccgaac                                       148

<210> SEQ ID NO 142
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

aggtctatat aagcagagct cgtttagtga accctcattc tggagacgga tcccgagccg     60

agtgttttga cctccataga a                                               81

<210> SEQ ID NO 143
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143

cagccgctaa atccaaggta aggtcagaag a                                    31

<210> SEQ ID NO 144
<211> LENGTH: 132
<212> TYPE: DNA
<213> ORGANISM: Simian virus 40

<400> SEQUENCE: 144

aacttgttta ttgcagctta taatggttac aaataaagca atagcatcac aaatttcaca     60

aataaagcat ttttttcact gcattctagt tgtggtttgt ccaaactcat caatgtatct    120

tatcatgtct gg                                                        132

<210> SEQ ID NO 145
<211> LENGTH: 275
<212> TYPE: DNA
<213> ORGANISM: Unknown
<220> FEATURE:
<223> OTHER INFORMATION: Description of Unknown:
      Bidirectional aCA polyA [bidirectional polyA] sequence

<400> SEQUENCE: 145

atcgattaat ctagcggccc tagacgagca gacatgataa gatacattga tgagtttgga     60

caaaccacaa ctagaatgca gtgaaaaaaa tgctttattt gtgaaatttg tgatgctatt    120

gctttatttg taaccattat aagctgcaat aaacaagtta acaacaacaa ttgcattcat    180

tttatgtttc aggttcaggg ggagatgtgg gaggtttttt aaagcaagta aaacctctac    240

aaatgtggta aaatccgata agcgtaccta gaggc                               275

<210> SEQ ID NO 146
<211> LENGTH: 73
```

<212> TYPE: DNA
<213> ORGANISM: Unknown
<220> FEATURE:
<223> OTHER INFORMATION: Description of Unknown:
2xRbm3 IRES sequence

<400> SEQUENCE: 146
actagtttta taatttcttc ttccagaatt tctgacattt tataatttct tcttccagaa 60
gactcacaac ctc 73

<210> SEQ ID NO 147
<211> LENGTH: 570
<212> TYPE: DNA
<213> ORGANISM: Unknown
<220> FEATURE:
<223> OTHER INFORMATION: Description of Unknown:
EMCV IRES sequence

<400> SEQUENCE: 147
ccccctctcc ctcccccccc cctaacgtta ctggccgaag ccgcttggaa taaggccggt 60
gtgcgtttgt ctatatgtta ttttccacca tattgccgtc ttttggcaat gtgagggccc 120
ggaaacctgg ccctgtcttc ttgacgagca ttcctagggg tctttcccct ctcgccaaag 180
gaatgcaagg tctgttgaat gtcgtgaagg aagcagttcc tctggaagct tcttgaagac 240
aaacaacgtc tgtagcgacc ctttgcaggc agcggaaccc cccacctggc gacaggtgcc 300
tctgcggcca aaagccacgt gtataagata cacctgcaaa ggcggcacaa ccccagtgcc 360
acgttgtgag ttggatagtt gtggaaagag tcaaatggct ctcctcaagc gtattcaaca 420
aggggctgaa ggatgcccag aaggtacccc attgtatggg atctgatctg gggcctcggt 480
gcacatgctt tacatgtgtt tagtcgaggt taaaaaacgt ctaggccccc cgaaccacgg 540
ggacgtggtt ttcctttgaa aaacacgatc 570

<210> SEQ ID NO 148
<211> LENGTH: 2811
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 148
atgcaccggc cgcgccgccg cgggacgcgc ccgccgctcc tggcgctgct ggccgcgctg 60
ctgctggccg cacgcggggc tgctgcccaa gaaacagagc tgtcagtcag tgctgaatta 120
gtgcctacct catcatggaa catctcaagt gaactcaaca aagattctta cctgaccctc 180
gatgaaccaa tgaataacat caccacgtct ctgggccaga cagcagaact gcactgcaaa 240
gtctctggga atccacctcc caccatccgc tggttcaaaa atgatgctcc tgtggtccag 300
gagccccgga ggctctcctt tcggtccacc atctatggct ctcggctgcg gattagaaac 360
ctcgacacca cagacacagg ctacttccag tgcgtggcaa caaacggcaa ggaggtggtt 420
tcttccactg gagtcttgtt tgtcaagttt ggcccccctc ccactgcaag tccaggatac 480
tcagatgagt atgaagaaga tggattctgt cagccataca gagggattgc atgtgcaaga 540
tttattggca accgcaccgt ctatatggag tctttgcaca tgcaagggga aatagaaaat 600
cagatcacag ctgccttcac tatgattggc acttccagtc acttatctga taagtgttct 660
cagttcgcca ttccttccct gtgccactat gccttcccgt actgcgatga aacttcatcc 720
gtcccaaagc cccgtgactt gtgtcgcgat gaatgtgaaa tcctggagaa tgtcctgtgt 780

```
caaacagagt acatttttgc aagatcaaat cccatgattc tgatgaggct gaaactgcca    840

aactgtgaag atctccccca gccagagagc ccagaagctg cgaactgtat ccggattgga    900

attcccatgg cagatcctat aaataaaaat cacaagtgtt ataacagcac aggtgtggac    960

taccggggga ccgtcagtgt gaccaaatca gggcgccagt gccagccatg gaattcccag   1020

tatccccaca cacacacttt caccgccctt cgtttcccag agctgaatgg aggccattcc   1080

tactgccgca acccagggaa tcaaaaggaa gctccctggt gcttcacctt ggatgaaaac   1140

tttaagtctg atctgtgtga catcccagcg tgcgattcaa aggattccaa ggagaagaat   1200

aaaatggaaa tcctgtacat actagtgcca agtgtggcca ttcccctggc cattgcttta   1260

ctcttcttct tcatttgcgt ctgtcggaat aaccagaagt catcgtcggc accagtccag   1320

aggcaaccaa aacacgtcag aggtcaaaat gtagagatgt caatgctgaa tgcatataaa   1380

cccaagagca aggctaaaga gctacctctt tctgctgtac gctttatgga agaattgggt   1440

gagtgtgcct ttggaaaaat ctataaaggc catctctatc tcccaggcat ggaccatgct   1500

cagctggttg ctatcaagac cttgaaagac tataacaacc cccagcaatg gacggaattt   1560

caacaagaag cctccctaat ggcagaactg caccacccca atattgtctg ccttctaggt   1620

gccgtcactc aggaacaacc tgtgtgcatg ctttttgagt atattaatca gggggatctc   1680

catgagttcc tcatcatgag atccccacac tctgatgttg gctgcagcag tgatgaagat   1740

gggactgtga aatccagcct ggaccacgga gattttctgc acattgcaat tcagattgca   1800

gctggcatgg aatacctgtc tagtcacttc tttgtccaca aggaccttgc agctcgcaat   1860

attttaatcg gagagcaact tcatgtaaag atttcagact tggggctttc cagagaaatt   1920

tactccgctg attactacag ggtccagagt aagtccttgc tgcccattcg ctggatgccc   1980

cctgaagcca tcatgtatgg caaattctct tctgattcag atatctggtc ctttggggtt   2040

gtcttgtggg agattttcag ttttggactc cagccatatt atggattcag taaccaggaa   2100

gtgattgaga tggtgagaaa acggcagctc ttaccatgct ctgaagactg cccacccaga   2160

atgtacagcc tcatgacaga gtgctggaat gagattcctt ctaggagacc aagatttaaa   2220

gatattcacg tccggcttcg gtcctgggag ggactctcaa gtcacacaag ctctactact   2280

ccttcagggg gaaatgccac cacacagaca acctccctca gtgccagccc agtgagtaat   2340

ctcagtaacc ccagatatcc taattacatg ttcccgagcc agggtattac accacagggc   2400

cagattgctg gtttcattgg cccgccaata cctcagaacc agcgattcat tcccatcaat   2460

ggatacccaa tacctcctgg atatgcagcg tttccagctg cccactacca gccaacaggt   2520

cctcccagag tgattcagca ctgcccacct cccaagagtc ggtccccaag cagtgccagt   2580

gggtcgacta gcactggcca tgtgactagc ttgccctcat caggatccaa tcaggaagca   2640

aatattcctt tactaccaca catgtcaatt ccaaatcatc ctggtggaat gggtatcacc   2700

gtttttggca acaaatctca aaaaccctac aaaattgact caaagcaagc atctttacta   2760

ggagacgcca atattcatgg acacaccgaa tctatgattt ctgcagaact g            2811
```

<210> SEQ ID NO 149
<211> LENGTH: 1311
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 149

-continued

```
atgcaccggc cgcgccgccg cgggacgcgc ccgccgctcc tggcgctgct ggccgcgctg     60
ctgctggccg cacgcggggc tgctgcccaa gaaacagagc tgtcagtcag tgctgaatta    120
gtgcctacct catcatggaa catctcaagt gaactcaaca aagattctta cctgaccctc    180
gatgaaccaa tgaataacat caccacgtct ctgggccaga cagcagaact gcactgcaaa    240
gtctctggga atccacctcc caccatccgc tggttcaaaa atgatgctcc tgtggtccag    300
gagccccgga ggctctcctt tcggtccacc atctatggct ctcggctgcg gattagaaac    360
ctcgacacca cagacacagg ctacttccag tgcgtggcaa caaacggcaa ggaggtggtt    420
tcttccactg gagtcttgtt tgtcaagttt ggcccccctc ccactgcaag tccaggatac    480
tcagatgagt atgaagaaga tggattctgt cagccataca gagggattgc atgtgcaaga    540
tttattggca accgcaccgt ctatatggag tctttgcaca tgcaagggga aatagaaaat    600
cagatcacag ctgccttcac tatgattggc acttccagtc acttatctga taagtgttct    660
cagttcgcca ttccttccct gtgccactat gccttcccgt actgcgatga aacttcatcc    720
gtcccaaagc cccgtgactt gtgtcgcgat gaatgtgaaa tcctggagaa tgtcctgtgt    780
caaacagagt acatttttgc aagatcaaat cccatgattc tgatgaggct gaaactgcca    840
aactgtgaag atctccccca gccagagagc ccagaagctg cgaactgtat ccggattgga    900
attcccatgg cagatcctat aaataaaaat cacaagtgtt ataacagcac aggtgtggac    960
taccggggga ccgtcagtgt gaccaaatca gggcgccagt gccagccatg gaattcccag   1020
tatccccaca cacacacttt caccgccctt cgtttcccag agctgaatgg aggccattcc   1080
tactgccgca acccagggaa tcaaaaggaa gctccctggt gcttcacctt ggatgaaaac   1140
tttaagtctg atctgtgtga catcccagcg tgcgattcaa aggattccaa ggagaagaat   1200
aaaatggaaa tcctgtacat actagtgcca agtgtggcca ttcccctggc cattgcttta   1260
ctcttcttct tcatttgcgt ctgtcggaat aaccagaagt catcgtcggc a            1311
```

<210> SEQ ID NO 150
<211> LENGTH: 1962
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150

```
gacatcaaga tgacccagag ccccagctct atgtacgcca gcctgggcga gcgcgtgacc     60
atcacatgca aggccagccc cgacatcaac agctacctgt cctggttcca gcagaagccc    120
ggcaagagcc ccaagaccct gatctaccgg gccaaccggc tggtggacgg cgtgccaagc    180
agattttccg gcggaggcag cggccaggac tacagcctga ccatcaacag cctggaatac    240
gaggacatgg gcatctacta ctgcctgcag tacgacgagt tcccctacac cttcggaggc    300
ggcaccaagc tggaaatgaa gggcagcacc tccggcagcg gcaagcctgg cagcggcgag    360
ggcagcacca agggcgaagt gaagctggtg gaaagcggcg gaggcctggt gaaacctggc    420
ggcagcctga agctgagctg cgccgccagc ggcttcacct tcagcagcta cgccatgagc    480
tgggtccgac agatccccga gaagcggctg gaatgggtgg ccagcatcag caggggcggc    540
accacctact accccgacag cgtgaagggc cggttcacca tcagccggga caacgtgcgg    600
aacatcctgt acctgcagat gagcagcctg cggagcgagg acaccgccat gtactactgc    660
ggcagatacg actacgacgg ctactacgcc atggattact ggggccaggg caccagcgtg    720
```

```
accgtgtcta gcgagagcaa gtacggccct ccctgccccc cttgccctgc cccgagttc    780
gagggcggac ccagcgtgtt cctgttcccc cccaagccca aggacaccct gatgatcagc    840
cggacccccg aggtgacctg tgtggtggtg gacgtgtccc aggaggaccc cgaggtccag    900
ttcaactggt acgtggacgg cgtggaggtg cacaacgcca agaccaagcc ccgggaggag    960
cagttccaga gcacctaccg ggtggtgtcc gtgctgaccg tgctgcacca ggactggctg   1020
aacggcaagg aatacaagtg taaggtgtcc aacaagggcc tgcccagcag catcgagaaa   1080
accatcagca aggccaaggg ccagcctcgg gagccccagg tgtacaccct gcccccctagc  1140
caagaggaga tgaccaagaa tcaggtgtcc ctgacctgcc tggtgaaggg cttctacccc   1200
agcgacatcg ccgtggagtg ggagagcaac ggccagcccg agaacaacta caagaccacc   1260
ccccctgtgc tggacagcga cggcagcttc ttcctgtaca gcaggctgac cgtggacaag   1320
agccggtggc aggagggcaa cgtctttagc tgctccgtga tgcacgaggc cctgcacaac   1380
cactacaccc agaagagcct gtccctgagc ctgggcaaga tgttctgggt gctggtcgtg   1440
gtgggtggcg tgctggcctg ctacagcctg ctggtgacag tggccttcat catcttttgg   1500
gtgaggagca agcggagcag aggcggccac agcgactaca tgaacatgac cccccggagg   1560
cctggcccca cccggaagca ctaccagccc tacgcccctc ccagggactt cgccgcctac   1620
cggagccggg tgaagttcag ccggagcgcc gacgcccctg cctaccagca gggccagaac   1680
cagctgtaca acgagctgaa cctgggccgg agggaggagt acgacgtgct ggacaagcgg   1740
agaggccggg accctgagat gggcggcaag ccccggagaa agaaccctca ggagggcctg   1800
tataacgaac tgcagaaaga caagatggcc gaggcctaca gcgagatcgg catgaagggc   1860
gagcggcgga ggggcaaggg ccacgacggc ctgtaccagg gcctgagcac cgccaccaag   1920
gatacctacg acgccctgca catgcaggcc ctgcccccca ga                      1962
```

<210> SEQ ID NO 151
<211> LENGTH: 1989
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 151

```
gacatcaaga tgacccagag ccccagctct atgtacgcca gcctgggcga gcgcgtgacc     60
atcacatgca aggccagccc cgacatcaac agctacctgt cctggttcca gcagaagccc    120
ggcaagagcc ccaagaccct gatctaccgg gccaaccggc tggtggacgg cgtgccaagc    180
agattttccg gcggaggcag cggccaggac tacagcctga ccatcaacag cctggaatac    240
gaggacatgg gcatctacta ctgcctgcag tacgacgagt tcccctacac cttcggaggc    300
ggcaccaagc tggaaatgaa gggcagcacc agcggcagcg gcaagcctgg aagcggcgag    360
ggctccacca agggcgaagt gaagctggtg gaaagcggcg gaggcctggt gaaacctggc    420
ggcagcctga agctgagctg cgccgccagc ggcttcacct tcagcagcta cgccatgagc    480
tgggtccgac agatccccga gaagcggctg gaatgggtgg ccagcatcag caggggcggc    540
accacctact accccgacag cgtgaagggc cggttcacca tcagccggga caacgtgcgg    600
aacatcctgt acctgcagat gagcagcctg cggagcgagg acaccgccat gtactactgc    660
ggcagatacg actacgacgg ctactacgcc atggattact ggggccaggg caccagcgtg    720
accgtgtcta gccagggaac ctccgtgaca gtgtccagcg agtccaaata tggtccccca    780
```

```
tgcccaccat gcccagcacc tgagttcctg gggggaccat cagtcttcct gttcccccca    840

aaacccaagg acactctcat gatctcccgg acccctgagg tcacgtgcgt ggtggtggac    900

gtgagccagg aagaccccga ggtccagttc aactggtacg tggatggcgt ggaggtgcat    960

aatgccaaga caaagccccg ggaggagcag ttcaatagca cctaccgggt ggtgtccgtg   1020

ctgaccgtgc tgcaccagga ctggctgaac ggcaaggaat acaagtgtaa ggtgtccaac   1080

aagggcctgc ccagcagcat cgagaaaacc atcagcaagg ccaagggcca gcctcgggag   1140

ccccaggtgt acaccctgcc ccctagccaa gaggagatga ccaagaatca ggtgtccctg   1200

acctgcctgg tgaagggctt ctaccccagc gacatcgccg tggagtggga gagcaacggc   1260

cagcccgaga acaactacaa gaccaccccc cctgtgctgg acagcgacgg cagcttcttc   1320

ctgtacagca ggctgaccgt ggacaagagc cggtggcagg agggcaacgt ctttagctgc   1380

tccgtgatgc acgaggccct gcacaaccac tacacccaga agagcctgtc cctgagcctg   1440

ggcaagatgt tctgggtgct ggtcgtggtg ggtggcgtgc tggcctgcta cagcctgctg   1500

gtgacagtgg ccttcatcat cttttgggtg aggagcaagc ggagcagagg cggccacagc   1560

gactacatga acatgacccc ccggaggcct ggccccaccc ggaagcacta ccagccctac   1620

gcccctccca gggacttcgc cgcctaccgg agccgggtga agttcagccg gagcgccgac   1680

gcccctgcct accagcaggg ccagaaccag ctgtacaacg agctgaacct gggccggagg   1740

gaggagtacg acgtgctgga caagcggaga ggccgggacc ctgagatggg cggcaagccc   1800

cggagaaaga accctcagga gggcctgtat aacgaactgc agaaagacaa gatggccgag   1860

gcctacagcg agatcggcat gaagggcgag cggcggaggg gcaagggcca cgacggcctg   1920

taccagggcc tgagcaccgc caccaaggat acctacgacg ccctgcacat gcaggccctg   1980

ccccccaga                                                            1989
```

```
<210> SEQ ID NO 152
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
```

```
gacatcaaga tgacccagag ccccagctct atgtacgcca gcctgggcga gcgcgtgacc     60

atcacatgca aggccagccc cgacatcaac agctacctgt cctggttcca gcagaagccc    120

ggcaagagcc ccaagaccct gatctaccgg gccaaccggc tggtggacgg cgtgccaagc    180

agattttccg gcggaggcag cggccaggac tacagcctga ccatcaacag cctggaatac    240

gaggacatgg gcatctacta ctgcctgcag tacgacgagt tcccctacac cttcggaggc    300

ggcaccaagc tggaaatgaa gggcagcacc tccggcagcg gcaagcctgg cagcggcgag    360

ggcagcacca agggcgaagt gaagctggtg gaaagcggcg gaggcctggt gaaacctggc    420

ggcagcctga agctgagctg cgccgccagc ggcttcacct tcagcagcta cgccatgagc    480

tgggtccgac agatccccga gaagcggctg gaatgggtgg ccagcatcag caggggcggc    540

accacctact accccgacag cgtgaagggc cggttcacca tcagccggga caacgtgcgg    600

aacatcctgt acctgcagat gagcagcctg cggagcgagg acaccgccat gtactactgc    660

ggcagatacg actacgacgg ctactacgcc atggattact ggggccaggg caccagcgtg    720

accgtgtcta gcaagcccac caccacccct gcccctagac ctccaacccc agcccctaca    780
```

atcgccagcc agcccctgag cctgaggccc gaagcctgta gacctgccgc tggcggagcc 840
gtgcacacca gaggcctgga tttcgcctgc gacatctaca tctgggcccc tctggccggc 900
acctgtggcg tgctgctgct gagcctggtc atcaccctgt actgcaacca ccggaatagg 960
agcaagcgga gcagaggcgg ccacagcgac tacatgaaca tgaccccccg gaggcctggc 1020
cccacccgga agcactacca gccctacgcc cctcccaggg acttcgccgc ctaccggagc 1080
cgggtgaagt tcagccggag cgccgacgcc cctgcctacc agcagggcca gaaccagctg 1140
tacaacgagc tgaacctggg ccggagggag gagtacgacg tgctggacaa gcggagaggc 1200
cgggaccctg agatgggcgg caagccccgg agaaagaacc ctcaggaggg cctgtataac 1260
gaactgcaga aagacaagat ggccgaggcc tacagcgaga tcggcatgaa gggcgagcgg 1320
cggaggggca agggccacga cggcctgtac cagggcctga gcaccgccac caaggatacc 1380
tacgacgccc tgcacatgca ggccctgccc cccaga 1416

<210> SEQ ID NO 153
<211> LENGTH: 1557
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153
gacatcaaga tgacccagag ccccagctct atgtacgcca gcctgggcga gcgcgtgacc 60
atcacatgca aggccagccc cgacatcaac agctacctgt cctggttcca gcagaagccc 120
ggcaagagcc ccaagaccct gatctaccgg gccaaccggc tggtggacgg cgtgccaagc 180
agattttccg gcggaggcag cggccaggac tacagcctga ccatcaacag cctggaatac 240
gaggacatgg gcatctacta ctgcctgcag tacgacgagt tcccctacac cttcggaggc 300
ggcaccaagc tggaaatgaa gggcagcacc tccggcagcg gcaagcctgg cagcggcgag 360
ggcagcacca agggcgaagt gaagctggtg gaaagcggcg gaggcctggt gaaacctggc 420
ggcagcctga agctgagctg cgccgccagc ggcttcacct tcagcagcta cgccatgagc 480
tgggtccgac agatccccga gaagcggctg gaatgggtgg ccagcatcag caggggcggc 540
accacctact accccgacag cgtgaagggc cggttcacca tcagccggga caacgtgcgg 600
aacatcctgt acctgcagat gagcagcctg cggagcgagg acaccgccat gtactactgc 660
ggcagatacg actacgacgg ctactacgcc atggattact ggggccaggg caccagcgtg 720
accgtgtcta gcaaacctac tacaactcct gcccccccggc ctcctacacc agctcctact 780
atcgcctccc agccactcag tctcagaccc gaggcttcta ggccagcggc cggaggcgcg 840
gtccacaccc gcgggctgga ctttgcatcc gataagccca ccaccacccc tgcccctaga 900
cctccaaccc cagcccctac aatcgccagc cagcccctga gcctgaggcc cgaagcctgt 960
agacctgccg ctggcggagc cgtgcacacc agaggcctgg atttcgcctg cgacatctac 1020
atctgggccc ctctggccgg cacctgtggc gtgctgctgc tgagcctggt catcaccctg 1080
tactgcaacc accggaatag gagcaagcgg agcagaggcg gccacagcga ctacatgaac 1140
atgacccccc ggaggcctgg ccccacccgg aagcactacc agccctacgc ccctcccagg 1200
gacttcgccg cctaccggag ccgggtgaag ttcagccgga gcgccgacgc ccctgcctac 1260
cagcagggcc agaaccagct gtacaacgag ctgaacctgg gccggaggga ggagtacgac 1320
gtgctggaca agcggagagg ccgggaccct gagatgggcg gcaagccccg gagaaagaac 1380
cctcaggagg gcctgtataa cgaactgcag aaagacaaga tggccgaggc ctacagcgag 1440
atcggcatga agggcgagcg gcggaggggc aagggccacg acggcctgta ccagggcctg 1500
agcaccgcca ccaaggatac ctacgacgcc ctgcacatgc aggccctgcc ccccaga 1557

<210> SEQ ID NO 154
<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 154
gacatcaaga tgacccagag ccccagctct atgtacgcca gcctgggcga gcgcgtgacc 60
atcacatgca aggccagccc cgacatcaac agctacctgt cctggttcca gcagaagccc 120
ggcaagagcc ccaagaccct gatctaccgg gccaaccggc tggtggacgg cgtgccaagc 180
agattttccg gcggaggcag cggccaggac tacagcctga ccatcaacag cctggaatac 240
gaggacatgg gcatctacta ctgcctgcag tacgacgagt tcccctacac cttcggaggc 300
ggcaccaagc tggaaatgaa gggcagcacc tccggcagcg gcaagcctgg cagcggcgag 360
ggcagcacca agggcgaagt gaagctggtg gaaagcggcg gaggcctggt gaaacctggc 420
ggcagcctga agctgagctg cgccgccagc ggcttcacct tcagcagcta cgccatgagc 480
tgggtccgac agatccccga gaagcggctg gaatgggtgg ccagcatcag caggggcggc 540
accacctact accccgacag cgtgaagggc cggttcacca tcagccggga caacgtgcgg 600
aacatcctgt acctgcagat gagcagcctg cggagcgagg acaccgccat gtactactgc 660
ggcagatacg actacgacgg ctactacgcc atggattact ggggccaggg caccagcgtg 720
accgtgtcta gcaagcctac caccaccccc gcacctcgtc ctccaacccc tgcacctacg 780
attgccagtc agcctctttc actgcggcct gaggccagca gaccagctgc cggcggtgcc 840
gtccatacaa gaggactgga cttcgcgtcc gataaaccta ctaccactcc agccccaagg 900
cccccaaccc cagcaccgac tatcgcatca cagcctttgt cactgcgtcc tgaagccagc 960
cggccagctg caggggggc cgtccacaca aggggactcg actttgcgag tgataagccc 1020
accaccaccc ctgcccctag acctccaacc ccagccccta caatcgccag ccagcccctg 1080
agcctgaggc ccgaagcctg tagacctgcc gctggcggag ccgtgcacac cagaggcctg 1140
gatttcgcct gcgacatcta catctgggcc cctctggccg gcacctgtgg cgtgctgctg 1200
ctgagcctgg tcatcaccct gtactgcaac caccggaata ggagcaagcg gagcagaggc 1260
ggccacagcg actacatgaa catgaccccc cggaggcctg gccccacccg gaagcactac 1320
cagccctacg cccctcccag ggacttcgcc gcctaccgga gccgggtgaa gttcagccgg 1380
agcgccgacg cccctgccta ccagcagggc cagaaccagc tgtacaacga gctgaacctg 1440
ggccggaggg aggagtacga cgtgctggac aagcggagag gccgggaccc tgagatgggc 1500
ggcaagcccc ggagaaagaa ccctcaggag ggcctgtata acgaactgca gaaagacaag 1560
atggccgagg cctacagcga gatcggcatg aagggcgagc ggcggagggg caagggccac 1620
gacggcctgt accagggcct gagcaccgcc accaaggata cctacgacgc cctgcacatg 1680
caggccctgc cccccaga 1698

<210> SEQ ID NO 155
<211> LENGTH: 1839

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 155

```
gacatcaaga tgacccagag ccccagctct atgtacgcca gcctgggcga gcgcgtgacc     60

atcacatgca aggccagccc cgacatcaac agctacctgt cctggttcca gcagaagccc    120

ggcaagagcc ccaagaccct gatctaccgg gccaaccggc tggtggacgg cgtgccaagc    180

agattttccg gcggaggcag cggccaggac tacagcctga ccatcaacag cctggaatac    240

gaggacatgg gcatctacta ctgcctgcag tacgacgagt tcccctacac cttcggaggc    300

ggcaccaagc tggaaatgaa gggcagcacc tccggcagcg gcaagcctgg cagcggcgag    360

ggcagcacca agggcgaagt gaagctggtg gaaagcggcg gaggcctggt gaaacctggc    420

ggcagcctga agctgagctg cgccgccagc ggcttcacct tcagcagcta cgccatgagc    480

tgggtccgac agatccccga gaagcggctg gaatgggtgg ccagcatcag caggggcggc    540

accacctact accccgacag cgtgaagggc cggttcacca tcagccggga caacgtgcgg    600

aacatcctgt acctgcagat gagcagcctg cggagcgagg acaccgccat gtactactgc    660

ggcagatacg actacgacgg ctactacgcc atggattact ggggccaggg caccagcgtg    720

accgtgtcta gcaagcctac caccaccccc gcacctcgtc ctccaacccc tgcacctacg    780

attgccagtc agcctctttc actgcggcct gaggccagca gaccagctgc cggcggtgcc    840

gtccatacaa gaggactgga cttcgcgtcc gataaaccta ctaccactcc agccccaagg    900

cccccaaccc cagcaccgac tatcgcatca cagcctttgt cactgcgtcc tgaagccagc    960

cggccagctg caggggggc cgtccacaca aggggactcg actttgcgag tgataaacct    1020

actacaactc ctgcccccg gcctcctaca ccagctccta ctatcgcctc ccagccactc    1080

agtctcagac ccgaggcttc taggccagcg gccggaggcg cggtccacac ccgcgggctg   1140

gactttgcat ccgataagcc caccaccacc cctgcccta gacctccaac cccagcccct    1200

acaatcgcca gccagcccct gagcctgagg cccgaagcct gtagacctgc cgctggcgga   1260

gccgtgcaca ccagaggcct ggatttcgcc tgcgacatct acatctgggc ccctctggcc   1320

ggcacctgtg gcgtgctgct gctgagcctg gtcatcaccc tgtactgcaa ccaccggaat   1380

aggagcaagc ggagcagagg cggccacagc gactacatga acatgacccc ccggaggcct   1440

ggccccaccc ggaagcacta ccagccctac gcccctccca gggacttcgc cgcctaccgg   1500

agccgggtga agttcagccg gagcgccgac gcccctgcct accagcaggg ccagaaccag   1560

ctgtacaacg agctgaacct gggccggagg gaggagtacg acgtgctgga caagcggaga   1620

ggccgggacc ctgagatggg cggcaagccc cggagaaaga accctcagga gggcctgtat   1680

aacgaactgc agaaagacaa gatggccgag gcctacagcg agatcggcat gaagggcgag   1740

cggcggaggg gcaagggcca cgacggcctg taccagggcc tgagcaccgc caccaaggat   1800

acctacgacg ccctgcacat gcaggccctg cccccaga                            1839
```

<210> SEQ ID NO 156
<211> LENGTH: 1941
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 156
gacatcaaga tgacccagag ccccagctct atgtacgcca gcctgggcga gcgcgtgacc 60
atcacatgca aggccagccc cgacatcaac agctacctgt cctggttcca gcagaagccc 120
ggcaagagcc ccaagaccct gatctaccgg gccaaccggc tggtggacgg cgtgccaagc 180
agattttccg gcggaggcag cggccaggac tacagcctga ccatcaacag cctggaatac 240
gaggacatgg gcatctacta ctgcctgcag tacgacgagt tcccctacac cttcggaggc 300
ggcaccaagc tggaaatgaa gggcagcacc tccggcagcg gcaagcctgg cagcggcgag 360
ggcagcacca agggcgaagt gaagctggtg gaaagcggcg gaggcctggt gaaacctggc 420
ggcagcctga agctgagctg cgccgccagc ggcttcacct tcagcagcta cgccatgagc 480
tgggtccgac agatccccga gaagcggctg gaatgggtgg ccagcatcag caggggcggc 540
accacctact accccgacag cgtgaagggc cggttcacca tcagccggga caacgtgcgg 600
aacatcctgt acctgcagat gagcagcctg cggagcgagg acaccgccat gtactactgc 660
ggcagatacg actacgacgg ctactacgcc atggattact ggggccaggg caccagcgtg 720
accgtgtcta gcaaggaggc atgccccaca ggcctgtaca cacacagcgg tgagtgctgc 780
aaagcctgca acctgggcga gggtgtggcc cagccttgtg gagccaacca gaccgtgtgt 840
gagccctgcc tggacagcgt gacgttctcc gacgtggtga gcgcgaccga gccgtgcaag 900
ccgtgcaccg agtgcgtggg gctccagagc atgtcggcgc cgtgcgtgga ggccgacgac 960
gccgtgtgcc gctgcgccta cggctactac caggatgaga cgactgggcg ctgcgaggcg 1020
tgccgcgtgt gcgaggcggg ctcgggcctc gtgttctcct gccaggacaa gcagaacacc 1080
gtgtgcgagg agtgccccga cggcacgtat tccgacgagg ccaaccacgt ggacccgtgc 1140
ctgccctgca ccgtgtgcga ggacaccgag cgccagctcc gcgagtgcac acgctgggcc 1200
gacgccgagt gcgaggagat ccctggccgt tggattacac ggtccacacc cccagagggc 1260
tcggacagca cagcccccag cacccaggag cctgaggcac ctccagaaca agacctcata 1320
gccagcacgg tggcaggtgt ggtgaccaca gtgatgggca gctcccagcc cgtggtgacc 1380
cgaggcacca ccgacaacat ctacatctgg gcccctctgg ccggcacctg tggcgtgctg 1440
ctgctgagcc tggtcatcac cctgtactgc aaccaccgga ataggagcaa gcggagcaga 1500
ggcggccaca gcgactacat gaacatgacc ccccggaggc ctggccccac ccggaagcac 1560
taccagccct acgcccctcc cagggacttc gccgcctacc ggagccgggt gaagttcagc 1620
cggagcgccg acgcccctgc ctaccagcag ggccagaacc agctgtacaa cgagctgaac 1680
ctgggccgga gggaggagta cgacgtgctg gacaagcgga gaggccggga ccctgagatg 1740
ggcggcaagc cccggagaaa gaaccctcag gagggcctgt ataacgaact gcagaaagac 1800
aagatggccg aggcctacag cgagatcggc atgaagggcg agcggcggag gggcaagggc 1860
cacgacggcc tgtaccaggg cctgagcacc gccaccaagg atacctacga cgccctgcac 1920
atgcaggccc tgccccccag a 1941

<210> SEQ ID NO 157
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 157

-continued

```
gaagtgaagc tggtggaaag cggcggaggc ctggtgaaac ctggcggcag cctgaagctg     60

agctgcgccg ccagcggctt caccttcagc agctacgcca tgagctgggt ccgacagatc    120

cccgagaagc ggctggaatg ggtggccagc atcagcaggg gcggcaccac ctactacccc    180

gacagcgtga agggccggtt caccatcagc cgggacaacg tgcggaacat cctgtacctg    240

cagatgagca gcctgcggag cgaggacacc gccatgtact actgcggcag atacgactac    300

gacggctact acgccatgga ttactggggc cagggcacca gcgtgaccgt gtctagcggc    360

agcacctccg gcagcggcaa gcctggcagc ggcgagggca gcaccaaggg cgacatcaag    420

atgacccaga gccccagctc tatgtacgcc agcctgggcg agcgcgtgac catcacatgc    480

aaggccagcc ccgacatcaa cagctacctg tcctggttcc agcagaagcc cggcaagagc    540

cccaagaccc tgatctaccg ggccaaccgg ctggtggacg gcgtgccaag cagattttcc    600

ggcggaggca gcggccagga ctacagcctg accatcaaca gcctggaata cgaggacatg    660

ggcatctact actgcctgca gtacgacgag ttcccctaca ccttcggagg cggcaccaag    720

ctggaaatga agaagcctac caccaccccc gcacctcgtc ctccaacccc tgcacctacg    780

attgccagtc agcctctttc actgcggcct gaggccagca gaccagctgc cggcggtgcc    840

gtccatacaa gaggactgga cttcgcgtcc gataaaccta ctaccactcc agccccaagg    900

cccccaaccc cagcaccgac tatcgcatca cagcctttgt cactgcgtcc tgaagccagc    960

cggccagctg caggggggc cgtccacaca aggggactcg actttgcgag tgataagccc   1020

accaccaccc ctgcccctag acctccaacc ccagccccta caatcgccag ccagcccctg   1080

agcctgaggc ccgaagcctg tagacctgcc gctggcggag ccgtgcacac cagaggcctg   1140

gatttcgcct gcgacatcta catctgggcc cctctggccg gcacctgtgg cgtgctgctg   1200

ctgagcctgg tcatcaccct gtactgcaac caccggaata agagaggccg gaagaaactg   1260

ctgtacatct tcaagcagcc cttcatgcgg cccgtgcaga ccacccagga agaggacggc   1320

tgcagctgcc ggttccccga ggaagaggaa ggcggctgcg aactgcgggt gaagttcagc   1380

cggagcgccg acgcccctgc ctaccagcag ggccagaacc agctgtacaa cgagctgaac   1440

ctgggccgga gggaggagta cgacgtgctg gacaagcgga gaggccggga ccctgagatg   1500

ggcggcaagc cccggagaaa gaaccctcag gagggcctgt ataacgaact gcagaaagac   1560

aagatggccg aggcctacag cgagatcggc atgaagggcg agcggcggag gggcaagggc   1620

cacgacggcc tgtaccaggg cctgagcacc gccaccaagg atacctacga cgccctgcac   1680

atgcaggccc tgccccccag a                                              1701
```

<210> SEQ ID NO 158
<211> LENGTH: 1968
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158

```
gaagtgaagc tggtggaaag cggcggaggc ctggtgaaac ctggcggcag cctgaagctg     60

agctgcgccg ccagcggctt caccttcagc agctacgcca tgagctgggt ccgacagatc    120

cccgagaagc ggctggaatg ggtggccagc atcagcaggg gcggcaccac ctactacccc    180

gacagcgtga agggccggtt caccatcagc cgggacaacg tgcggaacat cctgtacctg    240

cagatgagca gcctgcggag cgaggacacc gccatgtact actgcggcag atacgactac    300
```

-continued gacggctact acgccatgga ttactggggc cagggcacca gcgtgaccgt gtctagcggc 360
agcacctccg gcagcggcaa gcctggcagc ggcgagggca gcaccaaggg cgacatcaag 420
atgacccaga gccccagctc tatgtacgcc agcctgggcg agcgcgtgac catcacatgc 480
aaggccagcc ccgacatcaa cagctacctg tcctggttcc agcagaagcc cggcaagagc 540
cccaagaccc tgatctaccg ggccaaccgg ctggtggacg gcgtgccaag cagattttcc 600
ggcggaggca gcggccagga ctacagcctg accatcaaca gcctggaata cgaggacatg 660
ggcatctact actgcctgca gtacgacgag ttcccctaca ccttcggagg cggcaccaag 720
ctggaaatga aggagagcaa gtacggccct ccctgccccc cttgccctgc ccccgagttc 780
gagggcggac ccagcgtgtt cctgttcccc cccaagccca aggacaccct gatgatcagc 840
cggacccccg aggtgacctg tgtggtggtg gacgtgtccc aggaggaccc cgaggtccag 900
ttcaactggt acgtggacgg cgtggaggtg cacaacgcca agaccaagcc ccgggaggag 960
cagttccaga gcacctaccg ggtggtgtcc gtgctgaccg tgctgcacca ggactggctg 1020
aacggcaagg aatacaagtg taaggtgtcc aacaagggcc tgcccagcag catcgagaaa 1080
accatcagca aggccaaggg ccagcctcgg gagccccagg tgtacaccct gcccccctagc 1140 caagaggaga tgaccaagaa tcaggtgtcc ctgacctgcc tggtgaaggg cttctacccc 1200
agcgacatcg ccgtggagtg ggagagcaac ggccagcccg agaacaacta caagaccacc 1260 cccccctgtgc tggacagcga cggcagcttc ttcctgtaca gcaggctgac cgtggacaag 1320
agccggtggc aggagggcaa cgtctttagc tgctccgtga tgcacgaggc cctgcacaac 1380
cactacaccc agaagagcct gtccctgagc ctgggcaaga tgatctacat ctgggcccct 1440
ctggccggca cctgtggcgt gctgctgctg agcctggtca tcaccctgta ctgcaaccac 1500
cggaataaga gaggccggaa gaaactgctg tacatcttca agcagccctt catgcggccc 1560
gtgcagacca cccaggaaga ggacggctgc agctgccggt tccccgagga agaggaaggc 1620
ggctgcgaac tgcgggtgaa gttcagccgg agcgccgacg cccctgccta ccagcagggc 1680
cagaaccagc tgtacaacga gctgaacctg ggccggaggg aggagtacga cgtgctggac 1740
aagcggagag gccgggaccc tgagatgggc ggcaagcccc ggagaaagaa ccctcaggag 1800
ggcctgtata acgaactgca gaaagacaag atggccgagg cctacagcga gatcggcatg 1860
aagggcgagc ggcggagggg caagggccac gacggcctgt accagggcct gagcaccgcc 1920
accaaggata cctacgacgc cctgcacatg caggccctgc cccccaga 1968

<210> SEQ ID NO 159
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159
gacgtgcaga tcacccagag ccccagcagc ctgtatgcca gcctgggcga gagagtgacc 60
attacctgca aggccagccc cgacatcaac agctacctga gctggttcca gcagaagccc 120
ggcaagagcc ccaagaccct gatctaccgg gccaacagac tggtggatgg cgtgcccagc 180
agattcagcg gcggaggctc tggccaggac tacagcctga ccatcaactc cctggaatac 240
gaggacatgg gcatctacta ctgcctgcag tacgacgagt tcccctacac cttcggaggc 300
ggcaccaagc tggaaatgaa g 321

<210> SEQ ID NO 160
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 160
gaagtgaagc tggtggaatc tggcggcgga ctcgtgaagc ctggcggctc tctgaagctg 60
tcttgtgccg ccagcggctt caccttcagc agctacgcca tgagctgggt gcggcagatc 120
cccgagaagc ggctggaatg ggtggccagc atcagcagag gcggaaccac ctactacccc 180
gactctgtga agggccggtt caccatcagc cgggacaacg tgcggaacat cctgtacctg 240
cagatgagca gcctgcggag cgaggacacc gccatgtact actgtggcag atacgactac 300
gacggctact atgccatgga ttactggggc cagggcacca gcgtgaccgt gtcatct 357

<210> SEQ ID NO 161
<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 161
gacgtgcaga tcacccagag ccccagcagc ctgtatgcca gcctgggcga gagagtgacc 60
attacctgca aggccagccc cgacatcaac agctacctga gctggttcca gcagaagccc 120
ggcaagagcc ccaagaccct gatctaccgg gccaacagac tggtggatgg cgtgcccagc 180
agattcagcg gcggaggctc tggccaggac tacagcctga ccatcaactc cctggaatac 240
gaggacatgg gcatctacta ctgcctgcag tacgacgagt tcccctacac cttcggaggc 300
ggcaccaagc tggaaatgaa gggcagcaca agcggcagcg gcaagcctgg atctggcgag 360
ggaagcacca agggcgaagt gaagctggtg gaatctggcg gcggactcgt gaagcctggc 420
ggctctctga agctgtcttg tgccgccagc ggcttcacct tcagcagcta cgccatgagc 480
tgggtgcggc agatccccga gaagcggctg gaatgggtgg ccagcatcag cagaggcgga 540
accacctact accccgactc tgtgaagggc cggttcacca tcagccggga caacgtgcgg 600
aacatcctgt acctgcagat gagcagcctg cggagcgagg acaccgccat gtactactgt 660
ggcagatacg actacgacgg ctactatgcc atggattact ggggccaggg caccagcgtg 720
accgtgtcat ctaagcctac caccaccccc gcacctcgtc ctccaacccc tgcacctacg 780
attgccagtc agcctctttc actgcggcct gaggccagca gaccagctgc cggcggtgcc 840
gtccatacaa gaggactgga cttcgcgtcc gataaaccta ctaccactcc agccccaagg 900
cccccaaccc cagcaccgac tatcgcatca cagcctttgt cactgcgtcc tgaagccagc 960
cggccagctg caggggggc cgtccacaca aggggactcg actttgcgag tgataagccc 1020
accaccaccc ctgcccctag acctccaacc ccagccccta caatcgccag ccagcccctg 1080
agcctgaggc ccgaagcctg tagacctgcc gctggcggag ccgtgcacac cagaggcctg 1140
gatttcgcct gcgacatcta catctgggcc cctctggccg gcacctgtgg cgtgctgctg 1200
ctgagcctgg tcatcaccct gtactgcaac caccggaata ggagcaagcg gagcagaggc 1260
ggccacagcg actacatgaa catgaccccc cggaggcctg gccccacccg gaagcactac 1320
cagccctacg cccctcccag ggacttcgcc gcctaccgga gccgggtgaa gttcagccgg 1380
agcgccgacg cccctgccta ccagcagggc cagaaccagc tgtacaacga gctgaacctg 1440
ggccggaggg aggagtacga cgtgctggac aagcggagag gccgggaccc tgagatgggc 1500
ggcaagcccc ggagaaagaa ccctcaggag ggcctgtata acgaactgca gaaagacaag 1560
atggccgagg cctacagcga gatcggcatg aagggcgagc ggcggagggg caagggccac 1620
gacggcctgt accagggcct gagcaccgcc accaaggata cctacgacgc cctgcacatg 1680
caggccctgc cccccaga 1698

<210> SEQ ID NO 162
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162
gaggtgcagc tcgtggaatc cggcggtggc ctggtgcagc cgggcggcag tcttcgactc 60
tcctgtgcgg cgtcaggctt tacgttcagt tcttatgcca tgagctgggt gaggcaagct 120
cccggtaagg gactggagtg ggtctctgct atcagccggg gaggtacgac ctactacgct 180
gactccgtaa aaggaagatt taccataagt cgtgacaatt ccaaaaacac tctatactta 240
cagatgaact cgctcagggc cgaagatacc gcagtctact attgtgggag atacgattac 300
gacggctact atgctatgga ttattggggt cagggtacgc tcgtgacggt gtcctcc 357

<210> SEQ ID NO 163
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 163
gatattcaaa tgacgcaaag tcccagcagc ctctccgcct ccgttggaga cagggtgact 60
attacatgcc aagccagccc cgatattaat agctacttaa attggtatca gcagaaacct 120
gggaaggcac ctaaacttct catctaccgc gctaacaatc tggagaccgg cgtgccgtct 180
agattttccg gctctggatc agggaccgat tttactctga caattagttc cctgcaaccc 240
gaagacatcg ccacttatta ttgcctgcaa tatgatgagt ttccttacac atttggtcag 300
ggaactaaac tagagattaa g 321

<210> SEQ ID NO 164
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 164
gaagtgcaac tggtcgagtc tgggggcggc cttgtgcaac ctggaggcag ccttcgactc 60
agttgcgccg cgtctggttt taccttctcc tcttacgcga tgagctgggt tcgccaggcc 120
cccggcaagg gacttgagtg ggttagttcg atctcccgcg gaggcaccac atattatcct 180
gactcggtta agggacgctt cactatctct agggacaatt caaagaacac actgtatctc 240
caaatgaact ccttgcgggc cgaggacact gctgtgtatt attgcggacg atacgactac 300
gatgggtatt acgccatgga ttactggggg caaggtacac tggtcactgt gagttcg 357

<210> SEQ ID NO 165
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 165
gatattcaga tgacccagtc accttcgagt ctgagcgcat ccgtgggcga cagagtgacc 60
attacctgta aggccagccc ggacattaac agctacctat cgtggtatca gcaaaagcct 120
ggtaaggccc ctaaactcct tatctacagg gctaataggt tggtagacgg ggtgcctagc 180
cggttctctg gttccggcag cggtacggac tttactctga ccataagctc tctgcaacca 240
gaagacatcg caacatacta ctgtttacaa tacgacgaat ttccttatac ctttggccag 300
gggaccaagt tagagatcaa g 321

<210> SEQ ID NO 166
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 166
gaggttcagc tggtcgagtc cgggggaggc ttagtgcagc caggaggcag tctgcggctc 60
tcttgcgctg caagtggctt cacattcagt tcatacgcaa tcatctgggt tcgacaggct 120
cctggtaagg gcctcgaatg ggtcgcaagg atatcacgag gtggaaccac tagatacgca 180
gactctgtta agggcaggtt cacaattagc gcggatacct ccaaggagac tgcttattta 240
cagatgaact ctctgagagc cgaggacact gctgtttact actgcggccg atacgattac 300
gacggatatt acgcaatgga ttactggggc cagggcacgc tggtgacagt ttcatcg 357

<210> SEQ ID NO 167
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 167
gatatccaga tgactcagag tcccagtagc ctgtcggcaa gcgtcggaga tcgggtcaca 60
attacctgca aagctagtcc tgatattaat tcttacttgt cctggtatca gcagaagcct 120
ggtaaggccc ctaagttgct catctatcgg gctaaccggc tggtggacgg tgttccctct 180
agattctcag ggagtggaag cggcactgac ttcaccctga ctatatcgag ccttcagcca 240
gaggacattg ccacatacta ctgtctgcaa tatgatgaat ttccatatac attcggacaa 300
ggtacaaagt tagaaattaa g 321

<210> SEQ ID NO 168
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
gaagtccaac tggtggagtc tggcgggggc ttggtgcagc ccggtggctc ccttaggctg 60
tcttgcgctg ccagcgggtt cacattcagc tcctatgcga ttatatgggt ccgacaggca 120
cccggcaagg gattggagtg ggtggctcgc atcagcagag gcggcactac tcgttacgcc 180
gactccgtga aaggcagatt caccatcagt gcagacacat ccaaggaaac cgcatatctt 240
cagatgaata gcctgcgagc ggaggatacc gccgtctatt attgcggacg ctatgattac 300
gacggttatt atgctatgga ctactggggc cagggcacac ttgtgaccgt cagtagc 357

<210> SEQ ID NO 169
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 169
gacattcaaa tgacgcaaag ccctagtagc ttgtcagctt ctgtggggga ccgtgtcaca 60
atcacttgtc gggcctctcc agatataaac tcctacgttg cttggtatca gcagaagccc 120
ggaaaggctc cgaaattgtt gatttatcgc gctaatttct tagagtcagg agtgcccagc 180
cggttctcag ggtctcgctc tggaaccgac ttcacactca ctatttctag cctacagcct 240
gaggattttg caacttacta ctgtctacag tacgacgagt ttccgtacac tttcggacag 300
gggaccaagg tggagatcaa g 321

<210> SEQ ID NO 170
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 170
caagtacagc tcgtgcagag cggcggtggc ctggtgaagc caggaggtag tcttagactg 60
agctgtgcgg cttctggttt cacgttcagc agttatgcta tgtcctgggt taggcaaatc 120
cccggcaaag gattggagtg ggttagcagt atctcaaggg ggggaaccac atattatcct 180
gactctgtca aaggacggtt tacaatcagc cgcgataacg ttaaaaatac cctctacctc 240
cagatgtctt cgctccgcgc tgaagataca gcggtttact actgtggcag atacgactac 300
gacggttatt acgccatgga ctactgggga cagggaacta tggtcacagt tagctct 357

<210> SEQ ID NO 171
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 171
gacatcaaaa tgacgcagtc acctagtagc ctctccgcct cggttggcga tcgggtaacc 60
attacctgca aagcatctcc agacataaat agttatctta gttggtatca acagaaacct 120
ggcaaagctc ctaagaccct catctaccgc gctaaccgcc tcgtggatgg tgttccaagt 180

-continued

```
cggttctcag gaagcggcag tggcacagac tttacactga caattagttc cctccagtat    240

gaggatatgg ccatatatta ctgccttcag tatgatgagt ttccatacac attcggagac    300

ggtacaaagg tggagatcaa g                                              321
```

<210> SEQ ID NO 172
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 172

```
caagtgagcc tccgggagag tgggggcggt ctggtccaac caggacggtc actgcggctg     60

tcatgcactg ccagcggctt cacatttagc tcttacgcca tgacttgggt ccgccaagct    120

cccggtaagg gactggagtg ggtggccagc attagcaggg gtggtacaac ccacttcgcg    180

gattcagtta aggggagatt cactatctcc agggataatt ccaacaacac gctgtacctt    240

cagatggata acgtgagaga cgaggatacc gcgatatact actgtggccg ctatgactac    300

gatggttatt atgctatgga ttactggggg cggggcaccc tggtgactgt gtcctcg       357
```

<210> SEQ ID NO 173
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173

```
gatatcgtga tgacacagtc acctagctcc ctgagcgcaa gcgtggggga tagggttacc     60

ataacttgca gggccagtcc cgacatcaat agttatttgg cctggtatca acagaagcct    120

gggaaggcac ctaagttgct tatttatagg gctaactcgt tacagagcgg tgtgccaagt    180

cggttctcag gctcagggtc cgggaccgag ttcaccctga ccatcagtag cttgcagcca    240

gaagattttg ccacctacta ctgtcttcaa tacgatgagt ttccttacac ttttggacag    300

ggcaccaaac tagagatgaa g                                              321
```

<210> SEQ ID NO 174
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 174

```
caggttcaac tggtagaatc cggcggaggt gtagtgcagc ctggaaggtc attacggtta     60

agttgcgccg cctccgggtt cacatttagc agctatgcta tgaactgggt gcgccaggcc    120

cctgcgaaag gactcgaatg ggttgccatc atcagccgag gaggcacaca gtattatgcc    180

gattctgtga agggtcgttt tactatttcc agagacaaca gtaaaaatac gctgtacctg    240

caaatgaacg gattgagggc tgaggatacc gccgtgtact actgtggacg ctacgactat    300

gatgggtact acgcgatgga ctattggggg caaggaaccc ttgtaaccgt tagttca       357
```

<210> SEQ ID NO 175
<211> LENGTH: 321
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 175
gagatcgttt tgacacagag ccccgatttc cagagcgtca cgcccaagga gaaggtcacc 60
atcacctgcc gagccagccc cgacatcaac agttatcttt catggtatca acagaaacct 120
gatcagagcc ctaagctgct gattaagcgc gccaaccaga gcttctcagg ggttccttca 180
cggttttccg ggtcaggcag cgggactgac ttcacgttga ccattaactc tttggaggct 240
gaggatgctg ctgcctatta ctgccttcag tacgacgagt tcccctatac atttggtcct 300
ggaacaaaag tggatataaa g 321

<210> SEQ ID NO 176
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 176
caggtgcagc tcgtccagag cggagccgaa gtgaagaagc cgggagcatc agtgaaagtt 60
tcctgcaaag caagtggctt cactttcagc agttacgcga tgcactgggt gcggcaggca 120
ccaggtcagg gactggaatg gatggggaac atctctcgcg gcggaacaac caattacgca 180
gagaagttta agaatcgcgt tacgatgacc agagacactt ctattagtac agcctatatg 240
gagttgtcgc gtctgagaag cgacgatacc gctgtctact attgcggccg gtacgattat 300
gacggctact atgcaatgga ttactgggga cagggcacac ttgtgacagt gtctagt 357

<210> SEQ ID NO 177
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 177
gacattgtga tgactcagtc tccactcagc ctgcctgtca cgcccggcga acccgcttct 60
atctcttgta ggagtagccc tgatatcaac agctacctcg aatggtatct ccagaaacct 120
ggtcagagcc cccagctctt gatctataga gcaaacgaca ggttctctgg cgtgcctgat 180
aggttttccg gtagtggcag cggaaccgac ttcacactta agatttcaag ggtcgaggcc 240
gaggacgtgg gggtgtatta ctgcttacag tacgatgagt ttccgtatac attcgggcaa 300
ggcacaaagg tggaaattaa g 321

<210> SEQ ID NO 178
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 178
gaagtgcaac tggtcgaaag tggaggggga ctagtgcagc ccggagggtc actgaggcta 60
tcatgcaccg gctctggttt tactttttcc agctatgcca tgcactggct cagacaggtt 120
ccgggggaag gactggagtg ggttagcgga atctccagag gcggaactat tgactacgca 180
gacagcgtga aaggtaggtt taccatcagc agggacgatg ctaaaaagac cctgtcactt 240
caaatgaata gcctgagagc tgaggatacg gccgtgtatt actgtggacg ctatgactac 300
gatggatatt acgcaatgga ctactggggc cagggaacaa tggtgaccgt ctcaagc 357

<210> SEQ ID NO 179
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179
gagatcgtcc tgacccagag cccagctact ttgtcagttt cgccaggcga gcgggccaca 60
ctgagctgta gggcttctcc tgatatcaat tcttacctgg cctggtatca acagaaaccg 120
ggacaggccc ctcgcctgct gttctcccgc gccaacaata gggcgactgg cataccagct 180
cggtttactg ggagtgggtc aggcactgat ttcacgctta caatcagtag cctggagccc 240
gaagacttcg ccatctacta ctgtttacaa tacgatgagt tcccctatac cttcggccaa 300
gggaccaagg tggagatcaa g 321

<210> SEQ ID NO 180
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 180
gaagtgcagc tagtagaaag tggtggtggg gtcgtgcagc caggccgctc gctcaggctg 60
tcttgcgctg cgagtggttt cacattctct tcatacgcca tgagctgggt gagacaggct 120
cccggcaagg gcctcgaatg ggtcgcatct ataagcagag gcggaaccca gtactacgct 180
gacagtgtga agggtcgctt tacaatctca cgggacaaca gtaaaaacac cctctatcta 240
cagatgaatg gcttgcgagc tgaagacacg gctgtgtatt attgcgggcg ctatgactat 300
gatggttact acgctatgga ttactggggc cagggcaccc tggttactgt ttcatca 357

<210> SEQ ID NO 181
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181
gaaatagtcc tgacccagag cccagacttc cagtccgtga cccctaagga gaaggttact 60
atcacttgca gggcaagccc tgacataaat tcatacctgc catggtatca gcagaagcca 120
gaccagtcgc cgaagctatt aatcaaacgc gccaaccagt cttttagcgg cgtaccatcc 180
cgattctcag gttcggggtc cgggaccgat ttcacactca cgataaactc ccttgaggca 240
gaggatgcag cggcttacta ctgtttacag tacgacgagt ttccatatac gttcggcccc 300
ggcacgaagg tagatatcaa g 321

<210> SEQ ID NO 182
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 182
gaagtgcagc tggtggagtc tggcggcggt ctggtgcagc ccggcggctc tctgcgcctc 60
tcctgtgcca cctctggttt tacattctcc tcctacgcta tgtcctggat gcggcaagcc 120
cccggcaagg gcctagagtg ggtcgcctca atcagcaggg gcgggacgac ttattatgcc 180
gattcagtta aggggagatt cacaatttcc gtggataaat ccaagaatac cttatacctc 240
cagatgaact ctctgcgggc cgaagatacg gccgtatatt attgtgggag gtatgactac 300
gacggatatt acgccatgga ttattggggg caggggacac ttgttacagt gagttcc 357

<210> SEQ ID NO 183
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 183
gatatacaga tgacacagag cccttcaagt ttatctgcaa gcgtcggcga tcgtgttaca 60
ataacttgca aggcatctcc cgacatcaat tcctacctca actggtatca gcagaagcct 120
gggaaggctc ctaagctgct tatttacaga gcaaatcgcc tggtggacgg cgtgcccagt 180
cggttttccg ggtctgggag cggaacggat tacacactga ccatctcaag cctgcaaccc 240
gaagacttcg ctacatatta ctgccttcag tatgatgagt tcccatatac cttcggcgct 300
gggaccaagg tggagataaa g 321

<210> SEQ ID NO 184
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 184
gaggtccagc tcgtcgaatc tggcggaggt ttagtgcaac caggcgggtc gctccgatta 60
agttgtgcgt ccagtggctt caccttctcc agctacgcca tgtcgtggag gcgacaggct 120
cctggcaaag gcttggagtg ggttgctggt atctcccgag gaggcaccac tagttacgct 180
gacagtgtaa aaggacgttt cactatttcc tctgacgaca gcaagaacac actctatctg 240
caaatgaata gtctccgtgc tgaggacaca gccgtgtatt attgcgggcg gtatgattac 300
gacggctact acgctatgga ctactggggc cagggaactc tggtcactgt gagctct 357

<210> SEQ ID NO 185
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 185
gatatacaga tgactcaaag tcctagctcc ttgagcgcct cagtgggaga tcgggtcact 60
ataacttgta gagcctcacc agatataaac tcctatctct cttggtatca gcagaagccc 120
ggcaaagcac caaagctctt gatctataga gctaatacgc tagagagcgg agtgccttca 180
cggttttctg gttccgggag cggaaccgac tttaccctta caatttctag cctccagcca 240
gaggacttcg caacttacta ttgtctccag tatgatgaat ttccttacac cttcggccaa 300
gggaccaaga tcgagataaa g 321

<210> SEQ ID NO 186
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 186
gaggtgcagc tcgttgagtc cggtgggggg ctggtgcagc ctggcgggtc tctccgcctc 60
tcttgtgcct cctccggctt taccttcagc agctatgcta tgtcatgggt gcggcaggca 120
ccaggcaaag gtctggaatg ggtcgctggg atcagtagag gcggcacaac ctcctatgcc 180
gacagcgtta aggggaggtt cacaatctcg gctgatacaa gcaagaacac tctgtatctc 240
caaatgaaca gtctccgggc agaggacacc gcggtctatt actgcggccg gtacgactac 300
gacgggtact acgcaatgga ctattgggga cagggaactc tggttactgt cagctct 357

<210> SEQ ID NO 187
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 187
gatatccaga tgactcaaag cccatcttct ctcagcgcaa gcgtgggtga ccgagtgacc 60
atcacctgcc gggcgtctcc tgatatcaac tcatacctgt cctggtatca gcagaagccc 120
ggaaaggccc ctaagctgct gatctaccgc gcaaatacac tggagagcgg ggtcccaagc 180
agattcagtg ggtccggcag tggtacggac tttactctga ccatcagctc cctgcaaccg 240
gaggactttg ctacttatta ctgtctccag tacgacgagt tcccatacac tttcggaaca 300
ggcactaagc tggagatcaa a 321

<210> SEQ ID NO 188
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 188
gaggttcaac ttgtggaatc cggcggcggg ttagtccagc ccggcgggag cttgcggctg 60
tcctgcgccg cctctggatt cacttttagc tcctatgcta tgtcttgggt aaggcaggcc 120
cctggtaaag gactagagtg ggtggcctcg atctcccgtg gtggcactac atactacgcc 180
gactccgtta aaggccggtt taccatctcc cgtgacaact ctaaaaatac tttgtacctg 240
caaatgaact ccctgcgggc agaagacaca gccgtgtact attgcgggcg ttacgattac 300
gacggatatt acgcaatgga ctactggggc cagggcacac tggtcaccgt gagcagc 357

<210> SEQ ID NO 189
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 189
gatatacaaa tgactcagtc ccctagtagc cttagtgcta gtgtgggaga cagagtgacc 60
atcacctgca aagcatctcc tgatatcaat tcctacctta actggtatca acagaagcct 120
ggcaaagctc caaagctcct gatttatcgc gcgaacagat tggtcgatgg ggtcccttcc 180
agattcagcg gctcagggtc agggaccgat ttcaccctca caattagttc acttcagccc 240
gaggacatcg ccacgtatta ttgccttcag tacgatgagt tcccttacac ctttggcggg 300
ggaactaaag tcgaaattaa g 321

<210> SEQ ID NO 190
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 190
gaagtgcagc ttgtggagtc aggaggaggg ctagttcagc caggcggctc tctgagacta 60
tcttgtgctg cctccggctt cacatttagc tcttatgcaa tgtcctgggt ccgccaggcc 120
cctggtaaag gcctggaatg ggttgcttct atctctagag gcggaaccac ttactaccct 180
gattcagtga aggggagatt cacaattagt agggacaacg tgcggaacat cctctaccta 240
cagatgtcaa gtttacgcag tgaggacact gcgatgtatt actgcggtcg atacgattat 300
gatggatatt atgcaatgga ttattggggc cagggcactc tggtcacagt atcttcc 357

<210> SEQ ID NO 191
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 191
gacatccaga tgacccaatc accatcgagt cttagtgcat ccgttgggga tagagtgaca 60
atcacttgta aggcatcccc ggacatcaac tcatatctta attggtatca gcaaaagccg 120
ggcaaggccc ctaagctcct gatttatagg gccaaccgcc ttgtggatgg agtcccctcc 180
cgctttagtg gaagcggctc tggcacagac tacaccctga ctatcagctc cttgcagcct 240
gaggattttg ctacctacta ctgtcttcag tacgatgaat ttccatacac tttcggtgct 300
gggacaaaag tggagatcaa a 321

<210> SEQ ID NO 192
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 192
gaagtccagc tggttgagtc tggcggaggc ctcgtgcagc ccggtggttc cttgcgactg 60
tcatgcgcta ccagcgggtt cacattcagc tcttatgcaa tgtcctggat gcggaaggca 120
ccgggtaagg gcctggagta tgtggcctca atctcccgag gaggcaccac atactatgcc 180
gattctgtga aaggccgatt caccatttct gtggataagt ctaaaaacac tctctacctc 240
cagatgaact ccctacgtgc cgaagacaca gccgtgtatt attgcgggcg atacgattat 300
gacggttatt atgcgatgga ttactggggt caaggcacac tggtaacagt gtcttcc 357

<210> SEQ ID NO 193
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 193
gatattcaga tgacacaatc acctagctca ctgtcagcga gcgtcggtga ccgggttact 60
atcacatgca aagcctcacc cgatatcaat tcatacctta actggtatca acaaaaacca 120
ggaaaggctc caaagctgct aatttatcgg gccaatcggt tggtggatgg cgtcccgtcg 180
aggtttagtg gctccgggag cgggacagac tacactctta caatttcttc tctccagcca 240
gaggacttcg caacctacta ctgcttgcag tacgatgaat ttccatatac cttcggcgca 300
gggacaaaag tggaaatcaa a 321

<210> SEQ ID NO 194
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 194
gaggtgcagc ttgtagaaag cgggggggc ctggtgcaac ctggcgggtc cctgcggctt 60
agttgcgtta cgagcggatt tacattttcc agttatgcca tgtcttgggt gagacaagcc 120
cccggtaagg gtctggagtg ggtggcaagc attagccgag gcggcactac atactacagt 180
gatagtgtga aaggccgttt cacaatcagt agagataatt ctaaaaacac cctgtacttg 240
cagatgaaca gcctgcgcgc cgaggataca gccgtgtact actgtggaag atacgactac 300
gatggatatt atgcgatgga ttactgggga cagggaaccc ttgtcaccgt ttcctct 357

<210> SEQ ID NO 195
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 195
gacatagtgt tgacgcagtc ccctgccacc ctgagcctga gccccggaga gcgagcaacg 60
ttaagttgca aggccagtcc agatattaac tcatacatga attggtatca acagaaacca 120
ggccaggctc ctagacttct catatctcgg gcaaatcgac tggtggatgg agtacccgca 180
agattcagcg gcagcggcag cggaacggat ttcacgctca ccatctcttc ccttgagcct 240
gaggactttg cagtctatta ttgcttgcag tatgatgagt tcccctacac attcgggcaa 300
ggcacaaaag tggaaattaa g 321

<210> SEQ ID NO 196
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196
gaggtgcagc tggtggagag cggagggggc cttgtccaac caggaggtag cctcaggctg 60
tcttgcgctg cctcaggatt tactttttca tcctacgcaa tgagctgggt gcggcaagcc 120
ccagggaagg gattagaatg ggttgccagc atttctaggg gggggacgac ctactacgat 180
ccgaagtttc aggatcgcgc cactatctca gccgataact ccaagaatac tgcctactta 240
cagatgaaca gcctgcgggc cgaagacacg gccgtctact attgcggccg atatgattac 300
gacggctatt acgccatgga ttactggggg caagggactc tggtcacagt gagctct 357

<210> SEQ ID NO 197
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 197
gatattcaga tgacccagtc gcccagcagt ctctcggcct cagtgggcga ccgggtcact 60
atcacttgca aagcaagtcc tgatataaac tcctatctta attggtatca gcagaagccc 120
ggcaaggcac ctaaggttct gatatatcgc gcaaatcggc tcgtggatgg agtacccagc 180
cgattttccg gcagcggctc aggcactgac tacacactga caatcagcag cttgcagcct 240
gaagatttcg ccacatacta ttgtctacag tacgacgagt tcccttatac attcggccag 300
gggaccaagg tcgagatcaa g 321

<210> SEQ ID NO 198
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 198
gaggtccaac tcgtggagag cggagggggg ctagtgcaac caggtggctc cctccgcttg 60
tcctgtacgg gctcggggtt cacattttca tcctatgcca tgagctggct gagacaggtg 120
cctggcgagg gcctggaatg ggtgtctagt atcagcagag gggtacaac tgattacgca 180 gattccgtca agggacgttt taccatctca agagacgatg ccaagaagac attatcactc 240
caaatgaact cactgagggc cgaggacacc gctgtgtact attgtgggag atacgactac 300
gacggatact atgccatgga ctattgggga caaggcacga tggtgacggt atctagc 357

<210> SEQ ID NO 199
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199
gagatagtgc taacccagtc tcccgcaacc ctgtctgtgt cccccggaga gcgcgctact 60
ctgagctgca aagccagccc ggacattaat tcctaccttg cctggtatca gcagaagcct 120
ggacaggccc caagattgct cttttcacgc gccaaccgcc tggtagatgg tattccagct 180
aggtttacgg gctcaggcag cggaacagac ttcactctca ctattagctc attggagcct 240
gaggactttg caatttacta ttgtcttcag tacgacgagt tcccatatac tttcggccag 300
ggcacaaaag tagagatcaa g 321

<210> SEQ ID NO 200
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200
gaggttcaac tcgtggagtc tggaggcggg ctagtgcagc ctggcggctc cctgcgactg 60
tcttgcagcg catcaggctt tacattcagt tcttatgcca tgagctgggt gaggcaggtg 120
cccggcaagg gtctggtgtg gatcagctca atctccaggg gcgggactac atattacgcc 180
gattcggtca ggggtcgttt tatcattagc agggataatg ccaagaacac cttgtatttg 240
gagatgaaca acctaagagg cgaagacacc gctgtgtact attgtgcccg ttacgactac 300
gatgggtact acgccatgga ctattggggc cagggaacct tggtgactgt gtcaagt 357

<210> SEQ ID NO 201
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 201
gacatacagt tgactcagtc accggattcg ctggcagttt cgctgggtga gagagcaacc 60
atcaactgca aagcatctcc cgatatcaac tcttatctgt cttggtatca gcagcgtccg 120
ggacaacccc ctaggctgct tattcaccga gccaacaggc tggtggacgg ggtgccagac 180
cgcttctcgg gatcaggatt tggaaccgat tttaccctaa caattactag tctccaagcg 240
gaagacgtgg cgatctatta ttgtctacaa tatgacgagt tcccctacac cttcggccag 300
ggcacgaagt tggagatcaa g 321

<210> SEQ ID NO 202
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202
gaggtccagc tcgtcgaatc cggtggaggg ctagttcagc caggcggctc attgcgtttg 60
tcttgtgccg cctccggttt cacattctct tcttacgcta tgtcctgggt ccgacaagcc 120

-continued

```
ccaggaaaag gcttggaatg ggtggccagt atcagtagag gtgggactac atattatgcc    180

gactccgtga agggcagatt caccatctca gctgacacca gtaagaacac tgcctaccta    240

cagatgaaca gccttcgggc cgaggacacc gctgtgtatt actgtgcccg gtacgattat    300

gatggatatt atgctatgga ctattggggt caggggacct tggtgaccgt ctctagc       357


<210> SEQ ID NO 203
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203

gacattcaga tgactcaatc gccgagttct cttagcgctt ctgttgggga ccgggtgaca     60

atcacatgca aggcctctcc cgatataaac tcctatctaa gctggtatca gcagaagcca    120

gggaaggccc ccaagttgtt aatctatcgc gccaacagac tggtggatgg ggtgccctct    180

cgattctccg ggagtggcag tgggactgat tttacactga ccatttcctc attgcagccc    240

gaagacttcg ctacctatta ctgcttgcag tacgatgagt tcccatatac attcggtcag    300

gggactaaag tggagataaa a                                              321


<210> SEQ ID NO 204
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204

gaggtacagc tgctggaatc tggtgggggg ctggtccagc caggggggtc actacgactg     60

agctgcgctg cctccggttt tacattcagc agctatgcaa tgtcatgggt cagacaggca    120

ccaggtaaag gcctcgaatg ggtatcctcc atctcacgtg gtgggaccac ttactatgcc    180

gatagtgtga agggcaggtt cacgatctca agagataatt caaagaatac actctatcta    240

caaatgaaca gtttaagggc cgaggacacc gctgtttact attgtgccag atatgactac    300

gacggttatt atgctatgga ttactgggga caaggaacgc tggtaactgt tagctct       357


<210> SEQ ID NO 205
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205

gacatccaaa tgacccagtc gccttcctcc ttgtctgcat ctgtcggaga tcgggtgacg     60

atcacttgca aagcgagtcc agacatcaac tcatatctgt cctggtatca gcagaagccg    120

ggagaggcac ctaagctcct gatctacaga gcaaacagat tagtggatgg tgtgccctca    180

cggttttctg gctccgggtc cggcaccgat ttcaccttga ccatctcatc cctacagccc    240

gaggatttcg ctacttacta ttgcttacag tatgatgagt ttccatacac cttcggtcaa    300

ggcaccaagg ttgagattaa g                                              321


<210> SEQ ID NO 206
```

<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206
gaagttcaac tgcttgagac cggaggcggc ctggtaaaac ctgggggctc actgaggctg 60
agttgtgccg cttctgggtt caccttttca tcctatgcga tgtcatggat acggcaggct 120
cctgggaagg ggcttgagtg ggttgcatca atttcacgag gtgggacaac ttattatggg 180
gattccgtta aaggtagatt tacgatctct agagaccatg ccaaaaattc tctctatctc 240
cagatgaata gtcttagggt ggaggacacc gctgtgtact actgtgtccg gtacgactat 300
gatgggtact atgctatgga ctattggggg ctcggcactc tggtcactgt tagctct 357

<210> SEQ ID NO 207
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 207
gccatccgca tgacacaatc tccctccttc ctttctgcca gtgtcgggga cagagtgact 60
atcacatgca aagccagccc agatattaat tcgtacctgt cttggtatca gcagaggccc 120
ggcaaggcac caaagctgtt gatatatcgg gccaaccgct tagtggacgg tgtcccctct 180
cgattcagcg gaggcggtag cgggacggac tttacactga ccatctccag tctccaaccc 240
gaggatattg ccacttacta ttgtcttcag tatgacgagt tcccctacac atttggacag 300
ggcaccaagc tagaaattaa g 321

<210> SEQ ID NO 208
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208
gaggttcagc tggtggagtc tggtgggggg ctcgtacagc cgggtggctc cctaaggctg 60
agttgcgctg cctcaggctt taccttctca agctacgcga tgtcctgggt gagacaggcc 120
cctggcaaag gactggagtg ggtggcaagc attagccggg gcggaactac ctattacgct 180
gagtcgttag aggggcggtt tactatctcc agagacgatt caaagaactc gttatacttg 240
cagatgaaca gcctcaagac cgaggacacc gccgtgtact actgcgcccg gtacgactat 300
gacgggtact atgctatgga ttattgggga caaggcaccc tcgtgaccgt ctctagc 357

<210> SEQ ID NO 209
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209
gacatccaga tgacacagtc cccttcttca ctttccgctt ctgtgggcga cagggtgacg 60
atcacgtgta aggcctcgcc agacattaat tcgtacttat cgtggtatca gcagaaaccg 120
ggtaaagctc cgaagactct gatctataga gcaaataggc tcgtagacgg tgtcccatct 180
agatttagtg ggagcggcag cggaaccgac ttcactctca ccatctcatc cctgcaaccg 240
gaggatttcg ctacttacta ttgcttgcag tatgacgagt ttccatatac gtttggtcag 300
ggaaccaaat tagagatcaa a 321

<210> SEQ ID NO 210
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210
caggtaacac tccgagagag tgggccagct ctcgtgaagc ccacgcagac tttaacacta 60
acgtgtgcgg caagcggctt tacattttcg agctacgcga tgagctggat aaggcaacct 120
cctgggaagg cgttggagtg gttggcctca attagccggg gtggcaccac ttactacaat 180
cctagtctta aggacagact tactatttca aaagatacgt ccgccaacca ggtggtactg 240
aaggtcacaa atatggaccc agctgacact gctacttact actgcgcccg gtacgattac 300
gatggttact acgctatgga ttactggggt caaggaacca cagtgaccgt cagttca 357

<210> SEQ ID NO 211
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 211
gatatccaga tgacgcagtc cccttcaacc ctcagtgcca gcgttggtga ccgggttact 60
atcacctgta aggctagtcc cgatataaat tcctatttgt cttggtatca gcagaagcca 120
ggcaaggctc ctaagctgct catctaccgg gctaacaggt tagttgacgg tgtgccctcc 180
cgattttccg gcagtggcag cgggaccgct ttcactctta caatctcatc tcttcaaccg 240
gacgacttcg ctacgtacta ctgcctccaa tatgatgagt ttccatacac attcggagga 300
ggcacaaaag tcgaaatcaa g 321

<210> SEQ ID NO 212
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212
gaagtccagc tggtggagtc cggcggaggc ttggttcagc ccggaggatc tttgcgactg 60
tcttgcgccg ccagcggttt cactttcagc agctatgcca tgagttgggt tagacaagct 120
cccggcaagg ggctggaatg ggttagtgct attagccggg gagggacaac atattacgct 180
gactctgtca aaggccgatt caccatctct gctgacacga gcaaagaaac cgcctacctc 240
caaatgaaca gcctgcgagc tgaggacact gccgtctact attgtggtcg atatgattat 300
gatgggtact atgcaatgga ctattggggg cagggcacac tggtgaccgt gagctct 357

<210> SEQ ID NO 213
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213
gatattcaga tgacgcagag tccctcctcc ctatctgcct ctgttggaga tcgagtcacc 60
attacgtgta aagcgtctcc cgatatcaac agctacctct cttggtatca gcagaaacca 120
gggaaggccc ccaagctgct gatctataga gctaatcgct tagtggatgg agtgccaagc 180
aggttctccg ggtccggcag tggaaccgat ttcaccttga caataagtag cttgcaacct 240
gaggatattg caacatacta ctgtctacag tacgacgagt tcccctacac cttcggccaa 300
gggacaaagc tggagattaa g 321

<210> SEQ ID NO 214
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 214
gaagtgcagc tcgtggagag cggcggcggt ctggtacagc caggggggtc actgcgtctc 60
tcatgtgctg cgagtggctt tacgttctct tcctacgcta tgtcctgggt caggcaggca 120
ccggggaagg gcttagagtg ggttagtgca atctctaggg gcggtacaac ctactatgcc 180
gactctgtca agggcaggtt tacaatttca agagataatt ctaagaatac tctttaccta 240
cagatgaata gcttgcgggc ggaagacaca gcagtctatt attgtggccg ctatgactac 300
gacggatact atgccatgga ctactggggc caaggcactt tggtcacggt gagctct 357

<210> SEQ ID NO 215
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 215
gacatccaga tgacccagag ccctagttca ttgtctgcca gtgtggggga tagggtcact 60
atcacgtgta aggcttcccc tgacatcaat tcatacctgt catggtatca gcagaagcct 120
ggaaaagccc ctaaactgct gatctaccgc gcgaataggc ttgtggacgg cgttccaagc 180
cgcttctctg gctctggatc agggaccgac ttcaccctca cgatctccag cctccaaccc 240
gaggatatcg ccacctatta ttgccttcag tacgatgagt tcccctatac attcggccag 300
gggacaaagc tggaaatcaa a 321

<210> SEQ ID NO 216
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 216
gaggtccagc tcgtcgagtc gggtgggggc ttggtgcaac ccggtggcag tttgcgcctg 60
agctgcgccg cgagcgggtt cactttcagt tcgtatgcca tgagttgggt gcgacaagcg 120
cccggcaaag gactggagtg ggtgtcagcc attagccggg gcggtactac ctactatgcg 180
gactcggtca agggaagatt caccatcagc gctgatacca gtaaggaaac cgcttatctt 240
cagatgaact ccctgcgtgc cgaggataca gcagtctact attgcgggcg ctacgattat 300
gacggatatt atgccatgga ttactggggg cagggcactc tggtcacagt cagctct 357

<210> SEQ ID NO 217
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 217
gatattcaga tgacgcagtc tccctcttcc ctgagcgcct ccgtcggcga tagagttacg 60
atcacctgtc aggccagccc agatatcaac tcctatctga attggtatca gcaaaagcct 120
gggaaggctc ccaagttgct gatctacaga gccaataact tagagactgg cgtgccgtct 180
cggttcagcg ggtccggcag tggaaccgac tttacactga ccatttccag cctccaacct 240
gaggatatcg ccacatatta ttgtctccag tatgacgagt tcccttacac atttggtcaa 300
ggaactaaac tggaaatcaa a 321

<210> SEQ ID NO 218
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 218
gaggtgcagc tggtcgaaag tggaggcgga ctcgtgcagc ccggcggtag tctgcgattg 60
agctgtgccg cgtccggctt tactttctca tcttacgcta tgagttgggt ccgccaggcc 120
ccaggcaaag gactggagtg ggtatcagcc atcagtaggg ggggaactac ctattacgca 180
gattctgtga agggacgctt caccatcagc gcggacacta gcaaggagac tgcctacctg 240
caaatgaata gtctgagagc cgaggatacc gccgtgtact attgtggcag gtatgactac 300
gatggctatt atgctatgga ttactggggc caggggacgt tagtgacagt aagctct 357

<210> SEQ ID NO 219
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 219
gatattcaga tgacccaatc cccttcttct ctgagcgctt ctgtgggcga tagagttaca 60
ataacctgtc gggcgtcccc agacattaac tcttatgtag catggtatca gcaaaagcct 120
ggaaaggcac caaagttact gatctaccgg gccaattttc tggagtcggg cgtgccctca 180
cgatttagcg gtagcagatc aggcacagac tttactctga ccattagctc tctgcaaccc 240
gaggacttcg ccacctacta ctgtttgcag tatgacgagt ttccatacac ttttggtcaa 300
ggaaccaaag tcgaaatcaa a 321

<210> SEQ ID NO 220
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
cagatacagc tggtgcagtc tggtgccgag gttaaaaagc ccggagcctc ggttaaagtg 60
agttgtgcgg caagcggatt cacgttcagt tcctacgcta tgtcctgggt gcggcaggct 120
cctggcaagt catttaagtg gatggggtcg atctcacggg gtggaaccac ctattactct 180
gccgacttca aggggagatt tgcgattaca aaagatacaa gcgcctctac ggcctacatg 240
gagttaagta gccttagaag cgaagacacg gcggtgtact actgcgccag atatgactat 300
gacggctact acgccatgga ctactggggc cagggcacac tggttacagt cagctct 357

<210> SEQ ID NO 221
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
gatatcgtga tgacacaaag cccagacagt ctggcagtgt ccctcggcga gcgcgctacc 60
atctcatgca aagctagtcc cgacatcaat tcctatctgt cctggtatca gcaaaaacca 120
ggccaacccc ccaagctgct tatctatcgg gctaaccgat tagtcgatgg ggtgccagat 180
agattttcag gctctggttc ccggacagat tttactctca cgatctcctc actacaggca 240
gaagatgttg cagtgtatta ctgcctgcaa tacgacgagt tcccctacac cttcggccaa 300
ggcacgaaag tggagatcaa g 321

<210> SEQ ID NO 222
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
gaagtgcagc tggtggagtc tggcggcggt ctggtgcagc ccggcggctc tctgcgcctc 60
tcctgtgcca cctctggttt tacattctcc tcctacgcta tgtcctggat gcggcaagcc 120
cccggcaagg gcctagagtg ggtcgcctca atcagcaggg gcgggacgac ttattatgcc 180
gattcagtta aggggagatt cacaatttcc gtggataaat ccaagaatac cttatacctc 240
cagatgaact ctctgcgggc cgaagatacg gccgtatatt attgtgggag gtatgactac 300
gacggatatt acgccatgga ttattggggg caggggacac ttgttacagt gagttccggt 360
ggtggggggt ctggaggcgg gggcagtgga ggcggagggt ctgatataca gatgacacag 420
agcccttcaa gtttatctgc aagcgtcggc gatcgtgtta caataacttg caaggcatct 480
cccgacatca attcctacct caactggtat cagcagaagc ctgggaaggc tcctaagctg 540
cttatttaca gagcaaatcg cctggtggac ggcgtgccca gtcggttttc cgggtctggg 600
agcggaacgg attacacact gaccatctca agcctgcaac ccgaagactt cgctacatat 660
tactgccttc agtatgatga gttcccatat accttcggcg ctgggaccaa ggtggagata 720
aagaagccta ccaccacccc cgcacctcgt cctccaaccc ctgcacctac gattgccagt 780
cagcctcttt cactgcggcc tgaggccagc agaccagctg ccggcggtgc cgtccataca 840
agaggactgg acttcgcgtc cgataaacct actaccactc cagccccaag gcccccaacc 900
ccagcaccga ctatcgcatc acagcctttg tcactgcgtc ctgaagccag ccggccagct 960
gcaggggggg ccgtccacac aaggggactc gactttgcga gtgataagcc caccaccacc 1020
cctgccccta gacctccaac cccagcccct acaatcgcca gccagcccct gagcctgagg 1080
cccgaagcct gtagacctgc cgctggcgga gccgtgcaca ccagaggcct ggatttcgcc 1140
tgcgacatct acatctgggc ccctctggcc ggcacctgtg gcgtgctgct gctgagcctg 1200
gtcatcaccc tgtactgcaa ccaccggaat aggagcaagc ggagcagagg cggccacagc 1260
gactacatga acatgacccc ccggaggcct ggccccaccc ggaagcacta ccagccctac 1320
gcccctccca gggacttcgc cgcctaccgg agccgggtga agttcagccg gagcgccgac 1380
gcccctgcct accagcaggg ccagaaccag ctgtacaacg agctgaacct gggccggagg 1440
gaggagtacg acgtgctgga caagcggaga ggccgggacc ctgagatggg cggcaagccc 1500
cggagaaaga accctcagga gggcctgtat aacgaactgc agaaagacaa gatggccgag 1560
gcctacagcg agatcggcat gaagggcgag cggcggaggg gcaagggcca cgacggcctg 1620
taccagggcc tgagcaccgc caccaaggat acctacgacg ccctgcacat gcaggccctg 1680
ccccccaga 1689

<210> SEQ ID NO 223
<211> LENGTH: 1692
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 223
gatattcaga tgacccagtc accttcgagt ctgagcgcat ccgtgggcga cagagtgacc 60
attacctgta aggccagccc ggacattaac agctacctat cgtggtatca gcaaaagcct 120
ggtaaggccc ctaaactcct tatctacagg gctaataggt tggtagacgg ggtgcctagc 180
cggttctctg gttccggcag cggtacggac tttactctga ccataagctc tctgcaacca 240
gaagacatcg caacatacta ctgtttacaa tacgacgaat ttccttatac ctttggccag 300
gggaccaagt tagagatcaa ggggggcggc ggaagtggtg gagggggaag tggtggagga 360
ggaagcgaag tgcaactggt cgagtctggg ggcggccttg tgcaacctgg aggcagcctt 420
cgactcagtt gcgccgcgtc tggttttacc ttctcctctt acgcgatgag ctgggttcgc 480
caggcccccg gcaagggact tgagtgggtt agttcgatct cccgcggagg caccacatat 540
tatcctgact cggttaaggg acgcttcact atctctaggg acaattcaaa gaacacactg 600
tatctccaaa tgaactcctt gcgggccgag gacactgctg tgtattattg cggacgatac 660
gactacgatg ggtattacgc catggattac tgggggcaag gtacactggt cactgtgagt 720
tcgaagccta ccaccacccc cgcacctcgt cctccaaccc ctgcacctac gattgccagt 780
cagcctcttt cactgcggcc tgaggccagc agaccagctg ccggcggtgc cgtccataca 840
agaggactgg acttcgcgtc cgataaacct actaccactc cagccccaag gcccccaacc 900
ccagcaccga ctatcgcatc acagcctttg tcactgcgtc ctgaagccag ccggccagct 960
gcaggggggg ccgtccacac aaggggactc gactttgcga gtgataagcc caccaccacc 1020
cctgccccta gacctccaac cccagcccct acaatcgcca gccagcccct gagcctgagg 1080
cccgaagcct gtagacctgc cgctggcgga gccgtgcaca ccagaggcct ggatttcgcc 1140
tgcgacatct acatctgggc ccctctggcc ggcacctgtg gcgtgctgct gctgagcctg 1200
gtcatcaccc tgtactgcaa ccaccggaat aggagcaagc ggagcagagg cggccacagc 1260
gactacatga acatgacccc ccggaggcct ggccccaccc ggaagcacta ccagccctac 1320
gcccctccca gggacttcgc cgcctaccgg agccgggtga agttcagccg gagcgccgac 1380
gcccctgcct accagcaggg ccagaaccag ctgtacaacg agctgaacct gggccggagg 1440
gaggagtacg acgtgctgga caagcggaga ggccgggacc ctgagatggg cggcaagccc 1500
cggagaaaga accctcagga gggcctgtat aacgaactgc agaaagacaa gatggccgag 1560
gcctacagcg agatcggcat gaagggcgag cggcggaggg gcaagggcca cgacggcctg 1620
taccagggcc tgagcaccgc caccaaggat acctacgacg ccctgcacat gcaggccctg 1680
ccccccagat ga 1692

<210> SEQ ID NO 224
<211> LENGTH: 1689
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 224
gaggttcaac ttgtggaatc cggcggcggg ttagtccagc ccggcgggag cttgcggctg 60
tcctgcgccg cctctggatt cacttttagc tcctatgcta tgtcttgggt aaggcaggcc 120
cctggtaaag gactagagtg ggtggcctcg atctcccgtg gtggcactac atactacgcc 180
gactccgtta aaggccggtt taccatctcc cgtgacaact ctaaaaatac tttgtacctg 240
caaatgaact ccctgcgggc agaagacaca gccgtgtact attgcgggcg ttacgattac 300
gacggatatt acgcaatgga ctactggggc cagggcacac tggtcaccgt gagcagcggg 360
ggcggaggaa gtggaggagg cggtagtggt gggggaggaa gcgatataca aatgactcag 420
tcccctagta gccttagtgc tagtgtggga gacagagtga ccatcacctg caaagcatct 480
cctgatatca attcctacct taactggtat caacagaagc ctggcaaagc tccaaagctc 540
ctgatttatc gcgcgaacag attggtcgat ggggtccctt ccagattcag cggctcaggg 600
tcagggaccg atttcaccct cacaattagt tcacttcagc ccgaggacat cgccacgtat 660
tattgccttc agtacgatga gttcccttac acctttggcg ggggaactaa agtcgaaatt 720
aagaagccta ccaccacccc cgcacctcgt cctccaaccc ctgcacctac gattgccagt 780
cagcctcttt cactgcggcc tgaggccagc agaccagctg ccggcggtgc cgtccataca 840
agaggactgg acttcgcgtc cgataaacct actaccactc cagccccaag gcccccaacc 900
ccagcaccga ctatcgcatc acagcctttg tcactgcgtc ctgaagccag ccggccagct 960
gcaggggggg ccgtccacac aaggggactc gactttgcga gtgataagcc caccaccacc 1020
cctgccccta gacctccaac cccagcccct acaatcgcca gccagcccct gagcctgagg 1080
cccgaagcct gtagacctgc cgctggcgga gccgtgcaca ccagaggcct ggatttcgcc 1140

```
tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                          1689
```

```
<210> SEQ ID NO 225
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

gaagtgcagc ttgtggagtc aggaggaggg ctagttcagc caggcggctc tctgagacta     60

tcttgtgctg cctccggctt cacatttagc tcttatgcaa tgtcctgggt ccgccaggcc    120

cctggtaaag gcctggaatg ggttgcttct atctctagag gcggaaccac ttactaccct    180

gattcagtga aggggagatt cacaattagt agggacaacg tgcggaacat cctctaccta    240

cagatgtcaa gtttacgcag tgaggacact gcgatgtatt actgcggtcg atacgattat    300

gatggatatt atgcaatgga ttattggggc cagggcactc tggtcacagt atcttccggc    360

ggcggtggtt ctggcggtgg tggaagcgga ggggggggt ccgacatcca gatgacccaa    420

tcaccatcga gtcttagtgc atccgttggg gatagagtga caatcacttg taaggcatcc    480

ccggacatca actcatatct taattggtat cagcaaaagc cgggcaaggc ccctaagctc    540

ctgatttata gggccaaccg ccttgtggat ggagtcccct cccgctttag tggaagcggc    600

tctggcacag actacaccct gactatcagc tccttgcagc ctgaggattt tgctacctac    660

tactgtcttc agtacgatga atttccatac actttcggtg ctgggacaaa agtggagatc    720

aaaaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440
```

-continued

```
gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

```
<210> SEQ ID NO 226
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226

gaagtgcaac tggtcgagtc tgggggcggc cttgtgcaac ctggaggcag ccttcgactc     60

agttgcgccg cgtctggttt taccttctcc tcttacgcga tgagctgggt tcgccaggcc    120

cccggcaagg gacttgagtg ggttagttcg atctcccgcg gaggcaccac atattatcct    180

gactcggtta agggacgctt cactatctct agggacaatt caaagaacac actgtatctc    240

caaatgaact ccttgcgggc cgaggacact gctgtgtatt attgcggacg atacgactac    300

gatgggtatt acgccatgga ttactggggg caaggtacac tggtcactgt gagttcgggg    360

ggcggcggaa gtggtggagg gggaagtggt ggaggaggaa gcgatataca gatgacacag    420

agcccttcaa gtttatctgc aagcgtcggc gatcgtgtta caataacttg caaggcatct    480

cccgacatca attcctacct caactggtat cagcagaagc ctgggaaggc tcctaagctg    540

cttatttaca gagcaaatcg cctggtggac ggcgtgccca gtcggttttc cgggtctggg    600

agcggaacgg attacacact gaccatctca agcctgcaac ccgaagactt cgctacatat    660

tactgccttc agtatgatga gttcccatat accttcggcg ctgggaccaa ggtggagata    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

<210> SEQ ID NO 227
<211> LENGTH: 1689
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 227
gaagtgcaac tggtcgagtc tgggggcggc cttgtgcaac ctggaggcag ccttcgactc 60
agttgcgccg cgtctggttt taccttctcc tcttacgcga tgagctgggt tcgccaggcc 120
cccggcaagg gacttgagtg ggttagttcg atctcccgcg gaggcaccac atattatcct 180
gactcggtta agggacgctt cactatctct agggacaatt caaagaacac actgtatctc 240
caaatgaact ccttgcgggc cgaggacact gctgtgtatt attgcggacg atacgactac 300
gatgggtatt acgccatgga ttactggggg caaggtacac tggtcactgt gagttcgggg 360
ggcggcggaa gtggtggagg gggaagtggt ggaggaggaa gcgatattca gatgacccag 420
tcgcccagca gtctctcggc ctcagtgggc gaccgggtca ctatcacttg caaagcaagt 480
cctgatataa actcctatct taattggtat cagcagaagc ccggcaaggc acctaaggtt 540
ctgatatatc gcgcaaatcg gctcgtggat ggagtaccca gccgattttc cggcagcggc 600
tcaggcactg actacacact gacaatcagc agcttgcagc ctgaagattt cgccacatac 660
tattgtctac agtacgacga gttcccttat acattcggcc aggggaccaa ggtcgagatc 720
aagaagccta ccaccacccc cgcacctcgt cctccaaccc ctgcacctac gattgccagt 780
cagcctcttt cactgcggcc tgaggccagc agaccagctg ccggcggtgc cgtccataca 840
agaggactgg acttcgcgtc cgataaacct actaccactc cagccccaag gcccccaacc 900
ccagcaccga ctatcgcatc acagcctttg tcactgcgtc ctgaagccag ccggccagct 960
gcaggggggg ccgtccacac aaggggactc gactttgcga gtgataagcc caccaccacc 1020
cctgccccta gacctccaac cccagcccct acaatcgcca gccagcccct gagcctgagg 1080
cccgaagcct gtagacctgc cgctggcgga gccgtgcaca ccagaggcct ggatttcgcc 1140
tgcgacatct acatctgggc ccctctggcc ggcacctgtg gcgtgctgct gctgagcctg 1200
gtcatcaccc tgtactgcaa ccaccggaat aggagcaagc ggagcagagg cggccacagc 1260
gactacatga acatgacccc ccggaggcct ggccccaccc ggaagcacta ccagccctac 1320
gcccctccca gggacttcgc cgcctaccgg agccgggtga agttcagccg gagcgccgac 1380
gcccctgcct accagcaggg ccagaaccag ctgtacaacg agctgaacct gggccggagg 1440
gaggagtacg acgtgctgga caagcggaga ggccgggacc ctgagatggg cggcaagccc 1500
cggagaaaga accctcagga gggcctgtat aacgaactgc agaaagacaa gatggccgag 1560
gcctacagcg agatcggcat gaagggcgag cggcggaggg gcaagggcca cgacggcctg 1620
taccagggcc tgagcaccgc caccaaggat acctacgacg ccctgcacat gcaggccctg 1680
ccccccaga 1689

<210> SEQ ID NO 228
<211> LENGTH: 1689
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 228

```
gaggttcaac tcgtggagtc tggaggcggg ctagtgcagc ctggcggctc cctgcgactg     60

tcttgcagcg catcaggctt tacattcagt tcttatgcca tgagctgggt gaggcaggtg    120

cccggcaagg gtctggtgtg gatcagctca atctccaggg gcgggactac atattacgcc    180

gattcggtca ggggtcgttt tatcattagc agggataatg ccaagaacac cttgtatttg    240

gagatgaaca acctaagagg cgaagacacc gctgtgtact attgtgcccg ttacgactac    300

gatgggtact acgccatgga ctattggggc cagggaacct tggtgactgt gtcaagtggc    360

gggggcggca gcggaggcgg tggcagcgga ggcggcggtt ctgatattca aatgacgcaa    420

agtcccagca gcctctccgc ctccgttgga gacagggtga ctattacatg ccaagccagc    480

cccgatatta atagctactt aaattggtat cagcagaaac ctgggaaggc acctaaactt    540

ctcatctacc gcgctaacaa tctggagacc ggcgtgccgt ctagattttc cggctctgga    600

tcagggaccg attttactct gacaattagt tccctgcaac ccgaagacat cgccacttat    660

tattgcctgc aatatgatga gtttccttac acatttggtc agggaactaa actagagatt    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcagggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

<210> SEQ ID NO 229
<211> LENGTH: 1689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 229

```
gaggttcaac tcgtggagtc tggaggcggg ctagtgcagc ctggcggctc cctgcgactg     60

tcttgcagcg catcaggctt tacattcagt tcttatgcca tgagctgggt gaggcaggtg    120

cccggcaagg gtctggtgtg gatcagctca atctccaggg gcgggactac atattacgcc    180

gattcggtca ggggtcgttt tatcattagc agggataatg ccaagaacac cttgtatttg    240

gagatgaaca acctaagagg cgaagacacc gctgtgtact attgtgcccg ttacgactac    300
```

gatgggtact acgccatgga ctattggggc cagggaacct tggtgactgt gtcaagtggc 360
gggggcggca gcggaggcgg tggcagcgga ggcggcggtt ctgatataca gatgacacag 420
agcccttcaa gtttatctgc aagcgtcggc gatcgtgtta caataacttg caaggcatct 480
cccgacatca attcctacct caactggtat cagcagaagc ctgggaaggc tcctaagctg 540
cttatttaca gagcaaatcg cctggtggac ggcgtgccca gtcggttttc cgggtctggg 600
agcggaacgg attacacact gaccatctca agcctgcaac ccgaagactt cgctacatat 660
tactgccttc agtatgatga gttcccatat accttcggcg ctgggaccaa ggtggagata 720
aagaagccta ccaccacccc cgcacctcgt cctccaaccc ctgcacctac gattgccagt 780
cagcctcttt cactgcggcc tgaggccagc agaccagctg ccggcggtgc cgtccataca 840
agaggactgg acttcgcgtc cgataaacct actaccactc cagccccaag gcccccaacc 900
ccagcaccga ctatcgcatc acagcctttg tcactgcgtc ctgaagccag ccggccagct 960
gcaggggggg ccgtccacac aaggggactc gactttgcga gtgataagcc caccaccacc 1020
cctgccccta gacctccaac cccagcccct acaatcgcca gccagcccct gagcctgagg 1080
cccgaagcct gtagacctgc cgctggcgga gccgtgcaca ccagaggcct ggatttcgcc 1140
tgcgacatct acatctgggc ccctctggcc ggcacctgtg gcgtgctgct gctgagcctg 1200
gtcatcaccc tgtactgcaa ccaccggaat aggagcaagc ggagcagagg cggccacagc 1260
gactacatga acatgacccc ccggaggcct ggccccaccc ggaagcacta ccagccctac 1320
gcccctccca gggacttcgc cgcctaccgg agccgggtga agttcagccg gagcgccgac 1380
gcccctgcct accagcaggg ccagaaccag ctgtacaacg agctgaacct gggccggagg 1440
gaggagtacg acgtgctgga caagcggaga ggccgggacc ctgagatggg cggcaagccc 1500
cggagaaaga accctcagga gggcctgtat aacgaactgc agaaagacaa gatggccgag 1560
gcctacagcg agatcggcat gaagggcgag cggcggaggg gcaagggcca cgacggcctg 1620
taccagggcc tgagcaccgc caccaaggat acctacgacg ccctgcacat gcaggccctg 1680
ccccccaga 1689

<210> SEQ ID NO 230
<211> LENGTH: 141
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 230
aagcccacca ccacccctgc ccctagacct ccaaccccag cccctacaat cgccagccag 60
cccctgagcc tgaggcccga agcctgtaga cctgccgctg gcggagccgt gcacaccaga 120
ggcctggatt tcgcctgcga c 141

<210> SEQ ID NO 231
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 231
aaacctacta caactcctgc cccccggcct cctacaccag ctcctactat cgcctcccag 60
ccactcagtc tcagacccga ggcttctagg ccagcggccg gaggcgcggt ccacacccgc 120
gggctggact ttgcatccga taagcccacc accacccctg cccctagacc tccaacccca 180
gcccctacaa tcgccagcca gcccctgagc ctgaggcccg aagcctgtag acctgccgct 240
ggcggagccg tgcacaccag aggcctggat ttcgcctgcg ac 282

<210> SEQ ID NO 232
<211> LENGTH: 423
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 232
aagcctacca ccaccccgc acctcgtcct ccaacccctg cacctacgat tgccagtcag 60
cctctttcac tgcggcctga ggccagcaga ccagctgccg gcggtgccgt ccatacaaga 120
ggactggact tcgcgtccga taaacctact accactccag ccccaaggcc cccaacccca 180
gcaccgacta tcgcatcaca gcctttgtca ctgcgtcctg aagccagccg gccagctgca 240 ggggggccg tccacacaag ggactcgac tttgcgagtg ataagcccac caccacccct 300
gcccctagac ctccaacccc agcccctaca atcgccagcc agcccctgag cctgaggccc 360
gaagcctgta gacctgccgc tggcggagcc gtgcacacca gaggcctgga tttcgcctgc 420
gac 423

<210> SEQ ID NO 233
<211> LENGTH: 564
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233
aagcctacca ccaccccgc acctcgtcct ccaacccctg cacctacgat tgccagtcag 60
cctctttcac tgcggcctga ggccagcaga ccagctgccg gcggtgccgt ccatacaaga 120
ggactggact tcgcgtccga taaacctact accactccag ccccaaggcc cccaacccca 180
gcaccgacta tcgcatcaca gcctttgtca ctgcgtcctg aagccagccg gccagctgca 240 ggggggccg tccacacaag ggactcgac tttgcgagtg ataaacctac tacaactcct 300 gcccccggc ctcctacacc agctcctact atcgcctccc agccactcag tctcagaccc 360
gaggcttcta ggccagcggc cggaggcgcg gtccacaccc gcgggctgga ctttgcatcc 420
gataagccca ccaccacccc tgcccctaga cctccaaccc cagcccctac aatcgccagc 480
cagcccctga gcctgaggcc cgaagcctgt agacctgccg ctggcggagc cgtgcacacc 540
agaggcctgg atttcgcctg cgac 564

<210> SEQ ID NO 234
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
atctacatct gggcccctct ggccggcacc tgtggcgtgc tgctgctgag cctggtcatc 60
accctgtact gcaaccaccg gaat 84

<210> SEQ ID NO 235
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
ttttgggtgc tggtggtggt tggtggagtc ctggcttgct atagcttgct agtaacagtg 60
gcctttatta ttttctgggt g 81

<210> SEQ ID NO 236
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 236
aagagaggcc ggaagaaact gctgtacatc ttcaagcagc ccttcatgcg gcccgtgcag 60
accacccagg aagaggacgg ctgcagctgc cggttccccg aggaagagga aggcggctgc 120
gaactg 126

<210> SEQ ID NO 237
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 237
aggagcaagc ggagcagagg cggccacagc gactacatga acatgacccc ccggaggcct 60
ggccccaccc ggaagcacta ccagccctac gcccctccca gggacttcgc cgcctaccgg 120
agc 123

<210> SEQ ID NO 238
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238
ctgtgcgcac gcccacgccg cagccccgcc caagaagatg gcaaagtcta catcaacatg 60
ccaggcaggg gc 72

<210> SEQ ID NO 239
<211> LENGTH: 156
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 239
tacttcctgg gccggctggt ccctcggggg cgaggggctg cggaggcagc gacccggaaa 60
cagcgtatca ctgagaccga gtcgccttat caggagctcc agggtcagag gtcggatgtc 120
tacagcgacc tcaacacaca gaggccgtat tacaaa 156

<210> SEQ ID NO 240
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 240
cgggtgaagt tcagccggag cgccgacgcc cctgcctacc agcagggcca gaaccagctg 60
tacaacgagc tgaacctggg ccggagggag gagtacgacg tgctggacaa gcggagaggc 120
cgggaccctg agatgggcgg caagccccgg agaaagaacc ctcaggaggg cctgtataac 180
gaactgcaga aagacaagat ggccgaggcc tacagcgaga tcggcatgaa gggcgagcgg 240
cggaggggca agggccacga cggcctgtac cagggcctga gcaccgccac caaggatacc 300
tacgacgccc tgcacatgca ggccctgccc cccaga 336

<210> SEQ ID NO 241
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 241
atgcttctcc tggtgacaag ccttctgctc tgtgagttac cacacccagc attcctcctg 60
atccca 66

<210> SEQ ID NO 242
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 242
atgaggctcc ctgctcagct cctggggctg ctaatgctct gggtcccagg atccagtggg 60

<210> SEQ ID NO 243
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 243
atggattgga cctggattct gtttctggtg gccgctgcca caagagtgca cagc 54

<210> SEQ ID NO 244
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
atggcgctgc ccgtgaccgc cttgctcctg ccgctggcct tgctgctcca cgccgccagg 60
ccg 63

<210> SEQ ID NO 245
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 245
atgggcacca gcctcctctg ctggatggcc ctgtgtctcc tgggggcaga tcacgcagat 60
gct 63

<210> SEQ ID NO 246
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 246
atgaagcgct tcctcttcct cctactcacc atcagcctcc tggttatggt acagatacaa 60
actggactct ca 72

<210> SEQ ID NO 247
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 247
atgggggcag gtgccaccgg ccgcgccatg gacgggccgc gcctgctgct gttgctgctt 60
ctgggggtgt cccttggagg tgcc 84

<210> SEQ ID NO 248
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 248
atgggctggt cctgcatcat cctgtttctg gtggctaccg ccaccggcgt gcacagc 57

<210> SEQ ID NO 249
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 249
atgtctcgct ccgtggcctt agctgtgctc gcgctactct ctctttctgg cctggaggct 60

<210> SEQ ID NO 250
<211> LENGTH: 57
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 250
atgacccggc tgacagtcct ggccctgctg gctggtctgc tggcgtcctc gagggcc 57

<210> SEQ ID NO 251
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
atgaagtggg taacctttat ttcccttctt tttctcttta gctcggctta ttcc 54

<210> SEQ ID NO 252
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
atggggaaga acaaactcct tcatccaagt ctggttcttc tcctcttggt cctcctgccc 60
acagacgcc 69

<210> SEQ ID NO 253
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
atggagtttg ggctgagctg gctttttctt gtggctattt taaaaggtgt ccagtgt 57

<210> SEQ ID NO 254
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
atggacatga gggtccctgc tcagctcctg gggctcctgc tgctctggct ctcaggtgcc 60
agatgt 66

<210> SEQ ID NO 255
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
atggagtttg ggctgagctg ggttttcctc gttgctcttt ttagaggtgt ccagtgt 57

<210> SEQ ID NO 256
<211> LENGTH: 1005
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 256

```
cgcaaagtgt gtaacggaat aggtattggt gaatttaaag actcactctc cataaatgct      60
acgaatatta aacacttcaa aaactgcacc tccatcagtg gcgatctcca catcctgccg     120
gtggcattta ggggtgactc cttcacacat actcctcctc tggatccaca ggaactggat     180
attctgaaaa ccgtaaagga aatcacaggg tttttgctga ttcaggcttg gcctgaaaac     240
aggacggacc tccatgcctt tgagaaccta gaaatcatac gcggcaggac caagcaacat     300
ggtcagtttt ctcttgcagt cgtcagcctg aacataacat ccttgggatt acgctccctc     360
aaggagataa gtgatggaga tgtgataatt tcaggaaaca aaaatttgtg ctatgcaaat     420
acaataaact ggaaaaaact gtttgggacc tccggtcaga aaaccaaaat tataagcaac     480
agaggtgaaa acagctgcaa ggccacaggc caggtctgcc atgccttgtg ctcccccgag     540
ggctgctggg gcccggagcc cagggactgc gtctcttgcc ggaatgtcag ccgaggcagg     600
gaatgcgtgg acaagtgcaa ccttctggag ggtgagccaa gggagtttgt ggagaactct     660
gagtgcatac agtgccaccc agagtgcctg cctcaggcca tgaacatcac ctgcacagga     720
cggggaccag acaactgtat ccagtgtgcc cactacattg acggccccca ctgcgtcaag     780
acctgcccgg caggagtcat gggagaaaac aacaccctgg tctggaagta cgcagacgcc     840
ggccatgtgt gccacctgtg ccatccaaac tgcacctacg gatgcactgg gccaggtctt     900
gaaggctgtc caacgaatgg gcctaagatc ccgtccatcg ccactgggat ggtgggggcc     960
ctcctcttgc tgctggtggt ggccctgggg atcggcctct tcatg                    1005
```

<210> SEQ ID NO 257
<211> LENGTH: 732
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 257

```
cgcaaagtgt gtaacggaat aggtattggt gaatttaaag actcactctc cataaatgct      60
acgaatatta aacacttcaa aaactgcacc tccatcagtg gcgatctcca catcctgccg     120
gtggcattta ggggtgactc cttcacacat actcctcctc tggatccaca ggaactggat     180
attctgaaaa ccgtaaagga aatcacaggg tttttgctga ttcaggcttg gcctgaaaac     240
aggacggacc tccatgcctt tgagaaccta gaaatcatac gcggcaggac caagcaacat     300
ggtcagtttt ctcttgcagt cgtcagcctg aacataacat ccttgggatt acgctccctc     360
aaggagataa gtgatggaga tgtgataatt tcaggaaaca aaaatttgtg ctatgcaaat     420
acaataaact ggaaaaaact gtttgggacc tccggtcaga aaaccaaaat tataagcaac     480
agaggtgaaa acagctgcaa ggccacaggc caggtctgcc atgccttgtg ctcccccgag     540
ggctgctggg gcccggagcc cagggactgc gtctctggtg gcggtggctc gggcggtggt     600
gggtcgggtg gcggcggatc tggtggcggt ggctcgtttt gggtgctggt ggtggttggt     660
ggagtcctgg cttgctatag cttgctagta acagtggcct ttattatttt ctgggtgagg     720
```

agtaagagga gc 732

<210> SEQ ID NO 258
<211> LENGTH: 891
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 258
atgacaacac ccagaaattc agtaaatggg actttcccgg cagagccaat gaaaggccct 60
attgctatgc aatctggtcc aaaaccactc ttcaggagga tgtcttcact ggtgggcccc 120
acgcaaagct tcttcatgag ggaatctaag actttggggg ctgtccagat tatgaatggg 180
ctcttccaca ttgccctggg gggtcttctg atgatcccag cagggatcta tgcacccatc 240
tgtgtgactg tgtggtaccc tctctgggga ggcattatgt atattatttc cggatcactc 300
ctggcagcaa cggagaaaaa ctccaggaag tgtttggtca aaggaaaaat gataatgaat 360
tcattgagcc tctttgctgc catttctgga atgattcttt caatcatgga catacttaat 420
attaaaattt cccatttttt aaaaatggag agtctgaatt ttattagagc tcacacacca 480
tatattaaca tatacaactg tgaaccagct aatccctctg agaaaaactc cccatctacc 540
caatactgtt acagcataca atctctgttc ttgggcattt tgtcagtgat gctgatcttt 600
gccttcttcc aggaacttgt aatagctggc atcgttgaga atgaatggaa aagaacgtgc 660
tccagaccca aatctaacat agttctcctg tcagcagaag aaaaaaaaga acagactatt 720
gaaataaaag aagaagtggt tggctaact gaaacatctt cccaaccaaa gaatgaagaa 780
gacattgaaa ttattccaat ccaagaagag gaagaagaag aaacagagac gaactttcca 840
gaacctcccc aagatcagga atcctcacca atagaaaatg acagctctcc t 891

<210> SEQ ID NO 259
<211> LENGTH: 789
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 259
atgaccacac cacggaactc tgtgaatggc accttcccag cagagccaat gaagggacca 60
atcgcaatgc agagcggacc caagcctctg tttcggagaa tgagctccct ggtgggccca 120
acccagtcct tctttatgag agagtctaag acactgggcg ccgtgcagat catgaacgga 180
ctgttccaca tcgccctggg aggactgctg atgatcccag ccggcatcta cgcccctatc 240
tgcgtgaccg tgtggtaccc tctgtggggc ggcatcatgt atatcatctc cggctctctg 300
ctggccgcca cagagaagaa cagcaggaag tgtctggtga agggcaagat gatcatgaat 360
agcctgtccc tgtttgccgc catctctggc atgatcctga gcatcatgga catcctgaac 420
atcaagatca gccacttcct gaagatggag agcctgaact tcatcagagc ccacacccct 480
tacatcaaca tctataattg cgagcctgcc aacccatccg agaagaattc tccaagcaca 540
cagtactgtt attccatcca gtctctgttc ctgggcatcc tgtctgtgat gctgatcttt 600
gccttctttc aggagctggt catcgccggc atcgtggaga acgagtggaa gaggacctgc 660
agccgcccca agtccaatat cgtgctgctg tccgccgagg agaagaagga gcagacaatc 720
gagatcaagg aggaggtggt gggcctgacc gagacatcta gccagcctaa gaatgaggag 780
gatatcgag 789

<210> SEQ ID NO 260
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 260
atggattgga cctggattct gtttctggtg gccgctgcca caagagtgca cagcaactgg 60
gtgaatgtga tcagcgacct gaagaagatc gaggatctga tccagagcat gcacattgat 120
gccaccctgt acacagaatc tgatgtgcac cctagctgta aagtgaccgc catgaagtgt 180
tttctgctgg agctgcaggt gatttctctg gaaagcggag atgcctctat ccacgacaca 240
gtggagaatc tgatcatcct ggccaacaat agcctgagca gcaatggcaa tgtgacagag 300
tctggctgta aggagtgtga ggagctggag gagaagaaca tcaaggagtt tctgcagagc 360
tttgtgcaca tcgtgcagat gttcatcaat acaagctctg gcggaggatc tggaggaggc 420
ggatctggag gaggaggcag tggaggcgga ggatctggcg gaggatctct gcagattaca 480
tgccctcctc caatgtctgt ggagcacgcc gatatttggg tgaagtccta cagcctgtac 540
agcagagaga gatacatctg caacagcggc tttaagagaa aggccggcac ctcttctctg 600
acagagtgcg tgctgaataa ggccacaaat gtggcccact ggacaacacc tagcctgaag 660
tgcattagag atcctgccct ggtccaccag aggcctgccc ctccatctac agtgacaaca 720
gccggagtga cacctcagcc tgaatctctg agcccttctg gaaaagaacc tgccgccagc 780
tctcctagct ctaataatac cgccgccaca acagccgcca ttgtgcctgg atctcagctg 840
atgcctagca agtctcctag cacaggcaca acagagatca gcagccacga atcttctcac 900
ggaacacctt ctcagaccac cgccaagaat tgggagctga cagcctctgc ctctcaccag 960
cctccaggag tgtatcctca gggccactct gatacaacag tggccatcag cacatctaca 1020
gtgctgctgt gtggactgtc tgccgtgtct ctgctggcct gttacctgaa gtctagacag 1080
acacctcctc tggcctctgt ggagatggag gccatggaag ccctgcctgt gacatgggga 1140
acaagcagca gagatgagga cctggagaat tgttctcacc acctg 1185

<210> SEQ ID NO 261
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261
aactgggtga atgtgatcag cgacctgaag aagatcgagg atctgatcca gagcatgcac 60
attgatgcca ccctgtacac agaatctgat gtgcacccta gctgtaaagt gaccgccatg 120
aagtgttttc tgctggagct gcaggtgatt tctctggaaa gcggagatgc ctctatccac 180
gacacagtgg agaatctgat catcctggcc aacaatagcc tgagcagcaa tggcaatgtg 240
acagagtctg gctgtaagga gtgtgaggag ctggaggaga agaacatcaa ggagtttctg 300
cagagctttg tgcacatcgt gcagatgttc atcaatacaa gc 342

<210> SEQ ID NO 262

<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
attacatgcc ctcctccaat gtctgtggag cacgccgata tttgggtgaa gtcctacagc     60
ctgtacagca gagagagata catctgcaac agcggcttta agagaaaggc cggcacctct    120
tctctgacag agtgcgtgct gaataaggcc acaaatgtgg cccactggac aacacctagc    180
ctgaagtgca ttagagatcc tgccctggtc caccagaggc ctgcccctcc atctacagtg    240
acaacagccg gagtgacacc tcagcctgaa tctctgagcc cttctggaaa agaacctgcc    300
gccagctctc ctagctctaa taataccgcc gccacaacag ccgccattgt gcctggatct    360
cagctgatgc ctagcaagtc tcctagcaca ggcacaacag agatcagcag ccacgaatct    420
tctcacggaa caccttctca gaccaccgcc aagaattggg agctgacagc ctctgcctct    480
caccagcctc caggagtgta tcctcagggc cactctgata caacagtggc catcagcaca    540
tctacagtgc tgctgtgtgg actgtctgcc gtgtctctgc tggcctgtta cctgaagtct    600
agacagacac ctcctctggc ctctgtggag atggaggcca tggaagccct gcctgtgaca    660
tggggaacaa gcagcagaga tgaggacctg gagaattgtt ctcaccacct g             711

<210> SEQ ID NO 263
<211> LENGTH: 54
<212> TYPE: DNA
<213> ORGANISM: Thosea asigna virus

<400> SEQUENCE: 263
gagggcagag gaagtcttct aacatgcggt gacgtggagg agaatcccgg ccct           54

<210> SEQ ID NO 264
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
agagctaaga ggggaagcgg agagggcaga ggaagtctgc taacatgcgg tgacgtcgag     60
gagaatcctg gacct                                                      75

<210> SEQ ID NO 265
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
agggccaaga ggagtggcag cggcgagggc agaggaagtc ttctaacatg cggtgacgtg     60
gaggagaatc ccggccct                                                   78

<210> SEQ ID NO 266
<211> LENGTH: 57
<212> TYPE: DNA
<213> ORGANISM: Porcine teschovirus 1

<400> SEQUENCE: 266
gcaacgaact tctctctcct aaaacaggct ggtgatgtgg aggagaatcc tggtcca 57

<210> SEQ ID NO 267
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 267
ggaagcggag ctactaactt cagcctgctg aagcaggctg gagacgtgga ggagaaccct 60
ggacct 66

<210> SEQ ID NO 268
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
cgtgcaaagc gtgcaccggt gaaacaggga agcggagcta ctaacttcag cctgctgaag 60
caggctggag acgtggagga gaaccctgga cct 93

<210> SEQ ID NO 269
<211> LENGTH: 60
<212> TYPE: DNA
<213> ORGANISM: Equine rhinitis A virus

<400> SEQUENCE: 269
cagtgtacta attatgctct cttgaaattg gctggagatg ttgagagcaa ccctggacct 60

<210> SEQ ID NO 270
<211> LENGTH: 66
<212> TYPE: DNA
<213> ORGANISM: Foot-and-mouth disease virus

<400> SEQUENCE: 270
gtcaaacaga ccctaaactt tgatctgcta aaactggccg gggatgtgga aagtaatccc 60
ggcccc 66

<210> SEQ ID NO 271
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 271
cgtgcaaagc gt 12

<210> SEQ ID NO 272
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 272
agagccaaga gggcaccggt gaaacagact ttgaattttg accttctgaa gttggcagga 60
gacgttgagt ccaaccctgg gccc 84

<210> SEQ ID NO 273
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 273
ggtggcggtg gctcgggcgg tggtgggtcg ggtggcggcg gatct 45

<210> SEQ ID NO 274
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 274
ggcagcacct ccggcagcgg caagcctggc agcggcgagg gcagcaccaa gggc 54

<210> SEQ ID NO 275
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 275 ggaagcgga 9

<210> SEQ ID NO 276
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 276
agtggcagcg gc 12

<210> SEQ ID NO 277
<211> LENGTH: 258
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277
ggccccaaga agaaaaggaa ggtggccccc cccaccgacg tgagcctggg cgacgagctg 60
cacctggacg gcgaggacgt ggccatggcc cacgccgacg ccctggacga cttcgacctg 120
gacatgctgg gcgacggcga cagccccggc cccggcttca ccccccacga cagcgccccc 180
tacggcgccc tggacatggc cgacttcgag ttcgagcaga tgttcaccga cgccctgggc 240
atcgacgagt acggcggc 258

<210> SEQ ID NO 278
<211> LENGTH: 705
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 278
gagatgcccg tggacaggat tctggaggcc gaactcgccg tggagcagaa aagcgaccag 60
ggcgtggagg gccccggcgg aaccggcggc agcggcagca gccccaacga ccccgtgacc 120
aacatctgcc aggccgccga caagcagctg ttcaccctgg tggagtgggc caagaggatt 180
ccccacttca gcagcctgcc cctggacgac caggtgatcc tgctgagggc cggatggaac 240
gagctgctga tcgccagctt cagccacagg agcatcgacg tgagggacgg catcctgctg 300
gccaccggcc tgcacgtcca taggaacagc gcccacagcg ccggagtggg cgccatcttc 360
gacagggtgc tgaccgagct ggtgagcaag atgagggaca tgaggatgga caagaccgag 420
ctgggctgcc tgagggccat catcctgttc aaccccgagg tgaggggcct gaaaagcgcc 480
caggaggtgg agctgctgag ggagaaggtg tacgccgccc tggaggagta caccaggacc 540
acccaccccg acgagcccgg cagattcgcc aagctgctgc tgaggctgcc cagcctgagg 600
agcatcggcc tgaagtgcct ggagcacctg ttcttcttca ggctgatcgg cgacgtgccc 660
atcgacacct tcctgatgga gatgctggag agccccagcg acagc 705

<210> SEQ ID NO 279
<211> LENGTH: 969
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 279
ggccccaaga agaaaaggaa ggtggccccc cccaccgacg tgagcctggg cgacgagctg 60
cacctggacg gcgaggacgt ggccatggcc cacgccgacg ccctggacga cttcgacctg 120
gacatgctgg gcgacggcga cagccccggc cccggcttca ccccccacga cagcgccccc 180
tacggcgccc tggacatggc cgacttcgag ttcgagcaga tgttcaccga cgccctgggc 240
atcgacgagt acggcggcga attcgagatg cccgtggaca ggattctgga ggccgaactc 300
gccgtggagc agaaaagcga ccagggcgtg gagggccccg gcggaaccgg cggcagcggc 360
agcagcccca acgaccccgt gaccaacatc tgccaggccg ccgacaagca gctgttcacc 420
ctggtggagt gggccaagag gattccccac ttcagcagcc tgcccctgga cgaccaggtg 480
atcctgctga gggccggatg gaacgagctg ctgatcgcca gcttcagcca caggagcatc 540
gacgtgaggg acggcatcct gctggccacc ggcctgcacg tccataggaa cagcgcccac 600
agcgccggag tgggcgccat cttcgacagg gtgctgaccg agctggtgag caagatgagg 660
gacatgagga tggacaagac cgagctgggc tgcctgaggg ccatcatcct gttcaacccc 720
gaggtgaggg gcctgaaaag cgcccaggag gtggagctgc tgagggagaa ggtgtacgcc 780
gccctggagg agtacaccag gaccacccac cccgacgagc ccggcagatt cgccaagctg 840
ctgctgaggc tgcccagcct gaggagcatc ggcctgaagt gcctggagca cctgttcttc 900
ttcaggctga tcggcgacgt gcccatcgac accttcctga tggagatgct ggagagcccc 960
agcgacagc 969

<210> SEQ ID NO 280
<211> LENGTH: 450
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 280
atgaagctgc tgagcagcat cgagcaggct tgcgacatct gcaggctgaa gaagctgaag 60
tgcagcaagg agaagcccaa gtgcgccaag tgcctgaaga acaactggga gtgcagatac 120
agccccaaga ccaagaggag ccccctgacc agggcccacc tgaccgaggt ggagagcagg 180
ctggagaggc tggagcagct gttcctgctg atcttcccca gggaggacct ggacatgatc 240
ctgaagatgg acagcctgca agacatcaag gccctgctga ccggcctgtt cgtgcaggac 300
aacgtgaaca aggacgccgt gaccgacagg ctggccagcg tggagaccga catgcccctg 360
accctgaggc agcacaggat cagcgccacc agcagcagcg aggagagcag caacaagggc 420
cagaggcagc tgaccgtgag ccccgagttt 450

<210> SEQ ID NO 281
<211> LENGTH: 1008
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 281
atcaggcccg agtgcgtggt gcccgagacc cagtgcgcca tgaaaaggaa ggagaagaag 60
gcccagaagg agaaggacaa gctgcccgtg agcaccacca ccgtcgatga ccacatgccc 120
cccatcatgc agtgcgagcc cccccccccc gaggccgcca ggattcacga ggtcgtgccc 180
aggttcctga gcgacaagct gctggtgacc aacaggcaga agaacatccc ccagctgacc 240
gccaaccagc agttcctgat cgccaggctg atctggtatc aggacggcta cgagcagccc 300
agcgacgagg acctgaaaag gatcacccag acctggcagc aggccgacga cgagaacgag 360
gagagcgaca ccccccttcag gcagatcacc gagatgacca tcctgaccgt gcagctgatc 420
gtggagttcg ccaagggcct gcccggattc gccaagatca gccagcccga ccagatcacc 480
ctgctgaagg cttgcagcag cgaggtgatg atgctgaggg tggccaggag gtacgacgcc 540
gccagcgaca gcatcctgtt cgccaacaac caggcttaca ccagggacaa ctacaggaag 600
gctggcatgg ccgaggtgat cgaggacctc ctgcacttct gcagatgtat gtacagcatg 660
gccctggaca acatccacta cgccctgctg accgccgtgg tgatcttcag cgacaggccc 720
ggcctggagc agccccagct ggtggaggag atccagaggt actacctgaa caccctgagg 780
atctacatcc tgaaccagct gagcggcagc gccaggagca gcgtgatcta cggcaagatc 840
ctgagcatcc tgagcgagct gaggaccctg ggaatgcaga acagcaatat gtgtatcagc 900
ctgaagctga agaacaggaa gctgcccccc ttcctggagg agatttggga cgtggccgac 960
atgagccaca cccagccccc ccccatcctg gagagcccca ccaacctg 1008

<210> SEQ ID NO 282
<211> LENGTH: 1008
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 282

```
cggcctgagt gcgtagtacc cgagactcag tgcgccatga agcggaaaga gaagaaagca     60
cagaaggaga aggacaaact gcctgtcagc acgacgacgg tggacgacca catgccgccc    120
attatgcagt gtgaacctcc acctcctgaa gcagcaagga ttcacgaagt ggtcccaagg    180
tttctctccg acaagctgtt ggtgacaaac cggcagaaaa acatccccca gttgacagcc    240
aaccagcagt tccttatcgc caggctcatc tggtaccagg acgggtacga gcagccttct    300
gatgaagatt tgaagaggat tacgcagacg tggcagcaag cggacgatga aaacgaagag    360
tcggacactc ccttccgcca gatcacagag atgactatcc tcacggtcca acttatcgtg    420
gagttcgcga agggattgcc agggttcgcc aagatctcgc agcctgatca aattacgctg    480
cttaaggctt gctcaagtga ggtaatgatg ctccgagtcg cgcgacgata cgatgcggcc    540
tcagacagta ttctgttcgc gaacaaccaa gcgtacactc gcgacaacta ccgcaaggct    600
ggcatggccg aggtcatcga ggatctactg cacttctgcc ggtgcatgta ctctatggcg    660
ttggacaaca tccattacgc gctgctcacg gctgtcgtca tcttttctga ccggccaggg    720
ttggagcagc cgcaactggt ggaagagatc cagcggtact acctgaatac gctccgcatc    780
tatatcctga accagctgag cgggtcggcg cgttcgtccg tcatatacgg caagatcctc    840
tcaatcctct ctgagctacg cacgctcggc atgcaaaact ccaacatgtg catctccctc    900
aagctcaaga acagaaagct gccgcctttc ctcgaggaga tctgggatgt ggcggacatg    960
tcgcacaccc aaccgccgcc tatcctcgag tcccccacga atctctag                1008
```

<210> SEQ ID NO 283
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283

```
atgaagctac tgtcttctat cgaacaagca tgcgatattt gccgacttaa aaagctcaag     60
tgctccaaag aaaaaccgaa gtgcgccaag tgtctgaaga acaactggga gtgtcgctac    120
tctcccaaaa ccaaaaggtc tccgctgact agggcacatc tgacagaagt ggaatcaagg    180
ctagaaagac tggaacagct atttctactg atttttcctc gagaagacct tgacatgatt    240
ttgaaaatgg attctttaca ggatataaaa gcattgttaa caggattatt tgtacaagat    300
aatgtgaata aagatgccgt cacagataga ttggcttcag tggagactga tatgcctcta    360
acattgagac agcatagaat aagtgcgaca tcatcatcgg aagagagtag taacaaaggt    420
caaagacagt tgactgtatc gccggaattc ccggggatcc ggcctgagtg cgtagtaccc    480
gagactcagt gcgccatgaa gcggaaagag aagaaagcac agaaggagaa ggacaaactg    540
cctgtcagca cgacgacggt ggacgaccac atgccgccca ttatgcagtg tgaacctcca    600
cctcctgaag cagcaaggat tcacgaagtg gtcccaaggt ttctctccga caagctgttg    660
gtgacaaacc ggcagaaaaa catcccccag ttgacagcca accagcagtt ccttatcgcc    720
aggctcatct ggtaccagga cgggtacgag cagccttctg atgaagattt gaagaggatt    780
acgcagacgt ggcagcaagc ggacgatgaa aacgaagagt cggacactcc cttccgccag    840
atcacagaga tgactatcct cacggtccaa cttatcgtgg agttcgcgaa gggattgcca    900
```

-continued gggttcgcca agatctcgca gcctgatcaa attacgctgc ttaaggcttg ctcaagtgag 960
gtaatgatgc tccgagtcgc gcgacgatac gatgcggcct cagacagtat tctgttcgcg 1020
aacaaccaag cgtacactcg cgacaactac cgcaaggctg gcatggccga ggtcatcgag 1080
gatctactgc acttctgccg gtgcatgtac tctatggcgt tggacaacat ccattacgcg 1140
ctgctcacgg ctgtcgtcat cttttctgac cggccagggt tggagcagcc gcaactggtg 1200
gaagagatcc agcggtacta cctgaatacg ctccgcatct atatcctgaa ccagctgagc 1260
gggtcggcgc gttcgtccgt catatacggc aagatcctct caatcctctc tgagctacgc 1320
acgctcggca tgcaaaactc caacatgtgc atctccctca agctcaagaa cagaaagctg 1380
ccgcctttcc tcgaggagat ctgggatgtg gcggacatgt cgcacaccca accgccgcct 1440
atcctcgagt cccccacgaa tctctag 1467

<210> SEQ ID NO 284
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 284
atgaagctgc tgagcagcat cgagcaggct tgcgacatct gcaggctgaa gaagctgaag 60
tgcagcaagg agaagcccaa gtgcgccaag tgcctgaaga acaactggga gtgcagatac 120
agccccaaga ccaagaggag ccccctgacc agggcccacc tgaccgaggt ggagagcagg 180
ctggagaggc tggagcagct gttcctgctg atcttcccca gggaggacct ggacatgatc 240
ctgaagatgg acagcctgca agacatcaag gccctgctga ccggcctgtt cgtgcaggac 300
aacgtgaaca aggacgccgt gaccgacagg ctggccagcg tggagaccga catgcccctg 360
accctgaggc agcacaggat cagcgccacc agcagcagcg aggagagcag caacaagggc 420
cagaggcagc tgaccgtgag ccccgagttt cccgggcggc ctgagtgcgt agtacccgag 480
actcagtgcg ccatgaagcg gaaagagaag aaagcacaga aggagaagga caaactgcct 540
gtcagcacga cgacggtgga cgaccacatg ccgcccatta tgcagtgtga acctccacct 600
cctgaagcag caaggattca cgaagtggtc ccaaggtttc tctccgacaa gctgttggtg 660
acaaaccggc agaaaaacat cccccagttg acagccaacc agcagttcct tatcgccagg 720
ctcatctggt accaggacgg gtacgagcag ccttctgatg aagatttgaa gaggattacg 780
cagacgtggc agcaagcgga cgatgaaaac gaagagtcgg acactccctt ccgccagatc 840
acagagatga ctatcctcac ggtccaactt atcgtggagt tcgcgaaggg attgccaggg 900
ttcgccaaga tctcgcagcc tgatcaaatt acgctgctta aggcttgctc aagtgaggta 960
atgatgctcc gagtcgcgcg acgatacgat gcggcctcag acagtattct gttcgcgaac 1020
aaccaagcgt acactcgcga caactaccgc aaggctggca tggccgaggt catcgaggat 1080
ctactgcact tctgccggtg catgtactct atggcgttgg acaacatcca ttacgcgctg 1140
ctcacggctg tcgtcatctt ttctgaccgg ccagggttgg agcagccgca actggtggaa 1200
gagatccagc ggtactacct gaatacgctc cgcatctata tcctgaacca gctgagcggg 1260
tcggcgcgtt cgtccgtcat atacggcaag atcctctcaa tcctctctga gctacgcacg 1320
ctcggcatgc aaaactccaa catgtgcatc tccctcaagc tcaagaacag aaagctgccg 1380
cctttcctcg aggagatctg ggatgtggcg gacatgtcgc acacccaacc gccgcctatc 1440
ctcgagtccc ccacgaatct ctag 1464

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Glu Ser Lys Tyr Gly Pro Pro Cys Pro Pro Cys Pro
1 5 10

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 286

Asp Xaa Glu Xaa Asn Pro Gly Pro
1 5

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Gly Gly Gly Gly Ser
1 5

<210> SEQ ID NO 288
<211> LENGTH: 27
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (2)..(26)
<223> OTHER INFORMATION: This region may encompass 2-5 “Glu Ala Ala Ala Lys” repeating units

<400> SEQUENCE: 288

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 289
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 0-15 “Gly Ser” repeating units

<400> SEQUENCE: 289

```
Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30
```

<210> SEQ ID NO 290
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 0-15 “Ser Gly” repeating units

<400> SEQUENCE: 290

```
Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly
            20                  25                  30
```

<210> SEQ ID NO 291
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(45)
<223> OTHER INFORMATION: This sequence may encompass 0-15 “Gly Ser Gly” repeating units

<400> SEQUENCE: 291

```
Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly Gly Ser
            20                  25                  30

Gly Gly Ser Gly Gly Ser Gly Gly Ser Gly Gly Ser Gly
        35                  40                  45
```

<210> SEQ ID NO 292
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(60)
<223> OTHER INFORMATION: This sequence may encompass 0-15 “Ser Gly Ser Gly” repeating units

<400> SEQUENCE: 292

-continued

```
Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
            20                  25                  30

Ser Gly Ser Gly Ser Gly Ser Gly Ser Gly Ser Gly Ser Gly Ser Gly
        35                  40                  45

Ser Gly Ser Gly Ser Gly Ser Gly Ser Gly Ser Gly
    50                  55                  60


<210> SEQ ID NO 293
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Pro Val Lys Gln
1               5


<210> SEQ ID NO 294
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Gly Gly Gly Ser Gly Gly Gly Gly Ser Gly Gly Gly Gly Ser Gly
1               5                   10                  15

Gly Gly Gly Ser
            20
```

ROR-1 SPECIFIC CHIMERIC ANTIGEN RECEPTORS AND USES THEREOF

CROSS-REFERENCE

This application claims the benefit of U.S. Provisional Application No. 62/696,075, filed on Jul. 10, 2018, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 8, 2019, is named 50471_716_601_SL.txt and is 360,082 bytes in size.

BACKGROUND OF THE DISCLOSURE

Recombinant polypeptides such as chimeric polypeptides have been a valuable for research, diagnostic, manufacturing and therapeutic applications. Modified effector cells expressing antigen binding polypeptides such as CARs are useful in the treatment of diseases and disorders such as infectious disease, autoimmune disorders and cancers.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Disclosed herein, in certain embodiments, are isolated nucleic acids, vectors, immune effector cells, methods and systems comprising chimeric antigen receptors (CAR).

Provided herein is an isolated nucleic acid encoding a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and (e) a CD3 zeta signaling domain.

In some embodiments, the CAR comprises at least one of: (a) a polypeptide having at least 90%, 91%, 92%, 93%, 94%, 95%, 96%, 97%, 98%, 99% or 100% identity with at least one of amino acid sequences as shown in SEQ ID NOs: 3-11 and 14; or (b) a polypeptide having at least 90%, 91%, 92%, 93%, 94%, 95%, 96%, 97%, 98%, 99% or 100% identity with at least one of amino acid sequences as shown in SEQ ID NOs: 75-82. In some cases, the ROR-1 antigen binding domain comprises a polypeptide having at least 90%, 91%, 92%, 93%, 94%, 95%, 96%, 97%, 99% or 100% identity with at least one of amino acid sequences as shown in SEQ ID NOs: 15-74. In other cases, the ROR-1 antigen binding domain comprises a polypeptide having at least 90%, 91%, 92%, 93%, 94%, 95%, 96%, 97%, 99% or 100% identity with at least one of amino acid sequences as shown in SEQ ID NOs: 15, 17, 19, 21, 23, 25, 27, 29, 31, 33, 35, 37, 39, 41, 43, 45, 47, 49, 51, 53, 55, 57, 59, 61, 63, 65, 67, 69, 71, and 73. In some examples, the ROR-1 antigen binding domain comprises a polypeptide having at least 90%, 91%, 92%, 93%, 94%, 95%, 96%, 97%, 99% or 100% identity with at least one of amino acid sequences as shown in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74. In some embodiments, the spacer is a polypeptide having at least 90%, 91%, 92%, 93%, 94%, 95%, 96%, 97%, 98%, 99% or 100% identity with the amino acid sequence of SEQ ID NO: 83. In other embodiments, the spacer is a polypeptide having at least 90%, 91%, 92%, 93%, 94%, 95%, 96%, 97%, 98%, 99% or 100% identity with the amino acid sequence of SEQ ID NO: 84. In some cases, the spacer is a polypeptide having at least 90%, 91%, 92%, 93%, 94%, 95%, 96%, 97%, 98%, 99% or 100% identity with the amino acid sequence of SEQ ID NO: 85. In some examples, the spacer is a polypeptide having at least 90%, 91%, 92%, 93%, 94%, 95%, 96%, 97%, 98%, 99% or 100% identity with the amino acid sequence of SEQ ID NO: 86. In other embodiments, the transmembrane domain is a polypeptide having at least 90%, 91%, 92%, 93%, 94%, 95%, 96%, 97%, 98%, 99% or 100% identity with any one of the amino acid sequences as shown in SEQ ID NOs: 87-88.

In some cases, the costimulatory signaling domain comprises 4-1BB. In other embodiments, the costimulatory signaling domain of 4-1BB comprises a polypeptide having at least 90%, 91%, 92%, 93%, 94%, 95%, 96%, 97%, 98%, 99% or 100% identity with the amino acid sequence of SEQ ID NO: 89. In other cases, the costimulatory signaling domain comprises CD28. In some examples, the costimulatory signaling domain of CD28 comprises a polypeptide having at least 90%, 91%, 92%, 93%, 94%, 95%, 96%, 97%, 98%, 99% or 100% identity with the amino acid sequence of SEQ ID NO: 90. In some embodiments, the CD3 zeta signaling domain comprises a polypeptide having at least 90%, 91%, 92%, 93%, 94%, 95%, 96%, 97%, 98%, 99% or 100% identity with the amino acid sequence of SEQ ID NO: 93. In other embodiments, the isolated nuclei acid further comprises a polypeptide having at least 90%, 91%, 92%, 93%, 94%, 95%, 96%, 97%, 98%, 99% or 100% identity with the amino acid sequence of SEQ ID NOs: 94-108.

In some examples, the isolated nucleic acid further comprises a cell tag. In some embodiments, the cell tag is a truncated epidermal growth factor receptor. In some cases, the truncated epidermal growth factor receptor is HER1t and comprises a polypeptide having at least 90%, 91%, 92%, 93%, 94%, 95%, 96%, 97%, 98%, 99% or 100% identity with the amino acid sequence of SEQ ID NO: 109. In other embodiments, the truncated epidermal growth factor receptor is HER1t-1 and comprises a polypeptide having at least 90%, 91%, 92%, 93%, 94%, 95%, 96%, 97%, 98%, 99% or 100% identity with the amino acid sequence of SEQ ID NO: 110. In some embodiments, the cell tag comprises a polypeptide having at least 90%, 91%, 92%, 93%, 94%, 95%, 96%, 97%, 98%, 99% or 100% identity with the amino acid sequence of SEQ ID NO: 111. In other cases, the cell tag comprises a polypeptide having at least 90%, 91%, 92%, 93%, 94%, 95%, 96%, 97%, 98%, 99% or 100% identity with the amino acid sequence of SEQ ID NO: 112. In some examples, the isolated nucleic acid further comprises an additional polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

Provided herein is a vector comprising a backbone and a nucleic acid sequence encoding: (1) a cell tag; (2) a cytokine; and (3) a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and (e) a CD3 zeta signaling domain.

In some embodiments, the vector is a lentivirus vector, a retroviral vector, or a non-viral vector. In some cases, the cell tag is a truncated epidermal growth factor receptor. In some embodiments, the truncated epidermal growth factor receptor is a HER1t, HER1t-1 or a functional variant thereof. In some examples, the truncated epidermal growth factor receptor comprises a polypeptide having at least 90%, 91%, 92%, 93%, 94%, 95%, 96%, 97%, 98%, 99% or 100% identity with the amino acid sequence of SEQ ID NO: 109 or SEQ ID NO: 110. In other examples, the cell tag comprises a polypeptide having at least 90%, 91%, 92%, 93%, 94%, 95%, 96%, 97%, 98%, 99% or 100% identity with the amino acid sequence of SEQ ID NO: 111. In some examples, the cell tag comprises a polypeptide having at least 90%, 91%, 92%, 93%, 94%, 95%, 96%, 97%, 98%, 99% or 100% identity with the amino acid sequence of SEQ ID NO: 112.

In some cases, the cytokine is IL-15. In some embodiments, the IL-15 is a membrane bound IL-15. In some embodiments, the membrane bound IL-15 comprises a polypeptide having at least 90%, 91%, 92%, 93%, 94%, 95%, 96%, 97%, 98%, 99% or 100% identity with the amino acid sequence of SEQ ID NO: 113. In other cases, the vector further comprises a nucleotide sequence encoding a self-cleaving Thosea asigna virus (T2A) peptide. In some embodiments, the backbone is a SLEEPING BEAUTY® transposon DNA plasmid. In some examples, the vector further comprises a promoter. In some embodiments, the promoter is hEF1a1. In other embodiments, the CAR comprises at least one of: (a) a polypeptide having at least 90%, 91%, 92%, 93%, 94%, 95%, 96%, 97%, 98%, 99% or 100% identity with at least one of amino acid sequences as shown in SEQ ID NOs: 3-14; or (b) a polypeptide having at least 90%, 91%, 92%, 93%, 94%, 95%, 96%, 97%, 98%, 99% or 100% identity with at least one of amino acid sequences as shown in SEQ ID NOs: 75-82.

In some embodiments, ROR-1 antigen binding domain comprises a polypeptide having at least 90%, 91%, 92%, 93%, 94%, 95%, 96%, 97%, 99% or 100% identity with at least one of amino acid sequences as shown in SEQ ID NOs: 15-74. In some examples, the ROR-1 antigen binding domain comprises a polypeptide having at least 90%, 91%, 92%, 93%, 94%, 95%, 96%, 97%, 99% or 100% identity with at least one of amino acid sequences as shown in SEQ ID NOs: 15, 17, 19, 21, 23, 25, 27, 29, 31, 33, 35, 37, 39, 41, 43, 45, 47, 49, 51, 53, 55, 57, 59, 61, 63, 65, 67, 69, 71, and 73. In other examples, the ROR-1 antigen binding domain comprises a polypeptide having at least 90%, 91%, 92%, 93%, 94%, 95%, 96%, 97%, 99% or 100% identity with at least one of amino acid sequences as shown in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74. In some cases, the spacer is a polypeptide having at least 90%, 91%, 92%, 93%, 94%, 95%, 96%, 97%, 98%, 99% or 100% identity with the amino acid sequence of SEQ ID NO: 83. In other cases, the spacer is a polypeptide having at least 90%, 91%, 92%, 93%, 94%, 95%, 96%, 97%, 98%, 99% or 100% identity with the amino acid sequence of SEQ ID NO: 84.

In some cases, the spacer is a polypeptide having at least 90%, 91%, 92%, 93%, 94%, 95%, 96%, 97%, 98%, 99% or 100% identity with the amino acid sequence of SEQ ID NO: 85. In other cases, the spacer is a polypeptide having at least 90%, 91%, 92%, 93%, 94%, 95%, 96%, 97%, 98%, 99% or 100% identity with the amino acid sequence of SEQ ID NO: 86. In some embodiments, the transmembrane domain is a polypeptide having at least 90%, 91%, 92%, 93%, 94%, 95%, 96%, 97%, 98%, 99% or 100% identity with any one of the amino acid sequences as shown in SEQ ID NOs: 87-88.

In some examples, the costimulatory signaling domain comprises 4-1BB. In some embodiments, the costimulatory signaling domain of 4-1BB comprises a polypeptide having at least 90%, 91%, 92%, 93%, 94%, 95%, 96%, 97%, 98%, 99% or 100% identity with the amino acid sequence of SEQ ID NO: 89. In other embodiments, the CD3 zeta signaling domain comprises a polypeptide having at least 90%, 91%, 92%, 93%, 94%, 95%, 96%, 97%, 98%, 99% or 100% identity with the amino acid sequence of SEQ ID NO: 93. In some cases, the vector further comprises a polypeptide having at least 90%, 91%, 92%, 93%, 94%, 95%, 96%, 97%, 98%, 99% or 100% identity with the amino acid sequence of SEQ ID NOs: 94-108.

In some cases, the vector comprises a plasmid. In some embodiments, each vector comprises an expression plasmid. In some embodiments, the non-viral vector is a SLEEPING BEAUTY® transposon. In some examples, the vector further comprises an additional vector comprising a polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

Provided herein is an immune effector cell comprising the isolated nucleic acid. In some embodiments, an immune effector cell comprises the vector.

Further provided herein is an immune effector cell comprising (1) a cell tag; (2) a cytokine; and (3) a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and (e) a CD3 zeta signaling domain.

In some embodiments, the cytokine is IL-15. In some embodiments, the IL-15 is a membrane bound IL-15. In some cases, the membrane bound IL-15 comprises a polypeptide having at least 90%, 91%, 92%, 93%, 94%, 95%, 96%, 97%, 98%, 99% or 100% identity with the amino acid sequence of SEQ ID NO: 113. In other cases, the cell tag is a truncated epidermal growth factor receptor. In some embodiments, the truncated epidermal growth factor receptor is a HER1t, HER1t-1 or a functional variant thereof. In some cases, the truncated epidermal growth factor receptor comprises a polypeptide having at least 90%, 91%, 92%, 93%, 94%, 95%, 96%, 97%, 98%, 99% or 100% identity with the amino acid sequence of SEQ ID NO: 109 or SEQ ID NO: 110. In some examples, the cell tag comprises a polypeptide having at least 90%, 91%, 92%, 93%, 94%, 95%, 96%, 97%, 98%, 99% or 100% identity with the amino acid sequence of SEQ ID NO: 111. In other embodiments, the cell tag comprises a polypeptide having at least 90%, 91%, 92%, 93%, 94%, 95%, 96%, 97%, 98%, 99% or 100% identity with the amino acid sequence of SEQ ID NO: 112.

In some embodiments, the spacer is a polypeptide having at least 90%, 91%, 92%, 93%, 94%, 95%, 96%, 97%, 98%, 99% or 100% identity with the amino acid sequence of SEQ ID NO: 83. In other embodiments, the spacer is a polypeptide having at least 90%, 91%, 92%, 93%, 94%, 95%, 96%, 97%, 98%, 99% or 100% identity with the amino acid sequence of SEQ ID NO: 84. In some cases, the spacer is a polypeptide having at least 90%, 91%, 92%, 93%, 94%, 95%, 96%, 97%, 98%, 99% or 100% identity with the amino acid sequence of SEQ ID NO: 85. In other cases, the spacer is a polypeptide having at least 90%, 91%, 92%, 93%, 94%, 95%, 96%, 97%, 98%, 99% or 100% identity with the amino acid sequence of SEQ ID NO: 86.

In some examples, the cell is a T cell, a Natural Killer (NK) cell, a cytotoxic T lymphocyte (CTL), or a regulatory T cell. In other examples, the CAR comprises at least one of a polypeptide having amino acid sequences as shown in SEQ ID NOs: 3-14 or 75-82. In some cases, the CAR comprises at least one of a polypeptide having amino acid sequences as shown in SEQ ID NOs: 15-74. In other cases, the immune effector cell further comprises gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

Provided herein is a method for stimulating a T cell-mediated immune response to a target cell population or tissue in a human subject in need thereof, comprising administering to the human subject an effective amount of a cell genetically modified to express a CAR, wherein the CAR comprises (a) a ROR-1 antigen binding domain; (b) a spacer; (c) a transmembrane domain; (d) a costimulatory signaling domain comprising 4-1BB or CD28, or both; (e) a CD3 zeta signaling domain; and (f) a truncated epidermal growth factor receptor (HER1t).

In some embodiments, the human has been diagnosed with at least one of lung cancer, breast cancer, pancreatic cancer, ovarian cancer, prostate cancer, adrenal cancer, melanoma, uterine cancer, testicular cancer, or bladder cancer. In some cases, the human has been diagnosed with non-Hodgkin's lymphoma, acute lymphocytic leukemia (ALL), chronic lymphocytic leukemia (CLL), hairy cell leukemia (HCL), multiple myeloma (MM), acute myeloid leukemia (AML), or chronic myeloid leukemia (CML).

Provided herein is an isolated nucleic acid encoding a chimeric antigen receptor (CAR), wherein the CAR comprises: (a) a ROR-1 antigen binding domain with at least one of amino acid sequences of as shown in SEQ ID NO: 3-14, 75-82, or 15-74; (b) a spacer with at least one of amino acid sequences of SEQ ID NOs: 83-86; (c) a costimulatory signaling domain comprising CD28 with the amino acid sequence of SEQ ID NO: 90; (d) a HER1 tag which comprises at least one of HER1t with the amino acid sequence of SEQ ID NO: 109 and HER1t-1 with the amino acid sequence of SEQ ID NO: 110; and (e) a CD3 zeta signaling domain with the amino acid sequence of SEQ ID NO: 93.

Provided herein is an isolated nucleic acid encoding a chimeric antigen receptor (CAR), wherein the CAR comprises: (a) a ROR-1 antigen binding domain with at least one of amino acid sequences as shown in SEQ ID NO: 3-14, 85-82, or 15-74; (b) a spacer with at least one of amino acid sequences of SEQ ID NO: 83-86; (c) a costimulatory signaling domain comprising 4-1BB with the amino acid sequence of SEQ ID NO: 89; (d) a HER1 tag which comprises at least one of HER1t with the amino acid sequence of SEQ ID NO: 109 and HER1t-1 with the amino acid sequence of SEQ ID NO: 110; and (e) a CD3 zeta signaling domain with the amino acid sequence of SEQ ID NO: 93.

In some examples, a vector comprises any one or more of the isolated polynucleotides. In some embodiments, the vector is a lentivirus vector, a retroviral vector, or a non-viral vector. In some embodiments, the non-viral vector is a SLEEPING BEAUTY® transposon. In other examples, the vector is a plurality of vectors. In some embodiments, the vector further comprises an additional vector comprising a polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

Provided herein is a system for expressing a CAR in an immune effector cell, the system comprising one or more vectors encoding an isolated nucleic acid. In some examples, the immune effector cell is a T cell or NK cell. In some embodiments, the system further comprises a nucleic acid encoding at least one additional gene. In some embodiments, the additional gene comprises a cytokine. In some cases, the cytokine comprises at least one of IL-2, IL-15, IL-12, IL-21, and a fusion of IL-15 and IL-15Rα. In other embodiments, the cytokine is in secreted form. In some embodiments, the cytokine is in membrane bound form. In some embodiments, the system comprises at least one vector. In other cases, the at least one vector is a lentivirus vector, a retroviral vector, or a non-viral vector. In some embodiments, the non-viral vector is a SLEEPING BEAUTY® transposon. In some embodiments, the system further comprises a SLEEPING BEAUTY® Tc1/mariner-type transposase. In some examples, the transposase is SB11, SB100X or SB110. In other examples, the system further comprises an additional vector comprising a polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker. In some embodiments, the immune effector cell is a mammalian cell.

Provided herein is a system for expressing a CAR in an immune effector cell, the system comprising (1) a first vector comprising a backbone and a nucleic acid sequence encoding: (a) a cell tag; (b) a cytokine; and (c) a chimeric antigen receptor (CAR), wherein the CAR comprises (i) a ROR-1 antigen binding domain; (ii) a spacer; (iii) a transmembrane domain; (iv) a costimulatory signaling domain comprising 4-1BB or CD28, or both; and (v) a CD3 zeta signaling domain; and (2) a second vector comprising a polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

Provided herein is a method of expressing a CAR in an immune effector cell comprising contacting the immune effector cell with a system.

Provided herein is a method of stimulating the proliferation and/or survival of engineered T-cells comprising: (a) obtaining a sample of cells from a subject, the sample comprising T-cells or T-cell progenitors; (b) transfecting the cells with one or more vectors encoding an isolated nucleic acid and a vector encoding a transposase, to provide a population of engineered ROR-1 CAR-expressing T-cells; and (c) optionally culturing the population of ROR-1 CAR T-cells ex vivo for 2 days or less.

In some embodiments, the vector further encodes a cytokine and a cell tag. In some cases, the cytokine is a fusion protein comprising IL-15 and IL-15Rα. In other embodiments, the method further comprises an additional vector comprising a polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

In some examples, the DNA binding domain comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In other embodiments, the DNA binding domain comprises an amino acid sequence as shown in SEQ ID NO: 134. In some embodiments, the transactivation domain comprises at least one of a VP16 transactivation domain and a B42 acidic activator transactivation domain. In other cases, the transactivation domain comprises an amino acid sequence as shown in SEQ ID NO: 131. In some embodiments, at least one of the first nuclear receptor ligand binding domain and the second nuclear receptor ligand binding domain comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

In some cases, at least one of the first nuclear receptor ligand binding domain and the second nuclear receptor ligand binding domain comprise any one of amino acid sequences as shown in SEQ ID NOs: 135-136. In some examples, the first gene switch polypeptide comprises a GAL4 DBD fused to an EcR nuclear receptor ligand binding domain, and the second gene switch polypeptide comprises a VP16 transactivation domain fused to a retinoid receptor X (RXR) nuclear receptor ligand binding domain. In some embodiments, the Gal4 DBD fused to the EcR nuclear receptor ligand binding domain comprise an amino acid sequence as shown in any one of SEQ ID NOs: 137-138, and the VP16 transactivation domain fused to the retinoid receptor X (RXR) nuclear receptor ligand binding domain comprises an amino acid sequence as shown in SEQ ID NO: 133.

In some embodiments, the linker is a cleavable linker, a ribosome skipping linker sequence or an IRES linker. In some examples, the linker is an IRES linker and said IRES linker has a sequence as shown in any one of SEQ ID NOs: 146-147. In other embodiments, the linker is a cleavable linker or a ribosome skipping linker sequence. In other cases, the cleavable linker or the ribosome skipping linker sequence comprises one or more of a 2A linker, p2A linker, T2A linker, F2A linker, E2A linker, GSG-2A linker, GSG linker (SEQ ID NO: 129), SGSG linker (SEQ ID NO: 130), furinlink linker variants and derivatives thereof. In some embodiments, the cleavable linker or the ribosome skipping linker sequence has a sequence as shown in any one of SEQ ID NOs: 116-126. In some embodiments, at least one of the one or more vectors and the additional vector is a lentivirus vector, a retroviral vector, or a non-viral vector. In some cases, the non-viral vector is a SLEEPING BEAUTY® transposon. In some embodiments, the method further comprises a SLEEPING BEAUTY® Tc1/mariner-type transposase. In some embodiments, the transposase is SB11, SB100X or SB110.

Provided herein is a method of culturing engineered T-cells comprising: (a) obtaining a sample of cells from a subject, the sample comprising T-cells or T-cell progenitors; (b) transfecting the cells with one or more vectors encoding an isolated nucleic acid and a vector encoding a transposase, to provide a population of engineered ROR1 CAR-expressing T-cells; and (c) culturing the population of engineered ROR1 CAR-expressing T-cells ex vivo in a medium that selectively enhances proliferation of the engineered ROR1 CAR-expressing T-cells, wherein the engineered ROR1 CAR-expressing T-cells are cultured for no more than 21 days.

In some examples, the engineered ROR1 CAR-expressing T-cells are cultured for no more than 14 days. In some cases, the one or more vectors further encodes a cytokine and a cell tag. In some embodiments, the method further comprises an additional vector comprising a polynucleotide encoding gene switch polypeptides for ligand-inducible control of heterologous gene expression, wherein the gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker. In other embodiments, the DNA binding domain comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In some embodiments, the DNA binding domain comprises an amino acid sequence as shown in SEQ ID NO: 134.

In other embodiments, the transactivation domain comprises at least one of a VP16 transactivation domain and a B42 acidic activator transactivation domain. In some embodiments, the transactivation domain comprises an amino acid sequence as shown in SEQ ID NO: 131. In some cases, at least one of the first nuclear receptor ligand binding domain and the second nuclear receptor ligand binding domain comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In other cases, at least one of the first nuclear receptor ligand binding domain and the second nuclear receptor ligand binding domain comprise any one of amino acid sequences as shown in SEQ ID NOs: 135-136. In some embodiments, the first gene switch polypeptide comprises a GAL4 DBD fused to an EcR nuclear receptor ligand binding domain, and the second gene switch polypeptide comprises a VP16 transactivation domain fused to a retinoid receptor X (RXR) nuclear receptor ligand binding domain. In some examples, the Gal4 DBD fused to the EcR nuclear receptor ligand binding domain comprise an amino acid sequence as shown in any one of SEQ ID NOs: 137-138, and the VP16 transactivation domain fused to the retinoid receptor X (RXR) nuclear receptor ligand binding domain comprises an amino acid sequence as shown in SEQ ID NO: 133.

In some cases, the linker is a cleavable linker, a ribosome skipping linker sequence or an IRES linker. In other embodiments, the linker is an IRES linker and said IRES linker has a sequence as shown in any one of SEQ ID NOs: 146-147. In some embodiments, the linker is a cleavable linker or a ribosome skipping linker sequence. In some examples, the cleavable linker or the ribosome skipping linker sequence comprises one or more of a 2A linker, p2A linker, T2A linker, F2A linker, E2A linker, GSG-2A linker, GSG linker (SEQ ID NO: 129), SGSG linker (SEQ ID NO: 130), furinlink linker variants and derivatives thereof. In other examples, the cleavable linker or the ribosome skipping linker sequence has a sequence as shown in any one of SEQ ID NOs: 116-126. In some embodiments, at least one of the one or more vectors, the vector, and the additional vector is a lentivirus vector, a retroviral vector, or a non-viral vector. In some embodiments, the non-viral vector is a SLEEPING BEAUTY® transposon. In other embodiments, the method further comprises a SLEEPING BEAUTY® Tc1/mariner-type transposase. In some cases, the transposase is SB11, SB100X or SB110. In some embodiments, culturing the engineered ROR1 CAR-expressing T-cells in (c) comprises culturing the engineered ROR1 CAR-expressing T-cells in the presence of artificial antigen presenting cells (aAPCs) that stimulate expansion of the engineered ROR1 CAR-T expressing T-cells. In other cases, the aAPCs are engineered K562 cells. In some embodiments, the aAPCs comprises (i) a ROR1 antigen expressed on the engineered CAR cells; (ii) CD64; (ii) CD86; (iii) CD 137L; and/or (v) membrane-bound IL-15, expressed on the surface of the aAPCs.

Provided herein is a method of treating cancer in a subject in need thereof comprising administering to the subject one or more doses of an effective amount of engineered T-cells, wherein the engineered T-cells comprise ROR-1 CAR and membrane bound IL-15.

In some embodiments, a first dose of an effective amount of engineered T-cells is administered intraperitoneally. In other embodiments, a second dose of an effective amount of engineered T-cells is administered intravenously. In some embodiments, the cancer is non-Hodgkin's lymphoma, acute lymphocytic leukemia (ALL), chronic lymphocytic leukemia (CLL), hairy cell leukemia (HCL), multiple myeloma (MM), acute myeloid leukemia (AML), or chronic myeloid leukemia (CML). In some cases, the cancer is lung cancer, breast cancer, pancreatic cancer, ovarian cancer, prostate cancer, adrenal cancer, melanoma, uterine cancer, testicular cancer, or bladder cancer. In some examples, the ROR-1 CAR is encoded by any one of sequences as shown in SEQ ID NOs: 3-14, 75-82, or 15-74. In some embodiments, the membrane bound IL-15 is encoded by SEQ ID NO: 260. In some embodiments, the effective amount of engineered T-cells is at least $10^2$ cells/kg. In other embodiments, the effective amount of engineered T-cells is at least $10^4$ cells/kg. In some cases, the effective amount of engineered T-cells is at least $10^5$ cells/kg.

BRIEF DESCRIPTION OF THE FIGURES

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

Figure 10B:
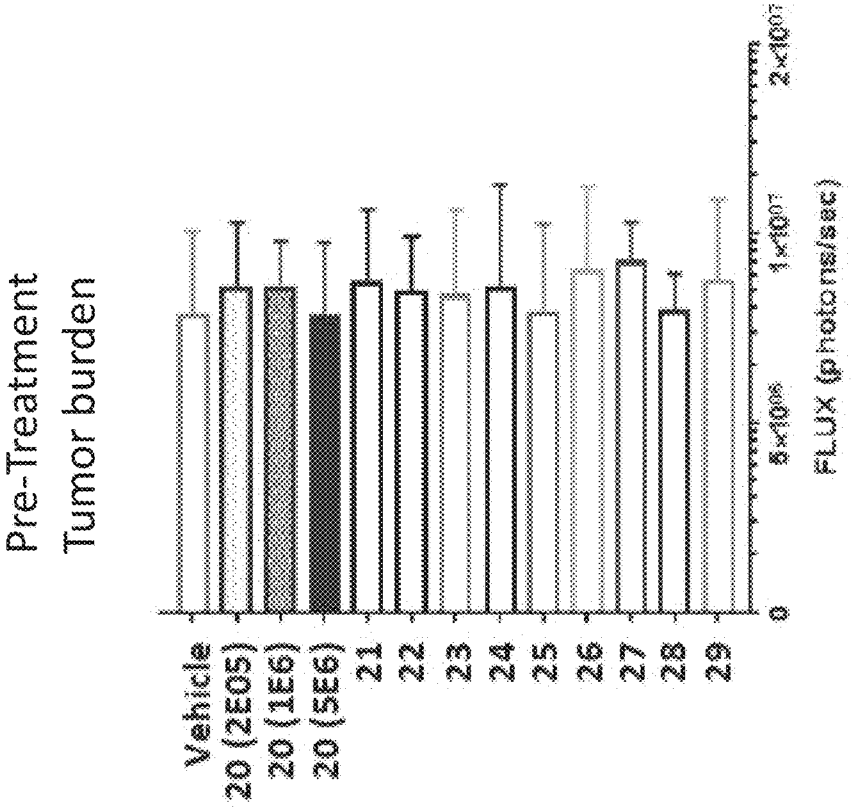
FIG. 10A shows quantitative analysis of JeKo-1 tumor burden as measured by in vivo bioluminescence (IVIS) imaging at day 7 post CAR-T treatment. NSG mice (N=5-7 mice per group) were administered with JeKo tumor cell line via i.p. injection on Day 0. Tumor bearing mice were treated with different hROR1 CAR-T cells treatment via single i.p. injection seven days after tumor cell administration and tumor burden was quantified via IVIS through the course of treatment. Data shown are mean±SEM.

FIG. 10B shows tumor burden pre-treatment.

Figure 11:
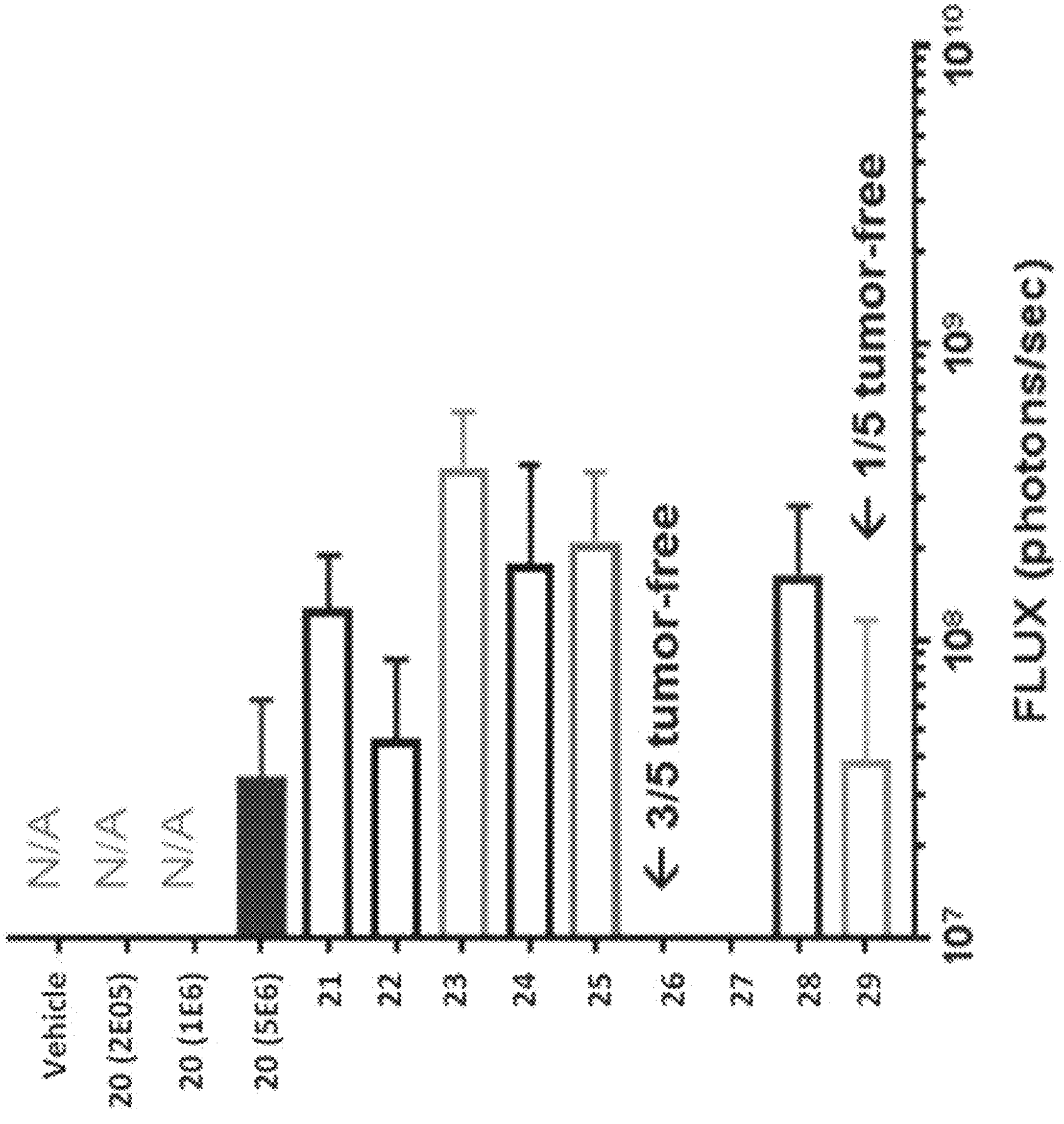

FIG. 11 shows quantitative analysis of JeKo-1 tumor burden as measured by in vivo bioluminescence (IVIS) imaging (as described above) at day 36.

Figure 12:
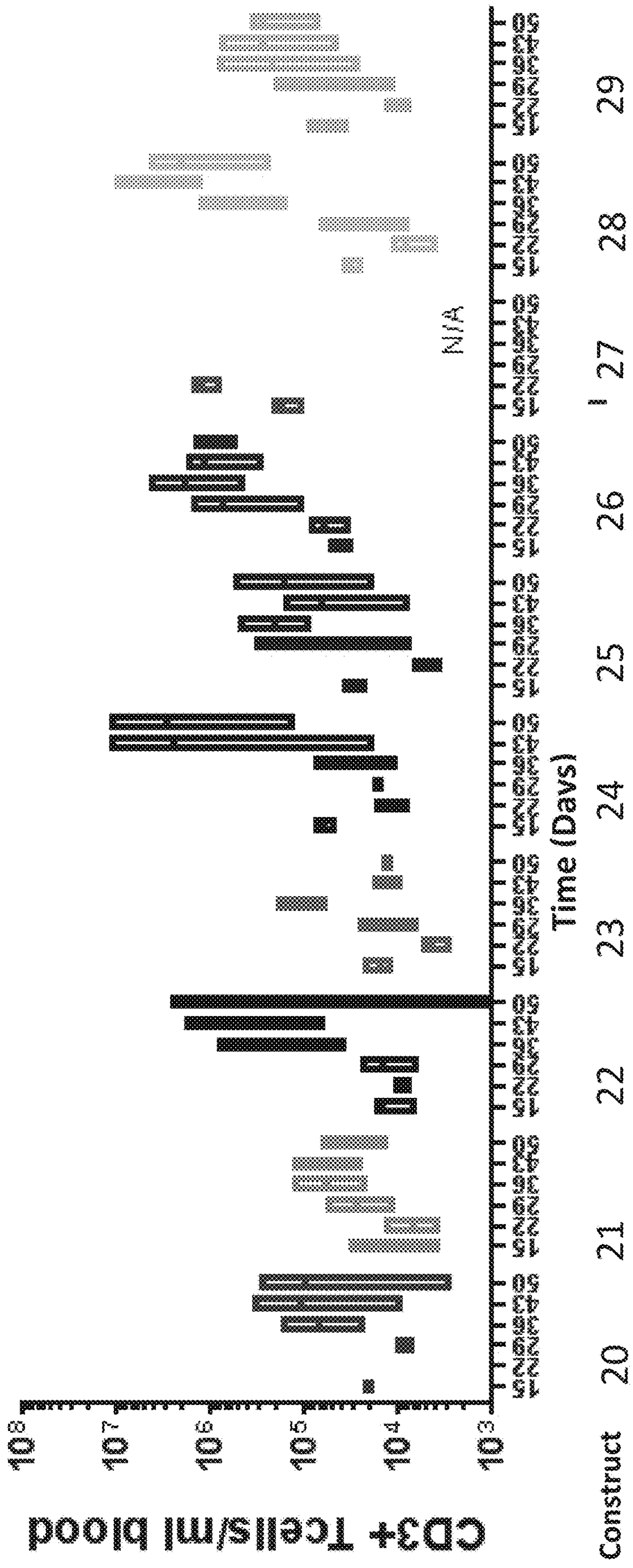

FIG. 12 shows quantification of human CD3+ T cells in peripheral blood of tumor bearing NSG mice treated with various hROR1 CAR-T cells. The CD3+ T cell expansion in blood was measured at days 15, 22, 29, 36, 43 and 50.

Figure 13B:
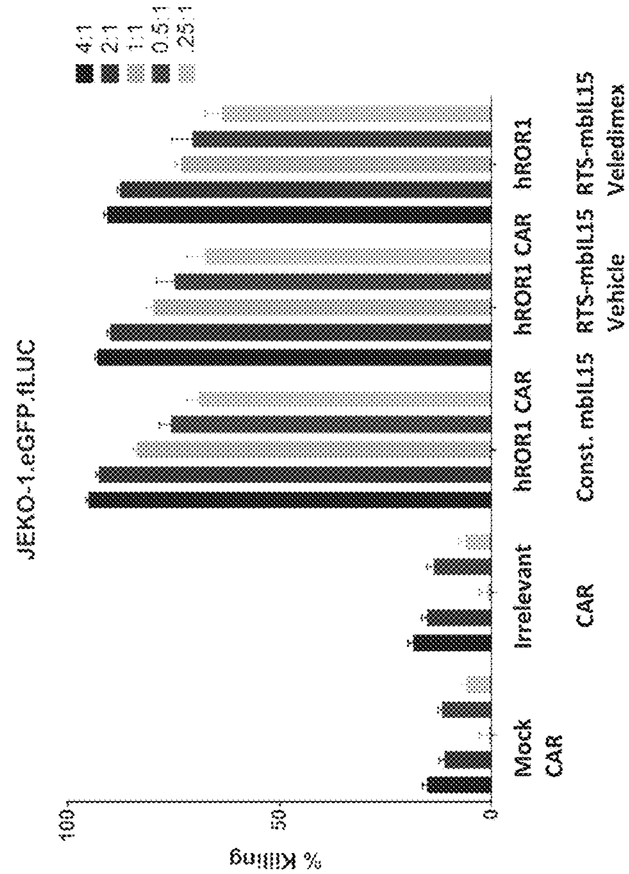
Figure 13A:
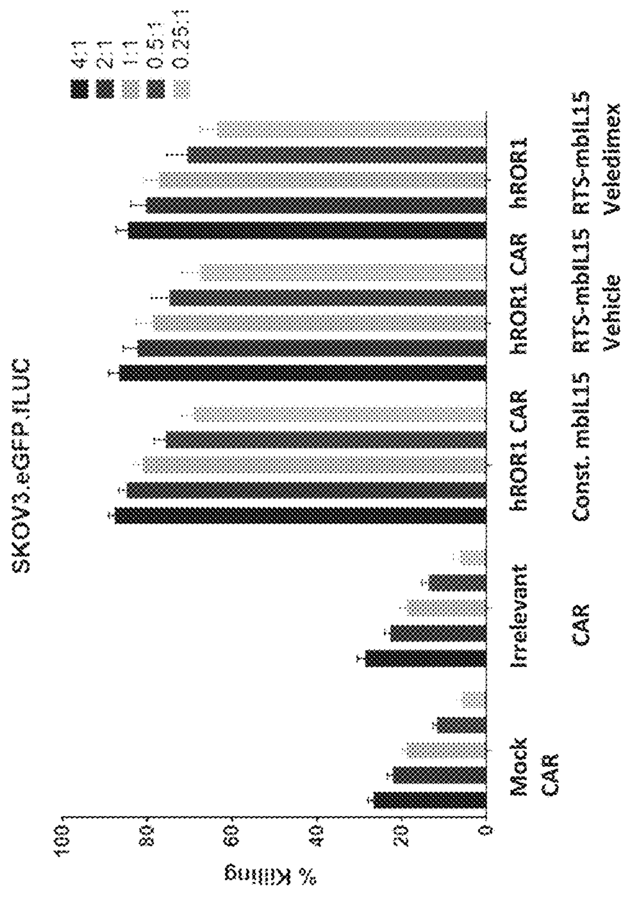

FIG. 13A and FIG. 13B demonstrates that ROR1+ tumor cell lines were equally killed by hROR1 CAR T cells co-expressing constitutive or RTS-mbIL-15 in vitro.

Figure 14:
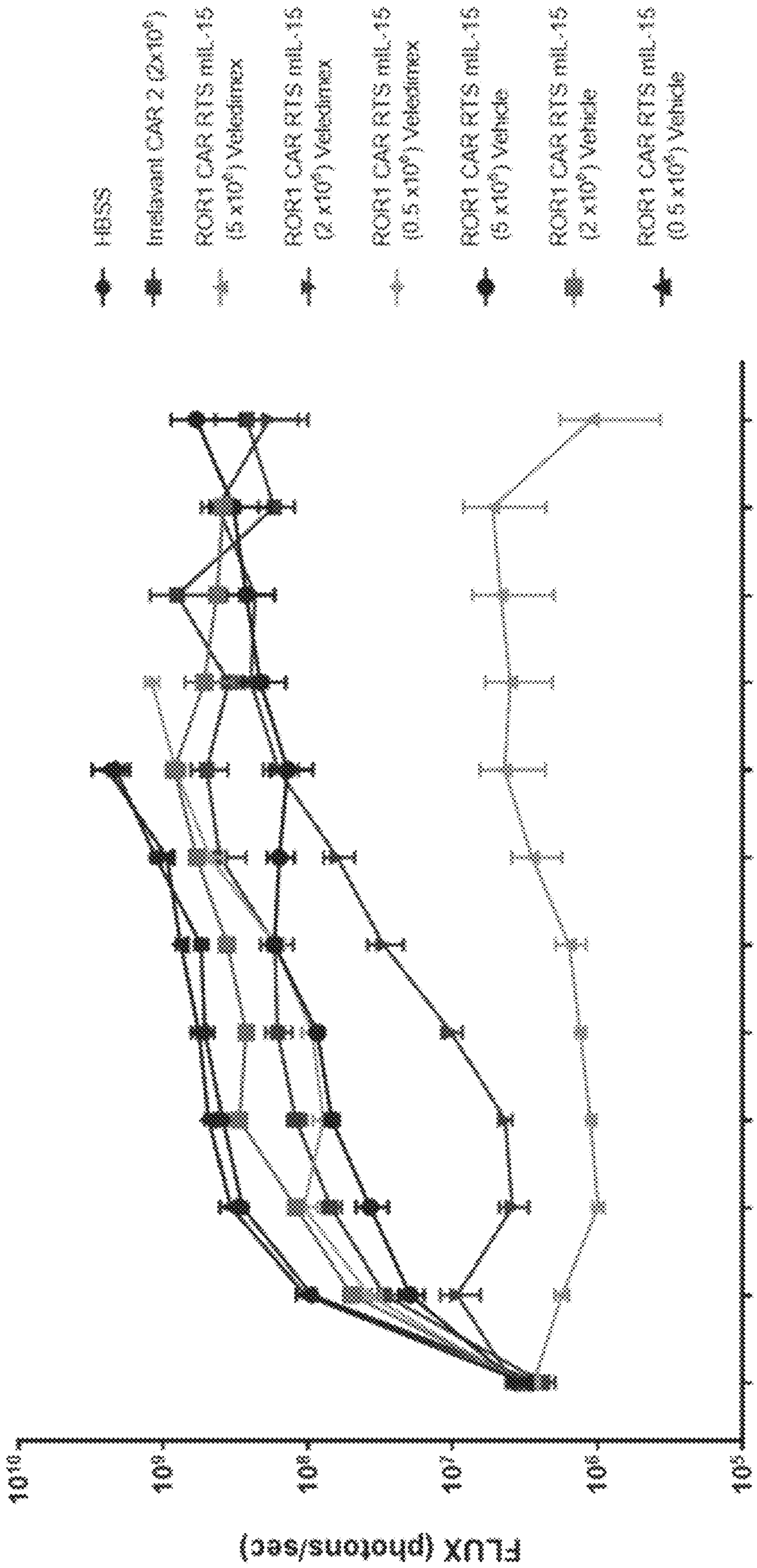

FIG. 14 demonstrates that administration of hROR1 CAR RTS-mbIL-15-T cells+ veledimex promotes anti-tumor effect in a JeKo-1 xenograft mouse model in a dose-dependent manner.

DETAILED DESCRIPTION OF THE DISCLOSURE

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention can be described in the context of a single embodiment, the features can also be provided separately or in any suitable combination. Conversely, although the invention can be described herein in the context of separate embodiments for clarity, the invention can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells.

"Polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Polypeptide" is used interchangeably with the terms "polypeptides" and "protein(s)," and refers to a polymer of amino acid residues. A "mature protein" is a protein which is full-length and which, optionally, includes glycosylation or other modifications typical for the protein in a given cellular environment.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology.

The terms "identical" or "sequence identity" in the context of two nucleic acid sequences or amino acid sequences of polypeptides refers to the residues in the two sequences which are the same when aligned for maximum correspondence over a specified comparison window. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is the to have certain percentage of sequence identity with a larger molecule, it means that when the two molecules are optimally aligned, the percentage of residues in the smaller molecule finds a match residue in the larger molecule in accordance with the order by which the two molecules are optimally aligned.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first, they are transcribed from DNA to RNA, and the RNA produced is then reverse transcribed to DNA. This copied DNA is then inserted at a new position into the genome. The reverse transcription step is catalyzed by a reverse transcriptase, which can be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the TE excision by transposase. Cut-and-paste TEs can be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome.

The nucleic acid sequences and vectors disclosed or contemplated herein can be introduced into a cell by "transfection," "transformation," "nucleofection" or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell Biol.,* 7: 2031-2034 (1987)); and nucleofection (Trompeter et al., *J. Immunol. Methods* 274:245-256 (2003). Phage or viral vectors can be introduced into host cells, after growth of infectious particles in suitable packaging cells, many of which are commercially available.

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter.

The term "promoter activity" refers to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch.

The term "enhancer," as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences.

Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), *Fundamental Immunology,* 3rd Edition, Raven Press, New York (1993), pages 353-363; and U.S. Pat. No. 5,885,827).

"Coding sequence" as used herein refers to a segment of a polynucleotide that codes for a polypeptide. The region or sequence is bounded nearer the 5' end by a start codon and nearer the 3' end with a stop codon. Coding sequences can also be referred to as open reading frames.

"Operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in nucleic acid sequence transcription, promoter activity and/or expression brought about by a transcriptional regulator, relative to some basal level of transcription.

A "target" gene or "heterologous" gene, or "gene of interest (GOI)" refers to a gene introduced into the host cell by gene transfer.

"Recombinase" as used herein refers to a group of enzymes that can facilitate site-specific recombination between defined sites, where the sites are physically separated on a single DNA molecule or where the sites reside on separate DNA molecules. The DNA sequences of the defined recombination sites are not necessarily identical. Initiation of recombination depends on protein-DNA interaction, within the group there are large number of proteins that catalyze phage integration and excision (e.g., λ integrase, ΦC31), resolution of circular plasmids (e.g., Tn3, gamma delta, Cre, Flp), DNA inversion for expression of alternate genes (e.g., Hin, Gin, Pin), assembly of genes during development (e.g., *Anabaena* nitrogen fixation genes), and transposition (e.g., IS607 transposon). Most site-specific recombinases fall into one of the two families, based on evolutionary and mechanistic relatedness. These are. λ integrase family or tyrosine recombinases (e.g., Cre, Flp, Xer D) and resolvase/integrase family or serine recombinase family (e.g., ΦC31, TP901-1, Tn3, gamma delta).

"Recombination attachment sites" are specific polynucleotide sequences that are recognized by the recombinase enzymes described herein. Typically, two different sites are involved (termed "complementary sites"), one present in the target nucleic acid (e.g., a chromosome or episome of a eukaryote or prokaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes can have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POB', respectively. In some representations herein, the "O" is omitted and attB and attP, for example, are designated as BB' and PP', respectively.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences.

Vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad. Sci. USA,* 77: 3567 (1980); O'Hare et al., *Proc. Natl. Acad. Sci. USA,* 78: 1527 (1981); Mulligan & Berg, *Proc. Natl. Acad. Sci. USA,* 78: 2072 (1981); Colberre-Garapin et al., *J. Mol. Biol.,* 150:1 (1981); Santerre et al., *Gene,* 30: 147 (1984); Kent et al., *Science,* 237: 901-903 (1987); Wigler et al., *Cell,* 11: 223 (1977); Szybalska &

Szybalski, *Proc. Natl. Acad. Sci. USA,* 48: 2026 (1962); Lowy et al., *Cell,* 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy,* 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

"Cancer cell" refers to a cell undergoing early, intermediate or advanced stages of multi-step neoplastic progression as previously described (Pitot et al., *Fundamentals of Oncology,* 15-28 (1978)). This includes cells in early, intermediate and advanced stages of neoplastic progression including "pre-neoplastic" cells (i.e., "hyperplastic" cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, leukemia, non-Hodgkin's lymphoma, acute lymphocytic leukemia (ALL), chronic lymphocytic leukemia (CLL), hairy cell leukemia (HCL), multiple myeloma (MM), acute myeloid leukemia (AML), or chronic myeloid leukemia (CML).

ROR-1

ROR1 is a transmembrane protein within the receptor tyrosine kinase (RTK) family. The ROR1 gene encodes two well-defined isoforms: a short 393 amino acid (aa) intracellular protein (isoform 2) and a long 937 aa type-1 transmembrane protein (isoform 1). The long cell surface isoform is expressed on primary human B-chronic lymphocytic leukemia (B-CLL) and mantle cell lymphomas, a subset of B-acute lymphocytic leukemia, and many tumors, including those associated with a metastatic phenotype.

ROR1 is principally expressed during embryonic development but its expression attenuates during fetal development. However, ROR1 is aberrantly expressed by some B-cell malignancies such as but not limited to, lymphomas, CLL, and B-ALL, and by many solid tumor malignancies, such as but not limited to, adrenal, bladder, breast, colon, lung, pancreas, prostate, ovary, skin, testes, uterus, and neuroblastoma.

Chimeric Antigen Receptors

In embodiments described herein, a CAR can comprise an extracellular antibody-derived single-chain variable domain (scFv) for target recognition, wherein the scFv can be connected by a flexible linker to a transmembrane domain and/or an intracellular signaling domain(s) that includes, for instance, CD3ζ for T-cell activation. Normally when T cells are activated in vivo they receive a primary antigen induced TCR signal with secondary costimulatory signaling from CD28 that induces the production of cytokines (i.e., IL-2 and IL-21), which then feed back into the signaling loop in an autocrine/paracrine fashion. As such, CARs can include a signaling domain, for instance, a CD28 cytoplasmic signaling domain or other costimulatory molecule signaling domains such as 4-1BB signaling domain. Chimeric CD28 co-stimulation improves T-cell persistence by up-regulation of anti-apoptotic molecules and production of IL-2, as well as expanding T cells derived from peripheral blood mononuclear cells (PBMC).

In one embodiment, CARs are fusions of single-chain variable fragments (scFv) derived from monoclonal antibodies specific for various epitopes of ROR-1 for example, fused to transmembrane domain and CD3-zeta endodomain. Such molecules result in the transmission of a zeta signal in response to recognition by the scFv of its target.

In an embodiment, a CAR can have an ectodomain (extracellular), a transmembrane domain and an endodomain (intracellular). In one embodiment of the CAR ectodomain, a signal peptide directs the nascent protein into the endoplasmic reticulum. This is if the receptor is to be glycosylated and anchored in the cell membrane for example. Any eukaryotic signal peptide sequence is envisaged to be functional. Generally, the signal peptide natively attached to the amino-terminal most component is used (e.g., in a scFv with orientation light chain—linker—heavy chain, the native signal of the light-chain is used). In embodiments, the signal peptide is GM-CSFRa (SEQ ID NO: 94) or IgK (SEQ ID NO: 95). Other signal peptides that can be used include signal peptides from CD8alpha (SEQ ID NO: 97) and CD28. In one embodiment, the signal peptide is Mouse Ig VH region 3 (SEQ ID NO: 101), Azurocidin (SEQ ID NO: 103), IGHV3-23 (SEQ ID NO: 106), IGKV1-D33 (HuL1) (SEQ ID NO: 107) or IGKV1-D33 (L14F) (HuH7) (SEQ ID NO: 108).

The antigen recognition domain can be a scFv. There can, however, be alternatives. An antigen recognition domain from native T-cell receptor (TCR) alpha and beta single chains are envisaged, as they have simple ectodomains (e.g. CD4 ectodomain) and as well as other recognition components such as a linked e.g., cytokine (which leads to recognition of cells bearing the cytokine receptor). Almost anything that binds a given target, such as e.g., viral associated antigen, with high affinity can be used as an antigen recognition region.

In general, CARs exist in a dimerized form and are expressed as a fusion protein that links the extracellular scFv (VH linked to VL) region, a spacer, a transmembrane domain, and intracellular signaling motifs. The endodomain of the first generation CAR induces T cell activation solely through CD3-ζ signaling. The second generation CAR provides activation signaling through CD3-ζ and CD28, or other endodomains such as 4-1BB or OX40. The 3rd generation CAR activates T cells via a CD3-ζ-containing combination of three signaling motifs such as CD28, 4-1BB, or OX40.

In embodiments, the present invention provides chimeric antigen receptor (CAR) comprising an extracellular domain, a transmembrane domain and an intracellular signaling domain. In embodiments, the extracellular domain comprises a target-specific binding element otherwise referred to as an antigen binding moiety or scFv and a spacer. In embodiments, the intracellular signaling domain or otherwise the cytoplasmic signaling domain comprises, a costimulatory signaling region and a zeta chain portion.

The costimulatory signaling region refers to a portion of the CAR comprising the intracellular signaling domain of a costimulatory molecule. Costimulatory molecules are cell surface molecules other than antigens receptors or their ligands that are required for an efficient response of lymphocytes to antigen.

In embodiments, between the extracellular domain and the transmembrane domain of the CAR, there is incorporated a stalk domain or stalk region. As used herein, the term "stalk domain" or "stalk region" generally means any oligonucleotide- or polypeptide that functions to link the transmembrane domain to, either the scFv or, the cytoplasmic domain in the polypeptide chain. A stalk domain can include a flexible hinge such as a Fc hinge and optionally one or two constant domains of Fc. In some instances, the stalk region comprises the hinge region from IgG1. In alternative instances, the stalk region comprises the CH2CH3 region of immunoglobulin and optionally portions of CD3. In some cases, the stalk region comprises a CD8α hinge region (SEQ ID NO: 83), an IgG4-Fc 12 amino acid hinge region (ESKYGPPCPPCP (SEQ ID NO: 285)) or IgG4 hinge regions as described in WO/2016/073755.

Figure 3:
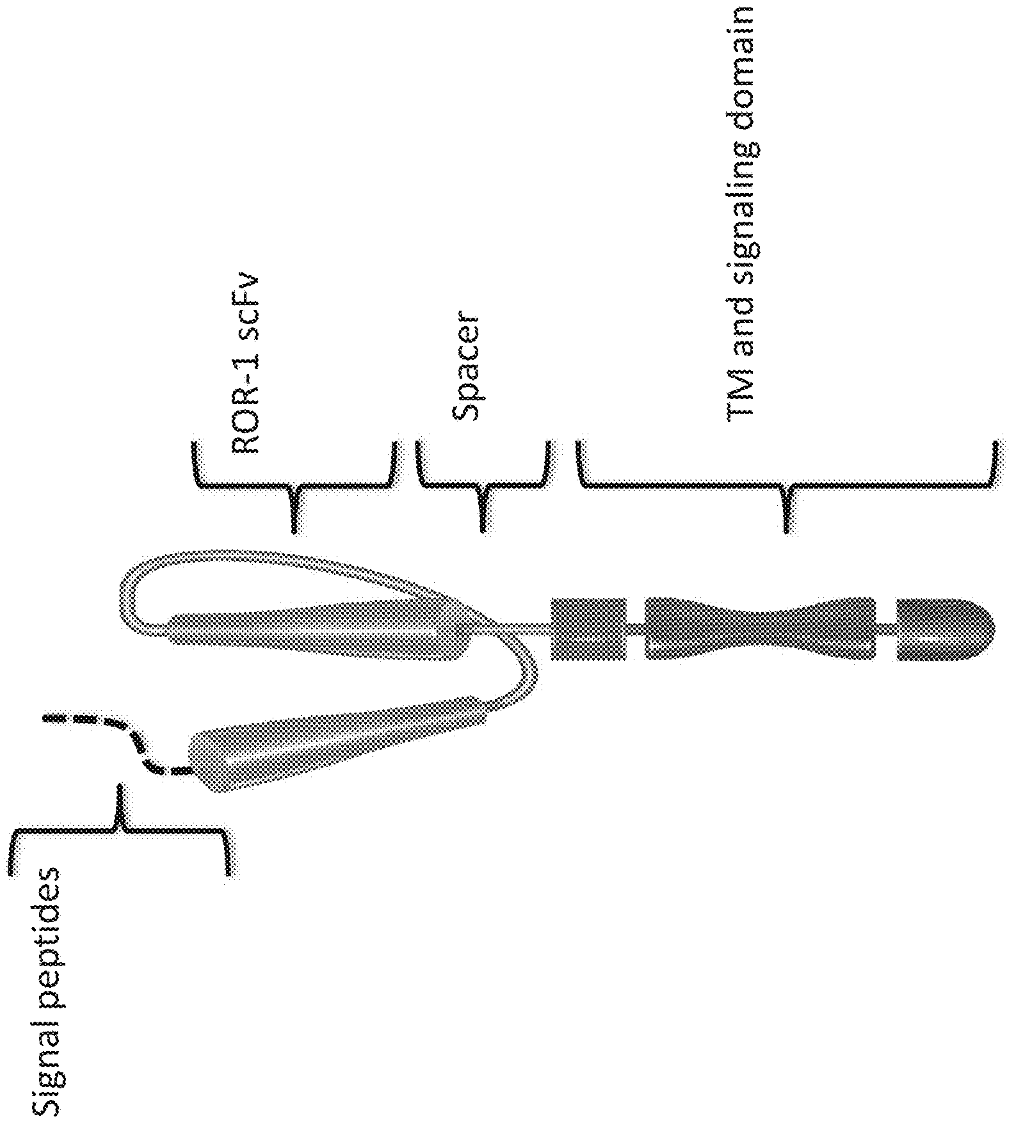
FIG. 3 depicts an exemplary ROR1 CAR design. ROR1 CAR based on the standard CAR design did not show any expression of ROR1 CAR after gene transfer. Various optimization strategies as described in Example 1 were employed to develop a surface expressed, functional ROR1 CAR.
Figure 4:
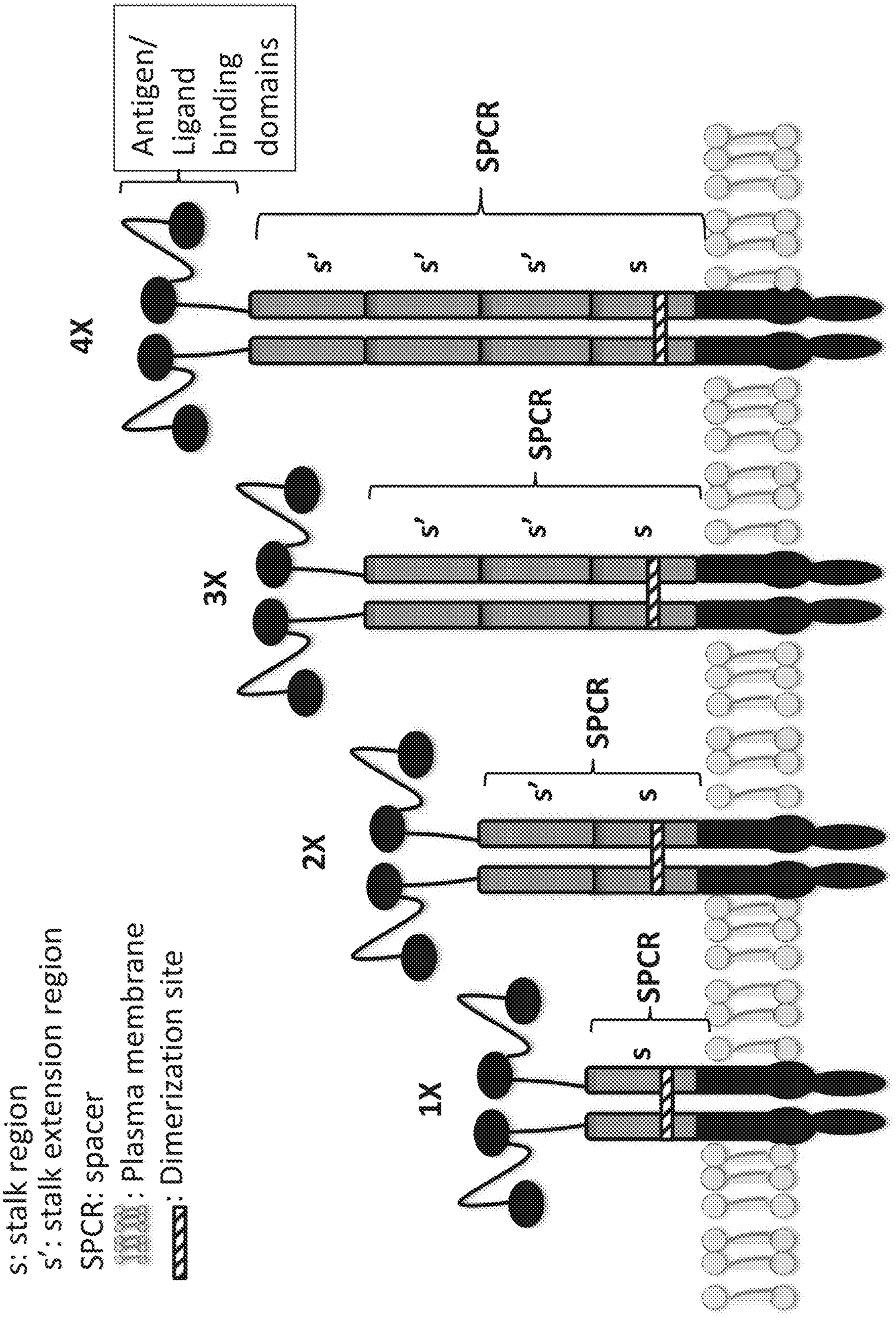
FIG. 4 depicts an illustration of ROR1 CARs with spacers of different lengths.

In other embodiments, between the extracellular domain and the transmembrane domain of the CAR, there is an incorporated spacer. A spacer can comprise a stalk region and a stalk extension region as depicted in FIGS. 3 and 4. In some embodiments, the spacer extends the distance between different domains of a chimeric polypeptide resulting in improved expression or functional activity of the polypeptide compared to an otherwise identical polypeptide lacking the spacer. In some instances, a spacer comprises any polypeptide that functions to link the transmembrane region to, either the extracellular region or, the cytoplasmic region in the chimeric polypeptide. In some embodiments, the spacer is flexible enough to allow the antigen or ligand-binding region to align in different orientations to facilitate antigen or ligand receptor recognition.

In some embodiments, the stalk region can be from about 20 to about 300 amino acids in length and comprises at least one dimerization site, and a stalk extension region can comprise from about 1 to about 10 times the length of the stalk region as measured by number of amino acids.

In some cases, a stalk region can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or greater amino acids in length. In other cases, the stalk region can be about: 100, 125, 150, 175, 200, 225, 250, 275 or 300 amino acids in length.

In one embodiment, a spacer can include a single stalk region. In another embodiment, a spacer can comprise a stalk region (designated as "S") and stalk extension region(s), which is herein designated as "S'n." For example, a spacer can comprise one (1) stalk region and S'n, wherein n can be 0, 1, 2, 3, 4, 5, 6, 7, 8, 9, 10, 11, 12, 13, 14, 15, 16, 17, 18, 19, or 20. In further embodiments, the stalk region can be linked to stalk extension region S'n via a linker. In one embodiment, when the CAR is a ROR1 CAR, n is not 0.

In some cases, a stalk extension region can comprise from about 1 to about 10 times the length of the stalk region as measured by number of amino acids. For example, a stalk extension region can comprise about 1, 2, 3, 4, 5, 6, 7, 8, 9, or 10 times the length of the stalk region as measured by number of amino acids. In some cases, a stalk extension region can comprise greater than 10 times the length of the stalk region as measured by number of amino acids. In some examples, a stalk extension region can comprise up to 2 times the length of the stalk region as measured by number of amino acids but comprise fewer dimerization sites than the stalk region.

A stalk extension region of a subject antigen-binding polypeptide can contain at least one fewer dimerization site as compared to a stalk region. For example, if a stalk region comprises two dimerization sites, a stalk extension region can comprise one or zero dimerization sites. As another example, if a stalk region comprises one dimerization site, a stalk extension region can comprise zero dimerization sites. In some examples, a stalk extension region lacks a dimerization site. In some examples, a stalk extension region can comprise up to 2 times the length of the stalk region as measured by number of amino acids but comprise no dimerization sites. In some examples, a stalk extension region can comprise up to 3 times the length of the stalk region as measured by number of amino acids but comprise no dimerization sites. In some examples, a stalk extension region can comprise up to 4 times the length of the stalk region as measured by number of amino acids but comprise zero dimerization sites. In some cases, one or more dimerization site(s) can be membrane proximal. In other cases, one or more dimerization site(s) can be membrane distal.

Each of the stalk extension regions can, in some examples, be from about 20 to about 60 amino acids in length. In other examples, stalk extension regions can be about 10, 15, 20, 25, 30, 35, 40, 45, 50, 55, 60, 65, greater amino acids in length, or any integer within or outside of that range. In some cases, each stalk extension region has a sequence which has at least about 60% identity to the stalk region. In some examples, each stalk extension region has a sequence which has at least about 65%, 70%, 75%, 80%, 85%, 90%, 95%, 96%, 97%, 98%, 99% or greater identity to the stalk region.

The transmembrane domain can be derived from either a natural or a synthetic source. Where the source is natural, the domain can be derived from any membrane-bound or transmembrane protein. Suitable transmembrane domains can include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length can form the linkage between the transmembrane domain and the cytoplasmic signaling domain of a CAR. In some embodiments, the linker is a glycine-serine linker. In some embodiments, the transmembrane domain comprises a CD8α transmembrane domain or a CD3ζ transmembrane domain. In some embodiments, the transmembrane domain comprises a CD8α transmembrane domain. In other embodiments, the transmembrane domain comprises a CD3ζ transmembrane domain.

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134), CD3-zeta or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), DAP10, DAP12 or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof. In some instances, a CAR described herein comprises at least one costimulatory domain DAP10 or a fragment thereof. In some instances, a CAR described herein comprises at least one costimulatory domain DAP12 or a fragment thereof.

The intracellular signaling domain, also known as cytoplasmic domain, of the CAR of the present disclosure, is responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal. In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

In embodiments, provided herein is an isolated nucleic acid encoding a chimeric antigen receptor (CAR), wherein the CAR comprises (a) a ROR-1 antigen binding domain; (b) a stalk domain; (c) a transmembrane domain; (d) a costimulatory signaling domain comprising 4-1BB or CD28, or both; (e) a CD3 zeta signaling domain; and optionally (f) a truncated epidermal growth factor receptor (HER1t or HER1t1).

Included in the scope of the invention are nucleic acid sequences that encode functional portions of the CAR described herein. Functional portions encompass, for example, those parts of a CAR that retain the ability to recognize target cells, or detect, treat, or prevent a disease, to a similar extent, the same extent, or to a higher extent, as the parent CAR. In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

In embodiments, the CAR contains additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

The term "functional variant," as used herein, refers to a polypeptide, or a protein having substantial or significant sequence identity or similarity to the reference polypeptide, and retains the biological activity of the reference polypeptide of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

A CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized, or conjugated.

Antigen Binding Moiety

In embodiments, a CAR described herein comprises a target-specific binding element otherwise referred to as an antigen-binding moiety. In embodiments, a CAR described herein engineered to target an antigen of interest by way of engineering a desired antigen-binding moiety that specifically binds to an antigen on a cell.

In embodiments, the antigen binding moiety of a CAR described herein is specific to ROR-1 (ROR-1 CAR). The ROR-1-specific CAR, when expressed on the cell surface, redirects the specificity of T cells to human ROR-1. In embodiments, the antigen binding domain comprises a single chain antibody fragment (scFv) comprising a variable domain light chain (VL) and variable domain heavy chain (VH) of a target antigen specific monoclonal anti-ROR-1 antibody joined by a flexible linker, such as a glycine-serine linker or a Whitlow linker. In embodiments, the scFv is mROR-1 that has been humanized. In some embodiments, the scFv is hROR1(VH-VL)_14, hROR1(VL-VH)_05, hROR1(VH-VL)_14-3, hROR1(VH-VL)_14-4, hROR1 (VH_5-VL_14), hROR1(VH_5-VL_16), hROR1(VH_18-VL_04), or hROR1(VH_18-VL_14). In some embodiments, the antigen binding moiety can comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with any one of amino acid sequences as shown in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74 (hROR1 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with any one of amino acid sequences as shown in SEQ ID NOs: 15, 17, 19, 21, 23, 25, 27, 29, 31, 33, 35, 37, 39, 41, 43, 45, 47, 49, 51, 53, 55, 57, 59, 61, 63, 65, 67, 69, 71, and 73 (hROR1 VH).

In embodiments, a CAR described herein comprises antigen binding moieties VL (SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74) and VH (SEQ ID NOs: 15, 17, 19, 21, 23, 25, 27, 29, 31, 33, 35, 37, 39, 41, 43, 45, 47, 49, 51, 53, 55, 57, 59, 61, 63, 65, 67, 69, 71, and 73) with a Gly-Ser linker (SEQ ID NOs: 127, 129, or 130) or functional variants of the linker.

In embodiments, a CAR described herein comprises a polypeptide having at least 90%, 91%, 92%, 93%, 94%, 95%, 96%, 97%, 98%, 99% or 100% identity with any one of amino acid sequences as shown in SEQ ID NOs: 3-14 and 75-82 (VH, VL and linker).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 15 (hROR1 VH_04).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 16 (hROR1 VL_04).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 17 (hROR1 VH_05).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 18 (hROR1 VL_05).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 19 (hROR1 VH_06).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 20 (hROR1 VL_06).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 21 (hROR1 VH_07).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 22 (hROR1 VL_07).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 23 (hROR1 VH_08).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 24 (hROR1 VL_08)

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 25 (hROR1 VH_09).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 26 (hROR1 VL_09).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 27 (hROR1 VH_10).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 28 (hROR1 VL_10).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 29 (hROR1 VH_11).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 30 (hROR1 VL_11).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 31 (hROR1 VH_12).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 32 (hROR1 VL_12).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 33 (hROR1 VH_13).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 34 (hROR1 VL_13).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 35 (hROR1 VH_14).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 36 (hROR1 VL_14).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 37 (hROR1 VH_14-1).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 38 (hROR1 VL_14-1).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 39 (hROR1 VH_14-2).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 40 (hROR1 VL_14-2).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 41 (hROR1 VH_14-3).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 42 (hROR1 VL_14-3).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 43 (hROR1 VH_14-4).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 44 (hROR1 VL_14-4).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 45 (hROR1 VH_14-5).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 46 (hROR1 VL_14-5).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 47 (hROR1 VH_15).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 48 (hROR1 VL_15).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 49 (hROR1 VH_16).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 50 (hROR1 VL_16).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 51 (hROR1 VH_17).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 52 (hROR1 VL_17).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 53 (hROR1 VH_18).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 54 (hROR1 VL_18).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 55 (hROR1 VH_19).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 56 (hROR1 VL_19).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 57 (hROR1 VH_20).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 58 (hROR1 VL_20).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 59 (hROR1 VH_21).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 60 (hROR1 VL_21).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 61 (hROR1 VH_22).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 62 (hROR1 VL_22).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 63 (hROR1 VH_23).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 64 (hROR1 VL_23).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 65 (hROR1 VH_24).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 66 (hROR1 VL_24).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 67 (hROR1 VH_25).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 68 (hROR1 VL_25).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 69 (hROR1 VH_26).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 70 (hROR1 VL_26).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 71 (hROR1 VH_27).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 72 (hROR1 VL_27).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 73 (hROR1 VH_28).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 74 (hROR1 VL_28).

In embodiments, a CAR described herein comprises an antigen-binding moiety comprising a VH polypeptide having the amino acid sequence of SEQ ID NO: 17 (hROR1 VH_5) and a VL polypeptide having the amino acid sequence of SEQ ID NO: 18 (hROR1 VL_5).

In embodiments, a CAR described herein comprises an antigen-binding moiety comprising a VH polypeptide having the amino acid sequence of SEQ ID NO: 35 (hROR1 VH_14) and a VL polypeptide having the amino acid sequence of SEQ ID NO: 36 (hROR1 VL_14).

In embodiments, a CAR described herein comprises an antigen-binding moiety comprising a VH polypeptide having the amino acid sequence of SEQ ID NO: 41 (hROR1 VH_14-3) and a VL polypeptide having the amino acid sequence of SEQ ID NO: 42 (hROR1 VL_14-3).

In embodiments, a CAR described herein comprises an antigen-binding moiety comprising a VH polypeptide having the amino acid sequence of SEQ ID NO: 43 (hROR1 VH_14-4) and a VL polypeptide having the amino acid sequence of SEQ ID NO: 44 (hROR1 VL_14-4).

In embodiments, a CAR described herein comprises an antigen-binding moiety comprising a VH polypeptide having the amino acid sequence of SEQ ID NO: 17 (hROR1 VH_5) and a VL polypeptide having the amino acid sequence of SEQ ID NO: 36 (hROR1 VL_14).

In embodiments, a CAR described herein comprises an antigen-binding moiety comprising a VH polypeptide having the amino acid sequence of SEQ ID NO: 53 (hROR1 VH_18) and a VL polypeptide having the amino acid sequence of SEQ ID NO: 16 (hROR1 VL_04).

In embodiments, a CAR described herein comprises an antigen-binding moiety comprising a VH polypeptide having the amino acid sequence of SEQ ID NO: 53 (hROR1 VH_18) and a VL polypeptide having the amino acid sequence of SEQ ID NO: 36 (hROR1 VL_14).

In embodiments, the antigen binding moiety has GM-CSFRa signal peptide having at least 90%, 91%, 92%, 93%, 94%, 95%, 96%, 97%, 98%, 99% or 100% identity with the amino acid sequence of SEQ ID NO: 94.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 3. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 4. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 5. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 6. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 7. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 8. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 9. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 10. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 11. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 12. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 13. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 14.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 75. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 76. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 77. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 78. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 79. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 80. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 81. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 82.

Spacer

In embodiments, the ROR-1 CAR of the present disclosure comprises a spacer comprising one or more stalk regions and optionally one or more stalk extension regions, that provides a separation between the antigen binding moiety and the T cell membrane. In embodiments, the spacer establishes an optimal effector-target inter-membrane distance. In embodiments, the stalk domain provides flexibility for antigen binding domain to reach its target. In one embodiment, the stalk domain is a CD8alpha hinge domain. In some embodiments, the term "spacer," "stalk regions" and "stalk domain" can be used interchangeably herein.

In embodiments, the CD8alpha hinge domain comprises a polypeptide having at least 90%, 91%, 92%, 93%, 94%, 95%, 96%, 97%, 98%, 99% or 100% identity with the amino acid sequence of SEQ ID NO: 88.

In other embodiments, between the extracellular domain and the transmembrane domain of the CAR, there is incorporated a spacer. As described herein, a spacer can comprise a stalk region and a stalk extension region as depicted in FIG. 3 and FIG. 4. In one embodiment, a spacer can include a single stalk region. In another embodiment, a spacer can comprise a stalk region (designated as "S") and stalk extension region(s), which is herein designated as "S'n." For example, a spacer can comprise one (1) stalk region and S'n, wherein n can be 0, 1, 2, 3, 4, 5, 6, 7, 8, 9, 10, 11, 12, 13, 14, 15, 16, 17, 18, 19, or 20. In one embodiment, when the scFv of the ROR1 CAR is mROR1 (SEQ ID NOs: 3-14) or hROR1 (SEQ ID NOs: 75-82), wherein n is not 0.

In further embodiments, the stalk region can be linked to stalk extension region S'n via a linker. A linker as described herein can include for instance, a GSG linker (SEQ ID NO: 129), SGSG linker (SEQ ID NO: 130), (G4S)3 linker (SEQ ID NO: 127), (G4S)4 linker (SEQ ID NO: 294) and/or a Whitlow linker (SEQ ID NO: 128).

In one embodiment, stalk region and stalk extension region(s) can be derived or designed from a polypeptide of natural or of synthetic origin. The stalk region and/or stalk extension region(s) can comprise hinge domain(s) derived from a cell surface protein or derivatives or variants thereof. In some embodiments, the stalk region and/or stalk extension region(s) can comprise a hinge domain derived from CD28 or CD8alpha (CD8α). In some embodiments, each of the stalk region and stalk extension region(s) can be derived from at least one of a CD8alpha hinge domain, a CD28 hinge domain, a CTLA-4 hinge domain, a LNGFR extracellular domain, IgG1 hinge, IgG4 hinge and CH2-CH3 domain. The stalk and stalk extension region(s) can be separately derived from any combination of CD8alpha hinge domain, CD28 hinge domain, CTLA-4 hinge domain, LNGFR extracellular domain, IgG1 hinge, IgG4 hinge or CH2-CH3 domain. As an example, the stalk region can be derived from CD8alpha hinge domain and at least one stalk extension region can be derived from CD28 hinge domain thus creating a hybrid spacer. As another example, the stalk region can be derived from an IgG1 hinge or IgG4 hinge and at least one stalk extension region can be derived from a CH2-CH3 domain of IgG.

In certain embodiments, the stalk region can comprise one or more dimerization sites to form homo or hetero dimerized chimeric polypeptides. In other embodiments, the stalk region or one or more stalk extension regions can contain mutations that eliminate dimerization sites altogether. In some embodiments, a stalk extension region(s) can contain at least one fewer dimerization site as compared to a stalk region. For example, if a stalk region comprises two dimerization sites, a stalk extension region can comprise one or zero dimerization sites. As another example, if a stalk region comprises one dimerization site, a stalk extension region can comprise zero dimerization sites. In some examples, the stalk extension region(s) lacks a dimerization site.

In some aspects of the embodiments disclosed herein, a stalk region of a subject antigen binding polypeptide comprises a sequence with at least about 65%, 70%, 75%, 80%, 85%, 90%, 95%, 99% or greater identity to a CD8alpha hinge domain. A CD8alpha hinge domain can comprise a polypeptide sequence with at least 65%, 70%, 75%, 80%, 85%, 90%, 95%, 99% or greater identity to the sequence shown in SEQ ID NO: 83. In some cases, a stalk extension region comprises a polypeptide sequence with at least 65%, 70%, 75%, 80%, 85%, 90%, 95%, or greater identity to the sequence shown in SEQ ID NO: 83. In some cases, a stalk extension region comprises a nucleotide sequence with at least 65%, 70%, 75%, 80%, 85%, 90%, 95%, or greater identity to the sequence shown in SEQ ID NO: 230. In some examples, a stalk region and stalk extension region can together comprise a polynucleotide sequence with at least 65%, 70%, 75%, 80%, 85%, 90%, 95%, or greater identity to any one of the sequences shown in SEQ ID NOs: 230-233.

Transmembrane Domain

In embodiments, the CAR comprises a transmembrane domain that is fused to the extracellular domain of the CAR stalk domain. In one embodiment, the transmembrane domain that naturally is associated with one of the domains in the CAR is used. In embodiments, the transmembrane domain is a hydrophobic alpha helix that spans the membrane.

The transmembrane domain can be derived from either a natural or a synthetic source. Where the source is natural, the domain can be derived from any membrane-bound or transmembrane protein. Transmembrane regions of particular use in this invention can be derived from (i.e. comprise at least the transmembrane region(s) of) the alpha, beta or zeta chain of the T-cell receptor, CD28, CD3 epsilon, CD45, CD4, CD5, CD8alpha, CD9, CD16, CD22, CD33, CD37, CD64, CD80, CD86, CD134, CD137, CD154. Alternatively the transmembrane domain can be synthetic, in which case it will comprise predominantly hydrophobic residues such as leucine and valine. In embodiments, a triplet of phenylalanine, tryptophan and valine will be found at each end of a synthetic transmembrane domain. Optionally, a short oligonucleotide or polypeptide linker, in embodiments, between 2 and 10 amino acids in length can form the linkage between the transmembrane domain and the cytoplasmic signaling domain of the CAR. In embodiments, the linker is a glycine-serine linker.

In embodiments, the transmembrane domain in a CAR described herein is the CD8alpha transmembrane domain. In embodiments, the CD8alpha transmembrane domain comprises a polypeptide having at least 90%, 91%, 92%, 93%, 94%, 95%, 96%, 97%, 98%, 99% or 100% identity with the amino acid sequence of SEQ ID NO: 87.

In embodiments, the transmembrane domain in a CAR described herein is the CD28 transmembrane domain. In embodiments, the CD28 transmembrane domain comprises a polypeptide having at least 90%, 91%, 92%, 93%, 94%, 95%, 96%, 97%, 98%, 99% or 100% identity with the amino acid sequence of SEQ ID NO: 88.

Cytoplasmic Domain (Co-Stimulatory Domain and Signaling Domain)

The cytoplasmic domain, also known as the intracellular signaling domain of a CAR described herein, is responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in a CAR described herein can include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through the TCR alone are generally insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner can contain signaling motifs which are known as immunoreceptor tyrosine-based activation motifs or ITAMs.

Examples of ITAM-containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In embodiments, the cytoplasmic signaling molecule in a CAR described herein comprises a cytoplasmic signaling sequence derived from CD3 zeta.

In embodiments, the cytoplasmic domain of the CAR can be designed to comprise the CD3-zeta signaling domain by itself or combined with any other desired cytoplasmic domain(s) useful in the context of a CAR described herein. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, DAP10, DAP12 and a ligand that specifically binds with CD83, and the like. In embodiments, costimulatory molecules can be used together, e.g., CD28 and 4-1BB or CD28 and OX40. Thus, while the invention in exemplified primarily with 4-1BB and CD28 as the co-stimulatory signaling element, other costimulatory elements are within the scope of the invention.

The cytoplasmic signaling sequences within the cytoplasmic signaling portion of a CAR described herein can be linked to each other in a random or specified order. Optionally, a short oligo- or polypeptide linker, between 2 and 10 amino acids in length can form the linkage. A glycine-serine doublet provides a particularly suitable linker.

In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB. In yet another embodiment, the cytoplasmic domain comprises the signaling domain of CD3-zeta and the signaling domains of CD28 and 4-1BB.

In one embodiment, the cytoplasmic domain in a CAR described herein comprises the signaling domain of 4-1BB and the signaling domain of CD3-zeta, wherein the signaling domain of 4-1BB comprises a polypeptide sequence having at least 90%, 91%, 92%, 93%, 94%, 95%, 96%, 97%, 98%, 99% or 100% identity with the polypeptide sequence of SEQ ID NO:89, and the signaling domain of CD3-zeta comprises a polypeptide sequence having at least 90%, 91%, 92%, 93%, 94%, 95%, 96%, 97%, 98%, 99% or 100% identity with the nucleic acid sequence of SEQ ID NO: 93.

In one embodiment, the cytoplasmic domain in a CAR described herein is designed to comprise the signaling domain of CD28 and the signaling domain of CD3-zeta, wherein the signaling domain of CD28 comprises a polypeptide sequence having at least 90%, 91%, 92%, 93%, 94%, 95%, 96%, 97%, 98%, 99% or 100% identity with the polypeptide sequence of SEQ ID NO: 90, and the signaling domain of CD3-zeta comprises a polypeptide sequence having at least 90%, 91%, 92%, 93%, 94%, 95%, 96%, 97%, 98%, 99% or 100% identity with the polypeptide sequence of SEQ ID NO: 93.

In one embodiment, the cytoplasmic domain in a CAR described herein is designed to comprise the signaling domain of DNAX-activation protein 10 (DAP10), wherein the signaling domain of DAP10 comprises a polypeptide sequence having at least 90%, 91%, 92%, 93%, 94%, 95%, 96%, 97%, 98%, 99% or 100% identity with the polypeptide sequence of SEQ ID NO: 91.

In one embodiment, the cytoplasmic domain in a CAR described herein is designed to comprise the signaling domain of DNAX-activation protein 12 (DAP12), wherein the signaling domain of DAP10 comprises a polypeptide sequence having at least 90%, 91%, 92%, 93%, 94%, 95%, 96%, 97%, 98%, 99% or 100% identity with the polypeptide sequence of SEQ ID NO: 92.

In one embodiment, the cytoplasmic domain in a CAR described herein comprises the signaling domain of 4-1BB and the signaling domain of CD3-zeta, wherein the signaling domain of 4-1BB comprises the amino acid sequence set forth in SEQ ID NO: 89 and the signaling domain of CD3-zeta comprises the amino acid sequence set forth in SEQ ID NO: 93.

Additional Genetic Elements

Although cellular therapies hold great promise for the treatment of human disease, significant toxicities from the cells themselves or from their transgene products have hampered clinical investigation. In embodiments described herein, immune effector cells comprising a CAR described herein that have been infused into a mammalian subject, e.g., a human, can be ablated in order to regulate the effect of such immune effector cells should toxicity arise from their use. Therefore, certain in embodiments, in addition to the therapeutic ROR-1-specific chimeric antigen receptor described herein, a second gene is also introduced into an engineered immune effector cell described herein. In some embodiments, the second gene is a "cell tag." In some embodiments, the cell tag is a "kill switch." In some embodiments, the second gene is effectively a "kill switch" that allows for the depletion of ROR-1 CAR or ROR-1 CAR/mbIL-15 containing cells. In certain embodiments, the "kill switch" is a HER1 tag or a CD20 tag which comprise a HER1 polypeptide or a CD20 polypeptide which comprises at least an antibody binding epitope of HER1 or CD20 or functional fragment thereof, and optionally a signal polypeptide sequence or fragment thereof.

In certain embodiments, the second gene is a HER1 tag which is Epidermal Growth Factor Receptor (HER1) or a fragment or variant thereof. In embodiments, the second gene is a HER1 tag which is truncated human Epidermal Growth Factor Receptor 1 (for instance HER1t or HER1t1). In some cases, the second gene is a variant of a truncated human Epidermal Growth Factor Receptor 1. In embodiments, at least one of HER1, HER1t and HER1t1 provides a safety mechanism by allowing for depletion of infused CAR-T cells through administering FDA approved cetuximab or any antibody that recognizes HER1, HER1t and/or HER1t1. In embodiments, the HER1t gene comprises a nucleotide sequence having at least 90%, 91%, 92%, 93%, 94%, 95%, 96%, 97%, 98%, 99% or 100% identity with the nucleic acid sequence of SEQ ID NO: 256. In embodiments, the HER1t1 gene comprises a nucleotide sequence having at least 90%, 91%, 92%, 93%, 94%, 95%, 96%, 97%, 98%, 99% or 100% identity with the nucleic acid sequence of SEQ ID NO: 257. The truncated HER1 sequence, for instance HER1t and HER1t1 eliminate the potential for EGF ligand binding, homo- and hetero- dimerization of EGFR, and EGFR mediated signaling while keeping cetuximab binding to the receptor intact (Ferguson, K., 2008. A structure-based view of Epidermal Growth Factor Receptor regulation. *Annu Rev Biophys*, Volume 37, pp. 353-373).

In some embodiments, the HER1t tag has a polypeptide sequence having at least 90%, 91%, 92%, 93%, 94%, 95%, 96%, 97%, 98%, 99% or 100% identity with the sequence of SEQ ID NO: 109. In some embodiments, the HER1t1 tag has a polypeptide sequence having at least 90%, 91%, 92%, 93%, 94%, 95%, 96%, 97%, 98%, 99% or 100% identity with the sequence of SEQ ID NO: 110.

In further embodiments, in addition to the therapeutic ROR-1-specific chimeric antigen receptor of the invention the second gene introduced is a CD20 tag. In some cases, the CD20 tag is a full-length CD20 polypeptide, or a truncated CD20 polypeptide (CD20t-1). In some cases, the CD20 tag, for instance CD20 or CD20t-1 also provides a safety mechanism by allowing for depletion of infused CAR-T cells through administering FDA-approved rituximab therapy. In certain embodiments, the CD20 tag has a polypeptide sequence having at least 90%, 91%, 92%, 93%, 94%, 95%, 96%, 97%, 98%, 99% or 100% identity with the sequence of SEQ ID NO: 111. In certain embodiments, the CD20 tag is a CD20t-1 tag and has a polypeptide sequence having at least 90%, 91%, 92%, 93%, 94%, 95%, 96%, 97%, 98%, 99% or 100% identity with the sequence of SEQ ID NO: 112. In some embodiments, the CD20 tag is encoded by a CD20 gene which comprises a nucleotide sequence having at least 90%, 91%, 92%, 93%, 94%, 95%, 96%, 97%, 98%, 99% or 100% identity with the nucleic acid sequence of SEQ ID NO: 258. In some embodiments, the CD20 tag is encoded by a CD20t-1 gene which comprises a nucleotide sequence having at least 90%, 91%, 92%, 93%, 94%, 95%, 96%, 97%, 98%, 99% or 100% identity with the nucleic acid sequence of SEQ ID NO: 259.

In embodiments, a CAR vector comprising a CAR described herein further comprises a full length CD20 tag comprising a nucleic acid sequence having at least 90%, 91%, 92%, 93%, 94%, 95%, 96%, 97%, 98%, 99% or 100% identity with the nucleic acid sequence of SEQ ID NO: 258.

In embodiments, the gene encoding the kill tag, for instance the HER1t, HER1t-1, CD20 or CD20t-1 tag, is genetically fused to the ROR-1 CAR at 3' end via in-frame with a self-cleaving peptide, for example but not restricted to Thosea asigna virus (T2A) peptide. In embodiments, the T2A peptide has an amino acid sequence having at least 90%, 91%, 92%, 93%, 94%, 95%, 96%, 97%, 98%, 99% or 100% identity with the amino acid sequence of SEQ ID NO: 116.

In embodiments, the kill tag gene is cloned into a lentiviral plasmid backbone in frame with the ROR-1 CAR gene. In other embodiments, the kill tag is cloned into a separate lentiviral vector. In other embodiments, both genes are cloned into a SLEEPING BEAUTY® transposon vector. In yet other embodiments, the kill tag such as HER1t, HER1t-1, CD20 or CD20t-1 is cloned into a separate SLEEPING BEAUTY® transposon vector. In certain embodiments, the kill tags have a signal peptide, for instance, GM-CSFRa signal peptide wherein the GM-CSFRa signal peptide has at least 90%, 91%, 92%, 93%, 94%, 95%, 96%, 97%, 98%, 99% or 100% identity with the amino acid sequence of SEQ ID NO: 94. In certain embodiments, the signal peptide is IgK having a sequence at least 90%, 91%, 92%, 93%, 94%, 95%, 96%, 97%, 98%, 99% or 100% identity with the nucleic acid sequence of SEQ ID NO: 95.

In one embodiment, the signal peptide is Mouse Ig VH region 3 (SEQ ID NO: 101), Azurocidin (SEQ ID NO: 103), IGHV3-23 (SEQ ID NO: 106), IGKV1-D33 (HuL1) (SEQ ID NO: 107) or IGKV1-D33 (L14F) (HuH7) (SEQ ID NO: 108).

Exemplary gene expression cassettes encoding a CAR and a kill tag as described herein are shown in FIG. 1 and FIG. 2.

Exemplary CAR Open Reading Frames

Exemplary CAR and human ROR-1 receptor open reading frames encompassed by methods and compositions described herein are in Table 1:

TABLE 1

| SEQ ID NO | CAR ORF |
|---|---|
| 75 | hROR1(VH-VL)__14.CD8a(3x).CD28z |
| 76 | hROR1(VL-VH)__05.CD8a(3x).CD28z |
| 77 | hROR1(VH-VL)__14-3.CD8a(3x).CD28z |
| 78 | hROR1(VH-VL)__14-4.CD8a(3x).CD28z |
| 79 | hROR1(VH__5-VL__14).CD8a(3x).CD28z |
| 80 | hROR1(VH__5-VL__16).CD8a(3x).CD28z |
| 82 | hROR1(VH__18-VL__04).CD8a(3x).CD28z |
| 82 | hROR1(VH__18-VL__14).CD8a(3x).CD28z |

In embodiments, provided herein is an isolated nucleic acid encoding a CAR, wherein the CAR comprises a polypeptide having at least 90%, 91%, 92%, 93%, 94%, 95%, 96%, 97%, 98%, 99% or 100% identity with an amino acid of SEQ ID NOs: 3-14 or SEQ ID NOs: 75-82.

In embodiments, the CAR hROR1(VH-VL)_14.CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 17 (hROR1 VH_5) and a VL polypeptide having at least 90%, 91%, 92%, 93%, 94%, 95%, 96%, 97%, 98%, 99% or 100% identity with the amino acid sequence of SEQ ID NO: 18 (hROR1 VL_5).

In embodiments, the CAR hROR1(VL-VH)_05.CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 35 (hROR1 VH_14) and a VL polypeptide having at least 90%, 91%, 92%, 93%, 94%, 95%, 96%, 97%, 98%, 99% or 100% identity with the amino acid sequence of SEQ ID NO: 36 (hROR1 VL_14).

In embodiments, the CAR hROR1(VH-VL)_14-3.CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 41 (hROR1 VH_14-3) and a VL polypeptide having at least 90%, 91%, 92%, 93%, 94%, 95%, 96%, 97%, 98%, 99% or 100% identity with the amino acid sequence of SEQ ID NO: 42 (hROR1 VL_14-3).

In embodiments, the CAR hROR1(VH-VL)_14-4.CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 43 (hROR1 VH_14-4) and a VL polypeptide having at least 90%, 91%, 92%, 93%, 94%, 95%, 96%, 97%, 98%, 99% or 100% identity with the amino acid sequence of SEQ ID NO: 44 (hROR1 VL_14-4).

In embodiments, the CAR hROR1(VH_5-VL_14).CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 17 (hROR1 VH_5) and a VL polypeptide having at least 90%, 91%, 92%, 93%, 94%, 95%, 96%, 97%, 98%, 99% or 100% identity with the amino acid sequence of SEQ ID NO: 36 (hROR1 VL_14).

In embodiments, the CAR hROR1(VH_5-VL_16).CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 17 (hROR1 VH_05) and a VL polypeptide having at least 90%, 91%, 92%, 93%, 94%, 95%, 96%, 97%, 98%, 99% or 100% identity with the amino acid sequence of SEQ ID NO: 50 (hROR1 VL_16).

In embodiments, the CAR hROR1(VH_18-VL_04).CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 53 (hROR1 VH_18) and a VL polypeptide having at least 90%, 91%, 92%, 93%, 94%, 95%, 96%, 97%, 98%, 99% or 100% identity with the amino acid sequence of SEQ ID NO: 16 (hROR1 VL_04).

In embodiments, the CAR hROR1(VH_18-VL_14).CD8a (3x).CD28z comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 53 (hROR1 VH_18) and a VL polypeptide having at least 90%, 91%, 92%, 93%, 94%, 95%, 96%, 97%, 98%, 99% or 100% identity with the amino acid sequence of SEQ ID NO: 36 (hROR1 VL_14).

In each of the embodiments in Table 1, the signal peptide of the CAR can comprise a polypeptide having at least 90%, 91%, 92%, 93%, 94%, 95%, 96%, 97%, 98%, 99% or 100% identity with the amino acid sequence of Mouse Ig VH region 3 (SEQ ID NO: 101), Azurocidin (SEQ ID NO: 103), IGHV3-23 (SEQ ID NO: 106), IGKV1-D33 (HuL1) (SEQ ID NO: 107) or IGKV1-D33 (L14F) (HuH7) (SEQ ID NO: 108).

In each of the embodiments in Table 1 with "CD8a," the transmembrane region of the CAR comprises CD8alpha transmembrane domain comprising a polypeptide having at least 90%, 91%, 92%, 93%, 94%, 95%, 96%, 97%, 98%, 99% or 100% identity with the amino acid sequence of SEQ ID NO: 87, and the spacer is CD8a comprising a polypeptide having at least 90%, 91%, 92%, 93%, 94%, 95%, 96%, 97%, 98%, 99% or 100% identity with any one of the amino acid sequences as shown in SEQ ID NOs: 83-86.

In each of the embodiments in Table 1 with "CD28m," the intracellular domain of the CAR comprises CD28 with an amino acid sequence having at least 90%, 91%, 92%, 93%, 94%, 95%, 96%, 97%, 98%, 99% or 100% identity with the amino acid sequence of SEQ ID NO: 90.

In each of the embodiments in Table 1 with "T2A", the CAR ORF comprises a self-cleaving Thosea asigna virus (T2A) peptide, which enables the production of multiple gene products from a single vector. In embodiments, the T2A peptide has an amino acid sequence having at least 90%, 91%, 92%, 93%, 94%, 95%, 96%, 97%, 98%, 99% or 100% identity with the amino acid sequence of SEQ ID NO: 116.

In the embodiments in Table 1 with "HER1t," the CAR ORF comprises truncated human Epidermal Growth Factor Receptor 1 (HER1t), which provides a safety mechanism by allowing for depletion of infused CAR-T cells through administering FDA approved cetuximab therapy. The HER1t gene as described herein can comprise a polypeptide sequence having at least 90%, 91%, 92%, 93%, 94%, 95%, 96%, 97%, 98%, 99% or 100% identity with the amino acid sequence of SEQ ID NO: 109. Unless otherwise noted in Table 1, HER1t tags have GM-CSFRa signal peptide ("GM-CSFRsp") (SEQ ID NO: 94). In one embodiment, the signal peptide is Mouse Ig VH region 3 (SEQ ID NO: 101), Azurocidin (SEQ ID NO: 103), IGHV3-23 (SEQ ID NO: 106), IGKV1-D33 (HuL1) (SEQ ID NO: 107) or IGKV1-D33 (L14F) (HuH7) (SEQ ID NO: 108). In certain embodiments, the HER1t can be substituted with another tag, for instance, HER1t-1. The HER1t-1 gene as described herein can comprise a polypeptide sequence having at least 90%, 91%, 92%, 93%, 94%, 95%, 96%, 97%, 98%, 99% or 100% identity with the amino acid sequence of SEQ ID NO: 110. In the embodiments in Table 1 with "IgKsp," the signal peptide is IgK having an amino acid sequence at least 90%, 91%, 92%, 93%, 94%, 95%, 96%, 97%, 98%, 99% or 100% identity with the amino acid sequence of SEQ ID NO: 95.

In embodiments in Table 1 with "4-1BB," the CAR ORF comprises costimulatory molecule having a polypeptide sequence having at least 90%, 91%, 92%, 93%, 94%, 95%, 96%, 97%, 98%, 99% or 100% identity with the amino acid sequence of SEQ ID NO: 89.

In embodiments in Table 1 with "FL CD20," the CAR ORF comprises a full length CD20 tag comprising a polypeptide sequence having at least 90%, 91%, 92%, 93%, 94%, 95%, 96%, 97%, 98%, 99% or 100% identity with the amino acid sequence of SEQ ID NO: 111. CD20 provides a safety mechanism by allowing for depletion of infused CAR-T cells through administering FDA-approved rituximab therapy. In other embodiments, FL CD20 can be substituted with CD20t-1 comprising a polypeptide sequence having at least 90%, 91%, 92%, 93%, 94%, 95%, 96%, 97%, 98%, 99% or 100% identity with the amino acid sequence of SEQ ID NO: 112.

In certain embodiments in Table 1, the CAR ORF can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch. In some embodiments, the CAR ORF and gene switch components can be configured as depicted in FIGS. 1A-1E and FIGS. 2A-2E.

Cytokines

In some embodiments, a CAR described herein is administered to a subject with one or more additional therapeutic agents that include but are not limited to cytokines. In some cases, the cytokine comprises at least one chemokine, interferon, interleukin, lymphokine, tumor necrosis factor, or variant or combination thereof. In some cases, the cytokine is an interleukin. In some cases the interleukin is at least one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 and functional variants and fragments thereof. In some embodiments, the cytokines can be membrane bound or secreted. In embodiments, the cytokine is soluble IL-15, soluble IL-15/IL-15Rα complex (e.g., ALT-803). In certain cases, the interleukin can comprise membrane bound IL-15 (mbIL-15) or a fusion of IL-15 and IL-15Rα. In some embodiments, a mbIL-15 is a membrane-bound chimeric IL-15 which can be co-expressed with a modified immune effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," *PNAS* 2016. In some cases, the cytokine is expressed in the same immune effector cell as the CAR.

In further embodiments, an immune effector cell expressing a CAR described herein expresses membrane-bound IL-15 ("mIL-15 or mbIL-15"). In aspects of the invention, the mbIL-15 comprises a fusion protein between IL-15 and IL-15Rα. In further embodiments, the mbIL-15 comprises an amino acid sequence having at least 90%, 91%, 92%, 93%, 94%, 95%, 96%, 97%, 98%, 99% or 100% identity with the amino acid sequence of SEQ ID NO: 113. In certain cases, the CAR and the cytokine is expressed in separate vectors. In specific cases, the vectors can be lentiviral vectors, retroviral vectors or transposons.

In some embodiments, the mbIL-15 is expressed with a cell tag such as HER1t, HER-1t-1, CD20t-1 or CD20 as described herein. The mbIL-15 can be expressed in-frame with HER1t, HER-it-1, CD20t-1 or CD20.

In some embodiments, the mbIL-15 can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In another aspect, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties.

In some embodiments, the cytokines described above can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Gene Switch

Provided herein are gene switch polypeptides, polynucleotides encoding ligand-inducible gene switch polypeptides, and methods and systems incorporating these polypeptides and/or polynucleotides. The term "gene switch" refers to the combination of a response element associated with a promoter, and for instance, an ecdysone receptor (EcR) based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

Certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., *A Unified Nomenclature System for the Nuclear Receptor Subfamily,* 1999; *Cell* 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter ("IP") can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919; each of which is incorporated by reference in its entirety.

Provided are systems for modulating the expression of a CAR and/or a cytokine in a host cell, comprising polynucelotides encoding for gene-switch polypeptides disclosed herein. Further provided herein are polynucleotides encoding gene switch polypeptides for ligand-inducible control of gene expression, wherein the gene switch polypeptides comprise (a) a first gene switch polypeptide comprising a DNA-binding domain (DBD) fused to a nuclear receptor ligand binding domain; and (b) a second gene switch polypeptide comprising a transactivation domain fused to a nuclear receptor ligand binding domain; wherein the first gene switch polypeptide and the second gene switch polypeptide are connected by a linker. In some embodiments, the linker is a cleavable or ribosome skipping linker sequence selected from the group consisting of 2A, GSG-2A, GSG linker (SEQ ID NO: 129), SGSG linker (SEQ ID NO: 130), furinlink variants and derivatives thereof. In certain embodiments, the 2A linker is a p2A linker, a T2A linker, F2A linker, or E2A linker.

In some embodiments, the DNA binding domain (DBD) comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In some cases, the transactivation domain comprises at least one of a VP16 transactivation domain, and a B42 acidic activator transactivation domain. In other cases, the nuclear receptor ligand binding domain comprises at least one of a ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In some embodiments, the nuclear receptor ligand binding domain is derived from the Ecdysone Receptor polypeptide sequence of SEQ ID NOs: 135 and 136.

In yet another embodiment, the first gene switch polypeptide comprises a GAL4 DBD fused to an EcR nuclear receptor ligand binding domain, and the second gene switch polypeptide comprises a VP16 transactivation domain fused to a retinoid receptor X (RXR) nuclear receptor ligand binding domain. In some cases, the first gene switch polypeptide and the second gene switch polypeptide are connected by a linker, which is selected from the group consisting of 2A, GSG-2A, GSG linker (SEQ ID NO: 129), SGSG linker (SEQ ID NO: 130), furinlink variants and derivatives thereof.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or more of: F/T2A, T2A, p2A, 2A, GSG-p2A, GSG linker (SEQ ID NO: 129), and furinlink variants. In certain embodiments, the linker polypeptide comprises any one of the amino acid sequences as shown in SEQ ID NOs: 116-130.

In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Val/Ile-Glu-X-Asn-Pro-Gly-Pro (SEQ ID NO: 286). A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston, Kallioinen et al. 2008). In some embodiments, a 2A sequence can include: F/T2A, T2A, p2A, 2A, T2A, E2A, F2A, and BmCPV2A, BmIFV2A, and any combination thereof.

In some cases, a vector can comprise an IRES sequence and a 2A linker sequence. In other cases, expression of multiple genes linked with 2A peptides can be facilitated by a spacer sequence (GSG (SEQ ID NO: 129)) ahead of the 2A peptides. In some cases, constructs can combine a spacers, linkers, adaptors, promotors, or combinations thereof. For example, a construct can have a spacer (SGSG (SEQ ID NO: 130) or GSG (SEQ ID NO: 129)) and furin linker (R-A-K-R (SEQ ID NO: 125)) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector. For example, genes of interest can be separated by at least two linkers.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described in SEQ ID NOs: 119, 120, 121, 125, and 128.

In some embodiments, a linker can be utilized in a polynucleotide described herein. A linker can be a flexible linker, a rigid linker, an in vivo cleavable linker, or any combination thereof. In some cases, a linker can link functional domains together (as in flexible and rigid linkers) or releasing free functional domain in vivo as in in vivo cleavable linkers.

Linkers can improve biological activity, increase expression yield, and achieving desirable pharmacokinetic profiles. A linker can also comprise hydrazone, peptide, disulfide, or thioesther.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of $(Gly-Gly-Gly-Gly-Ser)_n$ (SEQ ID NO: 287). By adjusting the copy number "n", the length of this exemplary GS linker can be optimized to achieve appropriate separation of functional domains, or to maintain necessary inter-domain interactions. For example, $(Gly-Gly-Gly-Gly-Ser)_n$, wherein n is 3 is (G4S)3 linker as shown in SEQ ID NO: 127. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers do not have rigid structures in some cases, they can serve as a passive linker to keep a distance between functional domains. The length of a flexible linkers can be adjusted to allow for proper folding or to achieve optimal biological activity of the fusion proteins.

A linker described herein can further include a rigid linker in some cases. A rigid linker can be utilized to maintain a fixed distance between domains of a polypeptide. Examples of rigid linkers can be: Alpha helix-forming linkers, Pro-rich sequence, $(XP)_n$, X-Pro backbone, $A(EAAAK)_nA$ (n=2-5) (SEQ ID NO: 288), to name a few. Rigid linkers can exhibit relatively stiff structures by adopting α-helical structures or by containing multiple Pro residues in some cases.

A linker described herein can be cleavable in some cases. In other cases a linker is not cleavable. Linkers that are not cleavable can covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein can also be carried out by proteases that can be expressed in vivo under pathological conditions (e.g., cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioesther. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO: 126. In certain embodiments, an fmdv linker polypeptide is one or more of the linkers encoded in a single vector linking two or more fusion proteins. In certain cases, an fmdv linker polypeptide can be encoded by a polynucleotide open reading frame (ORF) nucleic acid sequence. In some cases, an ORF encoding fmdv comprises or consists of a sequence of SEQ ID NO: 272. In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO: 272.

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 119. In certain embodiments, the p2a linker polypeptide can be one or more of the linkers encoded in a single vector linking two or more fusion proteins. In some cases, a p2a linker polypeptide can be encoded by a polynucleotide open reading frame (ORF) nucleic acid sequence. In certain embodiments, an ORF encoding p2a comprises or consists of the sequence of SEQ ID NO: 266. In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO: 266.

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 120. In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG p2a can comprises the sequence of SEQ ID NO: 267. In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO: 267.

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 121. In certain cases, an fp2a linker polypeptide can be one or more of the linkers encoded in a single vector linking two or more fusion proteins. In some cases, a fp2a linker polypeptide can be encoded by a polynucleotide open reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO: 268.

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99%, or 100% identical to a sequence of SEQ ID NO: 116 to SEQ ID NO: 130. In other cases, multiple linkers can be used in a vector. For example, genes of interest, and one or more gene switch polypeptide sequences described herein can be separated by at least two linkers. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W). In some cases, a polypeptide linker can also include one or more GS linker sequences, for instance $(GS)_n$ (SEQ ID NO: 289), $(SG)_n$ (SEQ ID NO: 290), $(GSG)_n$ (SEQ ID NO: 291) and $(SGSG)_n$ (SEQ ID NO: 292) wherein n can be any number from zero to fifteen.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ (SEQ ID NO: 293); and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ (SEQ ID NO: 293).

In other instances, the linker can be an IRES. The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith 1995).

Exemplary IRES sequences can be found in SEQ ID NO: 146 and 147. In certain cases, a polynucleotide encoding 2xRbm3 IRES a can be or can be about at least 45%, 50%, 55%, 60%, 65%, 70%, 75%, 80%, 85%, 90%, 95%, 97%, 98%, 99% or 100% identical to SEQ ID NO: 146. In certain cases, a polynucleotide encoding EMCV IRES a can be or can be about at least 45%, 50%, 55%, 60%, 65%, 70%, 75%, 80%, 85%, 90%, 95%, 97%, 98%, 99% or 100% identical to SEQ ID NO: 147.

In some embodiments are systems for modulating the expression of a CAR and a cytokine in a host cell, comprising a first gene expression cassette comprising a first polynucleotide encoding a first polypeptide; a second gene expression cassette comprising a second polynucleotide encoding a second polypeptide; and a ligand; wherein the first and second polypeptides comprise one or more of: (i) a transactivation domain; (ii) a DNA-binding domain; and (iii) a ligand binding domain; (iv) CAR; (vi) cytokine, and/or (vii) cell tag such that upon contacting the host cell with the first gene expression cassette and the second gene expression cassette in the presence of the ligand, the CAR and the cytokine are expressed in the host cell. In some cases, the CAR is a ROR-1 CAR and the cytokine is mbIL-15. In some cases, ROR-1CAR, mbIL-15 are co-expressed with one cell tag. In some cases, ROR-1 CAR and mbIL-15 are each co-expressed with a cell tag. In other cases, ROR-1 CAR is expressed with a cell tag and mbIL-15 is expressed with a second cell tag. Exemplary configurations of gene expression cassettes are depicted in FIGS. 1 and 2. In other cases, the CAR is a ROR-1 CAR and the cytokine is IL-12. In some cases, ROR-1 CAR, IL-12 are co-expressed with one cell tag. In some cases, ROR-1 CAR and IL-12 are each co-expressed with a cell tag. In other cases, ROR-1 CAR is expressed with a cell tag and IL-12 is expressed with a second cell tag.

In some embodiments are systems for modulating the expression of a CAR and a cytokine in a host cell, comprising a first gene expression cassette comprising a first polynucleotide encoding a first polypeptide; a second gene expression cassette comprising a second polynucleotide encoding a second polypeptide; and a ligand; wherein the first polypeptide comprise one or more of: (i) a transactivation domain; (ii) a DNA-binding domain; and (iii) a ligand binding domain and the second polypeptide comprise one or more of (i) CAR; (ii) cytokine, and/or (iii) cell tag such that upon contacting the host cell with the first gene expression cassette and the second gene expression cassette in the presence of the ligand, the CAR and/or the cytokine are expressed in the host cell. In some cases, the CAR is a ROR-1 CAR and the cytokine is mbIL-15. In some cases, ROR-1 CAR and mbIL-15 are each co-expressed with a cell tag. In other cases, ROR-1 CAR is expressed with a first cell tag and mbIL-15 is expressed with a second cell tag.

Exemplary configurations of systems for modulating the expression of a ROR-1 CAR and a cytokine in a host cell are depicted in FIGS. 1A-1E and FIGS. 2A-2E. In some embodiments, the gene expression cassettes are introduced into an immune effector cell using viral or viral based systems. Examples of non-viral based delivery systems as described herein include SB11 transposon system, the SB100X transposon system, the SB110 transposon system, the PIGGYBAC® transposon system. In one embodiment, the gene expression cassettes are introduced into an immune effector cell in one or more transposons.

Figure 1A:
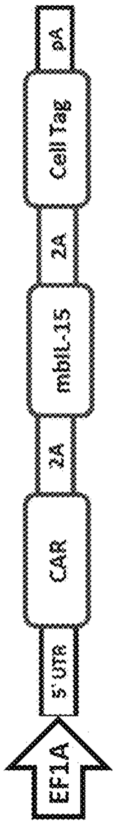
FIGS. 1A-1E depict exemplary gene expression cassettes for ROR1 CARs and cytokines in different configurations. In certain cases, the ROR1 CAR and/or cytokine can be co-expressed with a cell or kill tag for conditional in vivo ablation. Exemplary gene expression cassettes or combinations thereof for constitutive expression of ROR1 CAR and mbIL-15 can include c+e or d+e.
Figure 1B:
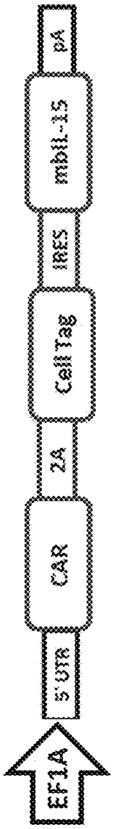
Figure 1C:
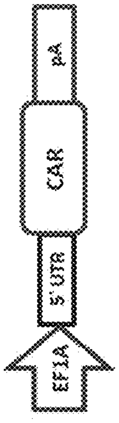
Figure 1D:
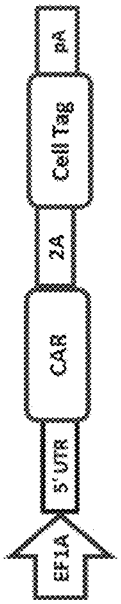
Figure 1E:
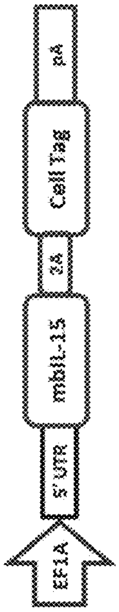

Exemplary embodiments of gene expression cassettes that encode for constitutive expression of ROR-1 CAR, cytokine (such as mbIL-15 or IL-12) and cell tag are depicted in FIGS. 1A-1E. FIGS. 1A-1B depict exemplary gene expression cassette designs for ROR-1 CAR, mbIL-15 and cell tag in various configurations. In this embodiment, the gene expression cassette is introduced into an immune effector cell in one transposon. FIGS. 1C-1D depict gene expression cassette configurations where ROR-1 CAR can be in one gene expression cassette and mbIL-15 and cell tag are in a second gene expression cassette. In this embodiment, the gene expression cassette is introduced into an immune effector cell in one or more transposons.

Figures 2A, 2B, 2C, 2D, 2E:
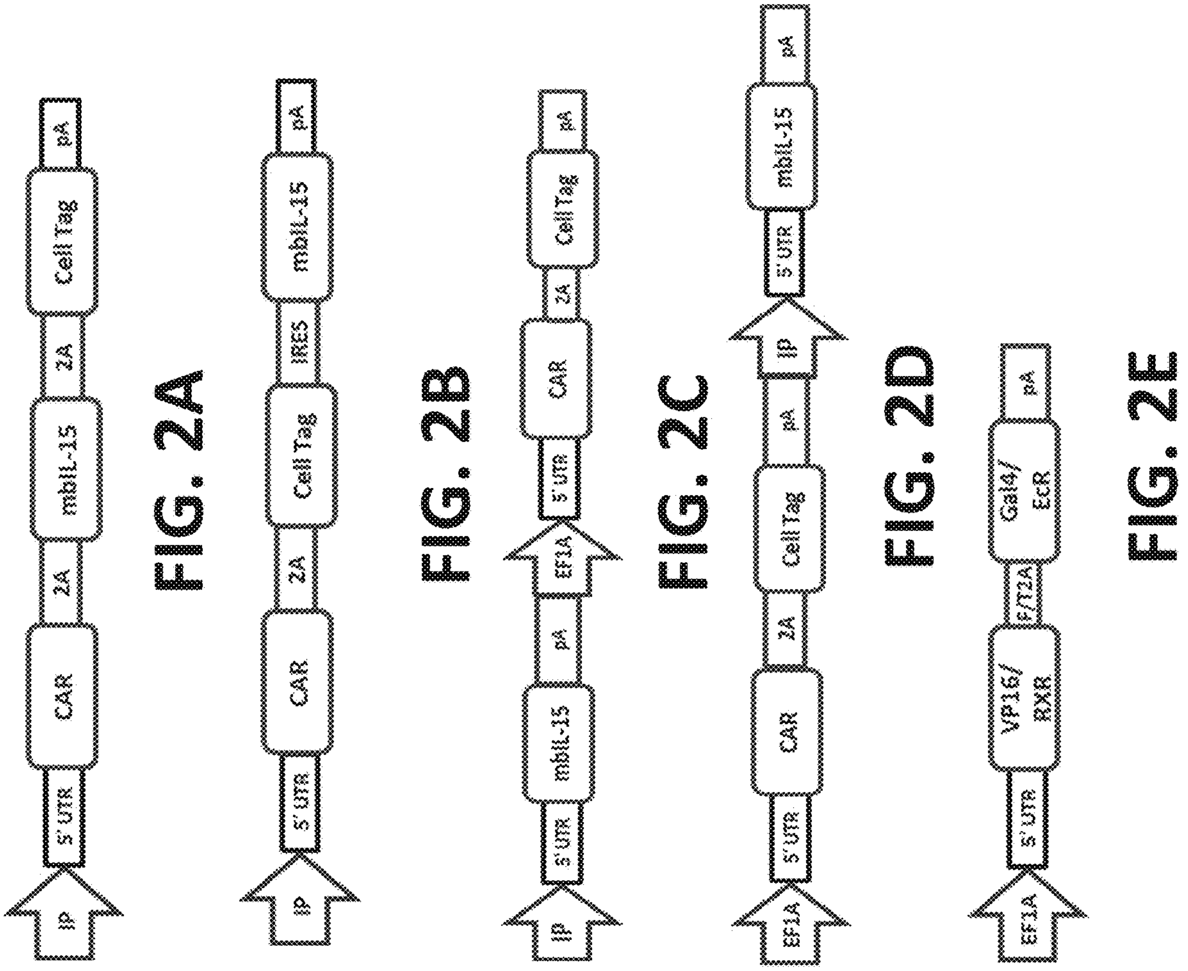
FIGS. 2A-2E depict exemplary gene expression cassettes for ROR1 CARs and cytokines in different configurations with gene switch components. Exemplary gene expression cassettes or combinations thereof for inducible expression can include a+e, b+e, c+e, or d+e.

Exemplary embodiments of gene expression cassettes that encode for expression of ROR-1 CAR, inducible cytokine (such as mbIL-15) and/or cell tag are depicted in FIGS. 2A-2E. FIGS. 2A-2D depict exemplary gene expression cassette designs for ROR-1 CAR, mbIL-15 and cell tag in various configurations under the control of an inducible promoter. FIG. 2E is an exemplary embodiment of a gene expression cassette encoding gene-switch polypeptides as described herein. In this embodiment, the gene expression cassette(s) is introduced into an immune effector cell in one or more transposons.

Ligands

In some embodiments, a ligand used for inducible gene switch regulation can be selected from any of, but without limitation to, following: N-[(1R)-1-(1,1-dimethylethyl) butyl]-N'-(2-ethyl-3-methoxybenzoyl)-3,5-dimethylbenzohydrazide (also referred to as veledimex), (2S,3R,5R,9R, 10R,13R,14S,17R)-17-[(2S,3R)-3,6-dihydroxy-6-methylheptan-2-yl]-2,3,14-trihydroxy-10,13-dimethyl-2,3, 4,5,9,11,12,15,16,17-decahydro-1H-cyclopenta[a] phenanthren-6-one; N'-(3,5-Dimethylbenzoyl)-N'-[(3R)-2, 2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1, 4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, a ligand used for dose-regulated control of ecdysone receptor-based inducible gene switch can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present disclosure include RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-b enzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

Non-Viral Based Delivery Systems

A nucleic acid encoding a CAR described invention can also be introduced into immune effector cells using non-viral based delivery systems, such as the "SLEEPING BEAUTY® (SB) Transposon System," which refers a synthetic DNA transposon system for introducing DNA sequences into the chromosomes of vertebrates. An exemplary SB transposon system is described for example, in U.S. Pat. Nos. 6,489,458 and 8,227,432. The SLEEPING BEAUTY® transposon system comprises a SLEEPING BEAUTY® Tc1/mariner-type (SB) transposase and SB transposon(s). As used herein, the SLEEPING BEAUTY® transposon system can comprise SLEEPING BEAUTY® Tc1/mariner-type transposase polypeptides as well as derivatives, variants and/or fragments that retain activity, and SLEEPING BEAUTY® transposon polynucleotides, derivatives, variants, and/or fragments that retain activity. In certain embodiments, the SLEEPING BEAUTY® transposase is provided as an mRNA. In some aspects, the mRNA encodes for a SB10, SB11, SB100X or SB110 transposase. In some aspects, the mRNA comprises a cap and a poly-A tail.

DNA transposons translocate from one DNA site to another in a simple, cut-and-paste manner. Transposition is a precise process in which a defined DNA segment is excised from one DNA molecule and moved to another site in the same or different DNA molecule or genome. As with other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy. Briefly, the SLEEPING BEAUTY® (SB) system (Hackett et al., *Mol Ther* 18:674-83, (2010)) was adapted to genetically modify the immune effector cells (Cooper et al., *Blood* 105:1622-31, (2005)). In one embodiment, this involved two steps: (i) the electro-transfer of DNA plasmids expressing a SB transposon [i.e., chimeric antigen receptor (CAR) to redirect T-cell specificity (Jin et al., *Gene Ther* 18:849-56, (2011); Kebriaei et al., *Hum Gene Ther* 23:444-50, (2012)) and SB transposase and (ii) the propagation and expansion of T cells stably expressing integrants on designer artificial antigen-presenting cells (AaPC) derived from the K562 cell line (also known as AaPCs (Activating and Propagating Cells). In another, embodiment, the second step (ii) is eliminated and the genetically modified T cells are cryopreserved or immediately infused into a patient.

In one embodiment, the SB transposon systems are described for example in Hudecek et al., *Critical Reviews in Biochemistry and Molecular Biology,* 52:4, 355-380 (2017), Singh et al., *Cancer Res* (8):68 (2008). Apr. 15, 2008 and Maiti et al., *J Immunother.* 36(2): 112-123 (2013), incorporated herein by reference in their entireties.

In certain embodiments, a ROR-1 CAR and mbIL-15 are encoded in a transposon DNA plasmid vector, and the SB transposase is encoded in a separate vector. In certain embodiments, a ROR-1 CAR described herein is encoded in a transposon DNA plasmid vector, mb-IL15 is encoded in a second transposon DNA plasmid vector, and the SB transposase is encoded in a third DNA plasmid vector. In some embodiment, the CAR is encoded with a kill tag, for instance, HER1, HER1t1, CD20 or CD20t-1. In some embodiments, the mbIL-15 is encoded with a kill tag, for instance, HER1t, HER1t1, CD20 or CD20t-1. Exemplary configurations of the ROR-1 CAR, kill tag and/or mbIL15 are depicted in FIG. 1.

In embodiments, the ROR-1 CAR can be co-expressed with mbIL-15 and the cell tag from a transposon DNA plasmid vector. In further embodiments, the ROR-1 CAR can be under the control of an inducible promoter. In another embodiment, the mbIL-15 can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch. In certain embodiments, the ROR-1 CAR, mbIL-15 and kill tag can be configured in one, two or more transposons. Exemplary configurations of the ROR-1 CAR or mbIL15 under the control of an inducible promoter are depicted in FIG. 2.

In embodiments, the ROR-1 CARs and other genetic elements are delivered to a cell using the SB11 transposon system, the SB100X transposon system, the SB110 transposon system, the PIGGYBAC® transposon system (see, e.g., U.S. Pat. No. 9,228,180, Wilson et al, "PiggyBac Transposon-mediated Gene Transfer in Human Cells," *Molecular Therapy* 15:139-145 (2007), incorporated herein by reference in its entirety) and/or the piggyBat transposon system (see, e.g., Mitra et al., "Functional characterization of piggyBat from the bat *Myotis lucifugus* unveils an active mammalian DNA transposon," *Proc. Natl. Acad. Sci USA* 110:234-239 (2013). Additional transposases and transposon systems are provided in U.S. Pat. Nos.; 7,148,203; 8,227,432; 2011/0117072; Mates et al., *Nat Genet,* 41(6):753-61 (2009). doi: 10.1038/ng.343. Epub 2009 May 3*, Gene Ther.,* 18(9):849-56 (2011). doi: 10.1038/gt.2011.40. Epub 2011 Mar. 31 and in Ivics et al., *Cell.* 91(4):501-10, (1997), each of which is incorporated herein by reference in their entirety.

In other embodiments, the ROR-1 CAR and other genetic elements such as cytokines, mbIL-15 and/or HER1t/HER1t1/CD20/CD20t-1 tag, can be integrated into the immune effector cell's DNA through a recombinase and integrating expression vectors. Such vectors can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

A recombinase can be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda (k) integrase. In the resolvase family, also known as the serine recombinase family, a conserved serine residue forms a covalent link to the DNA target site (Grindley, et al., (2006) *Ann Rev Biochem* 16:16).

In one embodiment, the recombinase is an isolated polynucleotide sequence comprising a nucleic acid sequence that encodes a recombinase selecting from the group consisting of a SPβc2 recombinase, a SF370.1 recombinase, a Bxbl recombinase, an A118 recombinase and a ΦRv1 recombinase. Examples of serine recombinases are described in detail in U.S. Pat. No. 9,034,652, hereby incorporated by reference in its entirety.

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, *Proc. Nat. Acad. Sci.* 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ΦRv1 recombinase, and a Bxbl recombinase. In one embodiment the recombination results in integration.

Regardless of the method used to introduce exogenous nucleic acids into a host cell, in order to confirm the presence of the recombinant DNA sequence in the host cell, a variety of assays can be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify peptides or proteins or nucleic acids falling within the scope of the invention.

Viral Based Delivery Systems

Also provided herein are viral-based delivery systems, in which a nucleic acid of the present invention is inserted. Representative viral expression vectors include, but are not limited to, the adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)) and retroviral vectors (e.g., the pFB-ERV plus pCFB-EGSH), herpes viruses. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, and in embodiments, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In embodiments, provided is a lentiviral vector comprising a backbone and a nucleic acid sequence encoding a chimeric antigen receptor (CAR), wherein the CAR comprises (a) a ROR-1 antigen binding domain; (b) a stalk domain; (c) a transmembrane domain; (d) a costimulatory signaling domain comprising 4-1BB or CD28, or both; (e) a CD3 zeta signaling domain. Optionally, the vector further comprises a nucleic acid encoding a truncated epidermal growth factor receptor (HER1t or HER1t1), CD20t-1 or a full length CD20.

In some cases is provided a vector comprising a backbone and a nucleic acid sequence encoding (1) a truncated epidermal growth factor receptor for instance HER1t or HERt-1 or a functional variant thereof; and (2) a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and (e) a CD3 zeta signaling domain.

In some cases is provided a vector comprising a backbone and a nucleic acid sequence encoding (1) full length CD20, truncated CD20 or functional variants thereof, and (2) a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and (e) a CD3 zeta signaling domain.

In embodiments, the nucleic acid encoding the ROR-1 specific CAR is cloned into a vector comprising lentiviral backbone components. Exemplary backbone components include, but are not limited to, pFUGW, and pSMPUW. The pFUGW lentiviral vector backbone is a self inactivating (SIN) lentiviral vector backbone and has unnecessary HIV-1 viral sequences removed resulting in reduced potential for the development of neoplasia, harmful mutations, and regeneration of infectious particles. In embodiments, the vector encoding the ROR-1 CAR also encodes mbIL-15 in a single construct. In embodiments, the ROR-1 CAR and mbIL-15 are encoded on two separate lentiviral vectors. In some embodiments, the mbIL-15 is expressed with a truncated epidermal growth factor receptor tag. In embodiments, the ROR-1 CAR can be co-expressed with mbIL-15 and the cell tag from a single lentiviral vector. In further embodiments, the ROR-1 CAR can be under the control of an inducible promoter. In another embodiment, the mbIL-15 can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In one embodiment, a ROR-1 CAR described herein comprises anti-ROR-1 scFv, human CD8 hinge and transmembrane domain, and human 4-1BB and CD3zeta signaling domains. In another embodiment, the ROR-1 CAR of the invention comprises anti-ROR-1 scFv, human CD8 hinge and transmembrane domain, human 4-1BB and CD3zeta signaling domains and optionally, a truncated epidermal growth factor receptor (HER1t or HER1t-1) tag. Other suitable vectors include integrating expression vectors, which can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is human elongation growth factor 1 alpha 1 (hEF1a1). In embodiments, the vector construct comprising a CAR described herein comprises hEF1a1 functional variants.

However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention as previously described. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In order to assess the expression of a CAR described herein or portions thereof, the expression vector to be introduced into a cell can also contain either a selectable marker gene or a reporter gene or both to facilitate identification and selection of expressing cells from the population of cells sought to be transfected or infected through viral vectors or non-viral vectors. In other aspects, the selectable marker can be carried on a separate piece of DNA and used in a co-transfection procedure. Both selectable markers and reporter genes can be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HER1t or HER1t-1) tag can be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes include genes encoding luciferase, beta-galactosidase, chloramphenicol acetyl transferase, secreted alkaline phosphatase, or the green fluorescent protein gene (e.g., Ui-Tei et al., *FEBS Letters* 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

In embodiments, a viral vector described herein can comprise a hEF1a1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

Methods of introducing and expressing genes into a cell are well known. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell, for instance an immune effector cell, include calcium phosphate precipitation, lipofection, particle bombardment, microinjection, electroporation, and the like. Methods for producing cells comprising vectors and/or exogenous nucleic acids are well-known in the art. See, for example, Sambrook et al. (*Molecular Cloning: A Laboratory Manual*, Cold Spring Harbor Laboratory, New York (2001)). In embodiments, a method for the introduction of a polynucleotide into a host cell is calcium phosphate transfection or polyethylenimine (PEI) Transfection. In some embodiments, a method for introduction of a polynucleotide into a host cell is electroporation.

Biological methods for introducing a polynucleotide of interest into a host cell, for instance an immune effector cell, include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a viral delivery system is utilized, an exemplary delivery vehicle is a liposome. Lipid formulations can be used for the introduction of the nucleic acids into a host cell (in vitro, ex vivo, or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., *Glycobiology* 5: 505-10 (1991)). However, compositions that have different structures in solution than the normal vesicular structure are also encompassed. For example, the lipids can assume a micellar structure or merely exist as nonuniform aggregates of lipid molecules. Also contemplated are lipofectamine-nucleic acid complexes.

Cells Comprising ROR-1 CARs and Vectors

Provided herein are engineered cells expressing a CAR described herein. In certain embodiments, an engineered cell described herein is an immune effector cell. In embodiments, provided herein is an immune effector cell comprising a vector comprising a backbone and a nucleic acid sequence encoding (1) a truncated epidermal growth factor receptor (HER1t or HER1t1) and (2) a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and e) a CD3 zeta signaling domain.

In certain embodiments is an immune effector cell comprising a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; e) a CD3 zeta signaling domain; and (f) a truncated epidermal growth factor receptor (HER1t or HER1t1).

In embodiments, provided herein is an immune effector cell comprising (1) a cell tag for use as a kill switch, selection marker, a biomarker, or a combination thereof, and (2) a chimeric antigen receptor (CAR), wherein the CAR comprises (a) a ROR-1 antigen binding domain; (b) a spacer; (c) a transmembrane domain; (d) a costimulatory signaling domain comprising 4-1BB or CD28, or both; and (e) a CD3 zeta signaling domain. In embodiments, the cell tag is HER1t, HER1t1, CD20t-1 or CD20.

In embodiments, an immune effector cell is a T cell, a Natural Killer (NK) cell, a cytotoxic T lymphocyte (CTL), and a regulatory T cell. In embodiments, the cell exhibits an anti-tumor activity when the ROR-1 antigen binding domain binds to ROR-1.

Modified Immune Effector Cells

Provided are immune effector cells modified to express one or more heterologous genes or polypeptides described herein. Provided are immune effector cells modified to express a ROR-1 CAR described herein and at least one of a HER1t, HER1t1, CD20 and CD20t-1 tag. In some cases is provided an immune effector cell modified to express ROR-1 CAR, mbIL-15 and at least one of a HER1t, HER1t1, CD20 and CD20t-1 tag disclosed herein.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

In some embodiments, modified immune effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, TH17 cells, stem memory T cells (TSCM), naïve T cells, memory T cells, effector T cells, regulatory T cells, or natural killer T cells.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

Cytotoxic T cells (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells can be either CD4+ or CD8+. Memory T cells can express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th (T helper) and Tc (cytotoxic T) cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

Modified Immune Effector Cell Doses

In some embodiments, an amount of modified immune effector cells is administered to a subject in need thereof and the amount is determined based on the efficacy and the potential of inducing a cytokine-associated toxicity. In some cases, an amount of modified immune effector cells comprises about $10^2$ to about $10^9$ modified immune effector cells/kg. In some cases, an amount of modified immune effector cells comprises about $10^3$ to about $10^9$ modified immune effector cells/kg. In some cases, an amount of modified immune effector cells comprises about $10^4$ to about $10^9$ modified immune effector cells/kg. In some cases, an amount of modified immune effector cells comprises about $10^5$ to about $10^9$ modified immune effector cells/kg. In some cases, an amount of modified immune effector cells comprises about $10^5$ to about $10^8$ modified immune effector cells/kg. In some cases, an amount of modified immune effector cells comprises about $10^5$ to about $10^7$ modified immune effector cells/kg. In some cases, an amount of modified immune effector cells comprises about $10^6$ to about $10^9$ modified immune effector cells/kg. In some cases, an amount of modified immune effector cells comprises about $10^6$ to about $10^8$ modified immune effector cells/kg. In some cases, an amount of modified immune effector cells comprises about $10^7$ to about $10^9$ modified immune effector cells/kg. In some cases, an amount of modified immune effector cells comprises about $10^5$ to about $10^6$ modified immune effector cells/kg. In some cases, an amount of modified immune effector cells comprises about $10^6$ to about $10^7$ modified immune effector cells/kg. In some cases, an amount of modified immune effector cells comprises about $10^7$ to about $10^8$ modified immune effector cells/kg. In some cases, an amount of modified immune effector cells comprises about $10^8$ to about $10^9$ modified immune effector cells/kg. In some instances, an amount of modified immune effector cells comprises about $10^9$ modified immune effector cells/kg. In some instances, an amount of modified immune effector cells comprises about $10^8$ modified immune effector cells/kg. In some instances, an amount of modified immune effector cells comprises about $10^7$ modified immune effector cells/kg. In some instances, an amount of modified immune effector cells comprises about $10^6$ modified immune effector cells/kg. In some instances, an amount of modified immune effector cells comprises about $10^5$ modified immune effector cells/kg.

In some embodiments, are CAR-T cells which are ROR-1-specific CAR-T cells. In some cases, an amount of ROR-1-specific CAR-T cells comprises about $10^2$ to about $10^9$ CAR-T cells/kg. In some cases, an amount of ROR-1-specific CAR-T cells comprises about $10^3$ to about $10^9$ CAR-T cells/kg. In some cases, an amount of ROR-1-specific CAR-T cells comprises about $10^4$ to about $10^9$ CAR-T cells/kg. In some cases, an amount of ROR-1-specific CAR-T cells comprises about $10^5$ to about $10^9$ CAR-T cells/kg. In some cases, an amount of ROR-1-specific CAR-T cells comprises about $10^5$ to about $10^8$ CAR-T cells/kg. In some cases, an amount of ROR-1-specific CAR-T cells comprises about $10^5$ to about $10^7$ CAR-T cells/kg. In some cases, an amount of ROR-1-specific CAR-T cells comprises about $10^6$ to about $10^9$ CAR-T cells/kg. In some cases, an amount of ROR-1-specific CAR-T cells comprises about $10^6$ to about $10^8$ CAR-T cells/kg. In some cases, an amount of ROR-1-specific CAR-T cells comprises about $10^7$ to about $10^9$ CAR-T cells/kg. In some cases, an amount of ROR-1-specific CAR-T cells comprises about $10^5$ to about $10^6$ CAR-T cells/kg. In some cases, an amount of ROR-1-specific CAR-T cells comprises about $10^6$ to about $10^7$ CAR-T cells/kg. In some cases, an amount of ROR-1-specific CAR-T cells comprises about $10^7$ to about $10^8$ CAR-T cells/kg. In some cases, an amount of ROR-1-specific CAR-T cells comprises about $10^8$ to about $10^9$ CAR-T cells/kg. In some instances, an amount of ROR-1-specific CAR-T cells comprises about $10^9$ CAR-T cells/kg. In some instances, an amount of ROR-1-specific CAR-T cells comprises about $10^8$ CAR-T cells/kg. In some instances, an amount of ROR-1-specific CAR-T cells comprises about $10^7$ CAR-T cells/kg. In some instances, an amount of ROR-1-specific CAR-T cells comprises about $10^6$ CAR-T cells/kg. In some instances, an amount of ROR-1-specific CAR-T cells comprises about $10^5$ CAR-T cells/kg. In some instances, an amount of ROR-1-specific CAR-T cells comprises about $10^4$ CAR-T cells/kg. In some instances, an amount of ROR-1-specific CAR-T cells comprises about $10^3$ CAR-T cells/kg. In some instances, an amount of ROR-1-specific CAR-T cells comprises about $10^2$ CAR-T cells/kg.

Immune Effector Cell Sources

In certain aspects, the embodiments described herein include methods of making and/or expanding the antigen-specific redirected immune effector cells (e.g., T-cells, Tregs, NK-cell or NK T-cells) that comprises transfecting the cells with an expression vector containing a DNA (or RNA) construct encoding the CAR, then, optionally, stimulating the cells with feeder cells, recombinant antigen, or an antibody to the receptor to cause the cells to proliferate. In certain aspects, the cell (or cell population) engineered to express a CAR is a stem cell, iPS cell, T cell differentiated from iPS cell, immune effector cell or a precursor of these cells.

Sources of immune effector cells can include both allogeneic and autologous sources. In some cases immune effector cells can be differentiated from stem cells or induced pluripotent stem cells (iPSCs). Thus, cell for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. In one aspect, the immune effector cells are Pan T cells. Following transfection or transduction (e.g., with a CAR expression construct), the cells can be immediately infused or can be cryo-preserved. In certain aspects, following transfection or transduction, the cells can be preserved in a cytokine bath that can include IL-2 and/or IL-21 until ready for infusion. In certain aspects, following transfection, the cells can be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells can be expanded by stimulation with IL-2, or other cytokines that bind the common gamma-chain (e.g., IL-7, IL-12, IL-15, IL-21, and others). The recombinant T cells can be expanded by stimulation with artificial antigen presenting cells. The recombinant T cells can be expanded on artificial antigen presenting cell or with an antibody, such as OKT3, which cross links CD3 on the T cell surface. Subsets of the recombinant T cells can be further selected with the use of magnetic bead based isolation methods and/or fluorescence activated cell sorting technology and further cultured with the AaPCs. In a further aspect, the genetically modified cells can be cryopreserved.

T cells can also be obtained from a number of sources, including bone marrow, lymph node tissue, cord blood, thymus tissue, tissue from a site of infection, ascites, pleural effusion, spleen tissue, and tumors. In certain embodiments of the present invention, any number of T cell lines available in the art, can be used. In certain embodiments of the present invention, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. Initial activation steps in the absence of calcium lead to magnified activation. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample can be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. In another embodiment, CD14+ cells are depleted from the T-cell population. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it can be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells, or from samples where there are many tumor cells present (i.e., leukemic blood, tumor tissue, etc.). Such populations of cells can have therapeutic value and would be desirable to obtain. For example, using high concentration of cells allows more efficient selection of $CD8^+$ T cells that normally have weaker CD28 expression.

In a related embodiment, it can be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells can be incubated on a rotator for varying lengths of time at varying speeds at either 2-10° C. or at room temperature.

T cells for stimulation can also be frozen after a washing step. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° C. per minute and stored in the vapor phase of a liquid nitrogen storage tank. Other methods of controlled freezing can be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also provided in certain embodiments is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells can be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, (1991); Henderson et al., *Immun* 73:316-321, (1991); Bierer et al., *Curr. Opin. Immun* 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained can be optimal or improved for their ability to expand ex vivo. Likewise, following ex vivo manipulation using the methods described herein, these cells can be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after engineering of the T cells to express a CAR described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells described herein are expanded by contact with a surface having attached thereto an agent that stimulates a CD3/TCR complex associated signal and a ligand that stimulates a co-stimulatory molecule on the surface of the T cells. In particular, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, (1998); Haanen et al., *J. Exp. Med.* 190(9):13191328, (1999); Garland et al., *J. Immunol Meth.* 227(1-2):53-63, (1999)).

In certain embodiments, the primary stimulatory signal and the co-stimulatory signal for the T cell can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between can be used to stimulate T cells or other target cells. As those of ordinary skill in the art can readily appreciate, the ratio of particles to cells can depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios can be suitable for use in the present invention. In particular, ratios will vary depending on particle size and on cell size and type.

In further embodiments described herein, the immune effector cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins can be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1, or MACS® MicroBeads from Miltenyi Biotec) are combined in a buffer, for example, PBS (without divalent cations such as, calcium and magnesium). Again, those of ordinary skill in the art can readily appreciate any cell concentration can be used. For example, the target cell can be very rare in the sample and comprise only 0.01% of the sample or the entire sample (i.e., 100%) can comprise the target cell of interest. Accordingly, any cell number is within the context of the present invention. In certain embodiments, it can be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells. Such populations of cells can have therapeutic value and would be desirable to obtain in certain embodiments. For example, using high concentration of cells allows more efficient selection of CD8+ T cells that normally have weaker CD28 expression.

In one embodiment described herein, the mixture can be cultured for several hours (about 3 hours) to about 14 days or any hourly integer value in between. In another embodiment, the mixture can be cultured for 21 days. In one embodiment of the invention the beads and the T cells are cultured together for about eight days. In another embodiment, the beads and T cells are cultured together for 2-3 days. Several cycles of stimulation can also be desired such that culture time of T cells can be 60 days or more. Conditions appropriate for T cell culture include an appropriate media (e.g., Minimal Essential Media or RPMI Media 1640 or, X-vivo 15, (Lonza)) that can contain factors necessary for proliferation and viability, including serum (e.g., fetal bovine or human serum), interleukin-2 (IL-2), insulin, IFN-.gamma., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times can exhibit different characteristics. For example, typical blood or apheresed peripheral blood mononuclear cell products have a helper T cell population ($T_H$, $CD4^+$) that is greater than the cytotoxic or suppressor T cell population (Tc, $CD8^+$). Ex vivo expansion of T cells by stimulating CD3 and CD28 receptors produces a population of T cells that prior to about days 8-9 consists predominately of TH cells, while after about days 8-9, the population of T cells comprises an increasingly greater population of Tc cells. Accordingly, depending on the purpose of treatment, infusing a subject with a T cell population comprising predominately of $T_H$ cells can be advantageous. Similarly, if an antigen-specific subset of Tc cells has been isolated it can be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (aAPCs). For example, antigen presenting cells (APCs) are useful in preparing therapeutic compositions and cell therapy products of the embodiments. In one aspect, the AaPCs can be genetically modified K562 cells. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference. In yet a further aspect of the embodiments, culturing the genetically modified CAR cells comprises culturing the genetically modified CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. The AaPCs can comprise additional molecules that activate or co-stimulate T-cells in some cases. The additional molecules can, in some cases, comprise membrane-bound Cy cytokines. In yet still further aspects, the AaPCs are inactivated or irradiated, or have been tested for and confirmed to be free of infectious material. In still further aspects, culturing the genetically modified CAR cells in the presence of AaPCs comprises culturing the genetically modified CAR cells in a medium comprising soluble cytokines, such as IL-15, IL-21 and/or IL-2. The cells can be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs can express CD137L. In some aspects, the AaPCs can further express the antigen that is targeted by the CAR cell, for example ROR-1 (full length, truncate or any variant thereof. In other aspects, the AaPCs can further express CD64, CD86, or mIL15. In certain aspects, the AaPCs can express at least one anti-CD3 antibody clone, such as, for example, OKT3 and/or UCHT1. In one aspect, the AaPCs can be inactivated (e.g., irradiated). In one aspect, the AaPCs can have been tested for and confirmed to be free of infectious material. Methods for producing such AaPCs are known in the art. In one aspect, culturing the CAR-modified T cell population with AaPCs can comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step can further comprise culturing with an aminobisphosphonate (e.g., zoledronic acid).

In one aspect, the population of genetically modified CAR cells is immediately infused into a subject or cryopreserved. In another aspect, the population of genetically modified CAR cells is placed in a cytokine bath prior to infusion into a subject. In a further aspect, the population of genetically modified CAR cells is cultured and/or stimulated for no more than 1, 2, 3, 4, 5, 6, 7, 14, 21, 28, 35 42 days, 49, 56, 63 or 70 days. In an embodiment, a stimulation includes the co-culture of the genetically modified CAR T cells with AaPCs to promote the growth of CAR positive T cells. In another aspect, the population of genetically modified CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the genetically modified cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching can comprise fluorescence-activated cell sorting (FACS) to sort for CAR-expressing cells. In a further aspect, the sorting for CAR-expressing cells comprises use of a CAR-binding antibody. The enriching can also comprise depletion of CD56+ cells. In yet still a further aspect of the embodiment, the method further comprises cryopreserving a sample of the population of genetically modified CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO/2014/190273, which is incorporated herein by reference. In addition to peptide-MHC molecules or antigens of interest, the AaPC systems can also comprise at least one exogenous assisting molecule. Any suitable number and combination of assisting molecules can be employed. The assisting molecule can be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2. Adhesion molecules can include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs) that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs can be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs can be frozen and stored for an extended period of time prior to thawing. Frozen AaPCs can also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, can be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain embodiments there are further provided an engineered antigen presenting cell (APC). Such cells can be used, for example, as described above, to propagate immune effector cells ex vivo. In further aspects, engineered APCs can, themselves be administered to a patient and thereby stimulate expansion of immune effector cells in vivo. Engineered APCs of the embodiments can, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term "engineered APC" refers to cell(s) that comprises at least a first transgene, wherein the first transgene encodes a HLA. Such engineered APCs can further comprise a second transgene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as "T-APC"). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments can further comprise at least a third transgene encoding co-stimulatory molecule. The co-stimulatory molecule can be a co-stimulatory cytokine that can be a membrane-bound Cy cytokine. In certain aspects, the co-stimulatory cytokine is IL-15, such as membrane-bound IL-15. In some further aspects, an engineered APC can comprise an edited (or deleted) gene. For example, an inhibitory gene, such as PD-1, LIM-3, CTLA-4 or a TCR, can be edited to reduce or eliminate expression of the gene. An engineered APC of the embodiments can further comprise a transgene encoding any target antigen of interest.

Point-of-Care

In one embodiment of the present disclosure, the immune effector cells described herein are modified at a point-of-care site. In some cases, modified immune effector cells are also referred to as engineered T cells. In some cases, the point-of-care site is at a hospital or at a facility (e.g., a medical facility) near a subject in need of treatment. The subject undergoes apheresis and peripheral blood mononuclear cells (PBMCs) or a sub population of PBMC can be enriched for example, by elutriation or Ficoll separation. Enriched PBMC or a subpopulation of PBMC can be cryopreserved in any appropriate cryopreservation solution prior to further processing. In one instance, the elutriation process is performed using a buffer solution containing human serum albumin. Immune effector cells, such as T cells can be isolated by selection methods described herein. In one instance, the selection method for T cells includes beads specific for CD3 or beads specific for CD4 and CD8 on T cells. In one case, the beads can be paramagnetic beads. The harvested immune effector cells can be cryopreserved in any appropriate cryopreservation solution prior to modification. The immune effector cells can be thawed up to 24 hours, 36 hours, 48 hours. 72 hours or 96 hours ahead of infusion. The thawed cells can be placed in cell culture buffer, for example in cell culture buffer (e.g. RPMI) supplemented with fetal bovine serum (FBS) or human serum AB or placed in a buffer that includes cytokines such as IL-2 and IL-21, prior to modification. In another aspect, the harvested immune effector cells can be modified immediately without the need for cryopreservation.

In some cases, the immune effector cells are modified by engineering/introducing a chimeric receptor, one or more cell tag(s), and/or cytokine(s) into the immune effector cells and then rapidly infused into a subject. In some cases, the sources of immune effector cells can include both allogeneic and autologous sources. In one case, the immune effector cells can be T cells or NK cells. In one case, the chimeric receptor can be a ROR-1 CAR. In another case, the cytokine can be mbIL-15. In one case, the mbIL-15 is of SEQ ID NO: 113, or variant or fragment thereof. In yet another case, expression of mbIL-15 is modulated by ligand inducible gene-switch expression systems described herein. For example, a ligand such as veledimex can be delivered to the subject to modulate the expression of mbIL-15. In another case, the cytokine can be IL-12. In yet another case, expression of IL-12 is modulated by ligand inducible gene-switch expression systems described herein. For example, a ligand such as veledimex can be delivered to the subject to modulate the expression of IL-12.

In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg. In one embodiment, veledimex is administered to the subject 0, 1, 2, 3, 4, 5, 6, 7, 8, 9, 10, 11, 12, 13, 14, 15, 16, 17, 18, 19, 20, or 21 days prior to infusion of the modified immune effector cells. In a further embodiment, veledimex is administered about once every 12 hours, about once every 24 hours, about once every 36 hours or about once every 48 hours, for an effective period of time to a subject post infusion of the modified immune effector cells. In one embodiment, an effective period of time for veledimex administration is about: 7, 8, 9, 10, 11, 12, 13, 14, 15, 16, 17, 18, 19, 20, 21, 22, 23, 24, 25, 26, 27, 28, 29, 30 days. In other embodiments, veledimex can be re-administered after a rest period, after a drug holiday or when the subject experiences a relapse.

In certain cases, where an adverse effect on a subject is observed or when treatment is not needed, the cell tag can be activated, for example via cetuximab, for conditional in vivo ablation of modified immune effector cells comprising cell tags such as truncated epidermal growth factor receptor tags as described herein.

In some embodiments, such immune effectors cells are modified by the constructs as described in FIGS. 1-2 through electroporation. In one instance, electroporation is performed with electroporators such as Lonza's Nucleofector™ electroporators. In other embodiments, the vector comprising the above-mentioned constructs is a non-viral or viral vector. In one case, the non-viral vector includes a SLEEPING BEAUTY® transposon-transposase system. In one instance, the immune effector cells are electroporated using a specific sequence. For example, the immune effector cells can be electroporated with one transposon followed by the DNA encoding the transposase followed by a second transposon. In another instance, the immune effector cells can be electroporated with all transposons and transposase at the same time. In another instance, the immune effector cells can be electroporated with a transposase followed by both transposons or one transposon at a time. While undergoing sequential electroporation, the immune effector cells can be rested for a period of time prior to the next electroporation step.

In some cases, the modified immune effector cells do not undergo a propagation and activation step. In some cases, the modified immune effector cells do not undergo an incubation or culturing step (e.g. ex vivo propagation). In certain cases, the modified immune effector cells are placed in a buffer that includes IL-2 and IL21 prior to infusion. In other instances, the modified immune effector cells are placed or rested in cell culture buffer, for example in cell culture buffer (e.g. RPMI) supplemented with fetal bovine serum (FBS) prior to infusion. Prior to infusion, the modified immune effector cells can be harvested, washed and formulated in saline buffer in preparation for infusion into the subject.

In one instance, the subject has been lymphodepleted prior to infusion. In other instances, lymphodepletion is not required and the modified immune effector cells are rapidly infused into the subject. Exemplary lymphodepletion regimens are listed in Tables 2 and 3 below:

TABLE 2

| Regimen 1 | |
|---|---|
| D-6 | Admit/IV Hydration |
| D-5 | Fludarabine 25 mg/m2, Cyclophosphamide 250 mg/m2 |
| D-4 | Fludarabine 25 mg/m2, Cyclophosphamide 250 mg/m2 |
| D-3 | Fludarabine 25 mg/m2 IV, Cyclophosphamide 250 mg/m2 |
| D-2 | REST |
| D-1 | REST |
| D0 | T-cell infusion |

TABLE 3

| Regimen 2 | |
|---|---|
| D-6 | Admit/IV Hydration |
| D-5 | Fludarabine 30 mg/m2, Cyclophosphamide 500 mg/m2 |
| D-4 | Fludarabine 30 mg/m2, Cyclophosphamide 500 mg/m2 |
| D-3 | Fludarabine 30 mg/m2 IV, Cyclophosphamide 500 mg/m2 |
| D-2 | REST |
| D-1 | REST |
| D0 | T-cell infusion |

In a further instance, the subject undergoes minimal lymphodepletion. Minimal lymphodepletion herein refers to a reduced lymphodepletion protocol such that the subject can be infused within 1 day, 2 days or 3 days following the lymphodepletion regimen. In one instance, a reduced lymphodepletion protocol can include lower doses of fludarabine and/or cyclophosphamide. In another instance, a reduced lymphodepletion protocol can include a shortened period of lymphodepletion, for example 1 day or 2 days.

In one embodiment, the immune effector cells are modified by engineering/introducing a chimeric receptor and a cytokine into said immune effector cells and then rapidly infused into a subject. In other cases, the immune effector cells are modified by engineering/introducing a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hours into a subject. In other cases, immune effector cells are modified by engineering/introducing a chimeric receptor and a cytokine into the immune effector cells and then infused in 0 days, <1 day, <2 days, <3 days, <4 days, <5 days, <6 days or <7 days into a subject.

In some embodiments, an amount of modified effector cells is administered to a subject in need thereof and the amount is determined based on the efficacy and the potential of inducing a cytokine-associated toxicity. In another embodiment, the modified effector cells are $CAR^+$ and $CD3^+$ cells. In some cases, an amount of modified effector cells comprises about $10^4$ to about $10^9$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises $>10^4$ but $\leq 10^5$ modified effector cells/kg. In some cases, an amount of modified effector cells comprises $>10^5$ but $\leq 10^6$ modified effector cells/kg. In some cases, an amount of modified effector cells comprises $>10^6$ but $\leq 10^7$ modified effector cells/kg.

In one embodiment, the modified immune effector cells are targeted to the cancer via regional delivery directly to the tumor tissue. For example, in ovarian cancer, the modified immune effector cells can be delivered intraperitoneally (IP) to the abdomen or peritoneal cavity. Such IP delivery can be performed via a port or pre-existing port placed for delivery of chemotherapy drugs. Other methods of regional delivery of modified immune effector cells can include catheter infusion into resection cavity, ultrasound guided intratumoral injection, hepatic artery infusion or intrapleural delivery.

In one embodiment, a subject in need thereof, can begin therapy with a first dose of modified immune effector cells delivered via IP followed by a second dose of modified immune effector cells delivered via IV. In a further embodiment, the second dose of modified immune effector cells can be followed by subsequent doses which can be delivered via IV or IP. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In another embodiment, the duration between the first and second or further subsequent dose can be about: 0, 1, 2, 3, 4, 5, 6, 7, 8, 9 or 10 years.

In another embodiment, a catheter can be placed at the tumor or metastasis site for further administration of 1, 2, 3, 4, 5, 6, 7, 8, 9, 10 doses of modified immune effector cells. In some cases, doses of modified effector cells can comprise about $10^2$ to about $10^9$ modified effector cells/kg. In cases where toxicity is observed, doses of modified effector cells can comprise about $10^2$ to about $10^5$ modified effector cells/kg. In some cases, doses of modified effector cells can start at about $10^2$ modified effector cells/kg and subsequent doses can be increased to about: $10^4$, $10^5$, $10^6$, $10^7$, $10^8$ or $10^9$ modified effector cells/kg.

In other embodiments, a method of stimulating the proliferation and/or survival of engineered cells comprises obtaining a sample of cells from a subject, and transfecting cells of the sample of cells with one or more polynucleotides that comprise one or more transposons. In one embodiment, the transposons encode a chimeric antigen receptor (CAR), a cytokine, one or more cell tags, and a transposase effective to integrate said one or more polynucleotides into the genome of said cells, to provide a population of engineered cells. In an embodiment, the transposons encode a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In one instance, a method of in vivo propagation of engineered cells comprises obtaining a sample of cells from a subject, and transfecting cells of the sample of cells with one or more polynucleotides that comprise one or more transposons. In one embodiment, the transposons encode a chimeric antigen receptor (CAR), a cytokine, one or more cell tags, and a transposase effective to integrate said one or more polynucleotides into the genome of said cells, to provide a population of engineered cells. In an embodiment, the transposons encode a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In another embodiment, a method of enhancing in vivo persistence of engineered cells in a subject in need thereof comprises obtaining a sample of cells from a subject, and transfecting cells of the sample of cells with one or more polynucleotides that comprise one or more transposons. In some cases, one or more transposons encode a chimeric antigen receptor (CAR), a cytokine, one or more cell tags, and a transposase effective to integrate the DNA into the genome of said cells, to provide a population of engineered cells. In some cases, one or more transposons encode a chimeric antigen receptor (CAR), a cytokine, one or more cell tags, gene switch polypeptides for ligand-inducible control of the cytokine and a transposase effective to integrate the DNA into the genome of said cells, to provide a population of engineered cells. In some cases, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and the second gene switch polypeptide are connected by a linker. In one instance, lymphodepletion is not required prior to administration of the engineered cells to a subject.

In another embodiment, a method of treating a subject with a solid tumor comprises obtaining a sample of cells from a subject, transfecting cells of the sample with one or more polynucleotides that comprise one or more transposons, and administering the population of engineered cells to the subject. In one instance, lymphodepletion is not required prior to administration of the engineered cells to a subject. In some cases, the one or more transposons encode a chimeric antigen receptor (CAR), a cytokine, one or more cell tags, and a transposase effective to integrate the DNA into the genome of the cells. In some cases, the one or more transposons encode a chimeric antigen receptor (CAR), a cytokine, one or more cell tags, gene switch polypeptides for ligand-inducible control of the cytokine and a transposase effective to integrate the DNA into the genome of the cells. In some cases, the gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and second gene switch polypeptide are connected by a linker. In some cases, the cells are transfected via electroporation. In some cases, the polynucleotides encoding the gene switch polypeptides are modulated by a promoter. In some cases, the promoter is a tissue-specific promoter or an EF1A promoter or functional variant thereof. In some cases, the tissue-specific promoter comprises a T cell specific response element or an NFAT response element. In some cases, the cytokine comprises at least one of IL-1, IL-2, IL-15, IL-12, IL-21, a fusion of IL-15, IL-15R or an IL-15 variant. In some cases, the cytokine is in secreted form. In some cases, the cytokine is in membrane-bound form. In some cases, the cells are NK cells, NKT cells, T-cells or T-cell progenitor cells. In some cases, the cells are administered to a subject (e.g. by infusing the subject with the engineered cells). In some cases, the method further comprises administering an effective amount of a ligand (e.g. veledimex) to induce expression of the cytokine. In some cases, the CAR is capable of binding at least ROR1. In some cases, the transposase is salmonid-type Tc1-like transposase. In some cases, the transposase is SB11 or SB100X transposase. In other cases, the transposase is a PIGGYBAC® transposase. In some cases, the cell tag comprises at least one of a HER1 truncated variant or a CD20 truncated variant.

Therapeutic Applications

In embodiments described herein, is an immune effector cell (e.g., T cell) transduced with SLEEPING BEAUTY® transposon(s) and a SLEEPING BEAUTY® Tc1/mariner-type transposase. For example, the SLEEPING BEAUTY® transposon or transposons can include a CAR that combines an antigen recognition domain of ROR-1 with a spacer of CD8 alpha hinge and variants thereof, an intracellular domain of CD3-zeta, CD28, 4-1BB, or any combinations thereof and the intracellular domain CD3zeta, one or more cell tags, one or more cytokines and optionally, components of the gene switch system as described herein. Therefore, in some instances, the transduced T cell can elicit a CAR-mediated T-cell response.

In embodiments described herein, is provided the use of a CAR to redirect the specificity of a primary T cell to a ROR-1 surface antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with ROR-1, a spacer, a zeta chain portion comprising for example the intracellular domain of human CD3zeta, and a costimulatory signaling region.

In one embodiment, the present disclosure includes a cellular therapy where T cells are genetically modified to express the ROR-1-specific CARs of the invention and the CAR T cell is infused to a recipient in need thereof. The infused cell is able to kill cells overexpressing ROR-1 in the recipient. Unlike antibody therapies, CAR T cells as described herein are able to replicate in vivo resulting in long-term persistence that can lead to sustained effect on tumor cells.

The invention additionally provides a method for detecting a disease that comprises overexpression of ROR-1 in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of ROR-1, comprising administering to a subject having the disease a therapeutically effective amount of any one or more of the antibodies, or antigen-binding fragments thereof, that are described herein. In one embodiment, the disease is cancer, as exemplified by ovarian cancer and breast cancer.

In one embodiment, the ROR-1 CAR T cells described herein can undergo robust in vivo T cell expansion and can persist for an extended amount of time. In another embodiment, the CAR T cells described herein can evolve into specific memory T cells that can be reactivated.

The CAR-modified T cells described herein can also serve as a type of vaccine for ex vivo immunization and/or in vivo therapy in a mammal. In embodiments, the mammal is a human. With respect to ex vivo immunization, at least one of the following occurs in vitro prior to administering the immune effector cell into a mammal: i) expansion of the cells, ii) introducing a nucleic acid encoding a CAR to the cells, and/or iii) cryopreservation of the cells.

Ex vivo procedures are well known and are discussed more fully below. Briefly, cells are isolated from a mammal (for example, a human) and genetically modified (i.e., transduced or transfected in vitro) with a vector expressing a CAR disclosed herein. The CAR-modified cell can be administered to a mammalian recipient to provide a therapeutic benefit. The mammalian recipient can be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein can be utilized in the treatment and prevention of diseases that arise in individuals who are immunocompromised. In particular, the CAR-modified T cells of the invention are used in the treatment of ROR-1 malignancies, such as for example, ROR-1. In certain embodiments, the cells of the invention are used in the treatment of patients at risk for developing ROR-1. Thus, the methods for the treatment or prevention of ROR-1 comprising administering to a subject in need thereof, a therapeutically effective amount of the CAR-modified T cells of the invention. In embodiments, the cells activated and expanded as described herein can be utilized in the treatment of ROR-1.

Briefly, pharmaceutical compositions described herein can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In embodiments, compositions of the present invention are formulated for intravenous administration.

Pharmaceutical compositions described herein can be administered in a manner appropriate to the disease to be treated (or prevented). The quantity and frequency of administration will be determined by such factors as the condition of the patient, and the type and severity of the patient's disease, although appropriate dosages can be determined by clinical trials.

When "an immunologically effective amount", or "therapeutic amount" is indicated, the precise amount of the compositions described herein to be administered can be determined by a physician with consideration of individual differences in age, weight, and condition of the patient (subject). It can generally be stated that a pharmaceutical composition comprising the T cells described herein can be administered at a dosage of $10^4$ to $10^9$ cells/kg body weight, $10^5$ to $10^6$ cells/kg body weight, including all integer values within those ranges. T cell compositions can also be administered multiple times at these dosages. The cells can be administered by using infusion techniques that are commonly known in immunotherapy (see, e.g., Rosenberg et al., *New Eng. J. of Med.* 319:1676, (1988)). The optimal dosage and treatment regime for a particular patient can readily be determined by one skilled in the art of medicine by monitoring the patient for signs of disease and adjusting the treatment accordingly.

In certain embodiments, it can be desired to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol can serve to select out certain populations of T cells. In another embodiment, it can be desired to administer activated T cells of the subject composition following lymphodepletion of the patient, either via radiation or chemotherapy.

The administration of compositions described herein can be carried out in any convenient manner, including by aerosol inhalation, injection, ingestion, transfusion, implantation or transplantation. The compositions described herein can be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the ROR-1 CAR-T cell compositions of the present invention are administered by i.v. injection. The compositions of T cells can be injected directly into a lymph node, or site of primary tumor or metastasis.

The dosage of the above treatments to be administered to a patient will vary with the precise nature of the condition being treated and the recipient of the treatment. The scaling of dosages for human administration can be performed according to art-accepted practices. For example, the dose of the above treatment can be in the range of $1\times10^4$ $CAR^+$ cells/kg to $5\times10^6$ $CAR^+$ cells/kg. Exemplary doses can be $1\times10^2$ $CAR^+$ cells/kg, $1\times10^3$ $CAR^+$ cells/kg, $1\times10^4$ $CAR^+$ cells/kg, $1\times10^5$ $CAR^+$ cells/kg, $3\times10^5$ $CAR^+$ cells/kg, $1\times10^6$ $CAR^+$ cells/kg, $5\times10^6$ $CAR^+$ cells/kg, $1\times10^7$ $CAR^+$ cells/kg, $1\times10^8$ $CAR^+$ cells/kg or $1\times10^9$ $CAR^+$ cells/kg. The appropriate dose can be adjusted accordingly for an adult or a pediatric patient.

Alternatively, a typical amount of immune effector cells administered to a mammal (e.g., a human) can be, for example, in the range of one hundred, one thousand, ten thousand, one million to 100 billion cells; however, amounts below or above this exemplary range are within the scope of the invention. For example, the dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens can be useful and are within the scope of the invention. The desired dosage can be delivered by a single bolus administration of the composition, by multiple bolus administrations of the composition, or by continuous infusion administration of the composition.

The composition comprising the immune effector cells expressing the disclosed nucleic acid sequences, or a vector comprising the those nucleic acid sequences, can be administered with one or more additional therapeutic agents, which can be co-administered to the mammal. By "co-administering" is meant administering one or more additional therapeutic agents and the composition comprising the inventive host cells or the inventive vector sufficiently close in time to enhance the effect of one or more additional therapeutic agents, or vice versa. In this regard, the composition comprising the immune effector cells described herein or a vector described herein can be administered simultaneously with one or more additional therapeutic agents, or first, and the one or more additional therapeutic agents can be administered second, or vice versa. Alternatively, the composition comprising the disclosed immune effector cells or the vectors described herein and the one or more additional therapeutic agents can be administered simultaneously.

An example of a therapeutic agents that can be included in or co-administered with the composition (or included in kits) comprising the inventive host cells and/or the inventive vectors are interleukins, cytokines, interferons, adjuvants and chemotherapeutic agents. In embodiments, the additional therapeutic agents are IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, and TLR10.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and an anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits and Compositions

One aspect of the disclosure relates to kits and compositions including a first vector including coding regions that encode the ROR-1-specific CARs of the invention and optionally genes included for safety reasons, e.g., HER1t or HER1t-1 and functional variants thereof, or CD20 or CD20t-1, and functional variants thereof. The kits and compositions can further include cytokines. In another aspect, the kits and compositions can include RHEO-SWITCH® gene switch components. These kits and compositions can include multiple vectors each encoding different proteins or subsets of proteins. These vectors can be viral, non-viral, episomal, or integrating. In some embodiments, the vectors are transposons, e.g., SLEEPING BEAUTY® transposons.

In some embodiments, the kits and compositions include not only vectors but also cells and agents such as interleukins, cytokines, interleukins and chemotherapeutics, adjuvants, wetting agents, or emulsifying agents. In one embodiment the cells are T cells. In one embodiment the kits and composition includes IL-2. In one embodiment, the kits and compositions include IL-21. In one embodiment, the kits and compositions include Bcl-2, STAT3 or STAT5 inhibitors. In embodiments, the kit includes IL-15, or mbIL-15.

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include CAR-T cells (e.g., ROR-1-specific CAR-T cells described herein), and optionally in addition with cytokines and/or chemotherapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1 Nucleofection of T Cells with SLEEPING BEAUTY® System

To generate the genetically modified T cells, cryopreserved pan T cells were thawed, washed and resuspended with pre-warmed Phenol Red free RPMI 1640 media supplemented with FBS and Glutamax (R20 media) and placed in in a humidified incubator at 37° C. with 5% C02. Cells were counted and centrifuged and resuspended in nucleofection buffer. To generate CAR-T cells, a total of 15 μg of the transposon plasmid(s) comprising CAR constructs were combined with 5 μg of plasmid encoding SB transposase for each nucleofection cuvette reaction. Electroporation of the T cells was achieved using the Amaxa 2b Nucleofection device or 4D Nucleofector (Lonza, Walkersville, MD). Following electroporation, the contents from each cuvette were transferred to pre-warmed R20 media and placed in incubator at 37° C. A sample of each T cell culture was taken for flow cytometric analysis to characterize CAR expression where applicable at a specified time point. $CAR^+$ T cells were numerically expanded ex vivo for further characterization. For ex vivo numerical expansion of the generated $CAR^+$ T cells, the T cells were further co-cultured with activating and propagating cells (AaPCs). Briefly, irradiated AaPCs derived from K562 cell line engineered to express CD86, 41BBL, mbIL15 along with ROR1 antigen were co-cultured with $CAR^+$ T cells in complete media with IL-21 and IL-2 for subsequent weekly AaPC additions.

Flow cytometric analysis for CAR expression was performed at Day 1 after electroporation and prior to each AaPC stimulation using fluorescently labeled recombinant ROR1-Fc fusion protein, biotin labelled soluble extracellular domain of ROR1 or Protein-L labelled with AF647. Cells were gated on live CD3+ cells.

TABLE 4

Murine ROR1 scFv CAR constructs with various signal peptides

| Construct No. | CAR ORF |
|---|---|
| 1 | mIgVH (SP)-Murine ROR1 scFv-CD8a-CD28z |
| 2 | IgKappa (SP)-Murine ROR1 scFv-CD8a-CD28z |
| 3 | CD28(SP)- Murine ROR1 scFv-CD8a-CD28z |
| 4 | CD8a(SP)- Murine ROR1 scFv-CD8a-CD28z |

Figure 5:
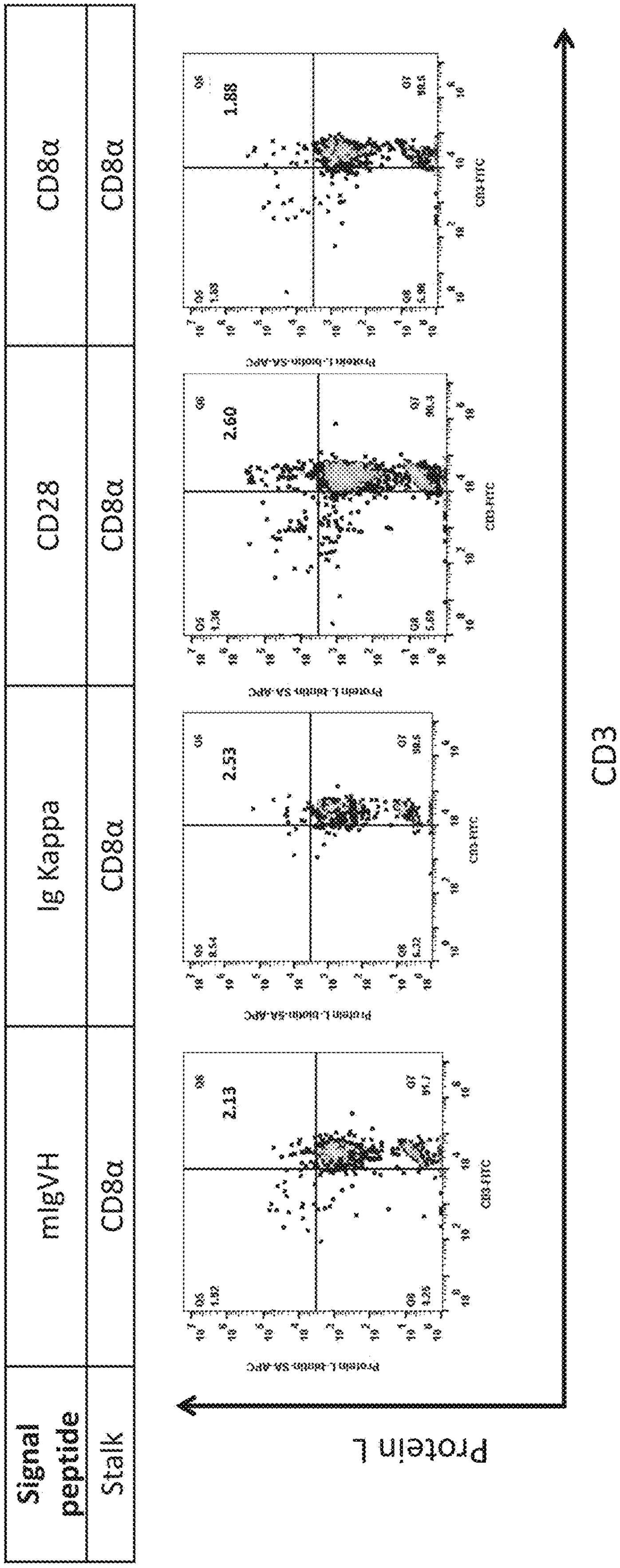
FIG. 5 depicts the combination of signal peptides tested in a ROR1 CAR (murine scFv) construct that utilized conventional CD8α stalk and shows expression of ROR1 CAR (murine scFv) with different signal peptides. Expression of transgenes was measured at Day 1 post nucleofection. Cells were gated as live CD3+ cells. Short CD8α (conventional) stalk does not permit surface expression regardless of signal peptide used (human or mouse).

The above mentioned CARs were constructed. FIG. 5 demonstrates that short CD8a stalk does not permit surface expression of ROR1 CAR regardless of signal peptide utilized. Other signal peptides that were tested included GM-CSFRα, β2M, azurocidin, Human Serum Albumin (HSA), A2M receptor associated protein, IgHV3-23, IgHV3-33, and IgKV1-D33.

Example 2: Optimization of ROR1 CAR

In all approximately 120 CAR vectors were designed and built based on various permutations of signal peptides, orientation of VL and VH chain of anti-ROR1 antibody, spacers of varying lengths, transmembrane and signaling domains. For example, 15 signal peptides, 2 orientations, and 7 different spacers of varying lengths, 2 different transmembrane and signaling domains were tested in various combinations. The expression of ROR1 CAR was found to be dependent on signal peptide, orientation and stalk type length. From these, 3 CAR constructs were identified with strong surface expression.

CAR-T cells expressing ROR1 CARs of different spacer lengths, signal peptides, and VH-VL orientation were generated by electroporation of SB system plasmids in healthy donor PBMCs as described in Example 1. CAR-T cells were numerically expanded ex vivo by co-culture with ROR1 expressing AaPC by once weekly stimulation as described in Example 1. Expression of CAR was measured by multi parameter flow cytometry at Day 1 and Day 8 post nucleofection. CAR-T test articles evaluated are listed in Table 5.

Figure 6:
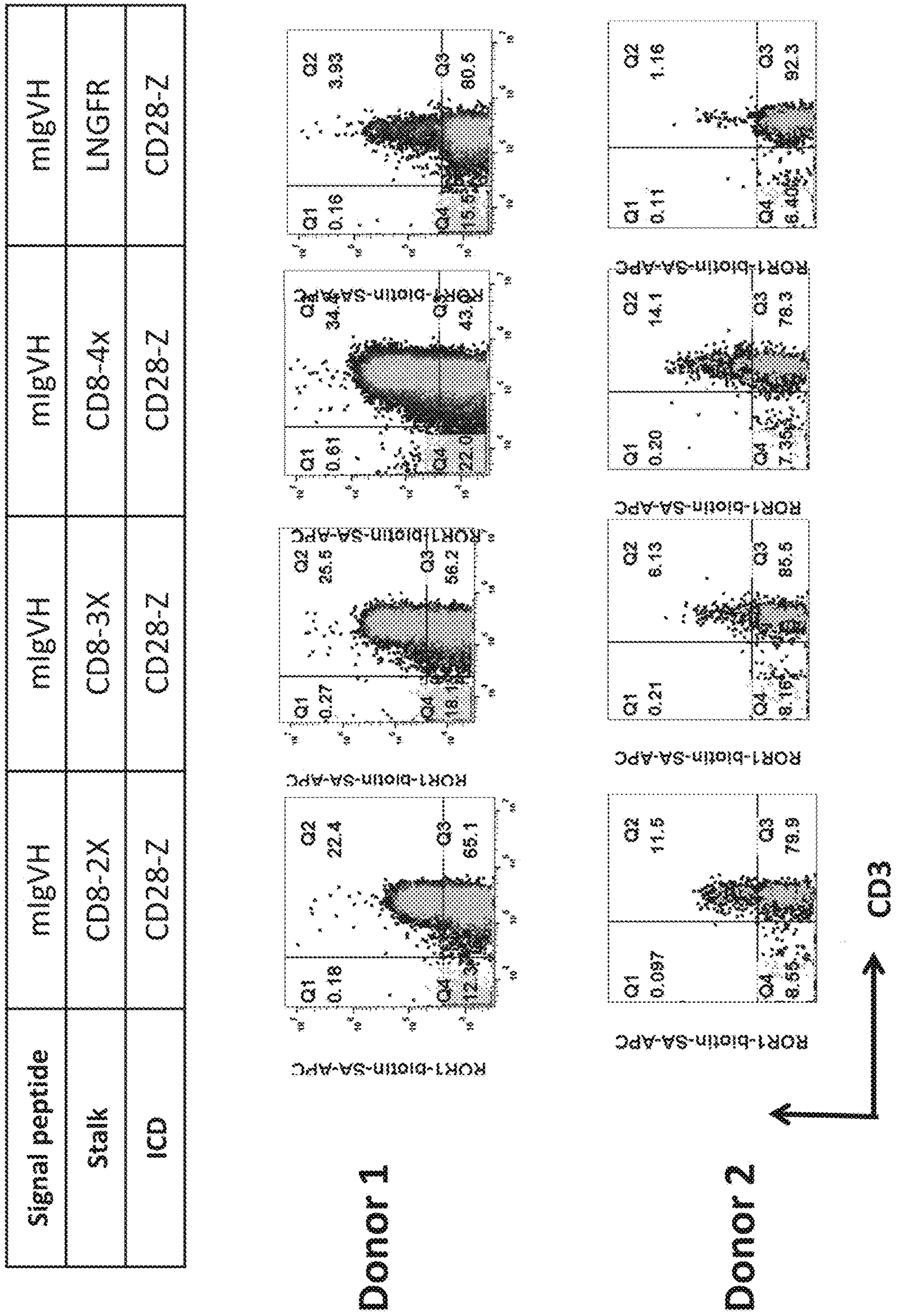
FIG. 6 shows expression of ROR1 CAR (murine scFv) with different combinations of signal peptides and different spacer and spacer lengths. ROR1 CARs utilizing three different longer spacer lengths with strong surface expressions were identified.

FIG. 6 shows flow cytometry data on ROR1 CAR expression of different ROR1 CAR (murine scFv)-T cells with. Cells were gated on live CD3+ cells. As shown in FIG. 6, varying degrees of murine ROR1 CAR expression was observed one day post gene transfer depending on the spacer utilized for construction of CAR molecule. Enrichment of $CAR^+$ T cells was observed upon co-culture of $CAR^+$ T cells with ROR1+ AaPC line in vitro. For murine ROR1 CAR-T, better surface expression of CAR on T cells was observed using longer spacers.

TABLE 5

Figure 7:
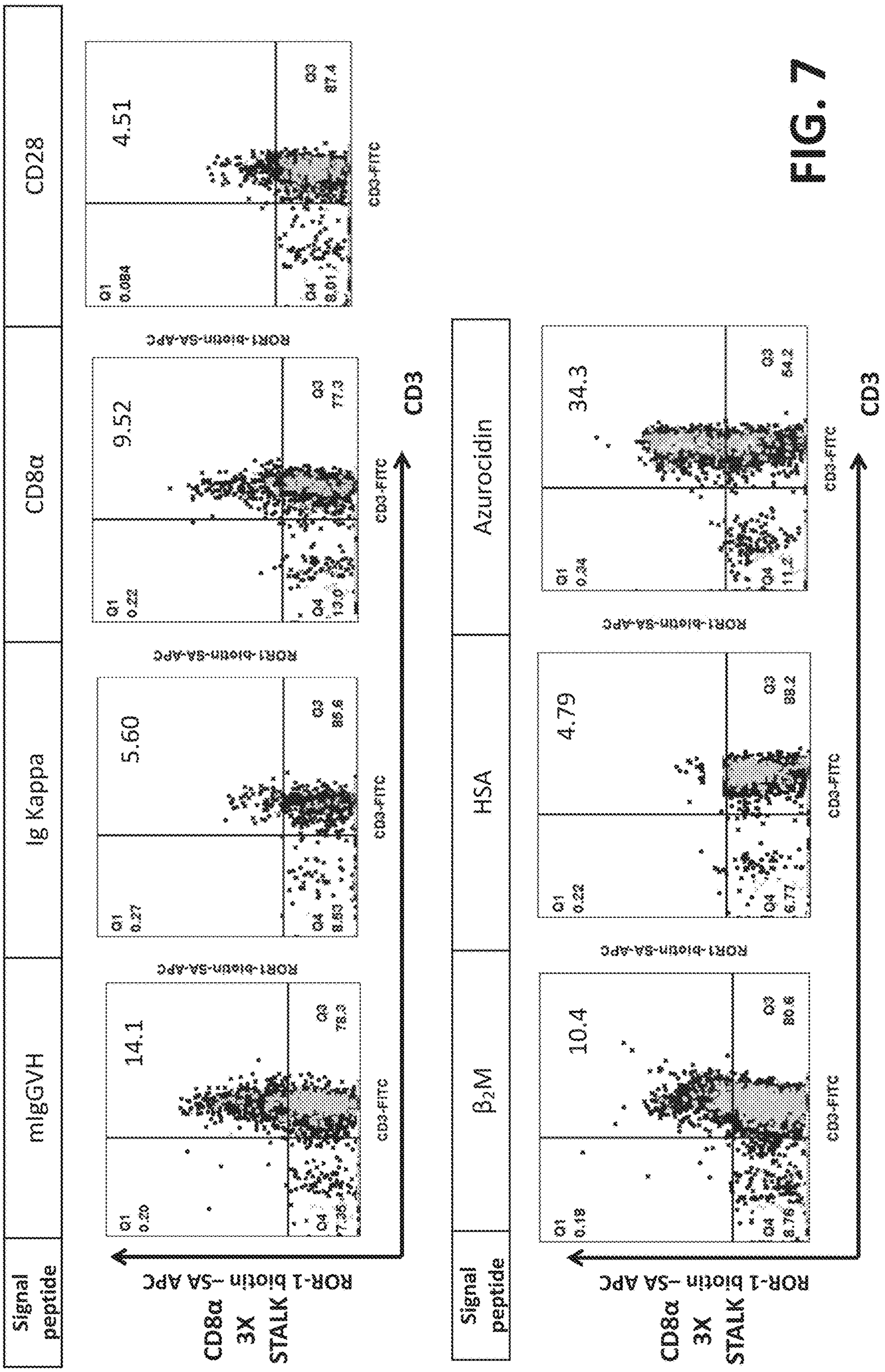
FIG. 7 shows expression of ROR1 CAR (murine scFv) with CD8α 3X stalk with different signal peptides. Expression of murine scFv based ROR1 CAR with 3X CD8α stalk was improved for certain (mIgGVH, β2M and Azurocidin) signal peptides.

ROR1 CAR constructs as utilized in FIGS. 6-7.

| Construct No. | CAR ORF |
|---|---|
| 5 | mIgVH (SP)-Murine ROR1 scFv-CD8a-2X-CD28z |
| 6 | mIgVH (SP)-Murine ROR1 scFv-CD8a-3X-CD28z |
| 7 | mIgVH (SP)-Murine ROR1 scFv-CD8a-4X-CD28z |
| 8 | mIgVH (SP)-Murine ROR1 scFv-LNGFR-CD28z |
| 9 | hIgK(SP)- Murine ROR1 scFv-CD8a-3X-CD28z |
| 10 | hCD8a(SP)-Murine ROR1 scFv-CD8a-3X-CD28z |
| 11 | hCD28(SP) -Murine ROR1 scFv-CD8a-3X-CD28z |
| 12 | hβ2M (SP)-Murine ROR1 scFv-CD8a-3X-CD28z |
| 13 | HAS(SP) -Murine ROR1 scFv-CD8a-3X-CD28z |
| 14 | hAzurocidin-Murine ROR1 scFv-CD8a-3X-CD28z |

FIG. 7 demonstrates varying degrees of ROR1 CAR expression using CD8a-3X spacer and different combinations of signal peptides. As shown in FIG. 7, signal peptides such as mIgVH, CD8a, β2M and Azurocidin allowed for better surface expression of CAR on T cells. The different signal peptides had no effect on surface expression of ROR1 CAR when CD8a-1X spacer was used.

TABLE 6

Figure 8:
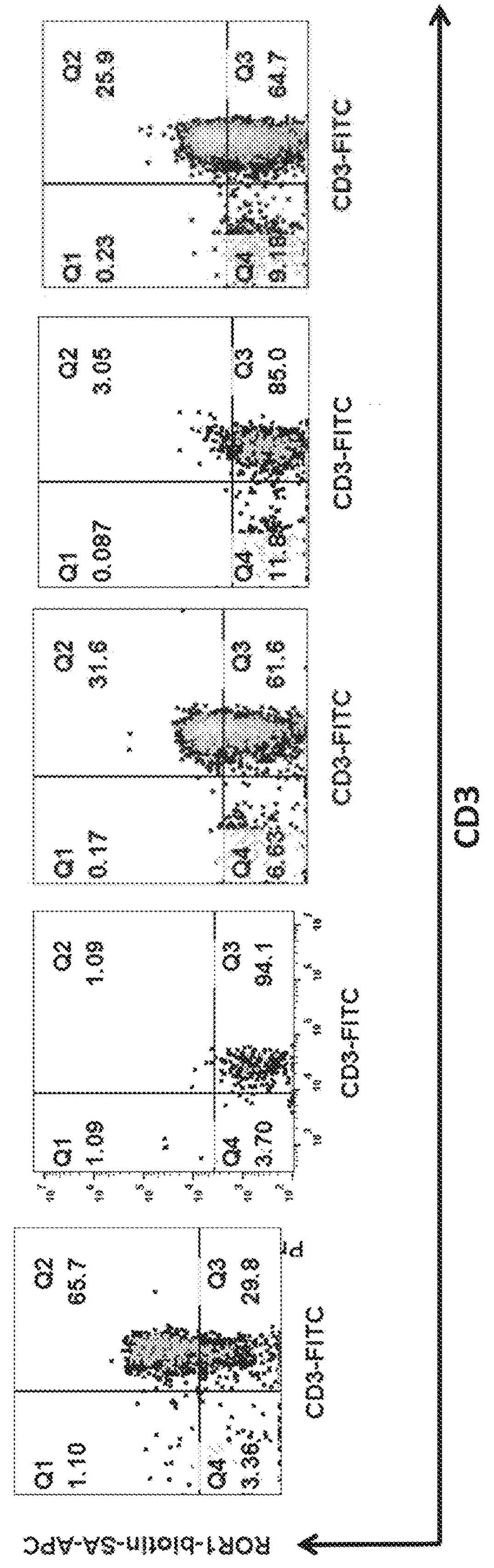
FIG. 8 shows different ROR 1 CAR (murine scFv) with various combinations of stalk, intracellular domain and orientations of the VH/VL chains evaluated and expression of ROR 1 CAR (murine scFv) with various combinations of stalk, intracellular domain and orientations of the VH/VL chains. As observed, reversing orientation from VL-VH to VH-VL enables surface expression form hGMCSFR and hIGHV3-23 signal peptides.

C ROR1 CAR constructs as utilized in FIG. 8.

| Construct No. | CAR ORF | Orientation |
|---|---|---|
| 15 | mgIVH(SP)-murine ROR1scFv -FcM-CD28z | VL-VH |
| 16 | hGMCSFR- murine ROR1scFv -FcM-CD28z | VL-VH |
| 17 | GM-CSFR(SP)-Murine ROR1 scFv-CD8a-3X-CD28z | VH-whitlow linker-VL |
| 18 | IgHV3-23- Murine ROR1 scFv-CD8a-3X-CD28z | VL-VH |
| 19 | IgHV3-23 (SP)- Murine ROR1 scFv-CD8a-3X-CD28z | VH-whitlow linker-VL |

FIG. 8 demonstrates that reversing orientation from VL-VH to VH-VL enables surface expression of murine ROR1CAR from GMCSFR and IGHV3-23 signal peptides.

Based on the above described data, CD8a-3X stalk was selected as a spacer, IgHV3-23 was selected as a signal peptide, with VL-VH as a preferred orientation, and CD8TM-CD28z signaling domain in the murine ROR1 CAR.

Example 3 Murine ROR1 CAR with CD8a-3x Stalk

The functional capability of murine ROR1 CAR-T cells was tested in an in vitro model. Mouse EL4 cell line was transduced to express human ROR1 on cell surface (EL4-ROR1), and secretion of IFN-γ and was measured upon co-culture of murine ROR1 scFv-CD8-3x-CD28z (CAR)+ T cells with $ROR1^+$ target cells. FIG. 9 shows murine ROR1 CAR with CD8-3x stalk demonstrates antigen specific IFN-γ expression upon coculture with ROR+ target cells.

Figure 9A:
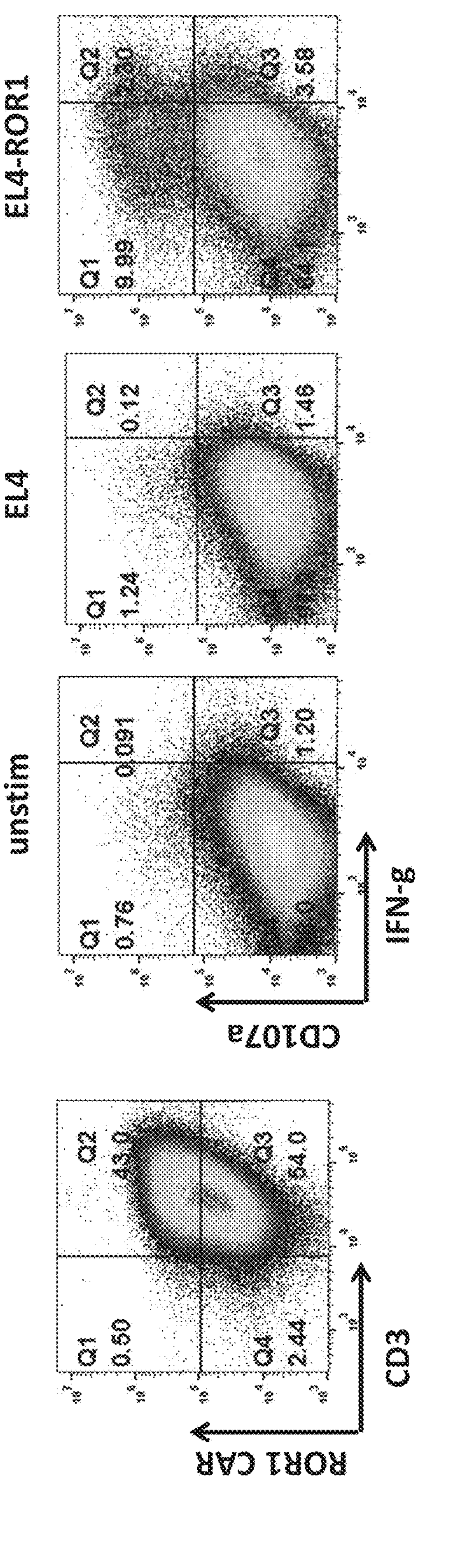
FIG. 9A and FIG. 9B show specificity of ROR1 (murine scFv)-CD8-3X stalk.CD28z CAR-T cells in various tumor cell lines as measured in CD107a degranulation assay and IFN-α expression assay.
Figure 9B:
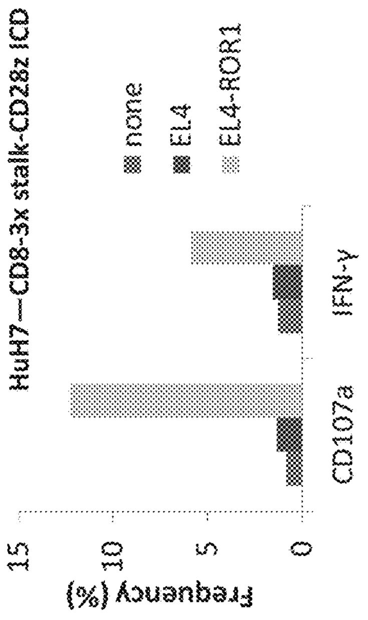

Furthermore, the capability of the ROR1 CAR-T to recognize target cells with or without ROR1 expression was assessed in CD107a degranulation assay. CD107a, also known as lysosomal-associate membrane protein-1 (LAMP-1), is constitutively expressed in the late endosomes-lysosomes of cells but transiently expressed on the cell surface on degranulating cells. As shown in FIGS. 9A-9B, significant expression of CD107a degranulation was observed upon coculture with EL4-ROR1 cell line while effector cells only and coculture with EL4 cell line had minimal degranulation observed.

Example 4 Humanization of ROR1 scFv

To reduce immunogenicity of murine ROR1 scFv and to prevent immune-mediated CAR T cell deletion in vivo, efforts were undertaken to humanize the murine ROR1 scFv.

A total of 168 humanized ROR1 scFvs were designed based on the sequence of murine ROR1 scFv and tested. 77 of the humanized antibody clones were successfully expressed. Out of the 77 humanized clones, 42 retained the ability to bind ROR1 antigen. 21 clones were further selected for affinity maturation. 10 humanized antibodies showed binding affinities ≤2.0 nM in IgG format. Additional scFv variants based on combination of different humanized VH and VL chains were also designed and tested.

Binding affinity of various humanized ROR1 scFv clones were assessed by surface plasmon resonance (SPR) assay using Biacore 3000. Variable regions of humanized ROR1 antibodies were fused to mouse constant chain regions to generate chimeric mouse IgG1 mAbs. Extracellular domain (ECD) of ROR1 fused to human Fc region was immobilized on sensor chip CM5. Different concentrations of humanized antibodies were injected in solution phase and data was analyzed using BIAevaluation to calculate Kd of the antibodies.

TABLE 7

Binding affinity of humanized clones of murine ROR1 scFv

| Humanized clones | Affinity (Kd) |
|---|---|
| Clone 04 | ~55 nM |
| Clone 05 | ~35 nM |
| Clone 07 | ~90 nM |

TABLE 7-continued

| Binding affinity of humanized clones of murine ROR1 scFv | |
|---|---|
| Humanized clones | Affinity (Kd) |
| Clone 14 | 1.45 nM |
| Clone 16 | 3.03 nM |
| Clone 18 | 12.7 nM |
| Hum ROR1_14VH_(G4S)3x_VL_16 | 131 nM |
| Hum ROR1_05VH_(G4S)3x_VL_14 | 3.55E−10M |
| Hum ROR1_05VH_(G4S)3x_VL_16 | 3.37E−10M |
| Hum ROR1_07VH_(G4S)3x_VL_05 | 7.16E−09M |
| Hum ROR1_07VH_(G4S)3x_VL_16 | 4.08E−09M |
| Hum ROR1_07VH_(G4S)3x_VL_18 | 1.17E−08M |
| Hum ROR1_18VH_(G4S)3x_VL_04 | 3.72E−10M |
| Hum ROR1_18VH_(G4S)3x_VL_07 | 3.87E−09M |
| Hum ROR1_18VH_(G4S)3x_VL_14 | 2.09E−10M |
| Hum ROR1_18VH_(G4S)3x_VL_16 | 1.60E−09M |
| Hum_design_14_variant3 | 1.3E−09M |
| Hum_design_14_variant4 | 4.08E−10M |
| Hum_design_14_variant5 | 4.52E−09M |

Based on top candidates from the humanization campaign, the following CAR constructs were designed and tested.

TABLE 8

| Humanized ROR1 CAR constructs as utilized in FIGS. 10A-10B, FIG. 11, FIG. 12 and Table 9. | |
|---|---|
| Construct No. | CAR ORF |
| 20 | MurineROR1_v2 (VL-VH). CD8a(3x).CD28z |
| 21 | IGVH3-33sp. hROR1(VH-VL)_14.CD8a(3x).CD28z |
| 22 | mIgVH3 sp. hROR1 (VH-VL)_14. CD8a(3x).CD28z |
| 23 | hROR1(VL-VH)_05.CD8a(3x).CD28z |
| 24 | hROR1(VH-VL)_14-3.CD8a(3x).CD28z |
| 25 | hROR1(VH-VL)_14-4.CD8a(3x).CD28z |
| 26 | hROR1(VH_5-VL_14).CD8a(3x).CD28z |
| 27 | hROR1(VH_5-VL_16).CD8a(3x).CD28z |
| 28 | hROR1(VH_18-VL_04).CD8a(3x).CD28z |
| 29 | hROR1(VH_18-VL_14).CD8a(3x).CD28z |
| 30 | Mock transfected T cells |

Figure 10A:
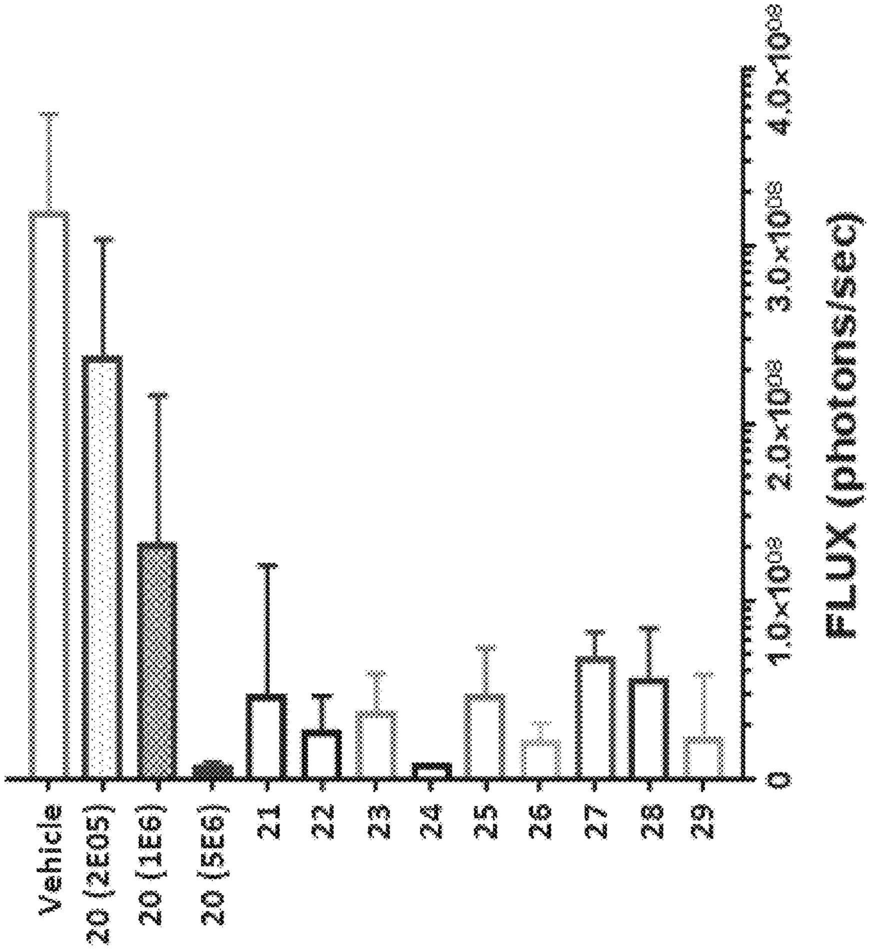

JeKo-1 tumor cells expressing fFLUC ($0.5\times10^6$ cells) were administered IP into NSG mice on Day 0. On Day 8, mice with established tumor burden (as confirmed by IVIS imaging) were randomized to receive a single IV injection with either: Saline (HBSS), or T cells transfected with CAR constructs as described above. CAR-T cells were numerically expanded by 2× weekly stimulations ex vivo by coculture with ROR1+ AaPC. Effectiveness against tumor growth was evaluated by in vivo bioluminescence (IVIS) imaging performed every 7 days and 36 days post CAR-T cell dosing to assess tumor burden (FIGS. 10A, 10B and 11). Whole blood samples in EDTA were collected once per week and subjected to multi-parameter flow cytometry for evaluation of humanized ROR1 CAR T cell persistence (FIG. 12), expansion and determination of the different T cell subsets.

A lead humanized ROR1 CAR (hROR1(VH_5-VL_14).CD8a(3x).CD28z) was selected based on similarity to the murine ROR1 CAR in scFv affinity, ROR1-Fc binding, CAR expression, CAR T-cell expression, in vitro ROR-1 specific cytokine production, in vitro ROR-1 specific cytotoxicity and in vivo ROR-1 anti-tumor activity.

A summary of the data is provided in Table 9 below.

TABLE 9

Summary of Constructs tested.

| | ROR1-His | ROR1-Fc | In vivo | | | In vitro | | | |
|---|---|---|---|---|---|---|---|---|---|
| | | | Tumor | | | | | | |
| Construct # | Affinity (KD, M) | Affinity (KD, M) | growth inhibition | CD8 in circulation | ROR1-CAR in circulation | ROR1-FC binding | Cytotoxicity | Cytokines | Expansion |
| 20 | 7.07E−08 | 2.31E−08 | 2 | 1 | 2 | 3 | 3 | 3 | 3 |
| 21 | 1.45E−09 | ND | 2 | 1 | 1 | 2 | 3 | 3 | 3 |
| 22 | 1.45E−09 | ND | 2 | 2 | 2 | 2 | 3 | 3 | 3 |
| 23 | 3.74E−08 | 3.50E−08 | 1 | 1 | 1 | 2 | 3 | 3 | 3 |
| 24 | 1.30E−09 | 9.59E−10 | 2 | 2 | 1 | 2 | 3 | 3 | 3 |
| 25 | 4.08E−10 | 2.84E−10 | 1 | 3 | 2 | 3 | 2 | 3 | 3 |
| 26 | 3.55E−10 | 1.93E−10 | 3 | 3 | 3 | 3 | 3 | 3 | 3 |
| 27 | 3.37E−10 | 2.73E−10 | 0 | 2 | 0 | 0 | 0 | 3 | 3 |
| 28 | 3.72E−10 | 2.71E−10 | 1 | 1 | 1 | 2 | 3 | 3 | 3 |
| 29 | 2.09E−10 | 2.01E−10 | 3 | 1 | 1 | 3 | 3 | 3 | 3 |

ND—not determined

Relative performance score from 0 to 3 with 0 being worst and 3 being the best performance

Example 5 In Vitro and In Vivo Experiments

Various DNA plasmids expressing a SB transposon system, i.e. SB11, membrane bound IL-15 (mbIL-15), cell tag and lead chimeric antigen receptor (CAR), were transfected into peripheral blood mononuclear cells (PBMC) via nucleofection to redirect T cell specificity. Constitutive expression of mbIL-15 or ligand inducible expression of mbIL-15 in combination with constitutive expression of lead ROR1 CAR was examined as described in Table 10.

TABLE 10

Combination of Transposons as utilized in FIGS. 13A-13B.

| Combination No. | Transposon #1 | Transposon #2 |
|---|---|---|
| 1 | Constitutive CAR (FIG. 1C) | Constitutive mbIL-15.HER1t (FIG. 1E) |
| 2 | Constitutive CAR.HER1t (FIG. 1D) | Constitutive mbIL-15.HER1t (FIG. 1E) |
| 3 | Constitutive CAR.HER1t. Inducible mbIL-15.HER1t | Gene Switch components (FIG. 2E) |

TABLE 11

Summary of combinations tested.

| Combination | 1 | 2 | 3 |
|---|---|---|---|
| CAR | hROR1 | hROR1 | hROR1 |
| mbIL-15 | const | const. | RTS ® |
| Expansion | ++ | + | + |
| CAR+ % | +++ | + | ++ |
| mbIL-15 (%) | + | + | ++ |
| CD107 | ++ | +/− | + |
| IFN-γ | ++ | +/− | + |
| TNF-α | + | − | +/− |

Relative performance score from − to +++, '−' being undetectable performance and +++ being the best performance.

RTS-mbIL-15 in combination with hROR1 CAR was further tested in vitro using SKOV3_fLUC (FIG. 13A) and JeKol_fLUC (FIG. 13B) tumor cell lines. As before, the 3 combinations of SB transposons encoding for hROR1 CAR and mbIL-15 were electroporated in healthy donor T cells. CAR+ T cells were numerically expanded ex vivo by co-culture with ROR1 expressing AaPC by once weekly stimulation as previously described for 2× stimulation. For ligand inducible mbIL-15 hROR1 CAR, the T cells were incubated in complete media containing IL-21 and IL-2 at following 2× stimulation of the cells. Two days after, the hROR1 CAR T cells were incubated in a cytokine free complete media and treated with veledimex or DMSO overnight. The next day, cells were counted and the frequency of ROR1 expressing T cells was estimated. T cells were then normalized for CAR expression.

For T cells constitutively expressing hROR1 CAR and mbIL-15, following ex vivo expansion using two weekly stimulations by coculture with AaPC, cells were cultured for an additional 3 days and counted. As before, T cells were normalized for CAR expression.

hROR1 CAR T cells were then mixed with each tumor cell line at different ratios: 4:1, 2:1, 0.5:1 and 0.25:1. 72 hours later, cells were removed from the incubator and pelleted. Supernatant was collected to measure cytokine production, and cell pellet was treated with OneGlo reagent for Luciferase assay. FIGS. 13A-13B demonstrates that ROR1+ tumor cell lines were equally killed by hROR1 CAR T cells with constitutive or RTS-mbIL-15 in vitro.

An in vivo study was conducted in mice treated with hROR-1 CAR T cells with RTS-mbIL-15. As before, JeKo-1 tumor cells ($10 \times 10^6$ cells) were administered IP into NSG mice on Day 0. On Day 8, mice with established tumor burden (as confirmed by IVIS imaging) were randomized to receive a single IP injection with either: Saline (HBSS), or hROR-1 CAR T cells with RTS-mbIL-15 (+/−veledimex). Effectiveness against tumor growth was evaluated by in vivo bioluminescence (IVIS) imaging performed at specific time points post CAR-T cell dosing to assess tumor burden (FIG. 14). Whole blood samples in EDTA were collected once per week and subjected to multi-parameter flow cytometry for evaluation of humanized ROR1 CAR T cell persistence, expansion and determination of the different T cell subsets.

FIG. 14 demonstrates that huROR1 RTS CART promotes an anti-tumor effect in a JEKO-1 xenograft mouse model in a dose-dependent manner.

Unless defined otherwise, all technical and scientific terms and any acronyms used herein have the same meanings as commonly understood by one of ordinary skill in the art in the field of this invention.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein can be employed in practicing the present disclosure. It is intended that the following claims define the scope of the present disclosure and that methods and structures within the scope of these claims and their equivalents be covered thereby.

Sequences

Provided in Table 12 is a representative list of certain sequences included in embodiments provided herein.

TABLE 12

Exemplary Sequences

| Name | SEQ ID NO | Amino Acid Sequence | SEQ ID NO | Nucleotide Sequence |
|---|---|---|---|---|
| CAR Sequences | | | | |
| Human ROR1 | 1 | PLLALLAALLLAARG AAAQETELSVSAELV PTSSWNISSELNKDSY LTLDEPMNNITTSLGQ TAELHCKVSGNPPPTI RWFKNDAPVVQEPR RLSFRSTIYGSRLRIRN LDTTDTGYFQCVATN GKEVVSSTGVLFVKF GPPPTASPGYSDEYEE DGFCQPYRGIACARFI GNRTVYMESLHMQG | 148 | ATGCACCGGCCGCGCCGCCGCGGGACG CGCCCGCCGCTCCTGGCGCTGCTGGCC GCGCTGCTGCTGGCCGCACGCGGGGCT GCTGCCCAAGAAACAGAGCTGTCAGTC AGTGCTGAATTAGTGCCTACCTCATCA TGGAACATCTCAAGTGAACTCAACAAA GATTCTTACCTGACCCTCGATGAACCA ATGAATAACATCACCACGTCTCTGGGC CAGACAGCAGAACTGCACTGCAAAGTC TCTGGGAATCCACCTCCCACCATCCGC TGGTTCAAAAATGATGCTCCTGTGGTC CAGGAGCCCCGGAGGCTCTCCTTTCGG |

TABLE 12-continued

| Exemplary Sequences | | |
|---|---|---|
| | EIENQITAAFTMIGTSS | TCCACCATCTATGGCTCTCGGCTGCGG |
| | HLSDKCSQFAIPSLCH | ATTAGAAACCTCGACACCACAGACACA |
| | YAFPYCDETSSVPKPR | GGCTACTTCCAGTGCGTGGCAACAAAC |
| | DLCRDECEILENVLC | GGCAAGGAGGTGGTTTCTTCCACTGGA |
| | QTEYIFARSNPMILMR | GTCTTGTTTGTCAAGTTTGGCCCCCCTC |
| | LKLPNCEDLPQPESPE | CCACTGCAAGTCCAGGATACTCAGATG |
| | AANCIRIGIPMADPIN | AGTATGAAGAAGATGGATTCTGTCAGC |
| | KNHKCYNSTGVDYR | CATACAGAGGGATTGCATGTGCAAGAT |
| | GTVSVTKSGRQCQPW | TTATTGGCAACCGCACCGTCTATATGG |
| | NSQYPHTHTFTALRFP | AGTCTTTGCACATGCAAGGGGAAATAG |
| | ELNGGHSYCRNPGNQ | AAAATCAGATCACAGCTGCCTTCACTA |
| | KEAPWCFTLDENFKS | TGATTGGCACTTCCAGTCACTTATCTGA |
| | DLCDIPACDSKDSKE | TAAGTGTTCTCAGTTCGCCATTCCTTCC |
| | KNKMEILYILVPSVAI | CTGTGCCACTATGCCTTCCCGTACTGCG |
| | PLAIALLFFFICVCRN | ATGAAACTTCATCCGTCCCAAAGCCCC |
| | NQKSSSAPVQRQPKH | GTGACTTGTGTCGCGATGAATGTGAAA |
| | VRGQNVEMSMLNAY | TCCTGGAGAATGTCCTGTGTCAAACAG |
| | KPKSKAKELPLSAVR | AGTACATTTTTGCAAGATCAAATCCCA |
| | FMEELGECAFGKIYK | TGATTCTGATGAGGCTGAAACTGCCAA |
| | GHLYLPGMDHAQLV | ACTGTGAAGATCTCCCCCAGCCAGAGA |
| | AIKTLKDYNNPQQWT | GCCCAGAAGCTGCGAACTGTATCCGGA |
| | EFQQEASLMAELHHP | TTGGAATTCCCATGGCAGATCCTATAA |
| | NIVCLLGAVTQEQPV | ATAAAAATCACAAGTGTTATAACAGCA |
| | CMLFEYINQGDLHEF | CAGGTGTGGACTACCGGGGGACCGTCA |
| | LIMRSPHSDVGCSSDE | GTGTGACCAAATCAGGGCGCCAGTGCC |
| | DGTVKSSLDHGDFLH | AGCCATGGAATTCCCAGTATCCCCACA |
| | IAIQIAAGMEYLSSHF | CACACACTTTCACCGCCCTTCGTTTCCC |
| | FVHKDLAARNILIGEQ | AGAGCTGAATGGAGGCCATTCCTACTG |
| | LHVKISDLGLSREIYS | CCGCAACCCAGGGAATCAAAAGGAAG |
| | ADYYRVQSKSLLPIR | CTCCCTGGTGCTTCACCTTGGATGAAA |
| | WMPPEAIMYGKFSSD | ACTTTAAGTCTGATCTGTGTGACATCCC |
| | SDIWSFGVVLWEIFSF | AGCGTGCGATTCAAAGGATTCCAAGGA |
| | GLQPYYGFSNQEVIE | GAAGAATAAAATGGAAATCCTGTACAT |
| | MVRKRQLLPCSEDCP | ACTAGTGCCAAGTGTGGCCATTCCCCT |
| | PRMYSLMTECWNEIP | GGCCATTGCTTTACTCTTCTTCTTCATT |
| | SRRPRFKDIHVRLRS | TGCGTCTGTCGGAATAACCAGAAGTCA |
| | WEGLSSHTSSTTPSGG | TCGTCGGCACCAGTCCAGAGGCAACCA |
| | NATTQTTSLSASPVSN | AAACACGTCAGAGGTCAAAATGTAGA |
| | LSNPRYPNYMFPSQGI | GATGTCAATGCTGAATGCATATAAACC |
| | TPQGQIAGFIGPPIPQN | CAAGAGCAAGGCTAAAGAGCTACCTCT |
| | QRFIPINGYPIPPGYAA | TTCTGCTGTACGCTTTATGGAAGAATT |
| | FPAAHYQPTGPPRVIQ | GGGTGAGTGTGCCTTTGGAAAAATCTA |
| | HCPPPKSRSPSSASGS | TAAAGGCCATCTCTATCTCCCAGGCAT |
| | TSTGHVTSLPSSGSNQ | GGACCATGCTCAGCTGGTTGCTATCAA |
| | EANIPLLPHMSIPNHP | GACCTTGAAAGACTATAACAACCCCCA |
| | GGMGITVFGNKSQKP | GCAATGGACGGAATTTCAACAAGAAG |
| | YKIDSKQASLLGDANI | CCTCCCTAATGGCAGAACTGCACCACC |
| | HGHTESMISAEL | CCAATATTGTCTGCCTTCTAGGTGCCGT |
| | | CACTCAGGAACAACCTGTGTGCATGCT |
| | | TTTTGAGTATATTAATCAGGGGGATCT |
| | | CCATGAGTTCCTCATCATGAGATCCCC |
| | | ACACTCTGATGTTGGCTGCAGCAGTGA |
| | | TGAAGATGGGACTGTGAAATCCAGCCT |
| | | GGACCACGGAGATTTTCTGCACATTGC |
| | | AATTCAGATTGCAGCTGGCATGGAATA |
| | | CCTGTCTAGTCACTTCTTTGTCCACAAG |
| | | GACCTTGCAGCTCGCAATATTTTAATC |
| | | GGAGAGCAACTTCATGTAAAGATTTCA |
| | | GACTTGGGGCTTTCCAGAGAAATTTAC |
| | | TCCGCTGATTACTACAGGGTCCAGAGT |
| | | AAGTCCTTGCTGCCCATTCGCTGGATG |
| | | CCCCCTGAAGCCATCATGTATGGCAAA |
| | | TTCTCTTCTGATTCAGATATCTGGTCCT |
| | | TTGGGGTTGTCTTGTGGGAGATTTTCA |
| | | GTTTTGGACTCCAGCCATATTATGGATT |
| | | CAGTAACCAGGAAGTGATTGAGATGGT |
| | | GAGAAAACGGCAGCTCTTACCATGCTC |
| | | TGAAGACTGCCCACCCAGAATGTACAG |
| | | CCTCATGACAGAGTGCTGGAATGAGAT |
| | | TCCTTCTAGGAGACCAAGATTTAAAGA |
| | | TATTCACGTCCGGCTTCGGTCCTGGGA |
| | | GGGACTCTCAAGTCACACAAGCTCTAC |
| | | TACTCCTTCAGGGGGAAATGCCACCAC |
| | | ACAGACAACCTCCCTCAGTGCCAGCCC |
| | | AGTGAGTAATCTCAGTAACCCCAGATA |
| | | TCCTAATTACATGTTCCCGAGCCAGGG |
| | | TATTACACCACAGGGCCAGATTGCTGG |
| | | TTTCATTGGCCCGCCAATACCTCAGAA |

TABLE 12-continued

| Exemplary Sequences | | | | |
|---|---|---|---|---|
| | | | | CCAGCGATTCATTCCCATCAATGGATA CCCAATACCTCCTGGATATGCAGCGTT TCCAGCTGCCCACTACCAGCCAACAGG TCCTCCCAGAGTGATTCAGCACTGCCC ACCTCCCAAGAGTCGGTCCCCAAGCAG TGCCAGTGGGTCGACTAGCACTGGCCA TGTGACTAGCTTGCCCTCATCAGGATC CAATCAGGAAGCAAATATTCCTTTACT ACCACACATGTCAATTCCAAATCATCC TGGTGGAATGGGTATCACCGTTTTTGG CAACAAATCTCAAAAACCCTACAAAAT TGACTCAAAGCAAGCATCTTTACTAGG AGACGCCAATATTCATGGACACACCGA ATCTATGATTTCTGCAGAACTG |
| Human ROR1 (1-437) | 2 | MHRPRRRGTRPPLLA LLLAALLLAARGAAAQ ETELSVSAELVPTSSW NISSELNKDSYLTLDE PMNNITTSLGQTAEL HCKVSGNPPPTIRWF KNDAPVVQEPRRLSF RSTIYGSRLRIRNLDT TDTGYFQCVATNGKE VVSSTGVLFVKFGPPP TASPGYSDEYEEDGF CQPYRGIACARFIGNR TVYMESLHMQGEIEN QITAAFTMIGTSSHLS DKCSQFAIPSLCHYAF PYCDETSSVPKPRDLC RDECEILENVLCQTEY IFARSNPMILMRLKLP NCEDLPQPESPEAAN CIRIGIPMADPINKNH KCYNSTGVDYRGTVS VTKSGRQCQPWNSQ YPHTHTFTALRFPELN GGHSYCRNPGNQKE APWCFTLDENFKSDL CDIPACDSKDSKEKN KMEILYILVPSVAIPL AIALLFFFICVCRNNQ KSSSA | 149 | ATGCACCGGCCGCGCCGCCGCGGGACG CGCCCGCCGCTCCTGGCGCTGCTGGCC GCGCTGCTGCTGGCCGCACGCGGGGCT GCTGCCCAAGAAACAGAGCTGTCAGTC AGTGCTGAATTAGTGCCTACCTCATCA TGGAACATCTCAAGTGAACTCAACAAA GATTCTTACCTGACCCTCGATGAACCA ATGAATAACATCACCACGTCTCTGGGC CAGACAGCAGAACTGCACTGCAAAGTC TCTGGGAATCCACCTCCCACCATCCGC TGGTTCAAAAATGATGCTCCTGTGGTC CAGGAGCCCCGGAGGCTCTCCTTTCGG TCCACCATCTATGGCTCTCGGCTGCGG ATTAGAAACCTCGACACCACAGACACA GGCTACTTCCAGTGCGTGGCAACAAAC GGCAAGGAGGTGGTTTCTTCCACTGGA GTCTTGTTTGTCAAGTTTGGCCCCCCTC CCACTGCAAGTCCAGGATACTCAGATG AGTATGAAGAAGATGGATTCTGTCAGC CATACAGAGGGATTGCATGTGCAAGAT TTATTGGCAACCGCACCGTCTATATGG AGTCTTTGCACATGCAAGGGGAAATAG AAAATCAGATCACAGCTGCCTTCACTA TGATTGGCACTTCCAGTCACTTATCTGA TAAGTGTTCTCAGTTCGCCATTCCTTCC CTGTGCCACTATGCCTTCCCGTACTGCG ATGAAACTTCATCCGTCCCAAAGCCCC GTGACTTGTGTCGCGATGAATGTGAAA TCCTGGAGAATGTCCTGTGTCAAACAG AGTACATTTTTGCAAGATCAAATCCCA TGATTCTGATGAGGCTGAAACTGCCAA ACTGTGAAGATCTCCCCCAGCCAGAGA GCCCAGAAGCTGCGAACTGTATCCGGA TTGGAATTCCCATGGCAGATCCTATAA ATAAAAATCACAAGTGTTATAACAGCA CAGGTGTGGACTACCGGGGGACCGTCA GTGTGACCAAATCAGGGCGCCAGTGCC AGCCATGGAATTCCCAGTATCCCCACA CACACACTTTCACCGCCCTTCGTTTCCC AGAGCTGAATGGAGGCCATTCCTACTG CCGCAACCCAGGGAATCAAAAGGAAG CTCCCTGGTGCTTCACCTTGGATGAAA ACTTTAAGTCTGATCTGTGTGACATCCC AGCGTGCGATTCAAAGGATTCCAAGGA GAAGAATAAAATGGAAATCCTGTACAT ACTAGTGCCAAGTGTGGCCATTCCCCT GGCCATTGCTTTACTCTTCTTCTTCATT TGCGTCTGTCGGAATAACCAGAAGTCA TCGTCGGCA |
| Murine ROR-1 (VL-VH).IgG4 Fc-CD28m-Z | 3 | DIKMTQSPSSMYASL GERVTITCKASPDINS YLSWFQQKPGKSPKT LIYRANRLVDGVPSR FSGGGSGQDYSLTINS LEYEDMGIYYCLQYD EFPYTFGGGTKLEMK GSTSGSGKPGSGEGST KGEVKLVESGGGLVK PGGSLKLSCAASGFTF SSYAMSWVRQIPEKR LEWVASISRGGTTYY PDSVKGRFTISRDNVR | 150 | GACATCAAGATGACCCAGAGCCCCAGC TCTATGTACGCCAGCCTGGGCGAGCGC GTGACCATCACATGCAAGGCCAGCCCC GACATCAACAGCTACCTGTCCTGGTTC CAGCAGAAGCCCGGCAAGAGCCCCAA GACCCTGATCTACCGGGCCAACCGGCT GGTGGACGGCGTGCCAAGCAGATTTTC CGGCGGAGGCAGCGGCCAGGACTACA GCCTGACCATCAACAGCCTGGAATACG AGGACATGGGCATCTACTACTGCCTGC AGTACGACGAGTTCCCCTACACCTTCG GAGGCGGCACCAAGCTGGAAATGAAG GGCAGCACCTCCGGCAGCGGCAAGCCT |

TABLE 12-continued

| Exemplary Sequences | | | | |
|---|---|---|---|---|
| | | NILYLQMSSLRSEDTA<br>MYYCGRYDYDGYYA<br>MDYWGQGTSVTVSS<br>ESKYGPPCPPCPAPEF<br>EGGPSVFLFPPKPKDT<br>LMISRTPEVTCVVVD<br>VSQEDPEVQFNWYV<br>DGVEVHNAKTKPREE<br>QFQSTYRVVSVLTVL<br>HQDWLNGKEYKCKV<br>SNKGLPSSIEKTISKA<br>KGQPREPQVYTLPPS<br>QEEMTKNQVSLTCLV<br>KGFYPSDIAVEWESN<br>GQPENNYKTTPPVLD<br>SDGSFFLYSRLTVDKS<br>RWQEGNVFSCSVMH<br>EALHNHYTQKSLSLS<br>LGKMFWVLVVVGGV<br>LACYSLLVTVAFIIFW<br>VRSKRSRGGHSDYM<br>NMTPRRPGPTRKHYQ<br>PYAPPRDFAAYRSRV<br>KFSRSADAPAYQQGQ<br>NQLYNELNLGRREEY<br>DVLDKRRGRDPEMG<br>GKPRRKNPQEGLYNE<br>LQKDKMAEAYSEIG<br>MKGERRRGKGHDGL<br>YQGLSTATKDTYDAL<br>HMQALPPR | | GGCAGCGGCGAGGGCAGCACCAAGGG<br>CGAAGTGAAGCTGGTGGAAAGCGGCG<br>GAGGCCTGGTGAAACCTGGCGGCAGCC<br>TGAAGCTGAGCTGCGCCGCCAGCGGCT<br>TCACCTTCAGCAGCTACGCCATGAGCT<br>GGGTCCGACAGATCCCCGAGAAGCGG<br>CTGGAATGGGTGGCCAGCATCAGCAGG<br>GGCGGCACCACCTACTACCCCGACAGC<br>GTGAAGGGCCGGTTCACCATCAGCCGG<br>GACAACGTGCGGAACATCCTGTACCTG<br>CAGATGAGCAGCCTGCGGAGCGAGGA<br>CACCGCCATGTACTACTGCGGCAGATA<br>CGACTACGACGGCTACTACGCCATGGA<br>TTACTGGGGCCAGGGCACCAGCGTGAC<br>CGTGTCTAGCGAGAGCAAGTACGGCCC<br>TCCCTGCCCCCCTTGCCCTGCCCCCGAG<br>TTCGAGGGCGGACCCAGCGTGTTCCTG<br>TTCCCCCCCAAGCCCAAGGACACCCTG<br>ATGATCAGCCGGACCCCCGAGGTGACC<br>TGTGTGGTGGTGGACGTGTCCCAGGAG<br>GACCCCGAGGTCCAGTTCAACTGGTAC<br>GTGGACGGCGTGGAGGTGCACAACGC<br>CAAGACCAAGCCCCGGGAGGAGCAGT<br>TCCAGAGCACCTACCGGGTGGTGTCCG<br>TGCTGACCGTGCTGCACCAGGACTGGC<br>TGAACGGCAAGGAATACAAGTGTAAG<br>GTGTCCAACAAGGGCCTGCCCAGCAGC<br>ATCGAGAAAACCATCAGCAAGGCCAA<br>GGGCCAGCCTCGGGAGCCCCAGGTGTA<br>CACCCTGCCCCCTAGCCAAGAGGAGAT<br>GACCAAGAATCAGGTGTCCCTGACCTG<br>CCTGGTGAAGGGCTTCTACCCCAGCGA<br>CATCGCCGTGGAGTGGGAGAGCAACG<br>GCCAGCCCGAGAACAACTACAAGACC<br>ACCCCCCCTGTGCTGGACAGCGACGGC<br>AGCTTCTTCCTGTACAGCAGGCTGACC<br>GTGGACAAGAGCCGGTGGCAGGAGGG<br>CAACGTCTTTAGCTGCTCCGTGATGCA<br>CGAGGCCCTGCACAACCACTACACCCA<br>GAAGAGCCTGTCCCTGAGCCTGGGCAA<br>GATGTTCTGGGTGCTGGTCGTGGTGGG<br>TGGCGTGCTGGCCTGCTACAGCCTGCT<br>GGTGACAGTGGCCTTCATCATCTTTTG<br>GGTGAGGAGCAAGCGGAGCAGAGGCG<br>GCCACAGCGACTACATGAACATGACCC<br>CCCGGAGGCCTGGCCCCACCCGGAAGC<br>ACTACCAGCCCTACGCCCCTCCCAGGG<br>ACTTCGCCGCCTACCGGAGCCGGGTGA<br>AGTTCAGCCGGAGCGCCGACGCCCCTG<br>CCTACCAGCAGGGCCAGAACCAGCTGT<br>ACAACGAGCTGAACCTGGGCCGGAGG<br>GAGGAGTACGACGTGCTGGACAAGCG<br>GAGAGGCCGGGACCCTGAGATGGGCG<br>GCAAGCCCCGGAGAAAGAACCCTCAG<br>GAGGGCCTGTATAACGAACTGCAGAA<br>AGACAAGATGGCCGAGGCCTACAGCG<br>AGATCGGCATGAAGGGCGAGCGGCGG<br>AGGGGCAAGGGCCACGACGGCCTGTA<br>CCAGGGCCTGAGCACCGCCACCAAGG<br>ATACCTACGACGCCCTGCACATGCAGG<br>CCCTGCCCCCCAGA |
| Murine ROR1<br>(VL-VH).IgG4<br>Fcm-CD28m-Z | 4 | DIKMTQSPSSMYASL<br>GERVTITCKASPDINS<br>YLSWFQQKPGKSPKT<br>LIYRANRLVDGVPSR<br>FSGGGSGQDYSLTINS<br>LEYEDMGIYYCLQYD<br>EFPYTFGGGTKLEMK<br>GSTSGSGKPGSGEGST<br>KGEVKLVESGGGLVK<br>PGGSLKLSCAASGFTF<br>SSYAMSWVRQIPEKR<br>LEWVASISRGGTTYY<br>PDSVKGRFTISRDNVR<br>NILYLQMSSLRSEDTA<br>MYYCGRYDYDGYYA<br>MDYWGQGTSVTVSS | 151 | GACATCAAGATGACCCAGAGCCCCAGC<br>TCTATGTACGCCAGCCTGGGCGAGCGC<br>GTGACCATCACATGCAAGGCCAGCCCC<br>GACATCAACAGCTACCTGTCCTGGTTC<br>CAGCAGAAGCCCGGCAAGAGCCCCAA<br>GACCCTGATCTACCGGGCCAACCGGCT<br>GGTGGACGGCGTGCCAAGCAGATTTTC<br>CGGCGGAGGCAGCGGCCAGGACTACA<br>GCCTGACCATCAACAGCCTGGAATACG<br>AGGACATGGGCATCTACTACTGCCTGC<br>AGTACGACGAGTTCCCCTACACCTTCG<br>GAGGCGGCACCAAGCTGGAAATGAAG<br>GGCAGCACCAGCGGCAGCGGCAAGCC<br>TGGAAGCGGCGAGGGCTCCACCAAGG<br>GCGAAGTGAAGCTGGTGGAAAGCGGC<br>GGAGGCCTGGTGAAACCTGGCGGCAG |

TABLE 12-continued

| Exemplary Sequences | | | | |
|---|---|---|---|---|
| | | QGTSVTVSSESKYGPP | | CCTGAAGCTGAGCTGCGCCGCCAGCGG |
| | | CPPCPAPEFLGGPSVF | | CTTCACCTTCAGCAGCTACGCCATGAG |
| | | LFPPKPKDTLMISRTP | | CTGGGTCCGACAGATCCCCGAGAAGCC |
| | | EVTCVVVDVSQEDPE | | GCTGGAATGGGTGGCCAGCATCAGCAC |
| | | VQFNWYVDGVEVHN | | GGGCGGCACCACCTACTACCCCGACAG |
| | | AKTKPREEQFNSTYR | | CGTGAAGGGCCGGTTCACCATCAGCCG |
| | | VVSVLTVLHQDWLN | | GGACAACGTGCGGAACATCCTGTACCT |
| | | GKEYKCKVSNKGLPS | | GCAGATGAGCAGCCTGCGGAGCGAGG |
| | | SIEKTISKAKGQPREP | | ACACCGCCATGTACTACTGCGGCAGAT |
| | | QVYTLPPSQEEMTKN | | ACGACTACGACGGCTACTACGCCATGG |
| | | QVSLTCLVKGFYPSDI | | ATTACTGGGGCCAGGGCACCAGCGTGA |
| | | AVEWESNGQPENNY | | CCGTGTCTAGCCAGGGAACCTCCGTGA |
| | | KTTPPVLDSDGSFFLY | | CAGTGTCCAGCGAGTCCAAATATGGTC |
| | | SRLTVDKSRWQEGN | | CCCCATGCCCACCATGCCCAGCACCTG |
| | | VFSCSVMHEALHNHY | | AGTTCCTGGGGGGACCATCAGTCTTCC |
| | | TQKSLSLSLGKMFWV | | TGTTCCCCCCAAAACCCAAGGACACTC |
| | | LVVVGGVLACYSLLV | | TCATGATCTCCCGGACCCCTGAGGTCA |
| | | TVAFIIFWVRSKRSRG | | CGTGCGTGGTGGTGGACGTGAGCCAGG |
| | | GHSDYMNMTPRRPG | | AAGACCCCGAGGTCCAGTTCAACTGGT |
| | | PTRKHYQPYAPPRDF | | ACGTGGATGGCGTGGAGGTGCATAATG |
| | | AAYRSRVKFSRSADA | | CCAAGACAAAGCCCCGGGAGGAGCAG |
| | | PAYQQGQNQLYNEL | | TTCAATAGCACCTACCGGGTGGTGTCC |
| | | NLGRREEYDVLDKRR | | GTGCTGACCGTGCTGCACCAGGACTGG |
| | | GRDPEMGGKPRRKNP | | CTGAACGGCAAGGAATACAAGTGTAA |
| | | QEGLYNELQKDKMA | | GGTGTCCAACAAGGGCCTGCCCAGCAG |
| | | EAYSEIGMKGERRRG | | CATCGAGAAAACCATCAGCAAGGCCA |
| | | KGHDGLYQGLSTATK | | AGGGCCAGCCTCGGGAGCCCCAGGTGT |
| | | DTYDALHMQALPPR | | ACACCCTGCCCCCTAGCCAAGAGGAGA |
| | | | | TGACCAAGAATCAGGTGTCCCTGACCT |
| | | | | GCCTGGTGAAGGGCTTCTACCCCAGCG |
| | | | | ACATCGCCGTGGAGTGGGAGAGCAAC |
| | | | | GGCCAGCCCGAGAACAACTACAAGAC |
| | | | | CACCCCCCCTGTGCTGGACAGCGACGG |
| | | | | CAGCTTCTTCCTGTACAGCAGGCTGAC |
| | | | | CGTGGACAAGAGCCGGTGGCAGGAGG |
| | | | | GCAACGTCTTTAGCTGCTCCGTGATGC |
| | | | | ACGAGGCCCTGCACAACCACTACACCC |
| | | | | AGAAGAGCCTGTCCCTGAGCCTGGGCA |
| | | | | AGATGTTCTGGGTGCTGGTCGTGGTGG |
| | | | | GTGGCGTGCTGGCCTGCTACAGCCTGC |
| | | | | TGGTGACAGTGGCCTTCATCATCTTTTG |
| | | | | GGTGAGGAGCAAGCGGAGCAGAGGCG |
| | | | | GCCACAGCGACTACATGAACATGACCC |
| | | | | CCCGGAGGCCTGGCCCCACCCGGAAGC |
| | | | | ACTACCAGCCCTACGCCCCTCCCAGGG |
| | | | | ACTTCGCCGCCTACCGGAGCCGGGTGA |
| | | | | AGTTCAGCCGGAGCGCCGACGCCCCTG |
| | | | | CCTACCAGCAGGGCCAGAACCAGCTGT |
| | | | | ACAACGAGCTGAACCTGGGCCGGAGG |
| | | | | GAGGAGTACGACGTGCTGGACAAGCG |
| | | | | GAGAGGCCGGGACCCTGAGATGGGCG |
| | | | | GCAAGCCCCGGAGAAAGAACCCTCAG |
| | | | | GAGGGCCTGTATAACGAACTGCAGAA |
| | | | | AGACAAGATGGCCGAGGCCTACAGCG |
| | | | | AGATCGGCATGAAGGGCGAGCGGCGG |
| | | | | AGGGGCAAGGGCCACGACGGCCTGTA |
| | | | | CCAGGGCCTGAGCACCGCCACCAAGG |
| | | | | ATACCTACGACGCCCTGCACATGCAGG |
| | | | | CCCTGCCCCCCAGA |
| Murine ROR1 | 5 | DIKMTQSPSSMYASL | 152 | GACATCAAGATGACCCAGAGCCCCAGC |
| (VL-VH).CD8α.CD28z | | GERVTITCKASPDINS | | TCTATGTACGCCAGCCTGGGCGAGCGC |
| | | YLSWFQQKPGKSPKT | | GTGACCATCACATGCAAGGCCAGCCCC |
| | | LIYRANRLVDGVPSR | | GACATCAACAGCTACCTGTCCTGGTTC |
| | | FSGGGSGQDYSLTINS | | CAGCAGAAGCCCGGCAAGAGCCCCAA |
| | | LEYEDMGIYYCLQYD | | GACCCTGATCTACCGGGCCAACCGGCT |
| | | EFPYTFGGGTKLEMK | | GGTGGACGGCGTGCCAAGCAGATTTTC |
| | | GSTSGSGKPGSGEGST | | CGGCGGAGGCAGCGGCCAGGACTACA |
| | | KGEVKLVESGGGLVK | | GCCTGACCATCAACAGCCTGGAATACG |
| | | PGGSLKLSCAASGFTF | | AGGACATGGGCATCTACTACTGCCTGC |
| | | SSYAMSWVRQIPEKR | | AGTACGACGAGTTCCCCTACACCTTCG |
| | | LEWVASISRGGTTYY | | GAGGCGGCACCAAGCTGGAAATGAAG |
| | | PDSVKGRFTISRDNVR | | GGCAGCACCTCCGGCAGCGGCAAGCCT |
| | | NILYLQMSSLRSEDTA | | GGCAGCGGCGAGGGCAGCACCAAGGG |
| | | MYYCGRYDYDGYYA | | CGAAGTGAAGCTGGTGGAAAGCGGCG |
| | | MDYWGQGTSVTVSS | | GAGGCCTGGTGAAACCTGGCGGCAGCC |
| | | KPTTTPAPRPPTPAPTI | | TGAAGCTGAGCTGCGCCGCCAGCGGCT |
| | | ASQPLSLRPEACRPAA | | TCACCTTCAGCAGCTACGCCATGAGCT |

TABLE 12-continued

| Exemplary Sequences | | | | |
|---|---|---|---|---|
| | | GGAVHTRGLDFACDI | | GGGTCCGACAGATCCCCGAGAAGCGG |
| | | YIWAPLAGTCGVLLL | | CTGGAATGGGTGGCCAGCATCAGCAGG |
| | | SLVITLYCNHRNRSK | | GGCGGCACCACCTACTACCCCGACAGC |
| | | RSRGGHSDYMNMTP | | GTGAAGGGCCGGTTCACCATCAGCCGG |
| | | RRPGPTRKHYQPYAP | | GACAACGTGCGGAACATCCTGTACCTG |
| | | PRDFAAYRSRVKFSR | | CAGATGAGCAGCCTGCGGAGCGAGGA |
| | | SADAPAYQQGQNQL | | CACCGCCATGTACTACTGCGGCAGATA |
| | | YNELNLGRREEYDVL | | CGACTACGACGGCTACTACGCCATGGA |
| | | DKRRGRDPEMGGKP | | TTACTGGGGCCAGGGCACCAGCGTGAC |
| | | RRKNPQEGLYNELQK | | CGTGTCTAGCAAGCCCACCACCACCCC |
| | | DKMAEAYSEIGMKG | | TGCCCCTAGACCTCCAACCCCAGCCCC |
| | | ERRRGKGHDGLYQG | | TACAATCGCCAGCCAGCCCCTGAGCCT |
| | | LSTATKDTYDALHM | | GAGGCCCGAAGCCTGTAGACCTGCCGC |
| | | QALPPR | | TGGCGGAGCCGTGCACACCAGAGGCCT |
| | | | | GGATTTCGCCTGCGACATCTACATCTG |
| | | | | GGCCCCTCTGGCCGGCACCTGTGGCGT |
| | | | | GCTGCTGCTGAGCCTGGTCATCACCCT |
| | | | | GTACTGCAACCACCGGAATAGGAGCA |
| | | | | AGCGGAGCAGAGGCGGCCACAGCGAC |
| | | | | TACATGAACATGACCCCCCGGAGGCCT |
| | | | | GGCCCCACCCGGAAGCACTACCAGCCC |
| | | | | TACGCCCCTCCCAGGGACTTCGCCGCC |
| | | | | TACCGGAGCCGGGTGAAGTTCAGCCGG |
| | | | | AGCGCCGACGCCCCTGCCTACCAGCAG |
| | | | | GGCCAGAACCAGCTGTACAACGAGCTG |
| | | | | AACCTGGGCCGGAGGGAGGAGTACGA |
| | | | | CGTGCTGGACAAGCGGAGAGGCCGGG |
| | | | | ACCCTGAGATGGGCGGCAAGCCCCGG |
| | | | | AGAAAGAACCCTCAGGAGGGCCTGTAT |
| | | | | AACGAACTGCAGAAAGACAAGATGGC |
| | | | | CGAGGCCTACAGCGAGATCGGCATGA |
| | | | | AGGGCGAGCGGCGGAGGGGCAAGGGC |
| | | | | CACGACGGCCTGTACCAGGGCCTGAGC |
| | | | | ACCGCCACCAAGGATACCTACGACGCC |
| | | | | CTGCACATGCAGGCCCTGCCCCCCAGA |
| Murine ROR1 | 6 | DIKMTQSPSSMYASL | 153 | GACATCAAGATGACCCAGAGCCCCAGC |
| (VL-VH).CD8α(2x).CD28z | | GERVTITCKASPDINS | | TCTATGTACGCCAGCCTGGGCGAGCGC |
| | | YLSWFQQKPGKSPKT | | GTGACCATCACATGCAAGGCCAGCCCC |
| | | LIYRANRLVDGVPSR | | GACATCAACAGCTACCTGTCCTGGTTC |
| | | FSGGGSGQDYSLTINS | | CAGCAGAAGCCCGGCAAGAGCCCCAA |
| | | LEYEDMGIYYCLQYD | | GACCCTGATCTACCGGGCCAACCGGCT |
| | | EFPYTFGGGTKLEMK | | GGTGGACGGCGTGCCAAGCAGATTTTC |
| | | GSTSGSGKPGSGEGST | | CGGCGGAGGCAGCGGCCAGGACTACA |
| | | KGEVKLVESGGGLVK | | GCCTGACCATCAACAGCCTGGAATACG |
| | | PGGSLKLSCAASGFTF | | AGGACATGGGCATCTACTACTGCCTGC |
| | | SSYAMSWVRQIPEKR | | AGTACGACGAGTTCCCCTACACCTTCG |
| | | LEWVASISRGGTTYY | | GAGGCGGCACCAAGCTGGAAATGAAG |
| | | PDSVKGRFTISRDNVR | | GGCAGCACCTCCGGCAGCGGCAAGCCT |
| | | NILYLQMSSLRSEDTA | | GGCAGCGGCGAGGGCAGCACCAAGGG |
| | | MYYCGRYDYDGYYA | | CGAAGTGAAGCTGGTGGAAAGCGGCG |
| | | MDYWGQGTSVTVSS | | GAGGCCTGGTGAAACCTGGCGGCAGCC |
| | | KPTTTPAPRPPTPAPTI | | TGAAGCTGAGCTGCGCCGCCAGCGGCT |
| | | ASQPLSLRPEASRPAA | | TCACCTTCAGCAGCTACGCCATGAGCT |
| | | GGAVHTRGLDFASDK | | GGGTCCGACAGATCCCCGAGAAGCGG |
| | | PTTTPAPRPPTPAPTIA | | CTGGAATGGGTGGCCAGCATCAGCAGG |
| | | SQPLSLRPEACRPAAG | | GGCGGCACCACCTACTACCCCGACAGC |
| | | GAVHTRGLDFACDIY | | GTGAAGGGCCGGTTCACCATCAGCCGG |
| | | IWAPLAGTCGVLLLS | | GACAACGTGCGGAACATCCTGTACCTG |
| | | LVITLYCNHRNRSKR | | CAGATGAGCAGCCTGCGGAGCGAGGA |
| | | SRGGHSDYMNMTPR | | CACCGCCATGTACTACTGCGGCAGATA |
| | | RPGPTRKHYQPYAPP | | CGACTACGACGGCTACTACGCCATGGA |
| | | RDFAAYRSRVKFSRS | | TTACTGGGGCCAGGGCACCAGCGTGAC |
| | | ADAPAYQQGQNQLY | | CGTGTCTAGCAAACCTACTACAACTCC |
| | | NELNLGRREEYDVLD | | TGCCCCCCGGCCTCCTACACCAGCTCC |
| | | KRRGRDPEMGGKPR | | TACTATCGCCTCCCAGCCACTCAGTCTC |
| | | RKNPQEGLYNELQKD | | AGACCCGAGGCTTCTAGGCCAGCGGCC |
| | | KMAEAYSEIGMKGER | | GGAGGCGCGGTCCACACCCGCGGGCTG |
| | | RRGKGHDGLYQGLST | | GACTTTGCATCCGATAAGCCCACCACC |
| | | ATKDTYDALHMQAL | | ACCCCTGCCCCTAGACCTCCAACCCCA |
| | | PPR | | GCCCCTACAATCGCCAGCCAGCCCCTG |
| | | | | AGCCTGAGGCCCGAAGCCTGTAGACCT |
| | | | | GCCGCTGGCGGAGCCGTGCACACCAGA |
| | | | | GGCCTGGATTTCGCCTGCGACATCTAC |
| | | | | ATCTGGGCCCCTCTGGCCGGCACCTGT |
| | | | | GGCGTGCTGCTGCTGAGCCTGGTCATC |
| | | | | ACCCTGTACTGCAACCACCGGAATAGG |
| | | | | AGCAAGCGGAGCAGAGGCGGCCACAG |

TABLE 12-continued

| Exemplary Sequences | | | | |
|---|---|---|---|---|
| | | | | CGACTACATGAACATGACCCCCCGGAG<br>GCCTGGCCCCACCCGGAAGCACTACCA<br>GCCCTACGCCCCTCCCAGGGACTTCGC<br>CGCCTACCGGAGCCGGGTGAAGTTCAG<br>CCGGAGCGCCGACGCCCCTGCCTACCA<br>GCAGGGCCAGAACCAGCTGTACAACG<br>AGCTGAACCTGGGCCGGAGGGAGGAG<br>TACGACGTGCTGGACAAGCGGAGAGG<br>CCGGGACCCTGAGATGGGCGGCAAGC<br>CCCGGAGAAAGAACCCTCAGGAGGGC<br>CTGTATAACGAACTGCAGAAAGACAA<br>GATGGCCGAGGCCTACAGCGAGATCG<br>GCATGAAGGGCGAGCGGCGGAGGGGC<br>AAGGGCCACGACGGCCTGTACCAGGG<br>CCTGAGCACCGCCACCAAGGATACCTA<br>CGACGCCCTGCACATGCAGGCCCTGCC<br>CCCCAGA |
| Murine ROR1<br>(VL-VH).CD8a(3x).CD28z | 7 | DIKMTQSPSSMYASL<br>GERVTITCKASPDINS<br>YLSWFQQKPGKSPKT<br>LIYRANRLVDGVPSR<br>FSGGGSGQDYSLTINS<br>LEYEDMGIYYCLQYD<br>EFPYTFGGGTKLEMK<br>GSTSGSGKPGSGEGST<br>KGEVKLVESGGGLVK<br>PGGSLKLSCAASGFTF<br>SSYAMSWVRQIPEKR<br>LEWVASISRGGTTYY<br>PDSVKGRFTISRDNVR<br>NILYLQMSSLRSEDTA<br>MYYCGRYDYDGYYA<br>MDYWGQGTSVTVSS<br>KPTTTPAPRPPTPAPTI<br>ASQPLSLRPEASRPAA<br>GGAVHTRGLDFASDK<br>PTTTPAPRPPTPAPTIA<br>SQPLSLRPEASRPAAG<br>GAVHTRGLDFASDKP<br>TTTPAPRPPTPAPTIAS<br>QPLSLRPEACRPAAG<br>GAVHTRGLDFACDIY<br>IWAPLAGTCGVLLLS<br>LVITLYCNHRNRSKR<br>SRGGHSDYMNMTPR<br>RPGPTRKHYQPYAPP<br>RDFAAYRSRVKFSRS<br>ADAPAYQQGQNQLY<br>NELNLGRREEYDVLD<br>KRRGRDPEMGGKPR<br>RKNPQEGLYNELQKD<br>KMAEAYSEIGMKGER<br>RRGKGHDGLYQGLST<br>ATKDTYDALHMQAL<br>PPR | 154 | GACATCAAGATGACCCAGAGCCCCAGC<br>TCTATGTACGCCAGCCTGGGCGAGCGC<br>GTGACCATCACATGCAAGGCCAGCCCC<br>GACATCAACAGCTACCTGTCCTGGTTC<br>CAGCAGAAGCCCGGCAAGAGCCCCAA<br>GACCCTGATCTACCGGGCCAACCGGCT<br>GGTGGACGGCGTGCCAAGCAGATTTTC<br>CGGCGGAGGCAGCGGCCAGGACTACA<br>GCCTGACCATCAACAGCCTGGAATACG<br>AGGACATGGGCATCTACTACTGCCTGC<br>AGTACGACGAGTTCCCCTACACCTTCG<br>GAGGCGGCACCAAGCTGGAAATGAAG<br>GGCAGCACCTCCGGCAGCGGCAAGCCT<br>GGCAGCGGCGAGGGCAGCACCAAGGG<br>CGAAGTGAAGCTGGTGGAAAGCGGCG<br>GAGGCCTGGTGAAACCTGGCGGCAGCC<br>TGAAGCTGAGCTGCGCCGCCAGCGGCT<br>TCACCTTCAGCAGCTACGCCATGAGCT<br>GGGTCCGACAGATCCCCGAGAAGCGG<br>CTGGAATGGGTGGCCAGCATCAGCAGG<br>GGCGGCACCACCTACTACCCCGACAGC<br>GTGAAGGGCCGGTTCACCATCAGCCGG<br>GACAACGTGCGGAACATCCTGTACCTG<br>CAGATGAGCAGCCTGCGGAGCGAGGA<br>CACCGCCATGTACTACTGCGGCAGATA<br>CGACTACGACGGCTACTACGCCATGGA<br>TTACTGGGGCCAGGGCACCAGCGTGAC<br>CGTGTCTAGCAAGCCTACCACCACCCC<br>CGCACCTCGTCCTCCAACCCCTGCACC<br>TACGATTGCCAGTCAGCCTCTTTCACTG<br>CGGCCTGAGGCCAGCAGACCAGCTGCC<br>GGCGGTGCCGTCCATACAAGAGGACTG<br>GACTTCGCGTCCGATAAACCTACTACC<br>ACTCCAGCCCCAAGGCCCCCAACCCCA<br>GCACCGACTATCGCATCACAGCCTTTG<br>TCACTGCGTCCTGAAGCCAGCCGGCCA<br>GCTGCAGGGGGGGCCGTCCACACAAG<br>GGGACTCGACTTTGCGAGTGATAAGCC<br>CACCACCACCCCTGCCCCTAGACCTCC<br>AACCCCAGCCCCTACAATCGCCAGCCA<br>GCCCCTGAGCCTGAGGCCCGAAGCCTG<br>TAGACCTGCCGCTGGCGGAGCCGTGCA<br>CACCAGAGGCCTGGATTTCGCCTGCGA<br>CATCTACATCTGGGCCCCTCTGGCCGG<br>CACCTGTGGCGTGCTGCTGCTGAGCCT<br>GGTCATCACCCTGTACTGCAACCACCG<br>GAATAGGAGCAAGCGGAGCAGAGGCG<br>GCCACAGCGACTACATGAACATGACCC<br>CCCGGAGGCCTGGCCCCACCCGGAAGC<br>ACTACCAGCCCTACGCCCCTCCCAGGG<br>ACTTCGCCGCCTACCGGAGCCGGGTGA<br>AGTTCAGCCGGAGCGCCGACGCCCCTG<br>CCTACCAGCAGGGCCAGAACCAGCTGT<br>ACAACGAGCTGAACCTGGGCCGGAGG<br>GAGGAGTACGACGTGCTGGACAAGCG<br>GAGAGGCCGGGACCCTGAGATGGGCG<br>GCAAGCCCCGGAGAAAGAACCCTCAG<br>GAGGGCCTGTATAACGAACTGCAGAA<br>AGACAAGATGGCCGAGGCCTACAGCG<br>AGATCGGCATGAAGGGCGAGCGGCGG |

TABLE 12-continued

| Exemplary Sequences | | | | |
|---|---|---|---|---|
| | | | | AGGGGCAAGGGCCACGACGGCCTGTA<br>CCAGGGCCTGAGCACCGCCACCAAGG<br>ATACCTACGACGCCCTGCACATGCAGG<br>CCCTGCCCCCCAGA |
| Murine ROR1<br>(VL-VH).CD8a(4x).CD28z | 8 | DIKMTQSPSSMYASL<br>GERVTITCKASPDINS<br>YLSWFQQKPGKSPKT<br>LIYRANRLVDGVPSR<br>FSGGGSGQDYSLTINS<br>LEYEDMGIYYCLQYD<br>EFPYTFGGGTKLEMK<br>GSTSGSGKPGSGEGST<br>KGEVKLVESGGGLVK<br>PGGSLKLSCAASGFTF<br>SSYAMSWVRQIPEKR<br>LEWVASISRGGTTYY<br>PDSVKGRFTISRDNVR<br>NILYLQMSSLRSEDTA<br>MYYCGRYDYDGYYA<br>MDYWGQGTSVTVSS<br>KPTTTPAPRPPTPAPTI<br>ASQPLSLRPEASRPAA<br>GGAVHTRGLDFASDK<br>PTTTPAPRPPTPAPTIA<br>SQPLSLRPEASRPAAG<br>GAVHTRGLDFASDKP<br>TTTPAPRPPTPAPTIAS<br>QPLSLRPEASRPAAG<br>GAVHTRGLDFASDKP<br>TTTPAPRPPTPAPTIAS<br>QPLSLRPEACRPAAG<br>GAVHTRGLDFACDIY<br>IWAPLAGTCGVLLLS<br>LVITLYCNHRNRSKR<br>SRGGHSDYMNMTPR<br>RPGPTRKHYQPYAPP<br>RDFAAYRSRVKFSRS<br>ADAPAYQQGQNQLY<br>NELNLGRREEYDVLD<br>KRRGRDPEMGGKPR<br>RKNPQEGLYNELQKD<br>KMAEAYSEIGMKGER<br>RRGKGHDGLYQGLST<br>ATKDTYDALHMQAL<br>PPR | 155 | GACATCAAGATGACCCAGAGCCCCAGC<br>TCTATGTACGCCAGCCTGGGCGAGCGC<br>GTGACCATCACATGCAAGGCCAGCCCC<br>GACATCAACAGCTACCTGTCCTGGTTC<br>CAGCAGAAGCCCGGCAAGAGCCCCAA<br>GACCCTGATCTACCGGGCCAACCGGCT<br>GGTGGACGGCGTGCCAAGCAGATTTTC<br>CGGCGGAGGCAGCGGCCAGGACTACA<br>GCCTGACCATCAACAGCCTGGAATACG<br>AGGACATGGGCATCTACTACTGCCTGC<br>AGTACGACGAGTTCCCCTACACCTTCG<br>GAGGCGGCACCAAGCTGGAAATGAAG<br>GGCAGCACCTCCGGCAGCGGCAAGCCT<br>GGCAGCGGCGAGGGCAGCACCAAGGG<br>CGAAGTGAAGCTGGTGGAAAGCGGCG<br>GAGGCCTGGTGAAACCTGGCGGCAGCC<br>TGAAGCTGAGCTGCGCCGCCAGCGGCT<br>TCACCTTCAGCAGCTACGCCATGAGCT<br>GGGTCCGACAGATCCCCGAGAAGCGG<br>CTGGAATGGGTGGCCAGCATCAGCAGG<br>GGCGGCACCACCTACTACCCCGACAGC<br>GTGAAGGGCCGGTTCACCATCAGCCGG<br>GACAACGTGCGGAACATCCTGTACCTG<br>CAGATGAGCAGCCTGCGGAGCGAGGA<br>CACCGCCATGTACTACTGCGGCAGATA<br>CGACTACGACGGCTACTACGCCATGGA<br>TTACTGGGGCCAGGGCACCAGCGTGAC<br>CGTGTCTAGCAAGCCTACCACCACCCC<br>CGCACCTCGTCCTCCAACCCCTGCACC<br>TACGATTGCCAGTCAGCCTCTTTCACTG<br>CGGCCTGAGGCCAGCAGACCAGCTGCC<br>GGCGGTGCCGTCCATACAAGAGGACTG<br>GACTTCGCGTCCGATAAACCTACTACC<br>ACTCCAGCCCCAAGGCCCCCAACCCCA<br>GCACCGACTATCGCATCACAGCCTTTG<br>TCACTGCGTCCTGAAGCCAGCCGGCCA<br>GCTGCAGGGGGGGCCGTCCACACAAG<br>GGGACTCGACTTTGCGAGTGATAAACC<br>TACTACAACTCCTGCCCCCCGGCCTCCT<br>ACACCAGCTCCTACTATCGCCTCCCAG<br>CCACTCAGTCTCAGACCCGAGGCTTCT<br>AGGCCAGCGGCCGGAGGCGCGGTCCA<br>CACCCGCGGGCTGGACTTTGCATCCGA<br>TAAGCCCACCACCACCCCTGCCCCTAG<br>ACCTCCAACCCCAGCCCCTACAATCGC<br>CAGCCAGCCCCTGAGCCTGAGGCCCGA<br>AGCCTGTAGACCTGCCGCTGGCGGAGC<br>CGTGCACACCAGAGGCCTGGATTTCGC<br>CTGCGACATCTACATCTGGGCCCCTCT<br>GGCCGGCACCTGTGGCGTGCTGCTGCT<br>GAGCCTGGTCATCACCCTGTACTGCAA<br>CCACCGGAATAGGAGCAAGCGGAGCA<br>GAGGCGGCCACAGCGACTACATGAAC<br>ATGACCCCCCGGAGGCCTGGCCCCACC<br>CGGAAGCACTACCAGCCCTACGCCCCT<br>CCCAGGGACTTCGCCGCCTACCGGAGC<br>CGGGTGAAGTTCAGCCGGAGCGCCGAC<br>GCCCCTGCCTACCAGCAGGGCCAGAAC<br>CAGCTGTACAACGAGCTGAACCTGGGC<br>CGGAGGGAGGAGTACGACGTGCTGGA<br>CAAGCGGAGAGGCCGGGACCCTGAGA<br>TGGGCGGCAAGCCCCGGAGAAAGAAC<br>CCTCAGGAGGGCCTGTATAACGAACTG<br>CAGAAAGACAAGATGGCCGAGGCCTA<br>CAGCGAGATCGGCATGAAGGGCGAGC<br>GGCGGAGGGGCAAGGGCCACGACGGC<br>CTGTACCAGGGCCTGAGCACCGCCACC<br>AAGGATACCTACGACGCCCTGCACATG<br>CAGGCCCTGCCCCCCAGA |
| Murine ROR1<br>(VL-VH).LNGFRECD.CD8TM.CD28z | 9 | DIKMTQSPSSMYASL<br>GERVTITCKASPDINS<br>YLSWFQQKPGKSPKT | 156 | GACATCAAGATGACCCAGAGCCCCAGC<br>TCTATGTACGCCAGCCTGGGCGAGCGC<br>GTGACCATCACATGCAAGGCCAGCCCC |

TABLE 12-continued

| Exemplary Sequences | | | | |
|---|---|---|---|---|
| | | LIYRANRLVDGVPSR | | GACATCAACAGCTACCTGTCCTGGTTC |
| | | FSGGGSGQDYSLTINS | | CAGCAGAAGCCCGGCAAGAGCCCCAA |
| | | LEYEDMGIYYCLQYD | | GACCCTGATCTACCGGGCCAACCGGCT |
| | | EFPYTFGGGTKLEMK | | GGTGGACGGCGTGCCAAGCAGATTTTC |
| | | GSTSGSGKPGSGEGST | | CGGCGGAGGCAGCGGCCAGGACTACA |
| | | KGEVKLVESGGGLVK | | GCCTGACCATCAACAGCCTGGAATACG |
| | | PGGSLKLSCAASGFTF | | AGGACATGGGCATCTACTACTGCCTGC |
| | | SSYAMSWVRQIPEKR | | AGTACGACGAGTTCCCCTACACCTTCG |
| | | LEWVASISRGGTTYY | | GAGGCGGCACCAAGCTGGAAATGAAG |
| | | PDSVKGRFTISRDNVR | | GGCAGCACCTCCGGCAGCGGCAAGCCT |
| | | NILYLQMSSLRSEDTA | | GGCAGCGGCGAGGGCAGCACCAAGGG |
| | | MYYCGRYDYDGYYA | | CGAAGTGAAGCTGGTGGAAAGCGGCG |
| | | MDYWGQGTSVTVSS | | GAGGCCTGGTGAAACCTGGCGGCAGCC |
| | | KEACPTGLYTHSGEC | | TGAAGCTGAGCTGCGCCGCCAGCGGCT |
| | | CKACNLGEGVAQPC | | TCACCTTCAGCAGCTACGCCATGAGCT |
| | | GANQTVCEPCLDSVT | | GGGTCCGACAGATCCCCGAGAAGCGG |
| | | FSDVVSATEPCKPCTE | | CTGGAATGGGTGGCCAGCATCAGCAGG |
| | | CVGLQSMSAPCVEAD | | GGCGGCACCACCTACTACCCCGACAGC |
| | | DAVCRCAYGYYQDE | | GTGAAGGGCCGGTTCACCATCAGCCGG |
| | | TTGRCEACRVCEAGS | | GACAACGTGCGGAACATCCTGTACCTG |
| | | GLVFSCQDKQNTVCE | | CAGATGAGCAGCCTGCGGAGCGAGGA |
| | | ECPDGTYSDEANHVD | | CACCGCCATGTACTACTGCGGCAGATA |
| | | PCLPCTVCEDTERQL | | CGACTACGACGGCTACTACGCCATGGA |
| | | RECTRWADAECEEIP | | TTACTGGGGCCAGGGCACCAGCGTGAC |
| | | GRWITRSTPPEGSDST | | CGTGTCTAGCAAGGAGGCATGCCCCAC |
| | | APSTQEPEAPPEQDLI | | AGGCCTGTACACACACAGCGGTGAGTG |
| | | ASTVAGVVTTVMGSS | | CTGCAAAGCCTGCAACCTGGGCGAGGG |
| | | QPVVTRGTTDNIYIW | | TGTGGCCCAGCCTTGTGGAGCCAACCA |
| | | APLAGTCGVLLLSLVI | | GACCGTGTGTGAGCCCTGCCTGGACAG |
| | | TLYCNHRNRSKRSRG | | CGTGACGTTCTCCGACGTGGTGAGCGC |
| | | GHSDYMNMTPRRPG | | GACCGAGCCGTGCAAGCCGTGCACCGA |
| | | PTRKHYQPYAPPRDF | | GTGCGTGGGGCTCCAGAGCATGTCGGC |
| | | AAYRSRVKFSRSADA | | GCCGTGCGTGGAGGCCGACGACGCCGT |
| | | PAYQQGQNQLYNEL | | GTGCCGCTGCGCCTACGGCTACTACCA |
| | | NLGRREEYDVLDKRR | | GGATGAGACGACTGGGCGCTGCGAGG |
| | | GRDPEMGGKPRRKNP | | CGTGCCGCGTGTGCGAGGCGGGCTCGG |
| | | QEGLYNELQKDKMA | | GCCTCGTGTTCTCCTGCCAGGACAAGC |
| | | EAYSEIGMKGERRRG | | AGAACACCGTGTGCGAGGAGTGCCCCG |
| | | KGHDGLYQGLSTATK | | ACGGCACGTATTCCGACGAGGCCAACC |
| | | DTYDALHMQALPPR | | ACGTGGACCCGTGCCTGCCCTGCACCG |
| | | | | TGTGCGAGGACACCGAGCGCCAGCTCC |
| | | | | GCGAGTGCACACGCTGGGCCGACGCCG |
| | | | | AGTGCGAGGAGATCCCTGGCCGTTGGA |
| | | | | TTACACGGTCCACACCCCCAGAGGGCT |
| | | | | CGGACAGCACAGCCCCCAGCACCCAG |
| | | | | GAGCCTGAGGCACCTCCAGAACAAGA |
| | | | | CCTCATAGCCAGCACGGTGGCAGGTGT |
| | | | | GGTGACCACAGTGATGGGCAGCTCCCA |
| | | | | GCCCGTGGTGACCCGAGGCACCACCGA |
| | | | | CAACATCTACATCTGGGCCCCTCTGGC |
| | | | | CGGCACCTGTGGCGTGCTGCTGCTGAG |
| | | | | CCTGGTCATCACCCTGTACTGCAACCA |
| | | | | CCGGAATAGGAGCAAGCGGAGCAGAG |
| | | | | GCGGCCACAGCGACTACATGAACATGA |
| | | | | CCCCCCGGAGGCCTGGCCCCACCCGGA |
| | | | | AGCACTACCAGCCCTACGCCCCTCCCA |
| | | | | GGGACTTCGCCGCCTACCGGAGCCGGG |
| | | | | TGAAGTTCAGCCGGAGCGCCGACGCCC |
| | | | | CTGCCTACCAGCAGGGCCAGAACCAGC |
| | | | | TGTACAACGAGCTGAACCTGGGCCGGA |
| | | | | GGGAGGAGTACGACGTGCTGGACAAG |
| | | | | CGGAGAGGCCGGGACCCTGAGATGGG |
| | | | | CGGCAAGCCCCGGAGAAAGAACCCTC |
| | | | | AGGAGGGCCTGTATAACGAACTGCAG |
| | | | | AAAGACAAGATGGCCGAGGCCTACAG |
| | | | | CGAGATCGGCATGAAGGGCGAGCGGC |
| | | | | GGAGGGGCAAGGGCCACGACGGCCTG |
| | | | | TACCAGGGCCTGAGCACCGCCACCAAG |
| | | | | GATACCTACGACGCCCTGCACATGCAG |
| | | | | GCCCTGCCCCCCAGA |
| Murine ROR1 | 10 | EVKLVESGGGLVKPG | 157 | GAAGTGAAGCTGGTGGAAAGCGGCGG |
| (VH-VL).CD8a(3x).41BBz | | GSLKLSCAASGFTFSS | | AGGCCTGGTGAAACCTGGCGGCAGCCT |
| | | YAMSWVRQIPEKRLE | | GAAGCTGAGCTGCGCCGCCAGCGGCTT |
| | | WVASISRGGTTYYPD | | CACCTTCAGCAGCTACGCCATGAGCTG |
| | | SVKGRFTISRDNVRNI | | GGTCCGACAGATCCCCGAGAAGCGGCT |
| | | LYLQMSSLRSEDTAM | | GGAATGGGTGGCCAGCATCAGCAGGG |
| | | YYCGRYDYDGYYAM | | GCGGCACCACCTACTACCCCGACAGCG |

TABLE 12-continued

| Exemplary Sequences | | | | |
|---|---|---|---|---|
| | | DYWGQGTSVTVSSGS | | TGAAGGGCCGGTTCACCATCAGCCGGG |
| | | TSGSGKPGSGEGSTK | | ACAACGTGCGGAACATCCTGTACCTGC |
| | | GDIKMTQSPSSMYAS | | AGATGAGCAGCCTGCGGAGCGAGGAC |
| | | LGERVTITCKASPDIN | | ACCGCCATGTACTACTGCGGCAGATAC |
| | | SYLSWFQQKPGKSPK | | GACTACGACGGCTACTACGCCATGGAT |
| | | TLIYRANRLVDGVPS | | TACTGGGGCCAGGGCACCAGCGTGACC |
| | | RFSGGGSGQDYSLTIN | | GTGTCTAGCGGCAGCACCTCCGGCAGC |
| | | SLEYEDMGIYYCLQY | | GGCAAGCCTGGCAGCGGCGAGGGCAG |
| | | DEFPYTFGGGTKLEM | | CACCAAGGGCGACATCAAGATGACCC |
| | | KKPTTTPAPRPPTPAP | | AGAGCCCCAGCTCTATGTACGCCAGCC |
| | | TIASQPLSLRPEASRP | | TGGGCGAGCGCGTGACCATCACATGCA |
| | | AAGGAVHTRGLDFAS | | AGGCCAGCCCCGACATCAACAGCTACC |
| | | DKPTTTPAPRPPTPAP | | TGTCCTGGTTCCAGCAGAAGCCCGGCA |
| | | TIASQPLSLRPEASRP | | AGAGCCCCAAGACCCTGATCTACCGGG |
| | | AAGGAVHTRGLDFAS | | CCAACCGGCTGGTGGACGGCGTGCCAA |
| | | DKPTTTPAPRPPTPAP | | GCAGATTTTCCGGCGGAGGCAGCGGCC |
| | | TIASQPLSLRPEACRP | | AGGACTACAGCCTGACCATCAACAGCC |
| | | AAGGAVHTRGLDFA | | TGGAATACGAGGACATGGGCATCTACT |
| | | CDIYIWAPLAGTCGV | | ACTGCCTGCAGTACGACGAGTTCCCCT |
| | | LLLSLVITLYCNHRNK | | ACACCTTCGGAGGCGGCACCAAGCTGG |
| | | RGRKKLLYIFKQPFM | | AAATGAAGAAGCCTACCACCACCCCCG |
| | | RPVQTTQEEDGCSCR | | CACCTCGTCCTCCAACCCCTGCACCTA |
| | | FPEEEEGGCELRVKFS | | CGATTGCCAGTCAGCCTCTTTCACTGC |
| | | RSADAPAYQQGQNQ | | GGCCTGAGGCCAGCAGACCAGCTGCCG |
| | | LYNELNLGRREEYDV | | GCGGTGCCGTCCATACAAGAGGACTGG |
| | | LDKRRGRDPEMGGK | | ACTTCGCGTCCGATAAACCTACTACCA |
| | | PRRKNPQEGLYNELQ | | CTCCAGCCCCAAGGCCCCCAACCCCAG |
| | | KDKMAEAYSEIGMK | | CACCGACTATCGCATCACAGCCTTTGT |
| | | GERRRGKGHDGLYQ | | CACTGCGTCCTGAAGCCAGCCGGCCAG |
| | | GLSTATKDTYDALH | | CTGCAGGGGGGGCCGTCCACACAAGG |
| | | MQALPPR | | GGACTCGACTTTGCGAGTGATAAGCCC |
| | | | | ACCACCACCCCTGCCCCTAGACCTCCA |
| | | | | ACCCCAGCCCCTACAATCGCCAGCCAG |
| | | | | CCCCTGAGCCTGAGGCCCGAAGCCTGT |
| | | | | AGACCTGCCGCTGGCGGAGCCGTGCAC |
| | | | | ACCAGAGGCCTGGATTTCGCCTGCGAC |
| | | | | ATCTACATCTGGGCCCCTCTGGCCGGC |
| | | | | ACCTGTGGCGTGCTGCTGCTGAGCCTG |
| | | | | GTCATCACCCTGTACTGCAACCACCGG |
| | | | | AATAAGAGAGGCCGGAAGAAACTGCT |
| | | | | GTACATCTTCAAGCAGCCCTTCATGCG |
| | | | | GCCCGTGCAGACCACCCAGGAAGAGG |
| | | | | ACGGCTGCAGCTGCCGGTTCCCCGAGG |
| | | | | AAGAGGAAGGCGGCTGCGAACTGCGG |
| | | | | GTGAAGTTCAGCCGGAGCGCCGACGCC |
| | | | | CCTGCCTACCAGCAGGGCCAGAACCAG |
| | | | | CTGTACAACGAGCTGAACCTGGGCCGG |
| | | | | AGGGAGGAGTACGACGTGCTGGACAA |
| | | | | GCGGAGAGGCCGGGACCCTGAGATGG |
| | | | | GCGGCAAGCCCCGGAGAAAGAACCCT |
| | | | | CAGGAGGGCCTGTATAACGAACTGCAG |
| | | | | AAAGACAAGATGGCCGAGGCCTACAG |
| | | | | CGAGATCGGCATGAAGGGCGAGCGGC |
| | | | | GGAGGGGCAAGGGCCACGACGGCCTG |
| | | | | TACCAGGGCCTGAGCACCGCCACCAAG |
| | | | | GATACCTACGACGCCCTGCACATGCAG |
| | | | | GCCCTGCCCCCCAGA |
| Murine ROR1 | 11 | EVKLVESGGGLVKPG | 158 | GAAGTGAAGCTGGTGGAAAGCGGCGG |
| (VH-VL).IgG4 | | GSLKLSCAASGFTFSS | | AGGCCTGGTGAAACCTGGCGGCAGCCT |
| Fcm.CD8aTM.41BBz | | YAMSWVRQIPEKRLE | | GAAGCTGAGCTGCGCCGCCAGCGGCTT |
| | | WVASISRGGTTYYPD | | CACCTTCAGCAGCTACGCCATGAGCTG |
| | | SVKGRFTISRDNVRNI | | GGTCCGACAGATCCCCGAGAAGCGGCT |
| | | LYLQMSSLRSEDTAM | | GGAATGGGTGGCCAGCATCAGCAGGG |
| | | YYCGRYDYDGYYAM | | GCGGCACCACCTACTACCCCGACAGCG |
| | | DYWGQGTSVTVSSGS | | TGAAGGGCCGGTTCACCATCAGCCGGG |
| | | TSGSGKPGSGEGSTK | | ACAACGTGCGGAACATCCTGTACCTGC |
| | | GDIKMTQSPSSMYAS | | AGATGAGCAGCCTGCGGAGCGAGGAC |
| | | LGERVTITCKASPDIN | | ACCGCCATGTACTACTGCGGCAGATAC |
| | | SYLSWFQQKPGKSPK | | GACTACGACGGCTACTACGCCATGGAT |
| | | TLIYRANRLVDGVPS | | TACTGGGGCCAGGGCACCAGCGTGACC |
| | | RFSGGGSGQDYSLTIN | | GTGTCTAGCGGCAGCACCTCCGGCAGC |
| | | SLEYEDMGIYYCLQY | | GGCAAGCCTGGCAGCGGCGAGGGCAG |
| | | DEFPYTFGGGTKLEM | | CACCAAGGGCGACATCAAGATGACCC |
| | | KESKYGPPCPPCPAPE | | AGAGCCCCAGCTCTATGTACGCCAGCC |
| | | FEGGPSVFLFPPKPKD | | TGGGCGAGCGCGTGACCATCACATGCA |
| | | TLMISRTPEVTCVVV | | AGGCCAGCCCCGACATCAACAGCTACC |
| | | DVSQEDPEVQFNWY | | TGTCCTGGTTCCAGCAGAAGCCCGGCA |

TABLE 12-continued

| Exemplary Sequences | | | | |
|---|---|---|---|---|
| | | VDGVEVHNAKTKPR EEQFQSTYRVVSVLT VLHQDWLNGKEYKC KVSNKGLPSSIEKTIS KAKGQPREPQVYTLP PSQEEMTKNQVSLTC LVKGFYPSDIAVEWE SNGQPENNYKTTPPV LDSDGSFFLYSRLTVD KSRWQEGNVFSCSV MHEALHNHYTQKSLS LSLGKMIYIWAPLAG TCGVLLLSLVITLYCN HRNKRGRKKLLYIFK QPFMRPVQTTQEEDG CSCRFPEEEEGGCELR VKFSRSADAPAYQQG QNQLYNELNLGRREE YDVLDKRRGRDPEM GGKPRRKNPQEGLYN ELQKDKMAEAYSEIG MKGERRRGKGHDGL YQGLSTATKDTYDAL HMQALPPR | | AGAGCCCCAAGACCCTGATCTACCGGG CCAACCGGCTGGTGGACGGCGTGCCAA GCAGATTTTCCGGCGGAGGCAGCGGCC AGGACTACAGCCTGACCATCAACAGCC TGGAATACGAGGACATGGGCATCTACT ACTGCCTGCAGTACGACGAGTTCCCCT ACACCTTCGGAGGCGGCACCAAGCTGG AAATGAAGGAGAGCAAGTACGGCCCT CCCTGCCCCCCTTGCCCTGCCCCCGAGT TCGAGGGCGGACCCAGCGTGTTCCTGT TCCCCCCCAAGCCCAAGGACACCCTGA TGATCAGCCGGACCCCCGAGGTGACCT GTGTGGTGGTGGACGTGTCCCAGGAGG ACCCCGAGGTCCAGTTCAACTGGTACG TGGACGGCGTGGAGGTGCACAACGCC AAGACCAAGCCCCGGGAGGAGCAGTT CCAGAGCACCTACCGGGTGGTGTCCGT GCTGACCGTGCTGCACCAGGACTGGCT GAACGGCAAGGAATACAAGTGTAAGG TGTCCAACAAGGGCCTGCCCAGCAGCA TCGAGAAAACCATCAGCAAGGCCAAG GGCCAGCCTCGGGAGCCCCAGGTGTAC ACCCTGCCCCCTAGCCAAGAGGAGATG ACCAAGAATCAGGTGTCCCTGACCTGC CTGGTGAAGGGCTTCTACCCCAGCGAC ATCGCCGTGGAGTGGGAGAGCAACGG CCAGCCCGAGAACAACTACAAGACCA CCCCCCCTGTGCTGGACAGCGACGGCA GCTTCTTCCTGTACAGCAGGCTGACCG TGGACAAGAGCCGGTGGCAGGAGGGC AACGTCTTTAGCTGCTCCGTGATGCAC GAGGCCCTGCACAACCACTACACCCAG AAGAGCCTGTCCCTGAGCCTGGGCAAG ATGATCTACATCTGGGCCCCTCTGGCC GGCACCTGTGGCGTGCTGCTGCTGAGC CTGGTCATCACCCTGTACTGCAACCAC CGGAATAAGAGAGGCCGGAAGAAACT GCTGTACATCTTCAAGCAGCCCTTCAT GCGGCCCGTGCAGACCACCCAGGAAG AGGACGGCTGCAGCTGCCGGTTCCCCG AGGAAGAGGAAGGCGGCTGCGAACTG CGGGTGAAGTTCAGCCGGAGCGCCGAC GCCCCTGCCTACCAGCAGGGCCAGAAC CAGCTGTACAACGAGCTGAACCTGGGC CGGAGGGAGGAGTACGACGTGCTGGA CAAGCGGAGAGGCCGGGACCCTGAGA TGGGCGGCAAGCCCCGGAGAAAGAAC CCTCAGGAGGGCCTGTATAACGAACTG CAGAAAGACAAGATGGCCGAGGCCTA CAGCGAGATCGGCATGAAGGGCGAGC GGCGGAGGGGCAAGGGCCACGACGGC CTGTACCAGGGCCTGAGCACCGCCACC AAGGATACCTACGACGCCCTGCACATG CAGGCCCTGCCCCCCAGA |
| Murine ROR1_v2 VL | 12 | DVQITQSPSSLYASLG ERVTITCKASPDINSY LSWFQQKPGKSPKTLI YRANRLVDGVPSRFS GGGSGQDYSLTINSLE YEDMGIYYCLQYDEF PYTFGGGTKLEMK | 159 | GACGTGCAGATCACCCAGAGCCCCAGC AGCCTGTATGCCAGCCTGGGCGAGAGA GTGACCATTACCTGCAAGGCCAGCCCC GACATCAACAGCTACCTGAGCTGGTTC CAGCAGAAGCCCGGCAAGAGCCCCAA GACCCTGATCTACCGGGCCAACAGACT GGTGGATGGCGTGCCCAGCAGATTCAG CGGCGGAGGCTCTGGCCAGGACTACAG CCTGACCATCAACTCCCTGGAATACGA GGACATGGGCATCTACTACTGCCTGCA GTACGACGAGTTCCCCTACACCTTCGG AGGCGGCACCAAGCTGGAAATGAAG |
| Murine ROR1_v2 VH | 13 | EVKLVESGGGLVKPG GSLKLSCAASGFTFSS YAMSWVRQIPEKRLE WVASISRGGTTYYPD SVKGRFTISRDNVRNI LYLQMSSLRSEDTAM YYCGRYDYDGYYAM DYWGQGTSVTVSS | 160 | GAAGTGAAGCTGGTGGAATCTGGCGGC GGACTCGTGAAGCCTGGCGGCTCTCTG AAGCTGTCTTGTGCCGCCAGCGGCTTC ACCTTCAGCAGCTACGCCATGAGCTGG GTGCGGCAGATCCCCGAGAAGCGGCTG GAATGGGTGGCCAGCATCAGCAGAGG CGGAACCACCTACTACCCCGACTCTGT GAAGGGCCGGTTCACCATCAGCCGGGA CAACGTGCGGAACATCCTGTACCTGCA GATGAGCAGCCTGCGGAGCGAGGACA |

TABLE 12-continued

| Exemplary Sequences | | | | |
|---|---|---|---|---|
| | | | | CCGCCATGTACTACTGTGGCAGATACG ACTACGACGGCTACTATGCCATGGATT ACTGGGGCCAGGGCACCAGCGTGACC GTGTCATCT |
| Murine ROR1_v2 (VL-VH).CD8a(3x).CD28z | 14 | DVQITQSPSSLYASLG ERVTITCKASPDINSY LSWFQQKPGKSPKTLI YRANRLVDGVPSRFS GGGSGQDYSLTINSLE YEDMGIYYCLQYDEF PYTFGGGTKLEMKGS TSGSGKPGSGEGSTK GEVKLVESGGGLVKP GGSLKLSCAASGFTFS SYAMSWVRQIPEKRL EWVASISRGGTTYYP DSVKGRFTISRDNVR NILYLQMSSLRSEDTA MYYCGRYDYDGYYA MDYWGQGTSVTVSS KPTTTPAPRPPTPAPTI ASQPLSLRPEASRPAA GGAVHTRGLDFASDK PTTTPAPRPPTPAPTIA SQPLSLRPEASRPAAG GAVHTRGLDFASDKP TTTPAPRPPTPAPTIAS QPLSLRPEACRPAAG GAVHTRGLDFACDIY IWAPLAGTCGVLLLS LVITLYCNHRNRSKR SRGGHSDYMNMTPR RPGPTRKHYQPYAPP RDFAAYRSRVKFSRS ADAPAYQQGQNQLY NELNLGRREEYDVLD KRRGRDPEMGGKPR RKNPQEGLYNELQKD KMAEAYSEIGMKGER RRGKGHDGLYQGLST ATKDTYDALHMQAL PPR | 161 | GACGTGCAGATCACCCAGAGCCCCAGC AGCCTGTATGCCAGCCTGGGCGAGAGA GTGACCATTACCTGCAAGGCCAGCCCC GACATCAACAGCTACCTGAGCTGGTTC CAGCAGAAGCCCGGCAAGAGCCCCAA GACCCTGATCTACCGGGCCAACAGACT GGTGGATGGCGTGCCCAGCAGATTCAG CGGCGGAGGCTCTGGCCAGGACTACAG CCTGACCATCAACTCCCTGGAATACGA GGACATGGGCATCTACTACTGCCTGCA GTACGACGAGTTCCCCTACACCTTCGG AGGCGGCACCAAGCTGGAAATGAAGG GCAGCACAAGCGGCAGCGGCAAGCCT GGATCTGGCGAGGGAAGCACCAAGGG CGAAGTGAAGCTGGTGGAATCTGGCGG CGGACTCGTGAAGCCTGGCGGCTCTCT GAAGCTGTCTTGTGCCGCCAGCGGCTT CACCTTCAGCAGCTACGCCATGAGCTG GGTGCGGCAGATCCCCGAGAAGCGGCT GGAATGGGTGGCCAGCATCAGCAGAG GCGGAACCACCTACTACCCCGACTCTG TGAAGGGCCGGTTCACCATCAGCCGGG ACAACGTGCGGAACATCCTGTACCTGC AGATGAGCAGCCTGCGGAGCGAGGAC ACCGCCATGTACTACTGTGGCAGATAC GACTACGACGGCTACTATGCCATGGAT TACTGGGGCCAGGGCACCAGCGTGACC GTGTCATCTAAGCCTACCACCACCCCC GCACCTCGTCCTCCAACCCCTGCACCT ACGATTGCCAGTCAGCCTCTTTCACTG CGGCCTGAGGCCAGCAGACCAGCTGCC GGCGGTGCCGTCCATACAAGAGGACTG GACTTCGCGTCCGATAAACCTACTACC ACTCCAGCCCCAAGGCCCCCAACCCCA GCACCGACTATCGCATCACAGCCTTTG TCACTGCGTCCTGAAGCCAGCCGGCCA GCTGCAGGGGGGGCCGTCCACACAAG GGGACTCGACTTTGCGAGTGATAAGCC CACCACCACCCCTGCCCCTAGACCTCC AACCCCAGCCCCTACAATCGCCAGCCA GCCCCTGAGCCTGAGGCCCGAAGCCTG TAGACCTGCCGCTGGCGGAGCCGTGCA CACCAGAGGCCTGGATTTCGCCTGCGA CATCTACATCTGGGCCCCTCTGGCCGG CACCTGTGGCGTGCTGCTGCTGAGCCT GGTCATCACCCTGTACTGCAACCACCG GAATAGGAGCAAGCGGAGCAGAGGCG GCCACAGCGACTACATGAACATGACCC CCCGGAGGCCTGGCCCCACCCGGAAGC ACTACCAGCCCTACGCCCCTCCCAGGG ACTTCGCCGCCTACCGGAGCCGGGTGA AGTTCAGCCGGAGCGCCGACGCCCCTG CCTACCAGCAGGGCCAGAACCAGCTGT ACAACGAGCTGAACCTGGGCCGGAGG GAGGAGTACGACGTGCTGGACAAGCG GAGAGGCCGGGACCCTGAGATGGGCG GCAAGCCCCGGAGAAAGAACCCTCAG GAGGGCCTGTATAACGAACTGCAGAA AGACAAGATGGCCGAGGCCTACAGCG AGATCGGCATGAAGGGCGAGCGGCGG AGGGGCAAGGGCCACGACGGCCTGTA CCAGGGCCTGAGCACCGCCACCAAGG ATACCTACGACGCCCTGCACATGCAGG CCCTGCCCCCCAGA |
| hROR1 VH_04 | 15 | EVQLVESGGGLVQPG GSLRLSCAASGFTFSS YAMSWVRQAPGKGL EWVSAISRGGTTYYA DSVKGRFTISRDNSK NTLYLQMNSLRAEDT AVYYCGRYDYDGYY AMDYWGQGTLVTVS | 162 | GAGGTGCAGCTCGTGGAATCCGGCGGT GGCCTGGTGCAGCCGGGCGGCAGTCTT CGACTCTCCTGTGCGGCGTCAGGCTTT ACGTTCAGTTCTTATGCCATGAGCTGG GTGAGGCAAGCTCCCGGTAAGGGACTG GAGTGGGTCTCTGCTATCAGCCGGGGA GGTACGACCTACTACGCTGACTCCGTA AAAGGAAGATTTACCATAAGTCGTGAC |

TABLE 12-continued

| Exemplary Sequences | | | | |
|---|---|---|---|---|
| | | S | | AATTCCAAAAACACTCTATACTTACAG<br>ATGAACTCGCTCAGGGCCGAAGATACC<br>GCAGTCTACTATTGTGGGAGATACGAT<br>TACGACGGCTACTATGCTATGGATTAT<br>TGGGGTCAGGGTACGCTCGTGACGGTG<br>TCCTCC |
| hROR1<br>VL_04 | 16 | DIQMTQSPSSLSASVG<br>DRVTITCQASPDINSY<br>LNWYQQKPGKAPKL<br>LIYRANNLETGVPSRF<br>SGSGSGTDFTLTISSL<br>QPEDIATYYCLQYDE<br>FPYTFGQGTKLEIK | 163 | GATATTCAAATGACGCAAAGTCCCAGC<br>AGCCTCTCCGCCTCCGTTGGAGACAGG<br>GTGACTATTACATGCCAAGCCAGCCCC<br>GATATTAATAGCTACTTAAATTGGTAT<br>CAGCAGAAACCTGGGAAGGCACCTAA<br>ACTTCTCATCTACCGCGCTAACAATCT<br>GGAGACCGGCGTGCCGTCTAGATTTTC<br>CGGCTCTGGATCAGGGACCGATTTTAC<br>TCTGACAATTAGTTCCCTGCAACCCGA<br>AGACATCGCCACTTATTATTGCCTGCA<br>ATATGATGAGTTTCCTTACACATTTGGT<br>CAGGGAACTAAACTAGAGATTAAG |
| hROR1<br>VH_05 | 17 | EVQLVESGGGLVQPG<br>GSLRLSCAASGFTFSS<br>YAMSWVRQAPGKGL<br>EWVSSISRGGTTYYP<br>DSVKGRFTISRDNSK<br>NTLYLQMNSLRAEDT<br>AVYYCGRYDYDGYY<br>AMDYWGQGTLVTVS<br>S | 164 | GAAGTGCAACTGGTCGAGTCTGGGGGC<br>GGCCTTGTGCAACCTGGAGGCAGCCTT<br>CGACTCAGTTGCGCCGCGTCTGGTTTT<br>ACCTTCTCCTCTTACGCGATGAGCTGG<br>GTTCGCCAGGCCCCCGGCAAGGGACTT<br>GAGTGGGTTAGTTCGATCTCCCGCGGA<br>GGCACCACATATTATCCTGACTCGGTT<br>AAGGGACGCTTCACTATCTCTAGGGAC<br>AATTCAAAGAACACACTGTATCTCCAA<br>ATGAACTCCTTGCGGGCCGAGGACACT<br>GCTGTGTATTATTGCGGACGATACGAC<br>TACGATGGGTATTACGCCATGGATTAC<br>TGGGGGCAAGGTACACTGGTCACTGTG<br>AGTTCG |
| hROR1<br>VL_05 | 18 | DIQMTQSPSSLSASVG<br>DRVTITCKASPDINSY<br>LSWYQQKPGKAPKLL<br>IYRANRLVDGVPSRFS<br>GSGSGTDFTLTISSLQ<br>PEDIATYYCLQYDEFP<br>YTFGQGTKLEIK | 165 | GATATTCAGATGACCCAGTCACCTTCG<br>AGTCTGAGCGCATCCGTGGGCGACAGA<br>GTGACCATTACCTGTAAGGCCAGCCCG<br>GACATTAACAGCTACCTATCGTGGTAT<br>CAGCAAAAGCCTGGTAAGGCCCCTAAA<br>CTCCTTATCTACAGGGCTAATAGGTTG<br>GTAGACGGGGTGCCTAGCCGGTTCTCT<br>GGTTCCGGCAGCGGTACGGACTTTACT<br>CTGACCATAAGCTCTCTGCAACCAGAA<br>GACATCGCAACATACTACTGTTTACAA<br>TACGACGAATTTCCTTATACCTTTGGCC<br>AGGGGACCAAGTTAGAGATCAAG |
| hROR1<br>VH_06 | 19 | EVQLVESGGGLVQPG<br>GSLRLSCAASGFTFSS<br>YAIIWVRQAPGKGLE<br>WVARISRGGTTRYAD<br>SVKGRFTISADTSKET<br>AYLQMNSLRAEDTA<br>VYYCGRYDYDGYYA<br>MDYWGQGTLVTVSS | 166 | GAGGTTCAGCTGGTCGAGTCCGGGGGA<br>GGCTTAGTGCAGCCAGGAGGCAGTCTG<br>CGGCTCTCTTGCGCTGCAAGTGGCTTC<br>ACATTCAGTTCATACGCAATCATCTGG<br>GTTCGACAGGCTCCTGGTAAGGGCCTC<br>GAATGGGTCGCAAGGATATCACGAGGT<br>GGAACCACTAGATACGCAGACTCTGTT<br>AAGGGCAGGTTCACAATTAGCGCGGAT<br>ACCTCCAAGGAGACTGCTTATTTACAG<br>ATGAACTCTCTGAGAGCCGAGGACACT<br>GCTGTTTACTACTGCGGCCGATACGAT<br>TACGACGGATATTACGCAATGGATTAC<br>TGGGGCCAGGGCACGCTGGTGACAGTT<br>TCATCG |
| hROR1<br>VL_06 | 20 | DIQMTQSPSSLSASVG<br>DRVTITCKASPDINSY<br>LSWYQQKPGKAPKLL<br>IYRANRLVDGVPSRFS<br>GSGSGTDFTLTISSLQ<br>PEDIATYYCLQYDEFP<br>YTFGQGTKLEIK | 167 | GATATCCAGATGACTCAGAGTCCCAGT<br>AGCCTGTCGGCAAGCGTCGGAGATCGG<br>GTCACAATTACCTGCAAAGCTAGTCCT<br>GATATTAATTCTTACTTGTCCTGGTATC<br>AGCAGAAGCCTGGTAAGGCCCCTAAGT<br>TGCTCATCTATCGGGCTAACCGGCTGG<br>TGGACGGTGTTCCCTCTAGATTCTCAG<br>GGAGTGGAAGCGGCACTGACTTCACCC<br>TGACTATATCGAGCCTTCAGCCAGAGG<br>ACATTGCCACATACTACTGTCTGCAAT<br>ATGATGAATTTCCATATACATTCGGAC<br>AAGGTACAAAGTTAGAAATTAAG |
| hROR1<br>VH_07 | 21 | EVQLVESGGGLVQPG<br>GSLRLSCAASGFTFSS | 168 | GAAGTCCAACTGGTGGAGTCTGGCGGG<br>GGCTTGGTGCAGCCCGGTGGCTCCCTT |

TABLE 12-continued

| Exemplary Sequences | | | | |
|---|---|---|---|---|
| | | YAIIWVRQAPGKGLE<br>WVARISRGGTTRYAD<br>SVKGRFTISADTSKET<br>AYLQMNSLRAEDTA<br>VYYCGRYDYDGYYA<br>MDYWGQGTLVTVSS | | AGGCTGTCTTGCGCTGCCAGCGGGTTC<br>ACATTCAGCTCCTATGCGATTATATGG<br>GTCCGACAGGCACCCGGCAAGGGATTG<br>GAGTGGGTGGCTCGCATCAGCAGAGGC<br>GGCACTACTCGTTACGCCGACTCCGTG<br>AAAGGCAGATTCACCATCAGTGCAGAC<br>VACATCCAAGGAAACCGCATATCTTCAG<br>ATGAATAGCCTGCGAGCGGAGGATACC<br>GCCGTCTATTATTGCGGACGCTATGAT<br>TACGACGGTTATTATGCTATGGACTAC<br>TGGGGCCAGGGCACACTTGTGACCGTC<br>AGTAGC |
| hROR1<br>VL_07 | 22 | DIQMTQSPSSLSASVG<br>DRVTITCRASPDINSY<br>VAWYQQKPGKAPKL<br>LIYRANFLESGVPSRF<br>SGSRSGTDFTLTISSL<br>QPEDFATYYCLQYDE<br>FPYTFGQGTKVEIK | 169 | GACATTCAAATGACGCAAAGCCCTAGT<br>AGCTTGTCAGCTTCTGTGGGGGACCGT<br>GTCACAATCACTTGTCGGGCCTCTCCA<br>GATATAAACTCCTACGTTGCTTGGTAT<br>CAGCAGAAGCCCGGAAAGGCTCCGAA<br>ATTGTTGATTTATCGCGCTAATTTCTTA<br>GAGTCAGGAGTGCCCAGCCGGTTCTCA<br>GGGTCTCGCTCTGGAACCGACTTCACA<br>CTCACTATTTCTAGCCTACAGCCTGAG<br>GATTTTGCAACTTACTACTGTCTACAGT<br>ACGACGAGTTTCCGTACACTTTCGGAC<br>AGGGGACCAAGGTGGAGATCAAG |
| hROR1<br>VH_08 | 23 | QVQLVQSGGGLVKP<br>GGSLRLSCAASGFTFS<br>SYAMSWVRQIPGKGL<br>EWVSSISRGGTTYYP<br>DSVKGRFTISRDNVK<br>NTLYLQMSSLRAEDT<br>AVYYCGRYDYDGYY<br>AMDYWGQGTMVTV<br>SS | 170 | CAAGTACAGCTCGTGCAGAGCGGCGGT<br>GGCCTGGTGAAGCCAGGAGGTAGTCTT<br>AGACTGAGCTGTGCGGCTTCTGGTTTC<br>ACGTTCAGCAGTTATGCTATGTCCTGG<br>GTTAGGCAAATCCCCGGCAAAGGATTG<br>GAGTGGGTTAGCAGTATCTCAAGGGGG<br>GGAACCACATATTATCCTGACTCTGTC<br>AAAGGACGGTTTACAATCAGCCGCGAT<br>AACGTTAAAAATACCCTCTACCTCCAG<br>ATGTCTTCGCTCCGCGCTGAAGATACA<br>GCGGTTTACTACTGTGGCAGATACGAC<br>TACGACGGTTATTACGCCATGGACTAC<br>TGGGGACAGGGAACTATGGTCACAGTT<br>AGCTCT |
| hROR1<br>VL_08 | 24 | DIKMTQSPSSLSASVG<br>DRVTITCKASPDINSY<br>LSWYQQKPGKAPKTL<br>IYRANRLVDGVPSRFS<br>GSGSGTDFTLTISSLQ<br>YEDMAIYYCLQYDEF<br>PYTFGDGTKVEIK | 171 | GACATCAAAATGACGCAGTCACCTAGT<br>AGCCTCTCCGCCTCGGTTGGCGATCGG<br>GTAACCATTACCTGCAAAGCATCTCCA<br>GACATAAATAGTTATCTTAGTTGGTAT<br>CAACAGAAACCTGGCAAAGCTCCTAAG<br>ACCCTCATCTACCGCGCTAACCGCCTC<br>GTGGATGGTGTTCCAAGTCGGTTCTCA<br>GGAAGCGGCAGTGGCACAGACTTTACA<br>CTGACAATTAGTTCCCTCCAGTATGAG<br>GATATGGCCATATATTACTGCCTTCAG<br>TATGATGAGTTTCCATACACATTCGGA<br>GACGGTACAAAGGTGGAGATCAAG |
| hROR1<br>VH_09 | 25 | QVSLRESGGGLVQPG<br>RSLRLSCTASGFTFSS<br>YAMTWVRQAPGKGL<br>EWVASISRGGTTHFA<br>DSVKGRFTISRDNSN<br>NTLYLQMDNVRDED<br>TAIYYCGRYDYDGYY<br>AMDYWGRGTLVTVS<br>S | 172 | CAAGTGAGCCTCCGGGAGAGTGGGGG<br>CGGTCTGGTCCAACCAGGACGGTCACT<br>GCGGCTGTCATGCACTGCCAGCGGCTT<br>CACATTTAGCTCTTACGCCATGACTTG<br>GGTCCGCCAAGCTCCCGGTAAGGGACT<br>GGAGTGGGTGGCCAGCATTAGCAGGG<br>GTGGTACAACCCACTTCGCGGATTCAG<br>TTAAGGGGAGATTCACTATCTCCAGGG<br>ATAATTCCAACAACACGCTGTACCTTC<br>AGATGGATAACGTGAGAGACGAGGAT<br>ACCGCGATATACTACTGTGGCCGCTAT<br>GACTACGATGGTTATTATGCTATGGAT<br>TACTGGGGGCGGGGCACCCTGGTGACT<br>GTGTCCTCG |
| hROR1<br>VL_09 | 26 | DIVMTQSPSSLSASVG<br>DRVTITCRASPDINSY<br>LAWYQQKPGKAPKL<br>LIYRANSLQSGVPSRF<br>SGSGSGTEFTLTISSLQ<br>PEDFATYYCLQYDEF<br>PYTFGQGTKLEMK | 173 | GATATCGTGATGACACAGTCACCTAGC<br>TCCCTGAGCGCAAGCGTGGGGGATAGG<br>GTTACCATAACTTGCAGGGCCAGTCCC<br>GACATCAATAGTTATTTGGCCTGGTAT<br>CAACAGAAGCCTGGGAAGGCACCTAA<br>GTTGCTTATTTATAGGGCTAACTCGTTA<br>CAGAGCGGTGTGCCAAGTCGGTTCTCA<br>GGCTCAGGGTCCGGGACCGAGTTCACC<br>CTGACCATCAGTAGCTTGCAGCCAGAA |

TABLE 12-continued

| Exemplary Sequences | | | | |
|---|---|---|---|---|
| | | | | GATTTTGCCACCTACTACTGTCTTCAAT ACGATGAGTTTCCTTACACTTTTGGAC AGGGCACCAAACTAGAGATGAAG |
| hROR1 VH_10 | 27 | QVQLVESGGGVVQP GRSLRLSCAASGFTFS SYAMNWVRQAPAKG LEWVAIISRGGTQYY ADSVKGRFTISRDNS KNTLYLQMNGLRAE DTAVYYCGRYDYDG YYAMDYWGQGTLVT VSS | 174 | CAGGTTCAACTGGTAGAATCCGGCGGA GGTGTAGTGCAGCCTGGAAGGTCATTA CGGTTAAGTTGCGCCGCCTCCGGGTTC ACATTTAGCAGCTATGCTATGAACTGG GTGCGCCAGGCCCCTGCGAAAGGACTC GAATGGGTTGCCATCATCAGCCGAGGA GGCACACAGTATTATGCCGATTCTGTG AAGGGTCGTTTTACTATTTCCAGAGAC AACAGTAAAAATACGCTGTACCTGCAA ATGAACGGATTGAGGGCTGAGGATACC GCCGTGTACTACTGTGGACGCTACGAC TATGATGGGTACTACGCGATGGACTAT TGGGGGCAAGGAACCCTTGTAACCGTT AGTTCA |
| hROR1 VL_10 | 28 | EIVLTQSPDFQSVTPK EKVTITCRASPDINSY LSWYQQKPDQSPKLL IKRANQSFSGVPSRFS GSGSGTDFTLTINSLE AEDAAAYYCLQYDE FPYTFGPGTKVDIK | 175 | GAGATCGTTTTGACACAGAGCCCCGAT TTCCAGAGCGTCACGCCCAAGGAGAAG GTCACCATCACCTGCCGAGCCAGCCCC GACATCAACAGTTATCTTTCATGGTAT CAACAGAAACCTGATCAGAGCCCTAAG CTGCTGATTAAGCGCGCCAACCAGAGC TTCTCAGGGGTTCCTTCACGGTTTTCCG GGTCAGGCAGCGGGACTGACTTCACGT TGACCATTAACTCTTTGGAGGCTGAGG ATGCTGCTGCCTATTACTGCCTTCAGTA CGACGAGTTCCCCTATACATTTGGTCCT GGAACAAAAGTGGATATAAAG |
| hROR1 VH_11 | 29 | QVQLVQSGAEVKKP GASVKVSCKASGFTF SSYAMHWVRQAPGQ GLEWMGNISRGGTTN YAEKFKNRVTMTRD TSISTAYMELSRLRSD DTAVYYCGRYDYDG YYAMDYWGQGTLVT VSS | 176 | CAGGTGCAGCTCGTCCAGAGCGGAGCC GAAGTGAAGAAGCCGGGAGCATCAGT GAAAGTTTCCTGCAAAGCAAGTGGCTT CACTTTCAGCAGTTACGCGATGCACTG GGTGCGGCAGGCACCAGGTCAGGGAC TGGAATGGATGGGGAACATCTCTCGCG GCGGAACAACCAATTACGCAGAGAAG TTTAAGAATCGCGTTACGATGACCAGA GACACTTCTATTAGTACAGCCTATATG GAGTTGTCGCGTCTGAGAAGCGACGAT ACCGCTGTCTACTATTGCGGCCGGTAC GATTATGACGGCTACTATGCAATGGAT TACTGGGGACAGGGCACACTTGTGACA GTGTCTAGT |
| hROR1 VL_11 | 30 | DIVMTQSPLSLPVTPG EPASISCRSSPDINSYL EWYLQKPGQSPQLLI YRANDRFSGVPDRFS GSGSGTDFTLKISRVE AEDVGVYYCLQYDE FPYTFGQGTKVEIK | 177 | GACATTGTGATGACTCAGTCTCCACTC AGCCTGCCTGTCACGCCCGGCGAACCC GCTTCTATCTCTTGTAGGAGTAGCCCTG ATATCAACAGCTACCTCGAATGGTATC TCCAGAAACCTGGTCAGAGCCCCCAGC TCTTGATCTATAGAGCAAACGACAGGT TCTCTGGCGTGCCTGATAGGTTTTCCGG TAGTGGCAGCGGAACCGACTTCACACT TAAGATTTCAAGGGTCGAGGCCGAGGA CGTGGGGGTGTATTACTGCTTACAGTA CGATGAGTTTCCGTATACATTCGGGCA AGGCACAAAGGTGGAAATTAAG |
| hROR1 VH_12 | 31 | EVQLVESGGGLVQPG GSLRLSCTGSGFTFSS YAMHWLRQVPGEGL EWVSGISRGGTIDYA DSVKGRFTISRDDAK KTLSLQMNSLRAEDT AVYYCGRYDYDGYY AMDYWGQGTMVTV SS | 178 | GAAGTGCAACTGGTCGAAAGTGGAGG GGGACTAGTGCAGCCCGGAGGGTCACT GAGGCTATCATGCACCGGCTCTGGTTT TACTTTTTCCAGCTATGCCATGCACTGG CTCAGACAGGTTCCGGGGGAAGGACTG GAGTGGGTTAGCGGAATCTCCAGAGGC GGAACTATTGACTACGCAGACAGCGTG AAAGGTAGGTTTACCATCAGCAGGGAC GATGCTAAAAAGACCCTGTCACTTCAA ATGAATAGCCTGAGAGCTGAGGATACG GCCGTGTATTACTGTGGACGCTATGAC TACGATGGATATTACGCAATGGACTAC TGGGGCCAGGGAACAATGGTGACCGTC TCAAGC |
| hROR1 VL_12 | 32 | EIVLTQSPATLSVSPG ERATLSCRASPDINSY LAWYQQKPGQAPRL | 179 | GAGATCGTCCTGACCCAGAGCCCAGCT ACTTTGTCAGTTTCGCCAGGCGAGCGG GCCACACTGAGCTGTAGGGCTTCTCCT |

TABLE 12-continued

| Exemplary Sequences | | | | |
|---|---|---|---|---|
| | | LFSRANNRATGIPARF<br>TGSGSGTDFTLTISSL<br>EPEDFAIYYCLQYDEF<br>PYTFGQGTKVEIK | | GATATCAATTCTTACCTGGCCTGGTATC<br>AACAGAAACCGGGACAGGCCCCTCGC<br>CTGCTGTTCTCCCGCGCCAACAATAGG<br>GCGACTGGCATACCAGCTCGGTTTACT<br>GGGAGTGGGTCAGGCACTGATTTCACG<br>CTTACAATCAGTAGCCTGGAGCCCGAA<br>GACTTCGCCATCTACTACTGTTTACAAT<br>ACGATGAGTTCCCCTATACCTTCGGCC<br>AAGGGACCAAGGTGGAGATCAAG |
| hROR1<br>VH_13 | 33 | EVQLVESGGGVVQPG<br>RSLRLSCAASGFTFSS<br>YAMSWVRQAPGKGL<br>EWVASISRGGTQYYA<br>DSVKGRFTISRDNSK<br>NTLYLQMNGLRAED<br>TAVYYCGRYDYDGY<br>YAMDYWGQGTLVTV<br>SS | 180 | GAAGTGCAGCTAGTAGAAAGTGGTGGT<br>GGGGTCGTGCAGCCAGGCCGCTCGCTC<br>AGGCTGTCTTGCGCTGCGAGTGGTTTC<br>ACATTCTCTTCATACGCCATGAGCTGG<br>GTGAGACAGGCTCCCGGCAAGGGCCTC<br>GAATGGGTCGCATCTATAAGCAGAGGC<br>GGAACCCAGTACTACGCTGACAGTGTG<br>AAGGGTCGCTTTACAATCTCACGGGAC<br>AACAGTAAAAACACCCTCTATCTACAG<br>ATGAATGGCTTGCGAGCTGAAGACACG<br>GCTGTGTATTATTGCGGGCGCTATGAC<br>TATGATGGTTACTACGCTATGGATTAC<br>TGGGGCCAGGGCACCCTGGTTACTGTT<br>TCATCA |
| hROR1<br>VL_13 | 34 | EIVLTQSPDFQSVTPK<br>EKVTITCRASPDINSY<br>LPWYQQKPDQSPKLL<br>IKRANQSFSGVPSRFS<br>GSGSGTDFTLTINSLE<br>AEDAAAYYCLQYDE<br>FPYTFGPGTKVDIK | 181 | GAAATAGTCCTGACCCAGAGCCCAGAC<br>TTCCAGTCCGTGACCCCTAAGGAGAAG<br>GTTACTATCACTTGCAGGGCAAGCCCT<br>GACATAAATTCATACCTGCCATGGTAT<br>CAGCAGAAGCCAGACCAGTCGCCGAA<br>GCTATTAATCAAACGCGCCAACCAGTC<br>TTTTAGCGGCGTACCATCCCGATTCTCA<br>GGTTCGGGGTCCGGGACCGATTTCACA<br>CTCACGATAAACTCCCTTGAGGCAGAG<br>GATGCAGCGGCTTACTACTGTTTACAG<br>TACGACGAGTTTCCATATACGTTCGGC<br>CCCGGCACGAAGGTAGATATCAAG |
| hROR1<br>VH_14 | 35 | EVQLVESGGGLVQPG<br>GSLRLSCATSGFTFSS<br>YAMSWMRQAPGKGL<br>EWVASISRGGTTYYA<br>DSVKGRFTISVDKSK<br>NTLYLQMNSLRAEDT<br>AVYYCGRYDYDGYY<br>AMDYWGQGTLVTVS<br>S | 182 | GAAGTGCAGCTGGTGGAGTCTGGCGGC<br>GGTCTGGTGCAGCCCGGCGGCTCTCTG<br>CGCCTCTCCTGTGCCACCTCTGGTTTTA<br>CATTCTCCTCCTACGCTATGTCCTGGAT<br>GCGGCAAGCCCCCGGCAAGGGCCTAG<br>AGTGGGTCGCCTCAATCAGCAGGGGCG<br>GGACGACTTATTATGCCGATTCAGTTA<br>AGGGGAGATTCACAATTTCCGTGGATA<br>AATCCAAGAATACCTTATACCTCCAGA<br>TGAACTCTCTGCGGGCCGAAGATACGG<br>CCGTATATTATTGTGGGAGGTATGACT<br>ACGACGGATATTACGCCATGGATTATT<br>GGGGGCAGGGGACACTTGTTACAGTGA<br>GTTCC |
| hROR1<br>VL_14 | 36 | DIQMTQSPSSLSASVG<br>DRVTITCKASPDINSY<br>LNWYQQKPGKAPKL<br>LIYRANRLVDGVPSR<br>FSGSGSGTDYTLTISS<br>LQPEDFATYYCLQYD<br>EFPYTFGAGTKVEIK | 183 | GATATACAGATGACACAGAGCCCTTCA<br>AGTTTATCTGCAAGCGTCGGCGATCGT<br>GTTACAATAACTTGCAAGGCATCTCCC<br>GACATCAATTCCTACCTCAACTGGTAT<br>CAGCAGAAGCCTGGGAAGGCTCCTAA<br>GCTGCTTATTTACAGAGCAAATCGCCT<br>GGTGGACGGCGTGCCCAGTCGGTTTTC<br>CGGGTCTGGGAGCGGAACGGATTACAC<br>ACTGACCATCTCAAGCCTGCAACCCGA<br>AGACTTCGCTACATATTACTGCCTTCA<br>GTATGATGAGTTCCCATATACCTTCGG<br>CGCTGGGACCAAGGTGGAGATAAAG |
| hROR1<br>VH_14-1 | 37 | EVQLVESGGGLVQPG<br>GSLRLSCASSGFTFSS<br>YAMSWRRQAPGKGL<br>EWVAGISRGGTTSYA<br>DSVKGRFTISSDDSKN<br>TLYLQMNSLRAEDTA<br>VYYCGRYDYDGYYA<br>MDYWGQGTLVTVSS | 184 | GAGGTCCAGCTCGTCGAATCTGGCGGA<br>GGTTTAGTGCAACCAGGCGGGTCGCTC<br>CGATTAAGTTGTGCGTCCAGTGGCTTC<br>ACCTTCTCCAGCTACGCCATGTCGTGG<br>AGGCGACAGGCTCCTGGCAAAGGCTTG<br>GAGTGGGTTGCTGGTATCTCCCGAGGA<br>GGCACCACTAGTTACGCTGACAGTGTA<br>AAAGGACGTTTCACTATTTCCTCTGAC<br>GACAGCAAGAACACACTCTATCTGCAA |

TABLE 12-continued

| Exemplary Sequences | | | | |
|---|---|---|---|---|
| | | | | ATGAATAGTCTCCGTGCTGAGGACACA GCCGTGTATTATTGCGGCGGTATGAT TACGACGGCTACTACGCTATGGACTAC TGGGGCCAGGGAACTCTGGTCACTGTG AGCTCT |
| hROR1 VL_14-1 | 38 | DIQMTQSPSSLSASVG DRVTITCRASPDINSY LSWYQQKPGKAPKLL IYRANTLESGVPSRFS GSGSGTDFTLTISSLQ PEDFATYYCLQYDEF PYTFGQGTKIEIK | 185 | GATATACAGATGACTCAAAGTCCTAGC TCCTTGAGCGCCTCAGTGGGAGATCGG GTCACTATAACTTGTAGAGCCTCACCA GATATAAACTCCTATCTCTCTTGGTATC AGCAGAAGCCCGGCAAAGCACCAAAG CTCTTGATCTATAGAGCTAATACGCTA GAGAGCGGAGTGCCTTCACGGTTTTCT GGTTCCGGGAGCGGAACCGACTTTACC CTTACAATTTCTAGCCTCCAGCCAGAG GACTTCGCAACTTACTATTGTCTCCAGT ATGATGAATTTCCTTACACCTTCGGCC AAGGGACCAAGATCGAGATAAAG |
| hROR1 VH_14-2 | 39 | EVQLVESGGGLVQPG GSLRLSCASSGFTFSS YAMSWVRQAPGKGL EWVAGISRGGTTSYA DSVKGRFTISADTSKN TLYLQMNSLRAEDTA VYYCGRYDYDGYYA MDYWGQGTLVTVSS | 186 | GAGGTGCAGCTCGTTGAGTCCGGTGGG GGGCTGGTGCAGCCTGGCGGGTCTCTC CGCCTCTCTTGTGCCTCCTCCGGCTTTA CCTTCAGCAGCTATGCTATGTCATGGG TGCGGCAGGCACCAGGCAAAGGTCTG GAATGGGTCGCTGGGATCAGTAGAGGC GGCACAACCTCCTATGCCGACAGCGTT AAGGGGAGGTTCACAATCTCGGCTGAT ACAAGCAAGAACACTCTGTATCTCCAA ATGAACAGTCTCCGGGCAGAGGACACC GCGGTCTATTACTGCGGCCGGTACGAC TACGACGGGTACTACGCAATGGACTAT TGGGGACAGGGAACTCTGGTTACTGTC AGCTCT |
| hROR1 VL_14-2 | 40 | DIQMTQSPSSLSASVG DRVTITCRASPDINSY LSWYQQKPGKAPKLL IYRANTLESGVPSRFS GSGSGTDFTLTISSLQ PEDFATYYCLQYDEF PYTFGTGTKLEIK | 187 | GATATCCAGATGACTCAAAGCCCATCT TCTCTCAGCGCAAGCGTGGGTGACCGA GTGACCATCACCTGCCGGGCGTCTCCT GATATCAACTCATACCTGTCCTGGTAT CAGCAGAAGCCCGGAAAGGCCCCTAA GCTGCTGATCTACCGCGCAAATACACT GGAGAGCGGGGTCCCAAGCAGATTCA GTGGGTCCGGCAGTGGTACGGACTTTA CTCTGACCATCAGCTCCCTGCAACCGG AGGACTTTGCTACTTATTACTGTCTCCA GTACGACGAGTTCCCATACACTTTCGG AACAGGCACTAAGCTGGAGATCAAA |
| hROR1 VH_14-3 | 41 | EVQLVESGGGLVQPG GSLRLSCAASGFTFSS YAMSWVRQAPGKGL EWVASISRGGTTYYA DSVKGRFTISRDNSK NTLYLQMNSLRAEDT AVYYCGRYDYDGYY AMDYWGQGTLVTVS S | 188 | GAGGTTCAACTTGTGGAATCCGGCGGC GGGTTAGTCCAGCCCGGCGGGAGCTTG CGGCTGTCCTGCGCCGCCTCTGGATTC ACTTTTAGCTCCTATGCTATGTCTTGGG TAAGGCAGGCCCCTGGTAAAGGACTAG AGTGGGTGGCCTCGATCTCCCGTGGTG GCACTACATACTACGCCGACTCCGTTA AAGGCCGGTTTACCATCTCCCGTGACA ACTCTAAAAATACTTTGTACCTGCAAA TGAACTCCCTGCGGGCAGAAGACACAG CCGTGTACTATTGCGGGCGTTACGATT ACGACGGATATTACGCAATGGACTACT GGGGCCAGGGCACACTGGTCACCGTGA GCAGC |
| hROR1 VL_14-3 | 42 | DIQMTQSPSSLSASVG DRVTITCKASPDINSY LNWYQQKPGKAPKL LIYRANRLVDGVPSR FSGSGSGTDFTLTISSL QPEDIATYYCLQYDE FPYTFGGGTKVEIK | 189 | GATATACAAATGACTCAGTCCCCTAGT AGCCTTAGTGCTAGTGTGGGAGACAGA GTGACCATCACCTGCAAAGCATCTCCT GATATCAATTCCTACCTTAACTGGTATC AACAGAAGCCTGGCAAAGCTCCAAAG CTCCTGATTTATCGCGCGAACAGATTG GTCGATGGGGTCCCTTCCAGATTCAGC GGCTCAGGGTCAGGGACCGATTTCACC CTCACAATTAGTTCACTTCAGCCCGAG GACATCGCCACGTATTATTGCCTTCAG TACGATGAGTTCCCTTACACCTTTGGC GGGGGAACTAAAGTCGAAATTAAG |
| hROR1 VH_14-4 | 43 | EVQLVESGGGLVQPG GSLRLSCAASGFTFSS YAMSWVRQAPGKGL | 190 | GAAGTGCAGCTTGTGGAGTCAGGAGG AGGGCTAGTTCAGCCAGGCGGCTCTCT GAGACTATCTTGTGCTGCCTCCGGCTTC |

TABLE 12-continued

| Exemplary Sequences | | | | |
|---|---|---|---|---|
| | | EWVASISRGGTTYYP DSVKGRFTISRDNVR NILYLQMSSLRSEDTA MYYCGRYDYDGYYA MDYWGQGTLVTVSS | | ACATTTAGCTCTTATGCAATGTCCTGG GTCCGCCAGGCCCCTGGTAAAGGCCTG GAATGGGTTGCTTCTATCTCTAGAGGC GGAACCACTTACTACCCTGATTCAGTG AAGGGGAGATTCACAATTAGTAGGGA CAACGTGCGGAACATCCTCTACCTACA GATGTCAAGTTTACGCAGTGAGGACAC TGCGATGTATTACTGCGGTCGATACGA TTATGATGGATATTATGCAATGGATTA TTGGGGCCAGGGCACTCTGGTCACAGT ATCTTCC |
| hROR1 VL_14-4 | 44 | DIQMTQSPSSLSASVG DRVTITCKASPDINSY LNWYQQKPGKAPKL LIYRANRLVDGVPSR FSGSGSGTDYTLTISS LQPEDFATYYCLQYD EFPYTFGAGTKVEIK | 191 | GACATCCAGATGACCCAATCACCATCG AGTCTTAGTGCATCCGTTGGGGATAGA GTGACAATCACTTGTAAGGCATCCCCG GACATCAACTCATATCTTAATTGGTAT CAGCAAAAGCCGGGCAAGGCCCCTAA GCTCCTGATTTATAGGGCCAACCGCCT TGTGGATGGAGTCCCCTCCCGCTTTAG TGGAAGCGGCTCTGGCACAGACTACAC CCTGACTATCAGCTCCTTGCAGCCTGA GGATTTTGCTACCTACTACTGTCTTCAG TACGATGAATTTCCATACACTTTCGGT GCTGGGACAAAAGTGGAGATCAAA |
| hROR1 VH_14-5 | 45 | EVQLVESGGGLVQPG GSLRLSCATSGFTFSS YAMSWMRKAPGKGL EYVASISRGGTTYYA DSVKGRFTISVDKSK NTLYLQMNSLRAEDT AVYYCGRYDYDGYY AMDYWGQGTLVTVS S | 192 | GAAGTCCAGCTGGTTGAGTCTGGCGGA GGCCTCGTGCAGCCCGGTGGTTCCTTG CGACTGTCATGCGCTACCAGCGGGTTC ACATTCAGCTCTTATGCAATGTCCTGG ATGCGGAAGGCACCGGGTAAGGGCCT GGAGTATGTGGCCTCAATCTCCCGAGG AGGCACCACATACTATGCCGATTCTGT GAAAGGCCGATTCACCATTTCTGTGGA TAAGTCTAAAAACACTCTCTACCTCCA GATGAACTCCCTACGTGCCGAAGACAC AGCCGTGTATTATTGCGGGCGATACGA TTATGACGGTTATTATGCGATGGATTA CTGGGGTCAAGGCACACTGGTAACAGT GTCTTCC |
| hROR1 VL_14-5 | 46 | DIQMTQSPSSLSASVG DRVTITCKASPDINSY LNWYQQKPGKAPKL LIYRANRLVDGVPSR FSGSGSGTDYTLTISS LQPEDFATYYCLQYD EFPYTFGAGTKVEIK | 193 | GATATTCAGATGACACAATCACCTAGC TCACTGTCAGCGAGCGTCGGTGACCGG GTTACTATCACATGCAAAGCCTCACCC GATATCAATTCATACCTTAACTGGTAT CAACAAAAACCAGGAAAGGCTCCAAA GCTGCTAATTTATCGGGCCAATCGGTT GGTGGATGGCGTCCCGTCGAGGTTTAG TGGCTCCGGGAGCGGGACAGACTACAC TCTTACAATTTCTTCTCTCCAGCCAGAG GACTTCGCAACCTACTACTGCTTGCAG TACGATGAATTTCCATATACCTTCGGC GCAGGGACAAAAGTGGAAATCAAA |
| hROR1 VH_15 | 47 | EVQLVESGGGLVQPG GSLRLSCVTSGFTFSS YAMSWVRQAPGKGL EWVASISRGGTTYYS DSVKGRFTISRDNSK NTLYLQMNSLRAEDT AVYYCGRYDYDGYY AMDYWGQGTLVTVS S | 194 | GAGGTGCAGCTTGTAGAAAGCGGGGG GGGCCTGGTGCAACCTGGCGGGTCCCT GCGGCTTAGTTGCGTTACGAGCGGATT TACATTTTCCAGTTATGCCATGTCTTGG GTGAGACAAGCCCCCGGTAAGGGTCTG GAGTGGGTGGCAAGCATTAGCCGAGG CGGCACTACATACTACAGTGATAGTGT GAAAGGCCGTTTCACAATCAGTAGAGA TAATTCTAAAAACACCCTGTACTTGCA GATGAACAGCCTGCGCGCCGAGGATAC AGCCGTGTACTACTGTGGAAGATACGA CTACGATGGATATTATGCGATGGATTA CTGGGGACAGGGAACCCTTGTCACCGT TTCCTCT |
| hROR1 VL_15 | 48 | DIVLTQSPATLSLSPG ERATLSCKASPDINSY MNWYQQKPGQAPRL LISRANRLVDGVPAR FSGSGSGTDFTLTISSL EPEDFAVYYCLQYDE FPYTFGQGTKVEIK | 195 | GACATAGTGTTGACGCAGTCCCCTGCC ACCCTGAGCCTGAGCCCCGGAGAGCGA GCAACGTTAAGTTGCAAGGCCAGTCCA GATATTAACTCATACATGAATTGGTAT CAACAGAAACCAGGCCAGGCTCCTAG ACTTCTCATATCTCGGGCAAATCGACT GGTGGATGGAGTACCCGCAAGATTCAG CGGCAGCGGCAGCGGAACGGATTTCAC GCTCACCATCTCTTCCCTTGAGCCTGAG GACTTTGCAGTCTATTATTGCTTGCAGT |

TABLE 12-continued

| Exemplary Sequences | | | | |
|---|---|---|---|---|
| | | | | ATGATGAGTTCCCCTACACATTCGGGC AAGGCACAAAAGTGGAAATTAAG |
| hROR1 VH_16 | 49 | EVQLVESGGGLVQPG GSLRLSCAASGFTFSS YAMSWVRQAPGKGL EWVASISRGGTTYYD PKFQDRATISADNSK NTAYLQMNSLRAEDT AVYYCGRYDYDGYY AMDYWGQGTLVTVS S | 196 | GAGGTGCAGCTGGTGGAGAGCGGAGG GGGCCTTGTCCAACCAGGAGGTAGCCT CAGGCTGTCTTGCGCTGCCTCAGGATT TACTTTTTCATCCTACGCAATGAGCTGG GTGCGGCAAGCCCCAGGGAAGGGATT AGAATGGGTTGCCAGCATTTCTAGGGG GGGGACGACCTACTACGATCCGAAGTT TCAGGATCGCGCCACTATCTCAGCCGA TAACTCCAAGAATACTGCCTACTTACA GATGAACAGCCTGCGGGCCGAAGACA CGGCCGTCTACTATTGCGGCCGATATG ATTACGACGGCTATTACGCCATGGATT ACTGGGGGCAAGGGACTCTGGTCACAG TGAGCTCT |
| hROR1 VL_16 | 50 | DIQMTQSPSSLSASVG DRVTITCKASPDINSY LNWYQQKPGKAPKV LIYRANRLVDGVPSR FSGSGSGTDYTLTISS LQPEDFATYYCLQYD EFPYTFGQGTKVEIK | 197 | GATATTCAGATGACCCAGTCGCCCAGC AGTCTCTCGGCCTCAGTGGGCGACCGG GTCACTATCACTTGCAAAGCAAGTCCT GATATAAACTCCTATCTTAATTGGTATC AGCAGAAGCCCGGCAAGGCACCTAAG GTTCTGATATATCGCGCAAATCGGCTC GTGGATGGAGTACCCAGCCGATTTTCC GGCAGCGGCTCAGGCACTGACTACACA CTGACAATCAGCAGCTTGCAGCCTGAA GATTTCGCCACATACTATTGTCTACAGT ACGACGAGTTCCCTTATACATTCGGCC AGGGGACCAAGGTCGAGATCAAG |
| hROR1 VH_17 | 51 | EVQLVESGGGLVQPG GSLRLSCTGSGFTFSS YAMSWLRQVPGEGL EWVSSISRGGTTDYA DSVKGRFTISRDDAK KTLSLQMNSLRAEDT AVYYCGRYDYDGYY AMDYWGQGTMVTV SS | 198 | GAGGTCCAACTCGTGGAGAGCGGAGG GGGGCTAGTGCAACCAGGTGGCTCCCT CCGCTTGTCCTGTACGGGCTCGGGGTT CACATTTTCATCCTATGCCATGAGCTG GCTGAGACAGGTGCCTGGCGAGGGCCT GGAATGGGTGTCTAGTATCAGCAGAGG GGGTACAACTGATTACGCAGATTCCGT CAAGGGACGTTTTACCATCTCAAGAGA CGATGCCAAGAAGACATTATCACTCCA AATGAACTCACTGAGGGCCGAGGACA CCGCTGTGTACTATTGTGGGAGATACG ACTACGACGGATACTATGCCATGGACT ATTGGGGACAAGGCACGATGGTGACG GTATCTAGC |
| hROR1 VL_17 | 52 | EIVLTQSPATLSVSPG ERATLSCKASPDINSY LAWYQQKPGQAPRL LFSRANRLVDGIPARF TGSGSGTDFTLTISSL EPEDFAIYYCLQYDEF PYTFGQGTKVEIK | 199 | GAGATAGTGCTAACCCAGTCTCCCGCA ACCCTGTCTGTGTCCCCCGGAGAGCGC GCTACTCTGAGCTGCAAAGCCAGCCCG GACATTAATTCCTACCTTGCCTGGTATC AGCAGAAGCCTGGACAGGCCCCAAGA TTGCTCTTTTCACGCGCCAACCGCCTGG TAGATGGTATTCCAGCTAGGTTTACGG GCTCAGGCAGCGGAACAGACTTCACTC TCACTATTAGCTCATTGGAGCCTGAGG ACTTTGCAATTTACTATTGTCTTCAGTA CGACGAGTTCCCATATACTTTCGGCCA GGGCACAAAAGTAGAGATCAAG |
| hROR1 VH_18 | 53 | EVQLVESGGGLVQPG GSLRLSCSASGFTFSS YAMSWVRQVPGKGL VWISSISRGGTTYYAD SVRGRFIISRDNAKNT LYLEMNNLRGEDTA VYYCARYDYDGYYA MDYWGQGTLVTVSS | 200 | GAGGTTCAACTCGTGGAGTCTGGAGGC GGGCTAGTGCAGCCTGGCGGCTCCCTG CGACTGTCTTGCAGCGCATCAGGCTTT ACATTCAGTTCTTATGCCATGAGCTGG GTGAGGCAGGTGCCCGGCAAGGGTCTG GTGTGGATCAGCTCAATCTCCAGGGGC GGGACTACATATTACGCCGATTCGGTC AGGGGTCGTTTTATCATTAGCAGGGAT AATGCCAAGAACACCTTGTATTTGGAG ATGAACAACCTAAGAGGCGAAGACAC CGCTGTGTACTATTGTGCCCGTTACGA CTACGATGGGTACTACGCCATGGACTA TTGGGGCCAGGGAACCTTGGTGACTGT GTCAAGT |

TABLE 12-continued

| Exemplary Sequences | | | | |
|---|---|---|---|---|
| hROR1 VL_18 | 54 | DIQLTQSPDSLAVSLG ERATINCKASPDINSY LSWYQQRPGQPPRLL IHRANRLVDGVPDRF SGSGFGTDFTLTITSL QAEDVAIYYCLQYDE FPYTFGQGTKLEIK | 201 | GACATACAGTTGACTCAGTCACCGGAT TCGCTGGCAGTTTCGCTGGGTGAGAGA GCAACCATCAACTGCAAAGCATCTCCC GATATCAACTCTTATCTGTCTTGGTATC AGCAGCGTCCGGGACAACCCCCTAGGC TGCTTATTCACCGAGCCAACAGGCTGG TGGACGGGGTGCCAGACCGCTTCTCGG GATCAGGATTTGGAACCGATTTTACCC TAACAATTACTAGTCTCCAAGCGGAAG ACGTGGCGATCTATTATTGTCTACAAT ATGACGAGTTCCCCTACACCTTCGGCC AGGGCACGAAGTTGGAGATCAAG |
| hROR1 VH_19 | 55 | EVQLVESGGGLVQPG GSLRLSCAASGFTFSS YAMSWVRQAPGKGL EWVASISRGGTTYYA DSVKGRFTISADTSKN TAYLQMNSLRAEDTA VYYCARYDYDGYYA MDYWGQGTLVTVSS | 202 | GAGGTCCAGCTCGTCGAATCCGGTGGA GGGCTAGTTCAGCCAGGCGGCTCATTG CGTTTGTCTTGTGCCGCCTCCGGTTTCA CATTCTCTTCTTACGCTATGTCCTGGGT CCGACAAGCCCCAGGAAAAGGCTTGG AATGGGTGGCCAGTATCAGTAGAGGTG GGACTACATATTATGCCGACTCCGTGA AGGGCAGATTCACCATCTCAGCTGACA CCAGTAAGAACACTGCCTACCTACAGA TGAACAGCCTTCGGGCCGAGGACACCG CTGTGTATTACTGTGCCCGGTACGATT ATGATGGATATTATGCTATGGACTATT GGGGTCAGGGGACCTTGGTGACCGTCT CTAGC |
| hROR1 VL_19 | 56 | DIQMTQSPSSLSASVG DRVTITCKASPDINSY LSWYQQKPGKAPKLL IYRANRLVDGVPSRFS GSGSGTDFTLTISSLQ PEDFATYYCLQYDEF PYTFGQGTKVEIK | 203 | GACATTCAGATGACTCAATCGCCGAGT TCTCTTAGCGCTTCTGTTGGGGACCGG GTGACAATCACATGCAAGGCCTCTCCC GATATAAACTCCTATCTAAGCTGGTAT CAGCAGAAGCCAGGGAAGGCCCCCAA GTTGTTAATCTATCGCGCCAACAGACT GGTGGATGGGGTGCCCTCTCGATTCTC CGGGAGTGGCAGTGGGACTGATTTTAC ACTGACCATTTCCTCATTGCAGCCCGA AGACTTCGCTACCTATTACTGCTTGCA GTACGATGAGTTCCCATATACATTCGG TCAGGGGACTAAAGTGGAGATAAAA |
| hROR1 VH_20 | 57 | EVQLLESGGGLVQPG GSLRLSCAASGFTFSS YAMSWVRQAPGKGL EWVSSISRGGTTYYA DSVKGRFTISRDNSK NTLYLQMNSLRAEDT AVYYCARYDYDGYY AMDYWGQGTLVTVS S | 204 | GAGGTACAGCTGCTGGAATCTGGTGGG GGGCTGGTCCAGCCAGGGGGGTCACTA CGACTGAGCTGCGCTGCCTCCGGTTTT ACATTCAGCAGCTATGCAATGTCATGG GTCAGACAGGCACCAGGTAAAGGCCTC GAATGGGTATCCTCCATCTCACGTGGT GGGACCACTTACTATGCCGATAGTGTG AAGGGCAGGTTCACGATCTCAAGAGAT AATTCAAAGAATACACTCTATCTACAA ATGAACAGTTTAAGGGCCGAGGACACC GCTGTTTACTATTGTGCCAGATATGACT ACGACGGTTATTATGCTATGGATTACT GGGGACAAGGAACGCTGGTAACTGTTA GCTCT |
| hROR1 VL_20 | 58 | DIQMTQSPSSLSASVG DRVTITCKASPDINSY LSWYQQKPGEAPKLL IYRANRLVDGVPSRFS GSGSGTDFTLTISSLQ PEDFATYYCLQYDEF PYTFGQGTKVEIK | 205 | GACATCCAAATGACCCAGTCGCCTTCC TCCTTGTCTGCATCTGTCGGAGATCGG GTGACGATCACTTGCAAAGCGAGTCCA GACATCAACTCATATCTGTCCTGGTAT CAGCAGAAGCCGGGAGAGGCACCTAA GCTCCTGATCTACAGAGCAAACAGATT AGTGGATGGTGTGCCCTCACGGTTTTC TGGCTCCGGGTCCGGCACCGATTTCAC CTTGACCATCTCATCCCTACAGCCCGA GGATTTCGCTACTTACTATTGCTTACAG TATGATGAGTTTCCATACACCTTCGGTC AAGGCACCAAGGTTGAGATTAAG |
| hROR1 VH_21 | 59 | EVQLLETGGGLVKPG GSLRLSCAASGFTFSS YAMSWIRQAPGKGLE WVASISRGGTTYYGD SVKGRFTISRDHAKN SLYLQMNSLRVEDTA VYYCVRYDYDGYYA MDYWGLGTLVTVSS | 206 | GAAGTTCAACTGCTTGAGACCGGAGGC GGCCTGGTAAAACCTGGGGGCTCACTG AGGCTGAGTTGTGCCGCTTCTGGGTTC ACCTTTTCATCCTATGCGATGTCATGGA TACGGCAGGCTCCTGGGAAGGGGCTTG AGTGGGTTGCATCAATTTCACGAGGTG GGACAACTTATTATGGGGATTCCGTTA AAGGTAGATTTACGATCTCTAGAGACC ATGCCAAAAATTCTCTCTATCTCCAGA |

TABLE 12-continued

| Exemplary Sequences | | | | |
|---|---|---|---|---|
| | | | | TGAATAGTCTTAGGGTGGAGGACACCG<br>CTGTGTACTACTGTGTCCGGTACGACT<br>ATGATGGGTACTATGCTATGGACTATT<br>GGGGGCTCGGCACTCTGGTCACTGTTA<br>GCTCT |
| hROR1<br>VL_21 | 60 | AIRMTQSPSFLSASVG<br>DRVTITCKASPDINSY<br>LSWYQQRPGKAPKLL<br>IYRANRLVDGVPSRFS<br>GGGSGTDFTLTISSLQ<br>PEDIATYYCLQYDEFP<br>YTFGQGTKLEIK | 207 | GCCATCCGCATGACACAATCTCCCTCC<br>TTCCTTTCTGCCAGTGTCGGGGACAGA<br>GTGACTATCACATGCAAAGCCAGCCCA<br>GATATTAATTCGTACCTGTCTTGGTATC<br>AGCAGAGGCCCGGCAAGGCACCAAAG<br>CTGTTGATATATCGGGCCAACCGCTTA<br>GTGGACGGTGTCCCCTCTCGATTCAGC<br>GGAGGCGGTAGCGGGACGGACTTTAC<br>ACTGACCATCTCCAGTCTCCAACCCGA<br>GGATATTGCCACTTACTATTGTCTTCAG<br>TATGACGAGTTCCCCTACACATTTGGA<br>CAGGGCACCAAGCTAGAAATTAAG |
| hROR1<br>VH_22 | 61 | EVQLVESGGGLVQPG<br>GSLRLSCAASGFTFSS<br>YAMSWVRQAPGKGL<br>EWVASISRGGTTYYA<br>ESLEGRFTISRDDSKN<br>SLYLQMNSLKTEDTA<br>VYYCARYDYDGYYA<br>MDYWGQGTLVTVSS | 208 | GAGGTTCAGCTGGTGGAGTCTGGTGGG<br>GGGCTCGTACAGCCGGGTGGCTCCCTA<br>AGGCTGAGTTGCGCTGCCTCAGGCTTT<br>ACCTTCTCAAGCTACGCGATGTCCTGG<br>GTGAGACAGGCCCCTGGCAAAGGACT<br>GGAGTGGGTGGCAAGCATTAGCCGGG<br>GCGGAACTACCTATTACGCTGAGTCGT<br>TAGAGGGGCGGTTTACTATCTCCAGAG<br>ACGATTCAAAGAACTCGTTATACTTGC<br>AGATGAACAGCCTCAAGACCGAGGAC<br>ACCGCCGTGTACTACTGCGCCCGGTAC<br>GACTATGACGGGTACTATGCTATGGAT<br>TATTGGGGACAAGGCACCCTCGTGACC<br>GTCTCTAGC |
| hROR1<br>VL_22 | 62 | DIQMTQSPSSLSASVG<br>DRVTITCKASPDINSY<br>LSWYQQKPGKAPKTL<br>IYRANRLVDGVPSRFS<br>GSGSGTDFTLTISSLQ<br>PEDFATYYCLQYDEF<br>PYTFGQGTKLEIK | 209 | GACATCCAGATGACACAGTCCCCTTCT<br>TCACTTTCCGCTTCTGTGGGCGACAGG<br>GTGACGATCACGTGTAAGGCCTCGCCA<br>GACATTAATTCGTACTTATCGTGGTATC<br>AGCAGAAACCGGGTAAAGCTCCGAAG<br>ACTCTGATCTATAGAGCAAATAGGCTC<br>GTAGACGGTGTCCCATCTAGATTTAGT<br>GGGAGCGGCAGCGGAACCGACTTCACT<br>CTCACCATCTCATCCCTGCAACCGGAG<br>GATTTCGCTACTTACTATTGCTTGCAGT<br>ATGACGAGTTTCCATATACGTTTGGTC<br>AGGGAACCAAATTAGAGATCAAA |
| hROR1<br>VH_23 | 63 | QVTLRESGPALVKPT<br>QTLTLTCAASGFTFSS<br>YAMSWIRQPPGKALE<br>WLASISRGGTTYYNP<br>SLKDRLTISKDTSANQ<br>VVLKVTNMDPADTA<br>TYYCARYDYDGYYA<br>MDYWGQGTTVTVSS | 210 | CAGGTAACACTCCGAGAGAGTGGGCC<br>AGCTCTCGTGAAGCCCACGCAGACTTT<br>AACACTAACGTGTGCGGCAAGCGGCTT<br>TACATTTTCGAGCTACGCGATGAGCTG<br>GATAAGGCAACCTCCTGGGAAGGCGTT<br>GGAGTGGTTGGCCTCAATTAGCCGGGG<br>TGGCACCACTTACTACAATCCTAGTCTT<br>AAGGACAGACTTACTATTTCAAAAGAT<br>ACGTCCGCCAACCAGGTGGTACTGAAG<br>GTCACAAATATGGACCCAGCTGACACT<br>GCTACTTACTACTGCGCCCGGTACGAT<br>TACGATGGTTACTACGCTATGGATTAC<br>TGGGGTCAAGGAACCACAGTGACCGTC<br>AGTTCA |
| hROR1<br>VL_23 | 64 | DIQMTQSPSTLSASVG<br>DRVTITCKASPDINSY<br>LSWYQQKPGKAPKLL<br>IYRANRLVDGVPSRFS<br>GSGSGTAFTLTISSLQ<br>PDDFATYYCLQYDEF<br>PYTFGGGTKVEIK | 211 | GATATCCAGATGACGCAGTCCCCTTCA<br>ACCCTCAGTGCCAGCGTTGGTGACCGG<br>GTTACTATCACCTGTAAGGCTAGTCCC<br>GATATAAATTCCTATTTGTCTTGGTATC<br>AGCAGAAGCCAGGCAAGGCTCCTAAG<br>CTGCTCATCTACCGGGCTAACAGGTTA<br>GTTGACGGTGTGCCCTCCCGATTTTCCG<br>GCAGTGGCAGCGGGACCGCTTTCACTC<br>TTACAATCTCATCTCTTCAACCGGACG<br>ACTTCGCTACGTACTACTGCCTCCAAT<br>ATGATGAGTTTCCATACACATTCGGAG<br>GAGGCACAAAAGTCGAAATCAAG |
| hROR1<br>VH_24 | 65 | EVQLVESGGGLVQPG<br>GSLRLSCAASGFTFSS<br>YAMSWVRQAPGKGL | 212 | GAAGTCCAGCTGGTGGAGTCCGGCGGA<br>GGCTTGGTTCAGCCCGGAGGATCTTTG<br>CGACTGTCTTGCGCCGCCAGCGGTTTC |

TABLE 12-continued

| Exemplary Sequences | | | | |
|---|---|---|---|---|
| | | EWVSAISRGGTTYYA<br>DSVKGRFTISADTSKE<br>TAYLQMNSLRAEDTA<br>VYYCGRYDYDGYYA<br>MDYWGQGTLVTVSS | | ACTTTCAGCAGCTATGCCATGAGTTGG<br>GTTAGACAAGCTCCCGGCAAGGGGCTG<br>GAATGGGTTAGTGCTATTAGCCGGGGA<br>GGGACAACATATTACGCTGACTCTGTC<br>AAAGGCCGATTCACCATCTCTGCTGAC<br>ACGAGCAAAGAAACCGCCTACCTCCAA<br>ATGAACAGCCTGCGAGCTGAGGACACT<br>GCCGTCTACTATTGTGGTCGATATGATT<br>ATGATGGGTACTATGCAATGGACTATT<br>GGGGGCAGGGCACACTGGTGACCGTG<br>AGCTCT |
| hROR1<br>VL_24 | 66 | DIQMTQSPSSLSASVG<br>DRVTITCKASPDINSY<br>LSWYQQKPGKAPKLL<br>IYRANRLVDGVPSRFS<br>GSGSGTDFTLTISSLQ<br>PEDIATYYCLQYDEFP<br>YTFGQGTKLEIK | 213 | GATATTCAGATGACGCAGAGTCCCTCC<br>TCCCTATCTGCCTCTGTTGGAGATCGA<br>GTCACCATTACGTGTAAAGCGTCTCCC<br>GATATCAACAGCTACCTCTCTTGGTAT<br>CAGCAGAAACCAGGGAAGGCCCCCAA<br>GCTGCTGATCTATAGAGCTAATCGCTT<br>AGTGGATGGAGTGCCAAGCAGGTTCTC<br>CGGGTCCGGCAGTGGAACCGATTTCAC<br>CTTGACAATAAGTAGCTTGCAACCTGA<br>GGATATTGCAACATACTACTGTCTACA<br>GTACGACGAGTTCCCCTACACCTTCGG<br>CCAAGGGACAAAGCTGGAGATTAAG |
| hROR1<br>VH_25 | 67 | EVQLVESGGGLVQPG<br>GSLRLSCAASGFTFSS<br>YAMSWVRQAPGKGL<br>EWVSAISRGGTTYYA<br>DSVKGRFTISRDNSK<br>NTLYLQMNSLRAEDT<br>AVYYCGRYDYDGYY<br>AMDYWGQGTLVTVS<br>S | 214 | GAAGTGCAGCTCGTGGAGAGCGGCGG<br>CGGTCTGGTACAGCCAGGGGGGTCACT<br>GCGTCTCTCATGTGCTGCGAGTGGCTTT<br>ACGTTCTCTTCCTACGCTATGTCCTGGG<br>TCAGGCAGGCACCGGGGAAGGGCTTA<br>GAGTGGGTTAGTGCAATCTCTAGGGGC<br>GGTACAACCTACTATGCCGACTCTGTC<br>AAGGGCAGGTTTACAATTTCAAGAGAT<br>AATTCTAAGAATACTCTTTACCTACAG<br>ATGAATAGCTTGCGGGCGGAAGACAC<br>AGCAGTCTATTATTGTGGCCGCTATGA<br>CTACGACGGATACTATGCCATGGACTA<br>CTGGGGCCAAGGCACTTTGGTCACGGT<br>GAGCTCT |
| hROR1<br>VL_25 | 68 | DIQMTQSPSSLSASVG<br>DRVTITCKASPDINSY<br>LSWYQQKPGKAPKLL<br>IYRANRLVDGVPSRFS<br>GSGSGTDFTLTISSLQ<br>PEDIATYYCLQYDEFP<br>YTFGQGTKLEIK | 215 | GACATCCAGATGACCCAGAGCCCTAGT<br>TCATTGTCTGCCAGTGTGGGGGATAGG<br>GTCACTATCACGTGTAAGGCTTCCCCT<br>GACATCAATTCATACCTGTCATGGTAT<br>CAGCAGAAGCCTGGAAAAGCCCCTAA<br>ACTGCTGATCTACCGCGCGAATAGGCT<br>TGTGGACGGCGTTCCAAGCCGCTTCTC<br>TGGCTCTGGATCAGGGACCGACTTCAC<br>CCTCACGATCTCCAGCCTCCAACCCGA<br>GGATATCGCCACCTATTATTGCCTTCA<br>GTACGATGAGTTCCCCTATACATTCGG<br>CCAGGGGACAAAGCTGGAAATCAAA |
| hROR1<br>VH_26 | 69 | EVQLVESGGGLVQPG<br>GSLRLSCAASGFTFSS<br>YAMSWVRQAPGKGL<br>EWVSAISRGGTTYYA<br>DSVKGRFTISADTSKE<br>TAYLQMNSLRAEDTA<br>VYYCGRYDYDGYYA<br>MDYWGQGTLVTVSS | 216 | GAGGTCCAGCTCGTCGAGTCGGGTGGG<br>GGCTTGGTGCAACCCGGTGGCAGTTTG<br>CGCCTGAGCTGCGCCGCGAGCGGGTTC<br>ACTTTCAGTTCGTATGCCATGAGTTGG<br>GTGCGACAAGCGCCCGGCAAAGGACT<br>GGAGTGGGTGTCAGCCATTAGCCGGGG<br>CGGTACTACCTACTATGCGGACTCGGT<br>CAAGGGAAGATTCACCATCAGCGCTGA<br>TACCAGTAAGGAAACCGCTTATCTTCA<br>GATGAACTCCCTGCGTGCCGAGGATAC<br>AGCAGTCTACTATTGCGGGCGCTACGA<br>TTATGACGGATATTATGCCATGGATTA<br>CTGGGGGCAGGGCACTCTGGTCACAGT<br>CAGCTCT |
| hROR1<br>VL_26 | 70 | DIQMTQSPSSLSASVG<br>DRVTITCQASPDINSY<br>LNWYQQKPGKAPKL<br>LIYRANNLETGVPSRF<br>SGSGSGTDFTLTISSL<br>QPEDIATYYCLQYDE<br>FPYTFGQGTKLEIK | 217 | GATATTCAGATGACGCAGTCTCCCTCT<br>TCCCTGAGCGCCTCCGTCGGCGATAGA<br>GTTACGATCACCTGTCAGGCCAGCCCA<br>GATATCAACTCCTATCTGAATTGGTAT<br>CAGCAAAAGCCTGGGAAGGCTCCCAA<br>GTTGCTGATCTACAGAGCCAATAACTT<br>AGAGACTGGCGTGCCGTCTCGGTTCAG<br>CGGGTCCGGCAGTGGAACCGACTTTAC<br>ACTGACCATTTCCAGCCTCCAACCTGA<br>GGATATCGCCACATATTATTGTCTCCA |

TABLE 12-continued

| Exemplary Sequences | | | | |
|---|---|---|---|---|
| | | | | GTATGACGAGTTCCCTTACACATTTGG TCAAGGAACTAAACTGGAAATCAAA |
| hROR1 VH_27 | 71 | EVQLVESGGGLVQPG GSLRLSCAASGFTFSS YAMSWVRQAPGKGL EWVSAISRGGTTYYA DSVKGRFTISADTSKE TAYLQMNSLRAEDTA VYYCGRYDYDGYYA MDYWGQGTLVTVSS | 218 | GAGGTGCAGCTGGTCGAAAGTGGAGG CGGACTCGTGCAGCCCGGCGGTAGTCT GCGATTGAGCTGTGCCGCGTCCGGCTT TACTTTCTCATCTTACGCTATGAGTTGG GTCCGCCAGGCCCCAGGCAAAGGACTG GAGTGGGTATCAGCCATCAGTAGGGGG GGAACTACCTATTACGCAGATTCTGTG AAGGGACGCTTCACCATCAGCGCGGAC ACTAGCAAGGAGACTGCCTACCTGCAA ATGAATAGTCTGAGAGCCGAGGATACC GCCGTGTACTATTGTGGCAGGTATGAC TACGATGGCTATTATGCTATGGATTAC TGGGGCCAGGGGACGTTAGTGACAGTA AGCTCT |
| hROR1 VL_27 | 72 | DIQMTQSPSSLSASVG DRVTITCRASPDINSY VAWYQQKPGKAPKL LIYRANFLESGVPSRF SGSRSGTDFTLTISSL QPEDFATYYCLQYDE FPYTFGQGTKVEIK | 219 | GATATTCAGATGACCCAATCCCCTTCTT CTCTGAGCGCTTCTGTGGGCGATAGAG TTACAATAACCTGTCGGGCGTCCCCAG ACATTAACTCTTATGTAGCATGGTATC AGCAAAAGCCTGGAAAGGCACCAAAG TTACTGATCTACCGGGCCAATTTTCTGG AGTCGGGCGTGCCCTCACGATTTAGCG GTAGCAGATCAGGCACAGACTTTACTC TGACCATTAGCTCTCTGCAACCCGAGG ACTTCGCCACCTACTACTGTTTGCAGTA TGACGAGTTTCCATACACTTTTGGTCA AGGAACCAAAGTCGAAATCAAA |
| hROR1 VH_28 | 73 | QIQLVQSGAEVKKPG ASVKVSCAASGFTFSS YAMSWVRQAPGKSF KWMGSISRGGTTYYS ADFKGRFAITKDTSAS TAYMELSSLRSEDTA VYYCARYDYDGYYA MDYWGQGTLVTVSS | 220 | CAGATACAGCTGGTGCAGTCTGGTGCC GAGGTTAAAAAGCCCGGAGCCTCGGTT AAAGTGAGTTGTGCGGCAAGCGGATTC ACGTTCAGTTCCTACGCTATGTCCTGG GTGCGGCAGGCTCCTGGCAAGTCATTT AAGTGGATGGGGTCGATCTCACGGGGT GGAACCACCTATTACTCTGCCGACTTC AAGGGGAGATTTGCGATTACAAAAGAT ACAAGCGCCTCTACGGCCTACATGGAG TTAAGTAGCCTTAGAAGCGAAGACACG GCGGTGTACTACTGCGCCAGATATGAC TATGACGGCTACTACGCCATGGACTAC TGGGGCCAGGGCACACTGGTTACAGTC AGCTCT |
| hROR1 VL_28 | 74 | DIVMTQSPDSLAVSL GERATISCKASPDINS YLSWYQQKPGQPPKL LIYRANRLVDGVPDR FSGSGSRTDFTLTISSL QAEDVAVYYCLQYD EFPYTFGQGTKVEIK | 221 | GATATCGTGATGACACAAAGCCCAGAC AGTCTGGCAGTGTCCCTCGGCGAGCGC GCTACCATCTCATGCAAAGCTAGTCCC GACATCAATTCCTATCTGTCCTGGTATC AGCAAAAACCAGGCCAACCCCCCAAG CTGCTTATCTATCGGGCTAACCGATTA GTCGATGGGGTGCCAGATAGATTTTCA GGCTCTGGTTCCCGGACAGATTTTACT CTCACGATCTCCTCACTACAGGCAGAA GATGTTGCAGTGTATTACTGCCTGCAA TACGACGAGTTCCCCTACACCTTCGGC CAAGGCACGAAAGTGGAGATCAAG |
| hROR1 (VH-VL)_14.CD8a(3x).CD28z | 75 | EVQLVESGGGLVQPG GSLRLSCATSGFTFSS YAMSWMRQAPGKGL EWVASISRGGTTYYA DSVKGRFTISVDKSK NTLYLQMNSLRAEDT AVYYCGRYDYDGYY AMDYWGQGTLVTVS SGGGGSGGGGSGGG GSDIQMTQSPSSLSAS VGDRVTITCKASPDIN SYLNWYQQKPGKAP KLLIYRANRLVDGVP SRFSGSGSGTDYTLTI SSLQPEDFATYYCLQ YDEFPYTFGAGTKVEI KKPTTTPAPRPPTPAP TIASQPLSLRPEASRP AAGGAVHTRGLDFAS | 222 | GAAGTGCAGCTGGTGGAGTCTGGCGGC GGTCTGGTGCAGCCCGGCGGCTCTCTG CGCCTCTCCTGTGCCACCTCTGGTTTTA CATTCTCCTCCTACGCTATGTCCTGGAT GCGGCAAGCCCCCGGCAAGGGCCTAG AGTGGGTCGCCTCAATCAGCAGGGGCG GGACGACTTATTATGCCGATTCAGTTA AGGGGAGATTCACAATTTCCGTGGATA AATCCAAGAATACCTTATACCTCCAGA TGAACTCTCTGCGGGCCGAAGATACGG CCGTATATTATTGTGGGAGGTATGACT ACGACGGATATTACGCCATGGATTATT GGGGGCAGGGGACACTTGTTACAGTGA GTTCCGGTGGTGGGGGGTCTGGAGGCG GGGGCAGTGGAGGCGGAGGGTCTGAT ATACAGATGACACAGAGCCCTTCAAGT TTATCTGCAAGCGTCGGCGATCGTGTT ACAATAACTTGCAAGGCATCTCCCGAC ATCAATTCCTACCTCAACTGGTATCAG |

TABLE 12-continued

| Exemplary Sequences | | | | |
|---|---|---|---|---|
| | | DKPTTTPAPRPPTPAP | | CAGAAGCCTGGGAAGGCTCCTAAGCTG |
| | | TIASQPLSLRPEASRP | | CTTATTTACAGAGCAAATCGCCTGGTG |
| | | AAGGAVHTRGLDFAS | | GACGGCGTGCCCAGTCGGTTTTCCGGG |
| | | DKPTTTPAPRPPTPAP | | TCTGGGAGCGGAACGGATTACACACTG |
| | | TIASQPLSLRPEACRP | | ACCATCTCAAGCCTGCAACCCGAAGAC |
| | | AAGGAVHTRGLDFA | | TTCGCTACATATTACTGCCTTCAGTATG |
| | | CDIYIWAPLAGTCGV | | ATGAGTTCCCATATACCTTCGGCGCTG |
| | | LLLSLVITLYCNHRNR | | GGACCAAGGTGGAGATAAAGAAGCCT |
| | | SKRSRGGHSDYMNM | | ACCACCACCCCCGCACCTCGTCCTCCA |
| | | TPRRPGPTRKHYQPY | | ACCCCTGCACCTACGATTGCCAGTCAG |
| | | APPRDFAAYRSRVKF | | CCTCTTTCACTGCGGCCTGAGGCCAGC |
| | | SRSADAPAYQQGQN | | AGACCAGCTGCCGGCGGTGCCGTCCAT |
| | | QLYNELNLGRREEYD | | ACAAGAGGACTGGACTTCGCGTCCGAT |
| | | VLDKRRGRDPEMGG | | AAACCTACTACCACTCCAGCCCCAAGG |
| | | KPRRKNPQEGLYNEL | | CCCCCAACCCCAGCACCGACTATCGCA |
| | | QKDKMAEAYSEIGM | | TCACAGCCTTTGTCACTGCGTCCTGAA |
| | | KGERRRGKGHDGLY | | GCCAGCCGGCCAGCTGCAGGGGGGGC |
| | | QGLSTATKDTYDALH | | CGTCCACACAAGGGGACTCGACTTTGC |
| | | MQALPPR | | GAGTGATAAGCCCACCACCACCCCTGC |
| | | | | CCCTAGACCTCCAACCCCAGCCCCTAC |
| | | | | AATCGCCAGCCAGCCCCTGAGCCTGAG |
| | | | | GCCCGAAGCCTGTAGACCTGCCGCTGG |
| | | | | CGGAGCCGTGCACACCAGAGGCCTGG |
| | | | | ATTTCGCCTGCGACATCTACATCTGGG |
| | | | | CCCCTCTGGCCGGCACCTGTGGCGTGC |
| | | | | TGCTGCTGAGCCTGGTCATCACCCTGT |
| | | | | ACTGCAACCACCGGAATAGGAGCAAG |
| | | | | CGGAGCAGAGGCGGCCACAGCGACTA |
| | | | | CATGAACATGACCCCCCGGAGGCCTGG |
| | | | | CCCCACCCGGAAGCACTACCAGCCCTA |
| | | | | CGCCCCTCCCAGGGACTTCGCCGCCTA |
| | | | | CCGGAGCCGGGTGAAGTTCAGCCGGA |
| | | | | GCGCCGACGCCCCTGCCTACCAGCAGG |
| | | | | GCCAGAACCAGCTGTACAACGAGCTGA |
| | | | | ACCTGGGCCGGAGGGAGGAGTACGAC |
| | | | | GTGCTGGACAAGCGGAGAGGCCGGGA |
| | | | | CCCTGAGATGGGCGGCAAGCCCCGGA |
| | | | | GAAAGAACCCTCAGGAGGGCCTGTATA |
| | | | | ACGAACTGCAGAAAGACAAGATGGCC |
| | | | | GAGGCCTACAGCGAGATCGGCATGAA |
| | | | | GGGCGAGCGGCGGAGGGGCAAGGGCC |
| | | | | ACGACGGCCTGTACCAGGGCCTGAGCA |
| | | | | CCGCCACCAAGGATACCTACGACGCCC |
| | | | | TGCACATGCAGGCCCTGCCCCCCAGA |
| hROR1 | 76 | DIQMTQSPSSLSASVG | 223 | GATATTCAGATGACCCAGTCACCTTCG |
| (VL-VH)_05.CD8a(3x).CD28z | | DRVTITCKASPDINSY | | AGTCTGAGCGCATCCGTGGGCGACAGA |
| | | LSWYQQKPGKAPKLL | | GTGACCATTACCTGTAAGGCCAGCCCG |
| | | IYRANRLVDGVPSRFS | | GACATTAACAGCTACCTATCGTGGTAT |
| | | GSGSGTDFTLTISSLQ | | CAGCAAAAGCCTGGTAAGGCCCCTAAA |
| | | PEDIATYYCLQYDEFP | | CTCCTTATCTACAGGGCTAATAGGTTG |
| | | YTFGQGTKLEIKGGG | | GTAGACGGGGTGCCTAGCCGGTTCTCT |
| | | GSGGGGSGGGGSEVQ | | GGTTCCGGCAGCGGTACGGACTTTACT |
| | | LVESGGGLVQPGGSL | | CTGACCATAAGCTCTCTGCAACCAGAA |
| | | RLSCAASGFTFSSYA | | GACATCGCAACATACTACTGTTTACAA |
| | | MSWVRQAPGKGLEW | | TACGACGAATTTCCTTATACCTTTGGCC |
| | | VSSISRGGTTYYPDSV | | AGGGGACCAAGTTAGAGATCAAGGGG |
| | | KGRFTISRDNSKNTLY | | GGCGGCGGAAGTGGTGGAGGGGGAAG |
| | | LQMNSLRAEDTAVY | | TGGTGGAGGAGGAAGCGAAGTGCAAC |
| | | YCGRYDYDGYYAMD | | TGGTCGAGTCTGGGGGCGGCCTTGTGC |
| | | YWGQGTLVTVSSKPT | | AACCTGGAGGCAGCCTTCGACTCAGTT |
| | | TTPAPRPPTPAPTIASQ | | GCGCCGCGTCTGGTTTTACCTTCTCCTC |
| | | PLSLRPEASRPAAGG | | TTACGCGATGAGCTGGGTTCGCCAGGC |
| | | AVHTRGLDFASDKPT | | CCCCGGCAAGGGACTTGAGTGGGTTAG |
| | | TTPAPRPPTPAPTIASQ | | TTCGATCTCCCGCGGAGGCACCACATA |
| | | PLSLRPEASRPAAGG | | TTATCCTGACTCGGTTAAGGGACGCTT |
| | | AVHTRGLDFASDKPT | | CACTATCTCTAGGGACAATTCAAAGAA |
| | | TTPAPRPPTPAPTIASQ | | CACACTGTATCTCCAAATGAACTCCTT |
| | | PLSLRPEACRPAAGG | | GCGGGCCGAGGACACTGCTGTGTATTA |
| | | AVHTRGLDFACDIYI | | TTGCGGACGATACGACTACGATGGGTA |
| | | WAPLAGTCGVLLLSL | | TTACGCCATGGATTACTGGGGGCAAGG |
| | | VITLYCNHRNRSKRS | | TACACTGGTCACTGTGAGTTCGAAGCC |
| | | RGGHSDYMNMTPRR | | TACCACCACCCCCGCACCTCGTCCTCC |
| | | PGPTRKHYQPYAPPR | | AACCCCTGCACCTACGATTGCCAGTCA |
| | | DFAAYRSRVKFSRSA | | GCCTCTTTCACTGCGGCCTGAGGCCAG |
| | | DAPAYQQGQNQLYN | | CAGACCAGCTGCCGGCGGTGCCGTCCA |
| | | ELNLGRREEYDVLDK | | TACAAGAGGACTGGACTTCGCGTCCGA |
| | | RRGRDPEMGGKPRR | | TAAACCTACTACCACTCCAGCCCCAAG |

TABLE 12-continued

| Exemplary Sequences | | | | |
|---|---|---|---|---|
| | | KNPQEGLYNELQKDK MAEAYSEIGMKGERR RGKGHDGLYQGLST ATKDTYDALHMQAL PPR | | GCCCCCAACCCCAGCACCGACTATCGC ATCACAGCCTTTGTCACTGCGTCCTGA AGCCAGCCGGCCAGCTGCAGGGGGGG CCGTCCACACAAGGGGACTCGACTTTG CGAGTGATAAGCCCACCACCACCCCTG CCCCTAGACCTCCAACCCCAGCCCCTA CAATCGCCAGCCAGCCCCTGAGCCTGA GGCCCGAAGCCTGTAGACCTGCCGCTG GCGGAGCCGTGCACACCAGAGGCCTG GATTTCGCCTGCGACATCTACATCTGG GCCCCTCTGGCCGGCACCTGTGGCGTG CTGCTGCTGAGCCTGGTCATCACCCTG TACTGCAACCACCGGAATAGGAGCAA GCGGAGCAGAGGCGGCCACAGCGACT ACATGAACATGACCCCCCGGAGGCCTG GCCCCACCCGGAAGCACTACCAGCCCT ACGCCCCTCCCAGGGACTTCGCCGCCT ACCGGAGCCGGGTGAAGTTCAGCCGG AGCGCCGACGCCCCTGCCTACCAGCAG GGCCAGAACCAGCTGTACAACGAGCTG AACCTGGGCCGGAGGGAGGAGTACGA CGTGCTGGACAAGCGGAGAGGCCGGG ACCCTGAGATGGGCGGCAAGCCCCGG AGAAAGAACCCTCAGGAGGGCCTGTAT AACGAACTGCAGAAAGACAAGATGGC CGAGGCCTACAGCGAGATCGGCATGA AGGGCGAGCGGCGGAGGGGCAAGGGC CACGACGGCCTGTACCAGGGCCTGAGC ACCGCCACCAAGGATACCTACGACGCC CTGCACATGCAGGCCCTGCCCCCCAGA TGA |
| hROR1 (VH-VL)_14-3.CD8a(3x).CD28z | 77 | EVQLVESGGGLVQPG GSLRLSCAASGFTFSS YAMSWVRQAPGKGL EWVASISRGGTTYYA DSVKGRFTISRDNSK NTLYLQMNSLRAEDT AVYYCGRYDYDGYY AMDYWGQGTLVTVS SGGGGSGGGGSGGG GSDIQMTQSPSSLSAS VGDRVTITCKASPDIN SYLNWYQQKPGKAP KLLIYRANRLVDGVP SRFSGSGSGTDFTLTIS SLQPEDIATYYCLQY DEFPYTFGGGTKVEIK KPTTTPAPRPPTPAPTI ASQPLSLRPEASRPAA GGAVHTRGLDFASDK PTTTPAPRPPTPAPTIA SQPLSLRPEASRPAAG GAVHTRGLDFASDKP TTTPAPRPPTPAPTIAS QPLSLRPEACRPAAG GAVHTRGLDFACDIY IWAPLAGTCGVLLLS LVITLYCNHRNRSKR SRGGHSDYMNMTPR RPGPTRKHYQPYAPP RDFAAYRSRVKFSRS ADAPAYQQGQNQLY NELNLGRREEYDVLD KRRGRDPEMGGKPR RKNPQEGLYNELQKD KMAEAYSEIGMKGER RRGKGHDGLYQGLST ATKDTYDALHMQAL PPR | 224 | GAGGTTCAACTTGTGGAATCCGGCGGC GGGTTAGTCCAGCCCGGCGGGAGCTTG CGGCTGTCCTGCGCCGCCTCTGGATTC ACTTTTAGCTCCTATGCTATGTCTTGGG TAAGGCAGGCCCCTGGTAAAGGACTAG AGTGGGTGGCCTCGATCTCCCGTGGTG GCACTACATACTACGCCGACTCCGTTA AAGGCCGGTTTACCATCTCCCGTGACA ACTCTAAAAATACTTTGTACCTGCAAA TGAACTCCCTGCGGGCAGAAGACACAG CCGTGTACTATTGCGGGCGTTACGATT ACGACGGATATTACGCAATGGACTACT GGGGCCAGGGCACACTGGTCACCGTGA GCAGCGGGGGCGGAGGAAGTGGAGGA GGCGGTAGTGGTGGGGGAGGAAGCGA TATACAAATGACTCAGTCCCCTAGTAG CCTTAGTGCTAGTGTGGGAGACAGAGT GACCATCACCTGCAAAGCATCTCCTGA TATCAATTCCTACCTTAACTGGTATCAA CAGAAGCCTGGCAAAGCTCCAAAGCTC CTGATTTATCGCGCGAACAGATTGGTC GATGGGGTCCCTTCCAGATTCAGCGGC TCAGGGTCAGGGACCGATTTCACCCTC ACAATTAGTTCACTTCAGCCCGAGGAC ATCGCCACGTATTATTGCCTTCAGTAC GATGAGTTCCCTTACACCTTTGGCGGG GGAACTAAAGTCGAAATTAAGAAGCCT ACCACCACCCCCGCACCTCGTCCTCCA ACCCCTGCACCTACGATTGCCAGTCAG CCTCTTTCACTGCGGCCTGAGGCCAGC AGACCAGCTGCCGGCGGTGCCGTCCAT ACAAGAGGACTGGACTTCGCGTCCGAT AAACCTACTACCACTCCAGCCCCAAGG CCCCCAACCCCAGCACCGACTATCGCA TCACAGCCTTTGTCACTGCGTCCTGAA GCCAGCCGGCCAGCTGCAGGGGGGC CGTCCACACAAGGGGACTCGACTTTGC GAGTGATAAGCCCACCACCACCCCTGC CCCTAGACCTCCAACCCCAGCCCCTAC AATCGCCAGCCAGCCCCTGAGCCTGAG GCCCGAAGCCTGTAGACCTGCCGCTGG CGGAGCCGTGCACACCAGAGGCCTGG ATTTCGCCTGCGACATCTACATCTGGG CCCCTCTGGCCGGCACCTGTGGCGTGC TGCTGCTGAGCCTGGTCATCACCCTGT ACTGCAACCACCGGAATAGGAGCAAG |

TABLE 12-continued

| Exemplary Sequences | | | | |
|---|---|---|---|---|
| | | | | CGGAGCAGAGGCGGCCACAGCGACTA<br>CATGAACATGACCCCCCGGAGGCCTGG<br>CCCCACCCGGAAGCACTACCAGCCCTA<br>CGCCCCTCCCAGGGACTTCGCCGCCTA<br>CCGGAGCCGGGTGAAGTTCAGCCGGA<br>GCGCCGACGCCCCTGCCTACCAGCAGG<br>GCCAGAACCAGCTGTACAACGAGCTGA<br>ACCTGGGCCGGAGGGAGGAGTACGAC<br>GTGCTGGACAAGCGGAGAGGCCGGGA<br>CCCTGAGATGGGCGGCAAGCCCCGGA<br>GAAAGAACCCTCAGGAGGGCCTGTATA<br>ACGAACTGCAGAAAGACAAGATGGCC<br>GAGGCCTACAGCGAGATCGGCATGAA<br>GGGCGAGCGGCGGAGGGGCAAGGGCC<br>ACGACGGCCTGTACCAGGGCCTGAGCA<br>CCGCCACCAAGGATACCTACGACGCCC<br>TGCACATGCAGGCCCTGCCCCCCAGA |
| hROR1<br>(VH-VL)_14-4.CD8a(3x).CD28z | 78 | EVQLVESGGGLVQPG<br>GSLRLSCAASGFTFSS<br>YAMSWVRQAPGKGL<br>EWVASISRGGTTYYP<br>DSVKGRFTISRDNVR<br>NILYLQMSSLRSEDTA<br>MYYCGRYDYDGYYA<br>MDYWGQGTLVTVSS<br>GGGGSGGGGSGGGG<br>SDIQMTQSPSSLSASV<br>GDRVTITCKASPDINS<br>YLNWYQQKPGKAPK<br>LLIYRANRLVDGVPS<br>RFSGSGSGTDYTLTIS<br>SLQPEDFATYYCLQY<br>DEFPYTFGAGTKVEIK<br>KPTTTPAPRPPTPAPTI<br>ASQPLSLRPEASRPAA<br>GGAVHTRGLDFASDK<br>PTTTPAPRPPTPAPTIA<br>SQPLSLRPEASRPAAG<br>GAVHTRGLDFASDKP<br>TTTPAPRPPTPAPTIAS<br>QPLSLRPEACRPAAG<br>GAVHTRGLDFACDIY<br>IWAPLAGTCGVLLLS<br>LVITLYCNHRNRSKR<br>SRGGHSDYMNMTPR<br>RPGPTRKHYQPYAPP<br>RDFAAYRSRVKFSRS<br>ADAPAYQQGQNQLY<br>NELNLGRREEYDVLD<br>KRRGRDPEMGGKPR<br>RKNPQEGLYNELQKD<br>KMAEAYSEIGMKGER<br>RRGKGHDGLYQGLST<br>ATKDTYDALHMQAL<br>PPR | 225 | GAAGTGCAGCTTGTGGAGTCAGGAGG<br>AGGGCTAGTTCAGCCAGGCGGCTCTCT<br>GAGACTATCTTGTGCTGCCTCCGGCTTC<br>ACATTTAGCTCTTATGCAATGTCCTGG<br>GTCCGCCAGGCCCCTGGTAAAGGCCTG<br>GAATGGGTTGCTTCTATCTCTAGAGGC<br>GGAACCACTTACTACCCTGATTCAGTG<br>AAGGGGAGATTCACAATTAGTAGGGA<br>CAACGTGCGGAACATCCTCTACCTACA<br>GATGTCAAGTTTACGCAGTGAGGACAC<br>TGCGATGTATTACTGCGGTCGATACGA<br>TTATGATGGATATTATGCAATGGATTA<br>TTGGGGCCAGGGCACTCTGGTCACAGT<br>ATCTTCCGGCGGCGGTGGTTCTGGCGG<br>TGGTGGAAGCGGAGGGGGGGGGTCCG<br>ACATCCAGATGACCCAATCACCATCGA<br>GTCTTAGTGCATCCGTTGGGGATAGAG<br>TGACAATCACTTGTAAGGCATCCCCGG<br>ACATCAACTCATATCTTAATTGGTATC<br>AGCAAAAGCCGGGCAAGGCCCCTAAG<br>CTCCTGATTTATAGGGCCAACCGCCTT<br>GTGGATGGAGTCCCCTCCCGCTTTAGT<br>GGAAGCGGCTCTGGCACAGACTACACC<br>CTGACTATCAGCTCCTTGCAGCCTGAG<br>GATTTTGCTACCTACTACTGTCTTCAGT<br>ACGATGAATTTCCATACACTTTCGGTG<br>CTGGGACAAAAGTGGAGATCAAAAAG<br>CCTACCACCACCCCCGCACCTCGTCCT<br>CCAACCCCTGCACCTACGATTGCCAGT<br>CAGCCTCTTTCACTGCGGCCTGAGGCC<br>AGCAGACCAGCTGCCGGCGGTGCCGTC<br>CATACAAGAGGACTGGACTTCGCGTCC<br>GATAAACCTACTACCACTCCAGCCCCA<br>AGGCCCCCAACCCCAGCACCGACTATC<br>GCATCACAGCCTTTGTCACTGCGTCCT<br>GAAGCCAGCCGGCCAGCTGCAGGGGG<br>GGCCGTCCACACAAGGGGACTCGACTT<br>TGCGAGTGATAAGCCCACCACCACCCC<br>TGCCCCTAGACCTCCAACCCCAGCCCC<br>TACAATCGCCAGCCAGCCCCTGAGCCT<br>GAGGCCCGAAGCCTGTAGACCTGCCGC<br>TGGCGGAGCCGTGCACACCAGAGGCCT<br>GGATTTCGCCTGCGACATCTACATCTG<br>GGCCCCTCTGGCCGGCACCTGTGGCGT<br>GCTGCTGCTGAGCCTGGTCATCACCCT<br>GTACTGCAACCACCGGAATAGGAGCA<br>AGCGGAGCAGAGGCGGCCACAGCGAC<br>TACATGAACATGACCCCCCGGAGGCCT<br>GGCCCCACCCGGAAGCACTACCAGCCC<br>TACGCCCCTCCCAGGGACTTCGCCGCC<br>TACCGGAGCCGGGTGAAGTTCAGCCGG<br>AGCGCCGACGCCCCTGCCTACCAGCAG<br>GGCCAGAACCAGCTGTACAACGAGCTG<br>AACCTGGGCCGGAGGGAGGAGTACGA<br>CGTGCTGGACAAGCGGAGAGGCCGGG<br>ACCCTGAGATGGGCGGCAAGCCCCGG<br>AGAAAGAACCCTCAGGAGGGCCTGTAT<br>AACGAACTGCAGAAAGACAAGATGGC<br>CGAGGCCTACAGCGAGATCGGCATGA<br>AGGGCGAGCGGCGGAGGGGCAAGGGC |

TABLE 12-continued

| Exemplary Sequences | | | | |
|---|---|---|---|---|
| | | | | CACGACGGCCTGTACCAGGGCCTGAGC ACCGCCACCAAGGATACCTACGACGCC CTGCACATGCAGGCCCTGCCCCCCAGA |
| hROR1 (VH_5-VL_14).CD8a(3x).CD28z | 79 | EVQLVESGGGLVQPG GSLRLSCAASGFTFSS YAMSWVRQAPGKGL EWVSSISRGGTTYYP DSVKGRFTISRDNSK NTLYLQMNSLRAEDT AVYYCGRYDYDGYY AMDYWGQGTLVTVS SGGGGSGGGGSGGG GSDIQMTQSPSSLSAS VGDRVTITCKASPDIN SYLNWYQQKPGKAP KLLIYRANRLVDGVP SRFSGSGSGTDYTLTI SSLQPEDFATYYCLQ YDEFPYTFGAGTKVEI KKPTTTPAPRPPTPAP TIASQPLSLRPEASRP AAGGAVHTRGLDFAS DKPTTTPAPRPPTPAP TIASQPLSLRPEASRP AAGGAVHTRGLDFAS DKPTTTPAPRPPTPAP TIASQPLSLRPEACRP AAGGAVHTRGLDFA CDIYIWAPLAGTCGV LLLSLVITLYCNHRNR SKRSRGGHSDYMNM TPRRPGPTRKHYQPY APPRDFAAYRSRVKF SRSADAPAYQQGQN QLYNELNLGRREEYD VLDKRRGRDPEMGG KPRRKNPQEGLYNEL QKDKMAEAYSEIGM KGERRRGKGHDGLY QGLSTATKDTYDALH MQALPPR | 226 | GAAGTGCAACTGGTCGAGTCTGGGGGC GGCCTTGTGCAACCTGGAGGCAGCCTT CGACTCAGTTGCGCCGCGTCTGGTTTT ACCTTCTCCTCTTACGCGATGAGCTGG GTTCGCCAGGCCCCCGGCAAGGGACTT GAGTGGGTTAGTTCGATCTCCCGCGGA GGCACCACATATTATCCTGACTCGGTT AAGGGACGCTTCACTATCTCTAGGGAC AATTCAAAGAACACACTGTATCTCCAA ATGAACTCCTTGCGGGCCGAGGACACT GCTGTGTATTATTGCGGACGATACGAC TACGATGGGTATTACGCCATGGATTAC TGGGGGCAAGGTACACTGGTCACTGTG AGTTCGGGGGGCGGCGGAAGTGGTGG AGGGGGAAGTGGTGGAGGAGGAAGCG ATATACAGATGACACAGAGCCCTTCAA GTTTATCTGCAAGCGTCGGCGATCGTG TTACAATAACTTGCAAGGCATCTCCCG ACATCAATTCCTACCTCAACTGGTATC AGCAGAAGCCTGGGAAGGCTCCTAAG CTGCTTATTTACAGAGCAAATCGCCTG GTGGACGGCGTGCCCAGTCGGTTTTCC GGGTCTGGGAGCGGAACGGATTACAC ACTGACCATCTCAAGCCTGCAACCCGA AGACTTCGCTACATATTACTGCCTTCA GTATGATGAGTTCCCATATACCTTCGG CGCTGGGACCAAGGTGGAGATAAAGA AGCCTACCACCACCCCCGCACCTCGTC CTCCAACCCCTGCACCTACGATTGCCA GTCAGCCTCTTTCACTGCGGCCTGAGG CCAGCAGACCAGCTGCCGGCGGTGCCG TCCATACAAGAGGACTGGACTTCGCGT CCGATAAACCTACTACCACTCCAGCCC CAAGGCCCCCAACCCCAGCACCGACTA TCGCATCACAGCCTTTGTCACTGCGTCC TGAAGCCAGCCGGCCAGCTGCAGGGG GGGCCGTCCACACAAGGGGACTCGACT TTGCGAGTGATAAGCCCACCACCACCC CTGCCCCTAGACCTCCAACCCCAGCCC CTACAATCGCCAGCCAGCCCCTGAGCC TGAGGCCCGAAGCCTGTAGACCTGCCG CTGGCGGAGCCGTGCACACCAGAGGCC TGGATTTCGCCTGCGACATCTACATCT GGGCCCCTCTGGCCGGCACCTGTGGCG TGCTGCTGCTGAGCCTGGTCATCACCC TGTACTGCAACCACCGGAATAGGAGCA AGCGGAGCAGAGGCGGCCACAGCGAC TACATGAACATGACCCCCCGGAGGCCT GGCCCCACCCGGAAGCACTACCAGCCC TACGCCCCTCCCAGGGACTTCGCCGCC TACCGGAGCCGGGTGAAGTTCAGCCGG AGCGCCGACGCCCCTGCCTACCAGCAG GGCCAGAACCAGCTGTACAACGAGCTG AACCTGGGCCGGAGGGAGGAGTACGA CGTGCTGGACAAGCGGAGAGGCCGGG ACCCTGAGATGGGCGGCAAGCCCCGG AGAAAGAACCCTCAGGAGGGCCTGTAT AACGAACTGCAGAAAGACAAGATGGC CGAGGCCTACAGCGAGATCGGCATGA AGGGCGAGCGGCGGAGGGGCAAGGGC CACGACGGCCTGTACCAGGGCCTGAGC ACCGCCACCAAGGATACCTACGACGCC CTGCACATGCAGGCCCTGCCCCCCAGA |
| hROR1 (VH_5-VL_16).CD8a(3x).CD28z | 80 | EVQLVESGGGLVQPG GSLRLSCAASGFTFSS YAMSWVRQAPGKGL EWVSSISRGGTTYYP DSVKGRFTISRDNSK NTLYLQMNSLRAEDT AVYYCGRYDYDGYY AMDYWGQGTLVTVS SGGGGSGGGGSGGG GSDIQMTQSPSSLSAS | 227 | GAAGTGCAACTGGTCGAGTCTGGGGGC GGCCTTGTGCAACCTGGAGGCAGCCTT CGACTCAGTTGCGCCGCGTCTGGTTTT ACCTTCTCCTCTTACGCGATGAGCTGG GTTCGCCAGGCCCCCGGCAAGGGACTT GAGTGGGTTAGTTCGATCTCCCGCGGA GGCACCACATATTATCCTGACTCGGTT AAGGGACGCTTCACTATCTCTAGGGAC AATTCAAAGAACACACTGTATCTCCAA ATGAACTCCTTGCGGGCCGAGGACACT |

TABLE 12-continued

| Exemplary Sequences | | | | |
|---|---|---|---|---|
| | | VGDRVTITCKASPDIN | | GCTGTGTATTATTGCGGACGATACGAC |
| | | SYLNWYQQKPGKAP | | TACGATGGGTATTACGCCATGGATTAC |
| | | KVLIYRANRLVDGVP | | TGGGGGCAAGGTACACTGGTCACTGTG |
| | | SRFSGSGSGTDYTLTI | | AGTTCGGGGGGCGGCGGAAGTGGTGG |
| | | SSLQPEDFATYYCLQ | | AGGGGGAAGTGGTGGAGGAGGAAGCG |
| | | YDEFPYTFGQGTKVEI | | ATATTCAGATGACCCAGTCGCCCAGCA |
| | | KKPTTTPAPRPPTPAP | | GTCTCTCGGCCTCAGTGGGCGACCGGG |
| | | TIASQPLSLRPEASRP | | TCACTATCACTTGCAAAGCAAGTCCTG |
| | | AAGGAVHTRGLDFAS | | ATATAAACTCCTATCTTAATTGGTATCA |
| | | DKPTTTPAPRPPTPAP | | GCAGAAGCCCGGCAAGGCACCTAAGG |
| | | TIASQPLSLRPEASRP | | TTCTGATATATCGCGCAAATCGGCTCG |
| | | AAGGAVHTRGLDFAS | | TGGATGGAGTACCCAGCCGATTTTCCG |
| | | DKPTTTPAPRPPTPAP | | GCAGCGGCTCAGGCACTGACTACACAC |
| | | TIASQPLSLRPEACRP | | TGACAATCAGCAGCTTGCAGCCTGAAG |
| | | AAGGAVHTRGLDFA | | ATTTCGCCACATACTATTGTCTACAGTA |
| | | CDIYIWAPLAGTCGV | | CGACGAGTTCCCTTATACATTCGGCCA |
| | | LLLSLVITLYCNHRNR | | GGGGACCAAGGTCGAGATCAAGAAGC |
| | | SKRSRGGHSDYMNM | | CTACCACCACCCCCGCACCTCGTCCTC |
| | | TPRRPGPTRKHYQPY | | CAACCCCTGCACCTACGATTGCCAGTC |
| | | APPRDFAAYRSRVKF | | AGCCTCTTTCACTGCGGCCTGAGGCCA |
| | | SRSADAPAYQQGQN | | GCAGACCAGCTGCCGGCGGTGCCGTCC |
| | | QLYNELNLGRREEYD | | ATACAAGAGGACTGGACTTCGCGTCCG |
| | | VLDKRRGRDPEMGG | | ATAAACCTACTACCACTCCAGCCCCAA |
| | | KPRRKNPQEGLYNEL | | GGCCCCCAACCCCAGCACCGACTATCG |
| | | QKDKMAEAYSEIGM | | CATCACAGCCTTTGTCACTGCGTCCTG |
| | | KGERRRGKGHDGLY | | AAGCCAGCCGGCCAGCTGCAGGGGGG |
| | | QGLSTATKDTYDALH | | GCCGTCCACACAAGGGGACTCGACTTT |
| | | MQALPPR | | GCGAGTGATAAGCCCACCACCACCCCT |
| | | | | GCCCCTAGACCTCCAACCCCAGCCCCT |
| | | | | ACAATCGCCAGCCAGCCCCTGAGCCTG |
| | | | | AGGCCCGAAGCCTGTAGACCTGCCGCT |
| | | | | GGCGGAGCCGTGCACACCAGAGGCCT |
| | | | | GGATTTCGCCTGCGACATCTACATCTG |
| | | | | GGCCCCTCTGGCCGGCACCTGTGGCGT |
| | | | | GCTGCTGCTGAGCCTGGTCATCACCCT |
| | | | | GTACTGCAACCACCGGAATAGGAGCA |
| | | | | AGCGGAGCAGAGGCGGCCACAGCGAC |
| | | | | TACATGAACATGACCCCCCGGAGGCCT |
| | | | | GGCCCCACCCGGAAGCACTACCAGCCC |
| | | | | TACGCCCCTCCCAGGGACTTCGCCGCC |
| | | | | TACCGGAGCCGGGTGAAGTTCAGCCGG |
| | | | | AGCGCCGACGCCCCTGCCTACCAGCAG |
| | | | | GGCCAGAACCAGCTGTACAACGAGCTG |
| | | | | AACCTGGGCCGGAGGGAGGAGTACGA |
| | | | | CGTGCTGGACAAGCGGAGAGGCCGGG |
| | | | | ACCCTGAGATGGGCGGCAAGCCCCGG |
| | | | | AGAAAGAACCCTCAGGAGGGCCTGTAT |
| | | | | AACGAACTGCAGAAAGACAAGATGGC |
| | | | | CGAGGCCTACAGCGAGATCGGCATGA |
| | | | | AGGGCGAGCGGCGGAGGGGCAAGGGC |
| | | | | CACGACGGCCTGTACCAGGGCCTGAGC |
| | | | | ACCGCCACCAAGGATACCTACGACGCC |
| | | | | CTGCACATGCAGGCCCTGCCCCCCAGA |
| hROR1 | 81 | EVQLVESGGGLVQPG | 228 | GAGGTTCAACTCGTGGAGTCTGGAGGC |
| (VH_18-VL_04).CD8a(3x).CD28z | | GSLRLSCSASGFTFSS | | GGGCTAGTGCAGCCTGGCGGCTCCCTG |
| | | YAMSWVRQVPGKGL | | CGACTGTCTTGCAGCGCATCAGGCTTT |
| | | VWISSISRGGTTYYAD | | ACATTCAGTTCTTATGCCATGAGCTGG |
| | | SVRGRFIISRDNAKNT | | GTGAGGCAGGTGCCCGGCAAGGGTCTG |
| | | LYLEMNNLRGEDTA | | GTGTGGATCAGCTCAATCTCCAGGGGC |
| | | VYYCARYDYDGYYA | | GGGACTACATATTACGCCGATTCGGTC |
| | | MDYWGQGTLVTVSS | | AGGGGTCGTTTTATCATTAGCAGGGAT |
| | | GGGGSGGGGSGGGG | | AATGCCAAGAACACCTTGTATTTGGAG |
| | | SDIQMTQSPSSLSASV | | ATGAACAACCTAAGAGGCGAAGACAC |
| | | GDRVTITCQASPDINS | | CGCTGTGTACTATTGTGCCCGTTACGA |
| | | YLNWYQQKPGKAPK | | CTACGATGGGTACTACGCCATGGACTA |
| | | LLIYRANNLETGVPSR | | TTGGGGCCAGGGAACCTTGGTGACTGT |
| | | FSGSGSGTDFTLTISSL | | GTCAAGTGGCGGGGGCGGCAGCGGAG |
| | | QPEDIATYYCLQYDE | | GCGGTGGCAGCGGAGGCGGCGGTTCTG |
| | | FPYTFGQGTKLEIKKP | | ATATTCAAATGACGCAAAGTCCCAGCA |
| | | TTTPAPRPPTPAPTIAS | | GCCTCTCCGCCTCCGTTGGAGACAGGG |
| | | QPLSLRPEASRPAAG | | TGACTATTACATGCCAAGCCAGCCCCG |
| | | GAVHTRGLDFASDKP | | ATATTAATAGCTACTTAAATTGGTATC |
| | | TTTPAPRPPTPAPTIAS | | AGCAGAAACCTGGGAAGGCACCTAAA |
| | | QPLSLRPEASRPAAG | | CTTCTCATCTACCGCGCTAACAATCTG |
| | | GAVHTRGLDFASDKP | | GAGACCGGCGTGCCGTCTAGATTTTCC |
| | | TTTPAPRPPTPAPTIAS | | GGCTCTGGATCAGGGACCGATTTTACT |
| | | QPLSLRPEACRPAAG | | CTGACAATTAGTTCCCTGCAACCCGAA |

TABLE 12-continued

| Exemplary Sequences | | | | |
|---|---|---|---|---|
| | | GAVHTRGLDFACDIY<br>IWAPLAGTCGVLLLS<br>LVITLYCNHRNRSKR<br>SRGGHSDYMNMTPR<br>RPGPTRKHYQPYAPP<br>RDFAAYRSRVKFSRS<br>ADAPAYQQGQNQLY<br>NELNLGRREEYDVLD<br>KRRGRDPEMGGKPR<br>RKNPQEGLYNELQKD<br>KMAEAYSEIGMKGER<br>RRGKGHDGLYQGLST<br>ATKDTYDALHMQAL<br>PPR | | GACATCGCCACTTATTATTGCCTGCAA<br>TATGATGAGTTTCCTTACACATTTGGTC<br>AGGGAACTAAACTAGAGATTAAGAAG<br>CCTACCACCACCCCCGCACCTCGTCCT<br>CCAACCCCTGCACCTACGATTGCCAGT<br>CAGCCTCTTTCACTGCGGCCTGAGGCC<br>AGCAGACCAGCTGCCGGCGGTGCCGTC<br>CATACAAGAGGACTGGACTTCGCGTCC<br>GATAAACCTACTACCACTCCAGCCCCA<br>AGGCCCCCAACCCCAGCACCGACTATC<br>GCATCACAGCCTTTGTCACTGCGTCCT<br>GAAGCCAGCCGGCCAGCTGCAGGGGG<br>GGCCGTCCACACAAGGGGACTCGACTT<br>TGCGAGTGATAAGCCCACCACCACCCC<br>TGCCCCTAGACCTCCAACCCCAGCCCC<br>TACAATCGCCAGCCAGCCCCTGAGCCT<br>GAGGCCCGAAGCCTGTAGACCTGCCGC<br>TGGCGGAGCCGTGCACACCAGAGGCCT<br>GGATTTCGCCTGCGACATCTACATCTG<br>GGCCCCTCTGGCCGGCACCTGTGGCGT<br>GCTGCTGCTGAGCCTGGTCATCACCCT<br>GTACTGCAACCACCGGAATAGGAGCA<br>AGCGGAGCAGAGGCGGCCACAGCGAC<br>TACATGAACATGACCCCCCGGAGGCCT<br>GGCCCCACCCGGAAGCACTACCAGCCC<br>TACGCCCCTCCCAGGGACTTCGCCGCC<br>TACCGGAGCCGGGTGAAGTTCAGCCGG<br>AGCGCCGACGCCCCTGCCTACCAGCAG<br>GGCCAGAACCAGCTGTACAACGAGCTG<br>AACCTGGGCCGGAGGGAGGAGTACGA<br>CGTGCTGGACAAGCGGAGAGGCCGGG<br>ACCCTGAGATGGGCGGCAAGCCCCGG<br>AGAAAGAACCCTCAGGAGGGCCTGTAT<br>AACGAACTGCAGAAAGACAAGATGGC<br>CGAGGCCTACAGCGAGATCGGCATGA<br>AGGGCGAGCGGCGGAGGGGCAAGGGC<br>CACGACGGCCTGTACCAGGGCCTGAGC<br>ACCGCCACCAAGGATACCTACGACGCC<br>CTGCACATGCAGGCCCTGCCCCCCAGA |
| hROR1<br>(VH_18-VL_14).CD8a(3x).CD28z | 82 | EVQLVESGGGLVQPG<br>GSLRLSCSASGFTFSS<br>YAMSWVRQVPGKGL<br>VWISSISRGGTTYYAD<br>SVRGRFIISRDNAKNT<br>LYLEMNNLRGEDTA<br>VYYCARYDYDGYYA<br>MDYWGQGTLVTVSS<br>GGGGSGGGGSGGGG<br>SDIQMTQSPSSLSASV<br>GDRVTITCKASPDINS<br>YLNWYQQKPGKAPK<br>LLIYRANRLVDGVPS<br>RFSGSGSGTDYTLTIS<br>SLQPEDFATYYCLQY<br>DEFPYTFGAGTKVEIK<br>KPTTTPAPRPPTPAPTI<br>ASQPLSLRPEASRPAA<br>GGAVHTRGLDFASDK<br>PTTTPAPRPPTPAPTIA<br>SQPLSLRPEASRPAAG<br>GAVHTRGLDFASDKP<br>TTTPAPRPPTPAPTIAS<br>QPLSLRPEACRPAAG<br>GAVHTRGLDFACDIY<br>IWAPLAGTCGVLLLS<br>LVITLYCNHRNRSKR<br>SRGGHSDYMNMTPR<br>RPGPTRKHYQPYAPP<br>RDFAAYRSRVKFSRS<br>ADAPAYQQGQNQLY<br>NELNLGRREEYDVLD<br>KRRGRDPEMGGKPR<br>RKNPQEGLYNELQKD<br>KMAEAYSEIGMKGER<br>RRGKGHDGLYQGLST<br>ATKDTYDALHMQAL<br>PPR | 229 | GAGGTTCAACTCGTGGAGTCTGGAGGC<br>GGGCTAGTGCAGCCTGGCGGCTCCCTG<br>CGACTGTCTTGCAGCGCATCAGGCTTT<br>ACATTCAGTTCTTATGCCATGAGCTGG<br>GTGAGGCAGGTGCCCGGCAAGGGTCTG<br>GTGTGGATCAGCTCAATCTCCAGGGGC<br>GGGACTACATATTACGCCGATTCGGTC<br>AGGGGTCGTTTTATCATTAGCAGGGAT<br>AATGCCAAGAACACCTTGTATTTGGAG<br>ATGAACAACCTAAGAGGCGAAGACAC<br>CGCTGTGTACTATTGTGCCCGTTACGA<br>CTACGATGGGTACTACGCCATGGACTA<br>TTGGGGCCAGGGAACCTTGGTGACTGT<br>GTCAAGTGGCGGGGGCGGCAGCGGAG<br>GCGGTGGCAGCGGAGGCGGCGGTTCTG<br>ATATACAGATGACACAGAGCCCTTCAA<br>GTTTATCTGCAAGCGTCGGCGATCGTG<br>TTACAATAACTTGCAAGGCATCTCCCG<br>ACATCAATTCCTACCTCAACTGGTATC<br>AGCAGAAGCCTGGGAAGGCTCCTAAG<br>CTGCTTATTTACAGAGCAAATCGCCTG<br>GTGGACGGCGTGCCCAGTCGGTTTTCC<br>GGGTCTGGGAGCGGAACGGATTACAC<br>ACTGACCATCTCAAGCCTGCAACCCGA<br>AGACTTCGCTACATATTACTGCCTTCA<br>GTATGATGAGTTCCCATATACCTTCGG<br>CGCTGGGACCAAGGTGGAGATAAAGA<br>AGCCTACCACCACCCCCGCACCTCGTC<br>CTCCAACCCCTGCACCTACGATTGCCA<br>GTCAGCCTCTTTCACTGCGGCCTGAGG<br>CCAGCAGACCAGCTGCCGGCGGTGCCG<br>TCCATACAAGAGGACTGGACTTCGCGT<br>CCGATAAACCTACTACCACTCCAGCCC<br>CAAGGCCCCCAACCCCAGCACCGACTA<br>TCGCATCACAGCCTTTGTCACTGCGTCC<br>TGAAGCCAGCCGGCCAGCTGCAGGGG<br>GGGCCGTCCACACAAGGGGACTCGACT<br>TTGCGAGTGATAAGCCCACCACCACCC |

TABLE 12-continued

Exemplary Sequences

| | | | | |
|---|---|---|---|---|
| | | | | CTGCCCCTAGACCTCCAACCCCAGCCC CTACAATCGCCAGCCAGCCCCTGAGCC TGAGGCCCGAAGCCTGTAGACCTGCCG CTGGCGGAGCCGTGCACACCAGAGGCC TGGATTTCGCCTGCGACATCTACATCT GGGCCCCTCTGGCCGGCACCTGTGGCG TGCTGCTGCTGAGCCTGGTCATCACCC TGTACTGCAACCACCGGAATAGGAGCA AGCGGAGCAGAGGCGGCCACAGCGAC TACATGAACATGACCCCCCGGAGGCCT GGCCCCACCCGGAAGCACTACCAGCCC TACGCCCCTCCCAGGGACTTCGCCGCC TACCGGAGCCGGGTGAAGTTCAGCCGG AGCGCCGACGCCCCTGCCTACCAGCAG GGCCAGAACCAGCTGTACAACGAGCTG AACCTGGGCCGGAGGGAGGAGTACGA CGTGCTGGACAAGCGGAGAGGCCGGG ACCCTGAGATGGGCGGCAAGCCCCGG AGAAAGAACCCTCAGGAGGGCCTGTAT AACGAACTGCAGAAAGACAAGATGGC CGAGGCCTACAGCGAGATCGGCATGA AGGGCGAGCGGCGGAGGGGCAAGGGC CACGACGGCCTGTACCAGGGCCTGAGC ACCGCCACCAAGGATACCTACGACGCC CTGCACATGCAGGCCCTGCCCCCCAGA |
| CD8α hinge | 83 | KPTTTPAPRPPTPAPTIA SQPLSLRPEACRPAAGG AVHTRGLDFACD | 230 | AAGCCCACCACCACCCCTGCCCCTAGACCT CCAACCCCAGCCCCTACAATCGCCAGCCAG CCCCTGAGCCTGAGGCCCGAAGCCTGTAG ACCTGCCGCTGGCGGAGCCGTGCACACCA GAGGCCTGGATTTCGCCTGCGAC |
| CD8α 2x | 84 | KPTTTPAPRPPTPAPTI ASQPLSLRPEASRPAA GGAVHTRGLDFASDK PTTTPAPRPPTPAPTIA SQPLSLRPEACRPAAG GAVHTRGLDFACD | 231 | AAACCTACTACAACTCCTGCCCCCCGG CCTCCTACACCAGCTCCTACTATCGCCT CCCAGCCACTCAGTCTCAGACCCGAGG CTTCTAGGCCAGCGGCCGGAGGCGCGG TCCACACCCGCGGGCTGGACTTTGCAT CCGATAAGCCCACCACCACCCCTGCCC CTAGACCTCCAACCCCAGCCCCTACAA TCGCCAGCCAGCCCCTGAGCCTGAGGC CCGAAGCCTGTAGACCTGCCGCTGGCG GAGCCGTGCACACCAGAGGCCTGGATT TCGCCTGCGAC |
| CD8α 3x | 85 | KPTTTPAPRPPTPAPTI ASQPLSLRPEASRPAA GGAVHTRGLDFASDK PTTTPAPRPPTPAPTIA SQPLSLRPEASRPAAG GAVHTRGLDFASDKP TTTPAPRPPTPAPTIAS QPLSLRPEACRPAAG GAVHTRGLDFACD | 232 | AAGCCTACCACCACCCCCGCACCTCGT CCTCCAACCCCTGCACCTACGATTGCC AGTCAGCCTCTTTCACTGCGGCCTGAG GCCAGCAGACCAGCTGCCGGCGGTGCC GTCCATACAAGAGGACTGGACTTCGCG TCCGATAAACCTACTACCACTCCAGCC CCAAGGCCCCCAACCCCAGCACCGACT ATCGCATCACAGCCTTTGTCACTGCGT CCTGAAGCCAGCCGGCCAGCTGCAGGG GGGGCCGTCCACACAAGGGGACTCGA CTTTGCGAGTGATAAGCCCACCACCAC CCCTGCCCCTAGACCTCCAACCCCAGC CCCTACAATCGCCAGCCAGCCCCTGAG CCTGAGGCCCGAAGCCTGTAGACCTGC CGCTGGCGGAGCCGTGCACACCAGAG GCCTGGATTTCGCCTGCGAC |
| CD8α 4x | 86 | TTPAPRPPTPAPTIASQ PLSLRPEASRPAAGG AVHTRGLDFASDKPT TTPAPRPPTPAPTIASQ PLSLRPEASRPAAGG AVHTRGLDFASDKPT TTPAPRPPTPAPTIASQ PLSLRPEASRPAAGG AVHTRGLDFASDKPT TTPAPRPPTPAPTIASQ PLSLRPEACRPAAGG AVHTRGLDFACD | 233 | AAGCCTACCACCACCCCCGCACCTCGT CCTCCAACCCCTGCACCTACGATTGCC AGTCAGCCTCTTTCACTGCGGCCTGAG GCCAGCAGACCAGCTGCCGGCGGTGCC GTCCATACAAGAGGACTGGACTTCGCG TCCGATAAACCTACTACCACTCCAGCC CCAAGGCCCCCAACCCCAGCACCGACT ATCGCATCACAGCCTTTGTCACTGCGT CCTGAAGCCAGCCGGCCAGCTGCAGGG GGGGCCGTCCACACAAGGGGACTCGA CTTTGCGAGTGATAAACCTACTACAAC TCCTGCCCCCCGGCCTCCTACACCAGC TCCTACTATCGCCTCCCAGCCACTCAGT CTCAGACCCGAGGCTTCTAGGCCAGCG GCCGGAGGCGCGGTCCACACCCGCGG GCTGGACTTTGCATCCGATAAGCCCAC CACCACCCCTGCCCCTAGACCTCCAAC |

TABLE 12-continued

| Exemplary Sequences | | | | |
|---|---|---|---|---|
| | | | | CCCAGCCCCTACAATCGCCAGCCAGCC CCTGAGCCTGAGGCCCGAAGCCTGTAG ACCTGCCGCTGGCGGAGCCGTGCACAC CAGAGGCCTGGATTTCGCCTGCGAC |
| CD8α TM | 87 | IYIWAPLAGTCGVLLLS LVITLYCNHRN | 234 | ATCTACATCTGGGCCCCTCTGGCCGGCACC TGTGGCGTGCTGCTGCTGAGCCTGGTCATC ACCCTGTACTGCAACCACCGGAAT |
| CD28 TM | 88 | FWVLVVVGGVLACYSL LVTVAFIIFWV | 235 | TTTTGGGTGCTGGTGGTGGTTGGTGGAGTC CTGGCTTGCTATAGCTTGCTAGTAACAGTG GCCTTTATTATTTTCTGGGTG |
| 4-1BB signaling domain | 89 | KRGRKKLLYIFKQPFMR PVQTTQEEDGCSCRFPE EEEGGCEL | 236 | AAGAGAGGCCGGAAGAAACTGCTGTACAT CTTCAAGCAGCCCTTCATGCGGCCCGTGCA GACCACCCAGGAAGAGGACGGCTGCAGCT GCCGGTTCCCCGAGGAAGAGGAAGGCGGC TGCGAACTG |
| CD28 signaling domain | 90 | RSKRSRGGHSDYMNMT PRRPGPTRKHYQPYAPP RDFAAYRS | 237 | AGGAGCAAGCGGAGCAGAGGCGGCCACAG CGACTACATGAACATGACCCCCCGGAGGC CTGGCCCCACCCGGAAGCACTACCAGCCCT ACGCCCCTCCCAGGGACTTCGCCGCCTACC GGAGC |
| DNAX-activation protein 10 (DAP10) Signaling Domain | 91 | LCARPRRSPAQEDGK VYINMPGRG | 238 | CTGTGCGCACGCCCACGCCGCAGCCCC GCCCAAGAAGATGGCAAAGTCTACATC AACATGCCAGGCAGGGGC |
| DNAX-activation protein 12 (DAP12) Signaling Domain | 92 | YFLGRLVPRGRGAAE AATRKQRITETESPYQ ELQGQRSDVYSDLNT QRPYYK | 239 | TACTTCCTGGGCCGGCTGGTCCCTCGG GGGCGAGGGGCTGCGGAGGCAGCGAC CCGGAAACAGCGTATCACTGAGACCGA GTCGCCTTATCAGGAGCTCCAGGGTCA GAGGTCGGATGTCTACAGCGACCTCAA CACACAGAGGCCGTATTACAAA |
| CD3ζ signaling domain | 93 | RVKFSRSADAPAYQQG QNQLYNELNLGRREEY DVLDKRRGRDPEMGGK PRRKNPQEGLYNELQK DKMAEAYSEIGMKGER RRGKGHDGLYQGLSTA TKDTYDALHMQALPPR | 240 | CGGGTGAAGTTCAGCCGGAGCGCCGACGC CCCTGCCTACCAGCAGGGCCAGAACCAGC TGTACAACGAGCTGAACCTGGGCCGGAGG GAGGAGTACGACGTGCTGGACAAGCGGAG AGGCCGGGACCCTGAGATGGGCGGCAAGC CCCGGAGAAAGAACCCTCAGGAGGGCCTG TATAACGAACTGCAGAAAGACAAGATGGC CGAGGCCTACAGCGAGATCGGCATGAAGG GCGAGCGGCGGAGGGGCAAGGGCCACGAC GGCCTGTACCAGGGCCTGAGCACCGCCAC CAAGGATACCTACGACGCCCTGCACATGC AGGCCCTGCCCCCCAGA |
| SIGNAL PEPTIDES | | | | |
| GMCSF R alpha | 94 | MLLLVTSLLLCELPHP AFLLIP | 241 | ATGCTTCTCCTGGTGACAAGCCTTCTGC TCTGTGAGTTACCACACCCAGCATTCC TCCTGATCCCA |
| Ig Kappa | 95 | MRLPAQLLGLLMLW VPGSSG | 242 | ATGAGGCTCCCTGCTCAGCTCCTGGGG CTGCTAATGCTCTGGGTCCCAGGATCC AGTGGG |
| Immuno-globulin E | 96 | MDWTWILFLVAAAT RVHS | 243 | ATGGATTGGACCTGGATTCTGTTTCTG GTGGCCGCTGCCACAAGAGTGCACAGC |
| CD8α | 97 | MALPVTALLLPLALL LHAARP | 244 | ATGGCGCTGCCCGTGACCGCCTTGCTC CTGCCGCTGGCCTTGCTGCTCCACGCC GCCAGGCCG |
| TVB2 (T21A) | 98 | MGTSLLCWMALCLL GADHADA | 245 | ATGGGCACCAGCCTCCTCTGCTGGATG GCCCTGTGTCTCCTGGGGGCAGATCAC GCAGATGCT |
| CD52 | 99 | MKRFLFLLLTISLLVM VQIQTGLS | 246 | ATGAAGCGCTTCCTCTTCCTCCTACTCA CCATCAGCCTCCTGGTTATGGTACAGA TACAAACTGGACTCTCA |

TABLE 12-continued

| Exemplary Sequences | | | | |
|---|---|---|---|---|
| Low-affinity nerve growth factor receptor (LNGFR, TNFRSF 16) | 100 | MGAGATGRAMDGPR LLLLLLLGVSLGGA | 247 | ATGGGGGCAGGTGCCACCGGCCGCGCC ATGGACGGGCCGCGCCTGCTGCTGTTG CTGCTTCTGGGGGTGTCCCTTGGAGGT GCC |
| Mouse Ig VH region 3 signal peptide | 101 | MGWSCIILFLVATAT GVHS | 248 | ATGGGCTGGTCCTGCATCATCCTGTTTC TGGTGGCTACCGCCACCGGCGTGCACA GC |
| β2M signal peptide | 102 | MSRSVALAVLALLSL SGLEA | 249 | ATGTCTCGCTCCGTGGCCTTAGCTGTGC TCGCGCTACTCTCTCTTTCTGGCCTGGA GGCT |
| Azurocidin signal peptide | 103 | MTRLTVLALLAGLLA SSRA | 250 | ATGACCCGGCTGACAGTCCTGGCCCTG CTGGCTGGTCTGCTGGCGTCCTCGAGG GCC |
| Human Serum Albumin signal peptide | 104 | MKWVTFISLLFLFSSA YS | 251 | ATGAAGTGGGTAACCTTTATTTCCCTTC TTTTTCTCTTTAGCTCGGCTTATTCC |
| A2M receptor associated protein signal peptide | 105 | MGKNKLLHPSLVLLL LVLLPTDA | 252 | ATGGGGAAGAACAAACTCCTTCATCCA AGTCTGGTTCTTCTCCTCTTGGTCCTCC TGCCCACAGACGCC |
| IGHV3-23 signal peptide | 106 | MEFGLSWLFLVAILK GVQC | 253 | ATGGAGTTTGGGCTGAGCTGGCTTTTT CTTGTGGCTATTTTAAAAGGTGTCCAG TGT |
| IGKV1-D33 (HuL1) signal peptide | 107 | MDMRVPAQLLGLLL LWLSGARC | 254 | ATGGACATGAGGGTCCCTGCTCAGCTC CTGGGGCTCCTGCTGCTCTGGCTCTCA GGTGCCAGATGT |
| IGHV3-33(L14F) (HuH7) signal peptide | 108 | MEFGLSWVFLVALFR GVQC | 255 | ATGGAGTTTGGGCTGAGCTGGGTTTTC CTCGTTGCTCTTTTTAGAGGTGTCCAGT GT |
| KILL SWITCH | | | | |
| HER1t | 109 | RKVCNGIGIGEFKDSL SINATNIKHFKNCTSIS GDLHILPVAFRGDSFT HTPPLDPQELDILKTV KEITGFLLIQAWPENR TDLHAFENLEIIRGRT KQHGQFSLAVVSLNI TSLGLRSLKEISDGDV IISGNKNLCYANTINW KKLFGTSGQKTKIISN RGENSCKATGQVCH ALCSPEGCWGPEPRD CVSCRNVSRGRECVD KCNLLEGEPREFVEN SECIQCHPECLPQAM NITCTGRGPDNCIQCA HYIDGPHCVKTCPAG VMGENNTLVWKYAD AGHVCHLCHPNCTY GCTGPGLEGCPTNGP KIPSIATGMVGALLLL LVVALGIGLFM | 256 | CGCAAAGTGTGTAACGGAATAGGTATT GGTGAATTTAAAGACTCACTCTCCATA AATGCTACGAATATTAAACACTTCAAA AACTGCACCTCCATCAGTGGCGATCTC CACATCCTGCCGGTGGCATTTAGGGGT GACTCCTTCACACATACTCCTCCTCTGG ATCCACAGGAACTGGATATTCTGAAAA CCGTAAAGGAAATCACAGGGTTTTTGC TGATTCAGGCTTGGCCTGAAAACAGGA CGGACCTCCATGCCTTTGAGAACCTAG AAATCATACGCGGCAGGACCAAGCAA CATGGTCAGTTTTCTCTTGCAGTCGTCA GCCTGAACATAACATCCTTGGGATTAC GCTCCCTCAAGGAGATAAGTGATGGAG ATGTGATAATTTCAGGAAACAAAAATT TGTGCTATGCAAATACAATAAACTGGA AAAAACTGTTTGGGACCTCCGGTCAGA AAACCAAAATTATAAGCAACAGAGGT GAAAACAGCTGCAAGGCCACAGGCCA GGTCTGCCATGCCTTGTGCTCCCCCGA GGGCTGCTGGGGCCCGGAGCCCAGGG ACTGCGTCTCTTGCCGGAATGTCAGCC GAGGCAGGGAATGCGTGGACAAGTGC AACCTTCTGGAGGGTGAGCCAAGGGA GTTTGTGGAGAACTCTGAGTGCATACA GTGCCACCCAGAGTGCCTGCCTCAGGC CATGAACATCACCTGCACAGGACGGGG ACCAGACAACTGTATCCAGTGTGCCCA CTACATTGACGGCCCCCACTGCGTCAA GACCTGCCCGGCAGGAGTCATGGGAG |

TABLE 12-continued

| Exemplary Sequences | | | | |
|---|---|---|---|---|
| | | | | AAAACAACACCCTGGTCTGGAAGTACG CAGACGCCGGCCATGTGTGCCACCTGT GCCATCCAAACTGCACCTACGGATGCA CTGGGCCAGGTCTTGAAGGCTGTCCAA CGAATGGGCCTAAGATCCCGTCCATCG CCACTGGGATGGTGGGGGCCCTCCTCT TGCTGCTGGTGGTGGCCCTGGGGATCG GCCTCTTCATG |
| HER1t-1 | 110 | RKVCNGIGIGEFKDSL SINATNIKHFKNCTSIS GDLHILPVAFRGDSFT HTPPLDPQELDILKTV KEITGFLLIQAWPENR TDLHAFENLEIIRGRT KQHGQFSLAVVSLNI TSLGLRSLKEISDGDV IISGNKNLCYANTINW KKLFGTSGQKTKIISN RGENSCKATGQVCH ALCSPEGCWGPEPRD CVSGGGGSGGGSGG GGSGGGGSFWVLVV VGGVLACYSLLVTVA FIIFWVRSKRS | 257 | CGCAAAGTGTGTAACGGAATAGGTATT GGTGAATTTAAAGACTCACTCTCCATA AATGCTACGAATATTAAACACTTCAAA AACTGCACCTCCATCAGTGGCGATCTC CACATCCTGCCGGTGGCATTTAGGGGT GACTCCTTCACACATACTCCTCCTCTGG ATCCACAGGAACTGGATATTCTGAAAA CCGTAAAGGAAATCACAGGGTTTTTGC TGATTCAGGCTTGGCCTGAAAACAGGA CGGACCTCCATGCCTTTGAGAACCTAG AAATCATACGCGGCAGGACCAAGCAA CATGGTCAGTTTTCTCTTGCAGTCGTCA GCCTGAACATAACATCCTTGGGATTAC GCTCCCTCAAGGAGATAAGTGATGGAG ATGTGATAATTTCAGGAAACAAAAATT TGTGCTATGCAAATACAATAAACTGGA AAAAACTGTTTGGGACCTCCGGTCAGA AAACCAAAATTATAAGCAACAGAGGT GAAAACAGCTGCAAGGCCACAGGCCA GGTCTGCCATGCCTTGTGCTCCCCCGA GGGCTGCTGGGGCCCGGAGCCCAGGG ACTGCGTCTCTGGTGGCGGTGGCTCGG GCGGTGGTGGGTCGGGTGGCGGCGGAT CTGGTGGCGGTGGCTCGTTTTGGGTGC TGGTGGTGGTTGGTGGAGTCCTGGCTT GCTATAGCTTGCTAGTAACAGTGGCCT TTATTATTTTCTGGGTGAGGAGTAAGA GGAGC |
| FL CD20 | 111 | MTTPRNSVNGTFPAE PMKGPIAMQSGPKPL FRRMSSLVGPTQSFF MRESKTLGAVQIMNG LFHIALGGLLMIPAGI YAPICVTVWYPLWG GIMYIISGSLLAATEK NSRKCLVKGKMIMNS LSLFAAISGMILSIMDI LNIKISHFLKMESLNFI RAHTPYINIYNCEPAN PSEKNSPSTQYCYSIQ SLFLGILSVMLIFAFFQ ELVIAGIVENEWKRT CSRPKSNIVLLSAEEK KEQTIEIKEEVVGLTE TSSQPKNEEDIEIIPIQE EEEEETETNFPEPPQD QESSPIENDSSP | 258 | ATGACAACACCCAGAAATTCAGTAAAT GGGACTTTCCCGGCAGAGCCAATGAAA GGCCCTATTGCTATGCAATCTGGTCCA AAACCACTCTTCAGGAGGATGTCTTCA CTGGTGGGCCCCACGCAAAGCTTCTTC ATGAGGGAATCTAAGACTTTGGGGGCT GTCCAGATTATGAATGGGCTCTTCCAC ATTGCCCTGGGGGGTCTTCTGATGATC CCAGCAGGGATCTATGCACCCATCTGT GTGACTGTGTGGTACCCTCTCTGGGGA GGCATTATGTATATTATTTCCGGATCAC TCCTGGCAGCAACGGAGAAAAACTCCA GGAAGTGTTTGGTCAAAGGAAAAATG ATAATGAATTCATTGAGCCTCTTTGCTG CCATTTCTGGAATGATTCTTTCAATCAT GGACATACTTAATATTAAAATTTCCCA TTTTTTAAAAATGGAGAGTCTGAATTTT ATTAGAGCTCACACACCATATATTAAC ATATACAACTGTGAACCAGCTAATCCC TCTGAGAAAAACTCCCCATCTACCCAA TACTGTTACAGCATACAATCTCTGTTCT TGGGCATTTTGTCAGTGATGCTGATCTT TGCCTTCTTCCAGGAACTTGTAATAGCT GGCATCGTTGAGAATGAATGGAAAAG AACGTGCTCCAGACCCAAATCTAACAT AGTTCTCCTGTCAGCAGAAGAAAAAAA AGAACAGACTATTGAAATAAAAGAAG AAGTGGTTGGGCTAACTGAAACATCTT CCCAACCAAAGAATGAAGAAGACATT GAAATTATTCCAATCCAAGAAGAGGAA GAAGAAGAAACAGAGACGAACTTTCC AGAACCTCCCCAAGATCAGGAATCCTC ACCAATAGAAAATGACAGCTCTCCT |
| CD20t-1 | 112 | MTTPRNSVNGTFPAE PMKGPIAMQSGPKPL FRRMSSLVGPTQSFF MRESKTLGAVQIMNG LFHIALGGLLMIPAGI YAPICVTVWYPLWG | 259 | ATGACCACACCACGGAACTCTGTGAAT GGCACCTTCCCAGCAGAGCCAATGAAG GGACCAATCGCAATGCAGAGCGGACC CAAGCCTCTGTTTCGGAGAATGAGCTC CCTGGTGGGCCCAACCCAGTCCTTCTTT ATGAGAGAGTCTAAGACACTGGGCGCC |

TABLE 12-continued

| Exemplary Sequences | | | | |
|---|---|---|---|---|
| | | GIMYIISGSLLAATEK<br>NSRKCLVKGKMIMNS<br>LSLFAAISGMILSIMDI<br>LNIKISHFLKMESLNFI<br>RAHTPYINIYNCEPAN<br>PSEKNSPSTQYCYSIQ<br>SLFLGILSVMLIFAFFQ<br>ELVIAGIVENEWKRT<br>CSRPKSNIVLLSAEEK<br>KEQTIEIKEEVVGLTE<br>TSSQPKNEEDIE | | GTGCAGATCATGAACGGACTGTTCCAC<br>ATCGCCCTGGGAGGACTGCTGATGATC<br>CCAGCCGGCATCTACGCCCCTATCTGC<br>GTGACCGTGTGGTACCCTCTGTGGGGC<br>GGCATCATGTATATCATCTCCGGCTCTC<br>TGCTGGCCGCCACAGAGAAGAACAGC<br>AGGAAGTGTCTGGTGAAGGGCAAGAT<br>GATCATGAATAGCCTGTCCCTGTTTGC<br>CGCCATCTCTGGCATGATCCTGAGCAT<br>CATGGACATCCTGAACATCAAGATCAG<br>CCACTTCCTGAAGATGGAGAGCCTGAA<br>CTTCATCAGAGCCCACACCCCTTACAT<br>CAACATCTATAATTGCGAGCCTGCCAA<br>CCCATCCGAGAAGAATTCTCCAAGCAC<br>ACAGTACTGTTATTCCATCCAGTCTCTG<br>TTCCTGGGCATCCTGTCTGTGATGCTGA<br>TCTTTGCCTTCTTTCAGGAGCTGGTCAT<br>CGCCGGCATCGTGGAGAACGAGTGGA<br>AGAGGACCTGCAGCCGCCCCAAGTCCA<br>ATATCGTGCTGCTGTCCGCCGAGGAGA<br>AGAAGGAGCAGACAATCGAGATCAAG<br>GAGGAGGTGGTGGGCCTGACCGAGAC<br>ATCTAGCCAGCCTAAGAATGAGGAGG<br>ATATCGAG |
| mbIL-15 | | | | |
| mbIL15 | 113 | MDWTWILFLVAAAT<br>RVHSNWVNVISDLKK<br>IEDLIQSMHIDATLYT<br>ESDVHPSCKVTAMKC<br>FLLELQVISLESGDASI<br>HDTVENLIIILANNSLS<br>SNGNVTESGCKECEE<br>LEEKNIKEFLQSFVHI<br>VQMFINTSSGGGSGG<br>GGSGGGGSGGGGSG<br>GGSLQITCPPPMSVEH<br>ADIWVKSYSLYSRER<br>YICNSGFKRKAGTSSL<br>TECVLNKATNVAHW<br>TTPSLKCIRDPALVHQ<br>RPAPPSTVTTAGVTPQ<br>PESLSPSGKEPAASSP<br>SSNNTAATTAAIVPGS<br>QLMPSKSPSTGTTEIS<br>SHESSHGTPSQTTAK<br>NWELTASASHQPPGV<br>YPQGHSDTTVAISTST<br>VLLCGLSAVSLLACY<br>LKSRQTPPLASVEME<br>AMEALPVTWGTSSRD<br>EDLENCSHHL | 260 | ATGGATTGGACCTGGATTCTGTTTCTG<br>GTGGCCGCTGCCACAAGAGTGCACAGC<br>AACTGGGTGAATGTGATCAGCGACCTG<br>AAGAAGATCGAGGATCTGATCCAGAG<br>CATGCACATTGATGCCACCCTGTACAC<br>AGAATCTGATGTGCACCCTAGCTGTAA<br>AGTGACCGCCATGAAGTGTTTTCTGCT<br>GGAGCTGCAGGTGATTTCTCTGGAAAG<br>CGGAGATGCCTCTATCCACGACACAGT<br>GGAGAATCTGATCATCCTGGCCAACAA<br>TAGCCTGAGCAGCAATGGCAATGTGAC<br>AGAGTCTGGCTGTAAGGAGTGTGAGGA<br>GCTGGAGGAGAAGAACATCAAGGAGT<br>TTCTGCAGAGCTTTGTGCACATCGTGC<br>AGATGTTCATCAATACAAGCTCTGGCG<br>GAGGATCTGGAGGAGGCGGATCTGGA<br>GGAGGAGGCAGTGGAGGCGGAGGATC<br>TGGCGGAGGATCTCTGCAGATTACATG<br>CCCTCCTCCAATGTCTGTGGAGCACGC<br>CGATATTTGGGTGAAGTCCTACAGCCT<br>GTACAGCAGAGAGAGATACATCTGCA<br>ACAGCGGCTTTAAGAGAAAGGCCGGC<br>ACCTCTTCTCTGACAGAGTGCGTGCTG<br>AATAAGGCCACAAATGTGGCCCACTGG<br>ACAACACCTAGCCTGAAGTGCATTAGA<br>GATCCTGCCCTGGTCCACCAGAGGCCT<br>GCCCCTCCATCTACAGTGACAACAGCC<br>GGAGTGACACCTCAGCCTGAATCTCTG<br>AGCCCTTCTGGAAAAGAACCTGCCGCC<br>AGCTCTCCTAGCTCTAATAATACCGCC<br>GCCACAACAGCCGCCATTGTGCCTGGA<br>TCTCAGCTGATGCCTAGCAAGTCTCCT<br>AGCACAGGCACAACAGAGATCAGCAG<br>CCACGAATCTTCTCACGGAACACCTTC<br>TCAGACCACCGCCAAGAATTGGGAGCT<br>GACAGCCTCTGCCTCTCACCAGCCTCC<br>AGGAGTGTATCCTCAGGGCCACTCTGA<br>TACAACAGTGGCCATCAGCACATCTAC<br>AGTGCTGCTGTGTGGACTGTCTGCCGT<br>GTCTCTGCTGGCCTGTTACCTGAAGTCT<br>AGACAGACACCTCCTCTGGCCTCTGTG<br>GAGATGGAGGCCATGGAAGCCCTGCCT<br>GTGACATGGGGAACAAGCAGCAGAGA<br>TGAGGACCTGGAGAATTGTTCTCACCA<br>CCTG |
| IL-15 | 114 | NWVNVISDLKKIEDLI<br>QSMHIDATLYTESDV<br>HPSCKVTAMKCFLLE<br>LQVISLESGDASIHDT<br>VENLIILANNSLSSNG | 261 | AACTGGGTGAATGTGATCAGCGACCTG<br>AAGAAGATCGAGGATCTGATCCAGAG<br>CATGCACATTGATGCCACCCTGTACAC<br>AGAATCTGATGTGCACCCTAGCTGTAA<br>AGTGACCGCCATGAAGTGTTTTCTGCT |

TABLE 12-continued

| Exemplary Sequences | | | | |
|---|---|---|---|---|
| | | NVTESGCKECEELEE<br>KNIKEFLQSFVHIVQM<br>FINTS | | GGAGCTGCAGGTGATTTCTCTGGAAAG<br>CGGAGATGCCTCTATCCACGACACAGT<br>GGAGAATCTGATCATCCTGGCCAACAA<br>TAGCCTGAGCAGCAATGGCAATGTGAC<br>AGAGTCTGGCTGTAAGGAGTGTGAGGA<br>GCTGGAGGAGAAGAACATCAAGGAGT<br>TTCTGCAGAGCTTTGTGCACATCGTGC<br>AGATGTTCATCAATACAAGC |
| IL-15Rα | 115 | ITCPPPMSVEHADIWV<br>KSYSLYSRERYICNSG<br>FKRKAGTSSLTECVL<br>NKATNVAHWTTPSL<br>KCIRDPALVHQRPAPP<br>STVTTAGVTPQPESLS<br>PSGKEPAASSPSSNNT<br>AATTAAIVPGSQLMP<br>SKSPSTGTTEISSHESS<br>HGTPSQTTAKNWELT<br>ASASHQPPGVYPQGH<br>SDTTVAISTSTVLLCG<br>LSAVSLLACYLKSRQ<br>TPPLASVEMEAMEAL<br>PVTWGTSSRDEDLEN<br>CSHHL | 262 | ATTACATGCCCTCCTCCAATGTCTGTGG<br>AGCACGCCGATATTTGGGTGAAGTCCT<br>ACAGCCTGTACAGCAGAGAGAGATAC<br>ATCTGCAACAGCGGCTTTAAGAGAAAG<br>GCCGGCACCTCTTCTCTGACAGAGTGC<br>GTGCTGAATAAGGCCACAAATGTGGCC<br>CACTGGACAACACCTAGCCTGAAGTGC<br>ATTAGAGATCCTGCCCTGGTCCACCAG<br>AGGCCTGCCCCTCCATCTACAGTGACA<br>ACAGCCGGAGTGACACCTCAGCCTGAA<br>TCTCTGAGCCCTTCTGGAAAAGAACCT<br>GCCGCCAGCTCTCCTAGCTCTAATAAT<br>ACCGCCGCCACAACAGCCGCCATTGTG<br>CCTGGATCTCAGCTGATGCCTAGCAAG<br>TCTCCTAGCACAGGCACAACAGAGATC<br>AGCAGCCACGAATCTTCTCACGGAACA<br>CCTTCTCAGACCACCGCCAAGAATTGG<br>GAGCTGACAGCCTCTGCCTCTCACCAG<br>CCTCCAGGAGTGTATCCTCAGGGCCAC<br>TCTGATACAACAGTGGCCATCAGCACA<br>TCTACAGTGCTGCTGTGTGGACTGTCT<br>GCCGTGTCTCTGCTGGCCTGTTACCTGA<br>AGTCTAGACACAGACACCTCCTCTGGCCT<br>CTGTGGAGATGGAGGCCATGGAAGCCC<br>TGCCTGTGACATGGGGAACAAGCAGCA<br>GAGATGAGGACCTGGAGAATTGTTCTC<br>ACCACCTG |
| LINKERS | | | | |
| T2A | 116 | EGRGSLLTCGDVEEN<br>PGP | 263 | GAGGGCAGAGGAAGTCTTCTAACATGCGG<br>TGACGTGGAGGAGAATCCCGGCCCT |
| Furin-<br>GSG-T2A | 117 | RAKRGSGEGRGSLLT<br>CGDVEENPGP | 264 | AGAGCTAAGAGGGGAAGCGGAGAGGGCA<br>GAGGAAGTCTGCTAACATGCGGTGACGTC<br>GAGGAGAATCCTGGACCT |
| Furin-SGSG-<br>T2A | 118 | RAKRSGSGEGRGSLL<br>TCGDVEENPGP | 265 | AGGGCCAAGAGGAGTGGCAGCGGCGAGGG<br>CAGAGGAAGTCTTCTAACATGCGGTGACGT<br>GGAGGAGAATCCCGGCCCT |
| Porcine<br>tescho-<br>virus-1 2A<br>region<br>(P2A) | 119 | ATNFSLLKQAGDVEE | 266 | GCAACGAACTTCTCTCTCCTAAAACAGGCT<br>GGTGATGTGGAGGAGAATCCTGGTCCA<br>NPGP |
| GSG-p2a | 120 | GSGATNFSLLKQAGD<br>VEENPGP | 267 | GGAAGCGGAGCTACTAACTTCAGCCTGCTG<br>AAGCAGGCTGGAGACGTGGAGGAGAACCC<br>TGGACCT |
| fp2a | 121 | RAKRAPVKQGSGAT<br>NFSLLKQAGDVEENP<br>GP | 268 | CGTGCAAAGCGTGCACCGGTGAAACAGGG<br>AAGCGGAGCTACTAACTTCAGCCTGCTGAA<br>GCAGGCTGGAGACGTGGAGGAGAACCCTG<br>GACCT |
| Equine<br>rhinitis A<br>virus 2A<br>region<br>(E2A) | 122 | QCTNYALLKLAGDVE<br>SNPGP | 269 | CAGTGTACTAATTATGCTCTCTTGAAATTG<br>GCTGGAGATGTTGAGAGCAACCCTGGACC<br>T |
| Foot-and-<br>mouth<br>disease<br>virus 2A<br>region<br>(F2A) | 123 | VKQTLNFDLLKLAGD<br>VESNPGP | 270 | GTCAAACAGACCCTAAACTTTGATCTGCTA<br>AAACTGGCCGGGGATGTGGAAAGTAATCC<br>CGGCCCC |

TABLE 12-continued

| Exemplary Sequences | | | | |
|---|---|---|---|---|
| Linker | 124 | APVKQGSG | | |
| Furinlink1 | 125 | RAKR | 271 | CGTGCAAAGCGT |
| Fmdv | 126 | RAKRAPVKQTLNFDL LKLAGDVESNPGP | 272 | AGAGCCAAGAGGGCACCGGTGAAACAGAC TTTGAATTTTGACCTTCTGAAGTTGGCAGG AGACGTTGAGTCCAACCCTGGGCCC |
| (G4S)3 Linker | 127 | GGGGSGGGGSGGGG S | 273 | GGTGGCGGTGGCTCGGGCGGTGGTGGGTC GGGTGGCGGCGGATCT |
| Whitlow Linker | 128 | GSTSGSGKPGSGEGST KG | 274 | GGCAGCACCTCCGGCAGCGGCAAGCCTGG CAGCGGCGAGGGCAGCACCAAGGGC |
| GSG linker | 129 | GSG | 275 | GGAAGCGGA |
| SGSG linker | 130 | SGSG | 276 | AGTGGCAGCGGC |
| RTS-COMPONENTS | | | | |
| VP16 activation domain | 131 | GPKKKRKVAPPTDVS LGDELHLDGEDVAM AHADALDDFDLDML GDGDSPGPGFTPHDS APYGALDMADFEFEQ MFTDALGIDEYGG | 277 | GGCCCCAAGAAGAAAAGGAAGGTGGCCCC CCCCACCGACGTGAGCCTGGGCGACGAGC TGCACCTGGACGGCGAGGACGTGGCCATG GCCCACGCCGACGCCCTGGACGACTTCGAC CTGGACATGCTGGGCGACGGCGACAGCCC CGGCCCCGGCTTCACCCCCCACGACAGCGC CCCCTACGGCGCCCTGGACATGGCCGACTT CGAGTTCGAGCAGATGTTCACCGACGCCCT GGGCATCGACGAGTACGGCGGC |
| Retinoid x receptor (RxR) | 132 | EMPVDRILEAELAVE QKSDQGVEGPGGTG GSGSSPNDPVTNICQA ADKQLFTLVEWAKRI PHFSSLPLDDQVILLR AGWNELLIASFSHRSI DVRDGILLATGLHVH RNSAHSAGVGAIFDR VLTELVSKMRDMRM DKTELGCLRAIILFNP EVRGLKSAQEVELLR EKVYAALEEYTRTTH PDEPGRFAKLLLRLPS LRSIGLKCLEHLFFFR LIGDVPIDTFLMEMLE SPSDS | 278 | GAGATGCCCGTGGACAGGATTCTGGAGGC CGAACTCGCCGTGGAGCAGAAAAGCGACC AGGGCGTGGAGGGCCCCGGCGGAACCGGC GGCAGCGGCAGCAGCCCCAACGACCCCGT GACCAACATCTGCCAGGCCGCCGACAAGC AGCTGTTCACCCTGGTGGAGTGGGCCAAG AGGATTCCCCACTTCAGCAGCCTGCCCCTG GACGACCAGGTGATCCTGCTGAGGGCCGG ATGGAACGAGCTGCTGATCGCCAGCTTCAG CCACAGGAGCATCGACGTGAGGGACGGCA TCCTGCTGGCCACCGGCCTGCACGTCCATA GGAACAGCGCCCACAGCGCCGGAGTGGGC GCCATCTTCGACAGGGTGCTGACCGAGCTG GTGAGCAAGATGAGGGACATGAGGATGGA CAAGACCGAGCTGGGCTGCCTGAGGGCCA TCATCCTGTTCAACCCCGAGGTGAGGGGCC TGAAAAGCGCCCAGGAGGTGGAGCTGCTG AGGGAGAAGGTGTACGCCGCCCTGGAGGA GTACACCAGGACCACCCACCCCGACGAGC CCGGCAGATTCGCCAAGCTGCTGCTGAGGC TGCCCAGCCTGAGGAGCATCGGCCTGAAG TGCCTGGAGCACCTGTTCTTCTTCAGGCTG ATCGGCGACGTGCCCATCGACACCTTCCTG ATGGAGATGCTGGAGAGCCCCAGCGACAG C |
| VP16-linker-RxR | 133 | GPKKKRKVAPPTDVS LGDELHLDGEDVAM AHADALDDFDLDML GDGDSPGPGFTPHDS APYGALDMADFEFEQ MFTDALGIDEYGGEF EMPVDRILEAELAVE QKSDQGVEGPGGTG GSGSSPNDPVTNICQA ADKQLFTLVEWAKRI PHFSSLPLDDQVILLR AGWNELLIASFSHRSI DVRDGILLATGLHVH RNSAHSAGVGAIFDR VLTELVSKMRDMRM DKTELGCLRAIILFNP EVRGLKSAQEVELLR EKVYAALEEYTRTTH PDEPGRFAKLLLRLPS LRSIGLKCLEHLFFFR | 279 | GGCCCCAAGAAGAAAAGGAAGGTGGCCCC CCCCACCGACGTGAGCCTGGGCGACGAGC TGCACCTGGACGGCGAGGACGTGGCCATG GCCCACGCCGACGCCCTGGACGACTTCGAC CTGGACATGCTGGGCGACGGCGACAGCCC CGGCCCCGGCTTCACCCCCCACGACAGCGC CCCCTACGGCGCCCTGGACATGGCCGACTT CGAGTTCGAGCAGATGTTCACCGACGCCCT GGGCATCGACGAGTACGGCGGCGAATTCG AGATGCCCGTGGACAGGATTCTGGAGGCC GAACTCGCCGTGGAGCAGAAAAGCGACCA GGGCGTGGAGGGCCCCGGCGGAACCGGCG GCAGCGGCAGCAGCCCCAACGACCCCGTG ACCAACATCTGCCAGGCCGCCGACAAGCA GCTGTTCACCCTGGTGGAGTGGGCCAAGA GGATTCCCCACTTCAGCAGCCTGCCCCTGG ACGACCAGGTGATCCTGCTGAGGGCCGGA TGGAACGAGCTGCTGATCGCCAGCTTCAGC CACAGGAGCATCGACGTGAGGGACGGCAT CCTGCTGGCCACCGGCCTGCACGTCCATAG |

TABLE 12-continued

| Exemplary Sequences | | | | |
|---|---|---|---|---|
| | | LIGDVPIDTFLMEMLE<br>SPSDS | | GAACAGCGCCCACAGCGCCGGAGTGGGCG<br>CCATCTTCGACAGGGTGCTGACCGAGCTGG<br>TGAGCAAGATGAGGGACATGAGGATGGAC<br>AAGACCGAGCTGGGCTGCCTGAGGGCCAT<br>CATCCTGTTCAACCCCGAGGTGAGGGGCCT<br>GAAAAGCGCCCAGGAGGTGGAGCTGCTGA<br>GGGAGAAGGTGTACGCCGCCCTGGAGGAG<br>TACACCAGGACCACCCACCCCGACGAGCC<br>CGGCAGATTCGCCAAGCTGCTGCTGAGGCT<br>GCCCAGCCTGAGGAGCATCGGCCTGAAGT<br>GCCTGGAGCACCTGTTCTTCTTCAGGCTGA<br>TCGGCGACGTGCCCATCGACACCTTCCTGA<br>TGGAGATGCTGGAGAGCCCCAGCGACAGC |
| GAL4 DNA Binding Domain | 134 | MKLLSSIEQACDICRL<br>KKLKCSKEKPKCAKC<br>LKNNWECRYSPKTKR<br>SPLTRAHLTEVESRLE<br>RLEQLFLLIFPREDLD<br>MILKMDSLQDIKALL<br>TGLFVQDNVNKDAV<br>TDRLASVETDMPLTL<br>RQHRISATSSSEESSN<br>KGQRQLTVSPEF | 280 | ATGAAGCTGCTGAGCAGCATCGAGCAGGC<br>TTGCGACATCTGCAGGCTGAAGAAGCTGA<br>AGTGCAGCAAGGAGAAGCCCAAGTGCGCC<br>AAGTGCCTGAAGAACAACTGGGAGTGCAG<br>ATACAGCCCCAAGACCAAGAGGAGCCCCC<br>TGACCAGGGCCCACCTGACCGAGGTGGAG<br>AGCAGGCTGGAGAGGCTGGAGCAGCTGTT<br>CCTGCTGATCTTCCCCAGGGAGGACCTGGA<br>CATGATCCTGAAGATGGACAGCCTGCAAG<br>ACATCAAGGCCCTGCTGACCGGCCTGTTCG<br>TGCAGGACAACGTGAACAAGGACGCCGTG<br>ACCGACAGGCTGGCCAGCGTGGAGACCGA<br>CATGCCCCTGACCCTGAGGCAGCACAGGA<br>TCAGCGCCACCAGCAGCAGCGAGGAGAGC<br>AGCAACAAGGGCCAGAGGCAGCTGACCGT<br>GAGCCCCGAGTTT |
| Ecdysone Receptor Ligand Binding Domain - VY variant (EcR) | 135 | IRPECVVPETQCAMK<br>RKEKKAQKEKDKLP<br>VSTTTVDDHMPPIMQ<br>CEPPPPEAARIHEVVP<br>RFLSDKLLVTNRQKN<br>IPQLTANQQFLIARLI<br>WYQDGYEQPSDEDL<br>KRITQTWQQADDENE<br>ESDTPFRQITEMTILT<br>VQLIVEFAKGLPGFA<br>KISQPDQITLLKACSS<br>EVMMLRVARRYDAA<br>SDSILFANNQAYTRD<br>NYRKAGMAEVIEDLL<br>HFCRCMYSMALDNIH<br>YALLTAVVIFSDRPGL<br>EQPQLVEEIQRYYLN<br>TLRIYILNQLSGSARS<br>SVIYGKILSILSELRTL<br>GMQNSNMCISLKLKN<br>RKLPPFLEEIWDVAD<br>MSHTQPPPILESPTNL | 281 | ATCAGGCCCGAGTGCGTGGTGCCCGAG<br>ACCCAGTGCGCCATGAAAAGGAAGGA<br>GAAGAAGGCCCAGAAGGAGAAGGACA<br>AGCTGCCCGTGAGCACCACCACCGTCG<br>ATGACCACATGCCCCCCATCATGCAGT<br>GCGAGCCCCCCCCCCCCGAGGCCGCCA<br>GGATTCACGAGGTCGTGCCCAGGTTCC<br>TGAGCGACAAGCTGCTGGTGACCAACA<br>GGCAGAAGAACATCCCCCAGCTGACCG<br>CCAACCAGCAGTTCCTGATCGCCAGGC<br>TGATCTGGTATCAGGACGGCTACGAGC<br>AGCCCAGCGACGAGGACCTGAAAAGG<br>ATCACCCAGACCTGGCAGCAGGCCGAC<br>GACGAGAACGAGGAGAGCGACACCCC<br>CTTCAGGCAGATCACCGAGATGACCAT<br>CCTGACCGTGCAGCTGATCGTGGAGTT<br>CGCCAAGGGCCTGCCCGGATTCGCCAA<br>GATCAGCCAGCCCGACCAGATCACCCT<br>GCTGAAGGCTTGCAGCAGCGAGGTGAT<br>GATGCTGAGGGTGGCCAGGAGGTACG<br>ACGCCGCCAGCGACAGCATCCTGTTCG<br>CCAACAACCAGGCTTACACCAGGGACA<br>ACTACAGGAAGGCTGGCATGGCCGAG<br>GTGATCGAGGACCTCCTGCACTTCTGC<br>AGATGTATGTACAGCATGGCCCTGGAC<br>AACATCCACTACGCCCTGCTGACCGCC<br>GTGGTGATCTTCAGCGACAGGCCCGGC<br>CTGGAGCAGCCCCAGCTGGTGGAGGA<br>GATCCAGAGGTACTACCTGAACACCCT<br>GAGGATCTACATCCTGAACCAGCTGAG<br>CGGCAGCGCCAGGAGCAGCGTGATCTA<br>CGGCAAGATCCTGAGCATCCTGAGCGA<br>GCTGAGGACCCTGGGAATGCAGAACA<br>GCAATATGTGTATCAGCCTGAAGCTGA<br>AGAACAGGAAGCTGCCCCCCTTCCTGG<br>AGGAGATTTGGGACGTGGCCGACATGA<br>GCCACACCCAGCCCCCCCCCATCCTGG<br>AGAGCCCCACCAACCTG |
| Ecdysone Receptor Ligand Binding Domain - VY variant (EcR) | 136 | RPECVVPETQCAMKR<br>KEKKAQKEKDKLPVS<br>TTTVDDHMPPIMQCE<br>PPPPEAARIHEVVPRF<br>LSDKLLVTNRQKNIP<br>QLTANQQFLIARLIW<br>YQDGYEQPSDEDLKR<br>ITQTWQQADDENEES | 282 | CGGCCTGAGTGCGTAGTACCCGAGACT<br>CAGTGCGCCATGAAGCGGAAAGAGAA<br>GAAAGCACAGAAGGAGAAGGACAAAC<br>TGCCTGTCAGCACGACGACGGTGGACG<br>ACCACATGCCGCCCATTATGCAGTGTG<br>AACCTCCACCTCCTGAAGCAGCAAGGA<br>TTCACGAAGTGGTCCCAAGGTTTCTCT<br>CCGACAAGCTGTTGGTGACAAACCGGC |

TABLE 12-continued

| Exemplary Sequences | | | | |
|---|---|---|---|---|
| | | DTPFRQITEMTILTVQ<br>LIVEFAKGLPGFAKIS<br>QPDQITLLKACSSEV<br>MMLRVARRYDAASD<br>SILFANNQAYTRDNY<br>RKAGMAEVIEDLLHF<br>CRCMYSMALDNIHY<br>ALLTAVVIFSDRPGLE<br>QPQLVEEIQRYYLNT<br>LRIYILNQLSGSARSS<br>VIYGKILSILSELRTLG<br>MQNSNMCISLKLKNR<br>KLPPFLEEIWDVADM<br>SHTQPPPILESPTNL | | AGAAAAACATCCCCCAGTTGACAGCCA<br>ACCAGCAGTTCCTTATCGCCAGGCTCA<br>TCTGGTACCAGGACGGGTACGAGCAGC<br>CTTCTGATGAAGATTTGAAGAGGATTA<br>CGCAGACGTGGCAGCAAGCGGACGAT<br>GAAAACGAAGAGTCGGACACTCCCTTC<br>CGCCAGATCACAGAGATGACTATCCTC<br>ACGGTCCAACTTATCGTGGAGTTCGCG<br>AAGGGATTGCCAGGGTTCGCCAAGATC<br>TCGCAGCCTGATCAAATTACGCTGCTT<br>AAGGCTTGCTCAAGTGAGGTAATGATG<br>CTCCGAGTCGCGCGACGATACGATGCG<br>GCCTCAGACAGTATTCTGTTCGCGAAC<br>AACCAAGCGTACACTCGCGACAACTAC<br>CGCAAGGCTGGCATGGCCGAGGTCATC<br>GAGGATCTACTGCACTTCTGCCGGTGC<br>ATGTACTCTATGGCGTTGGACAACATC<br>CATTACGCGCTGCTCACGGCTGTCGTC<br>ATCTTTTCTGACCGGCCAGGGTTGGAG<br>CAGCCGCAACTGGTGGAAGAGATCCA<br>GCGGTACTACCTGAATACGCTCCGCAT<br>CTATATCCTGAACCAGCTGAGCGGGTC<br>GGCGCGTTCGTCCGTCATATACGGCAA<br>GATCCTCTCAATCCTCTCTGAGCTACGC<br>ACGCTCGGCATGCAAAACTCCAACATG<br>TGCATCTCCCTCAAGCTCAAGAACAGA<br>AAGCTGCCGCCTTTCCTCGAGGAGATC<br>TGGGATGTGGCGGACATGTCGCACACC<br>CAACCGCCGCCTATCCTCGAGTCCCCC<br>ACGAATCTCTAG |
| GAL4-<br>Linker-<br>EcR | 137 | MKLLSSIEQACDICRL<br>KKLKCSKEKPKCAKC<br>LKNNWECRYSPKTKR<br>SPLTRAHLTEVESRLE<br>RLEQLFLLIFPREDLD<br>MILKMDSLQDIKALL<br>TGLFVQDNVNKDAV<br>TDRLASVETDMPLTL<br>RQHRISATSSSEESSN<br>KGQRQLTVSPEFPGIR<br>PECVVPETQCAMKRK<br>EKKAQKEKDKLPVST<br>TTVDDHMPPIMQCEP<br>PPPEAARIHEVVPRFL<br>SDKLLVTNRQKNIPQ<br>LTANQQFLIARLIWY<br>QDGYEQPSDEDLKRI<br>TQTWQQADDENEES<br>DTPFRQITEMTILTVQ<br>LIVEFAKGLPGFAKIS<br>QPDQITLLKACSSEV<br>MMLRVARRYDAASD<br>SILFANNQAYTRDNY<br>RKAGMAEVIEDLLHF<br>CRCMYSMALDNIHY<br>ALLTAVVIFSDRPGLE<br>QPQLVEEIQRYYLNT<br>LRIYILNQLSGSARSS<br>VIYGKILSILSELRTLG<br>MQNSNMCISLKLKNR<br>KLPPFLEEIWDVADM<br>SHTQPPPILESPTNL | 283 | ATGAAGCTACTGTCTTCTATCGAACAA<br>GCATGCGATATTTGCCGACTTAAAAAG<br>CTCAAGTGCTCCAAAGAAAAACCGAA<br>GTGCGCCAAGTGTCTGAAGAACAACTG<br>GGAGTGTCGCTACTCTCCCAAAACCAA<br>AAGGTCTCCGCTGACTAGGGCACATCT<br>GACAGAAGTGGAATCAAGGCTAGAAA<br>GACTGGAACAGCTATTTCTACTGATTTT<br>TCCTCGAGAAGACCTTGACATGATTTT<br>GAAAATGGATTCTTTACAGGATATAAA<br>AGCATTGTTAACAGGATTATTTGTACA<br>AGATAATGTGAATAAAGATGCCGTCAC<br>AGATAGATTGGCTTCAGTGGAGACTGA<br>TATGCCTCTAACATTGAGACAGCATAG<br>AATAAGTGCGACATCATCATCGGAAGA<br>GAGTAGTAACAAAGGTCAAAGACAGT<br>TGACTGTATCGCCGGAATTCCCGGGGA<br>TCCGGCCTGAGTGCGTAGTACCCGAGA<br>CTCAGTGCGCCATGAAGCGGAAAGAG<br>AAGAAAGCACAGAAGGAGAAGGACAA<br>ACTGCCTGTCAGCACGACGACGGTGGA<br>CGACCACATGCCGCCCATTATGCAGTG<br>TGAACCTCCACCTCCTGAAGCAGCAAG<br>GATTCACGAAGTGGTCCCAAGGTTTCT<br>CTCCGACAAGCTGTTGGTGACAAACCG<br>GCAGAAAAACATCCCCCAGTTGACAGC<br>CAACCAGCAGTTCCTTATCGCCAGGCT<br>CATCTGGTACCAGGACGGGTACGAGCA<br>GCCTTCTGATGAAGATTTGAAGAGGAT<br>TACGCAGACGTGGCAGCAAGCGGACG<br>ATGAAAACGAAGAGTCGGACACTCCCT<br>TCCGCCAGATCACAGAGATGACTATCC<br>TCACGGTCCAACTTATCGTGGAGTTCG<br>CGAAGGGATTGCCAGGGTTCGCCAAGA<br>TCTCGCAGCCTGATCAAATTACGCTGC<br>TTAAGGCTTGCTCAAGTGAGGTAATGA<br>TGCTCCGAGTCGCGCGACGATACGATG<br>CGGCCTCAGACAGTATTCTGTTCGCGA<br>ACAACCAAGCGTACACTCGCGACAACT<br>ACCGCAAGGCTGGCATGGCCGAGGTCA<br>TCGAGGATCTACTGCACTTCTGCCGGT<br>GCATGTACTCTATGGCGTTGGACAACA<br>TCCATTACGCGCTGCTCACGGCTGTCG<br>TCATCTTTTCTGACCGGCCAGGGTTGG<br>AGCAGCCGCAACTGGTGGAAGAGATC<br>CAGCGGTACTACCTGAATACGCTCCGC<br>ATCTATATCCTGAACCAGCTGAGCGGG |

TABLE 12-continued

| Exemplary Sequences | | | | |
|---|---|---|---|---|
| | | | | TCGGCGCGTTCGTCCGTCATATACGGC<br>AAGATCCTCTCAATCCTCTCTGAGCTA<br>CGCACGCTCGGCATGCAAAACTCCAAC<br>ATGTGCATCTCCCTCAAGCTCAAGAAC<br>AGAAAGCTGCCGCCTTTCCTCGAGGAG<br>ATCTGGGATGTGGCGGACATGTCGCAC<br>ACCCAACCGCCGCCTATCCTCGAGTCC<br>CCCACGAATCTCTAG |
| GAL4-<br>Linker-<br>EcR | 138 | MKLLSSIEQACDICRL<br>KKLKCSKEKPKCAKC<br>LKNNWECRYSPKTKR<br>SPLTRAHLTEVESRLE<br>RLEQLFLLIFPREDLD<br>MILKMDSLQDIKALL<br>TGLFVQDNVNKDAV<br>TDRLASVETDMPLTL<br>RQHRISATSSSEESSN<br>KGQRQLTVSPEFPGR<br>PECVVPETQCAMKRK<br>EKKAQKEKDKLPVST<br>TTVDDHMPPIMQCEP<br>PPPEAARIHEVVPRFL<br>SDKLLVTNRQKNIPQ<br>LTANQQFLIARLIWY<br>QDGYEQPSDEDLKRI<br>TQTWQQADDENEES<br>DTPFRQITEMTILTVQ<br>LIVEFAKGLPGFAKIS<br>QPDQITLLKACSSEV<br>MMLRVARRYDAASD<br>SILFANNQAYTRDNY<br>RKAGMAEVIEDLLHF<br>CRCMYSMALDNIHY<br>ALLTAVVIFSDRPGLE<br>QPQLVEEIQRYYLNT<br>LRIYILNQLSGSARSS<br>VIYGKILSILSELRTLG<br>MQNSNMCISLKLKNR<br>KLPPFLEEIWDVADM<br>SHTQPPPILESPTNL | 284 | ATGAAGCTGCTGAGCAGCATCGAGCAG<br>GCTTGCGACATCTGCAGGCTGAAGAAG<br>CTGAAGTGCAGCAAGGAGAAGCCCAA<br>GTGCGCCAAGTGCCTGAAGAACAACTG<br>GGAGTGCAGATACAGCCCCAAGACCA<br>AGAGGAGCCCCCTGACCAGGGCCCACC<br>TGACCGAGGTGGAGAGCAGGCTGGAG<br>AGGCTGGAGCAGCTGTTCCTGCTGATC<br>TTCCCCAGGGAGGACCTGGACATGATC<br>CTGAAGATGGACAGCCTGCAAGACATC<br>AAGGCCCTGCTGACCGGCCTGTTCGTG<br>CAGGACAACGTGAACAAGGACGCCGT<br>GACCGACAGGCTGGCCAGCGTGGAGA<br>CCGACATGCCCCTGACCCTGAGGCAGC<br>ACAGGATCAGCGCCACCAGCAGCAGC<br>GAGGAGAGCAGCAACAAGGGCCAGAG<br>GCAGCTGACCGTGAGCCCCGAGTTTCC<br>CGGGCGGCCTGAGTGCGTAGTACCCGA<br>GACTCAGTGCGCCATGAAGCGGAAAG<br>AGAAGAAAGCACAGAAGGAGAAGGAC<br>AAACTGCCTGTCAGCACGACGACGGTG<br>GACGACCACATGCCGCCCATTATGCAG<br>TGTGAACCTCCACCTCCTGAAGCAGCA<br>AGGATTCACGAAGTGGTCCCAAGGTTT<br>CTCTCCGACAAGCTGTTGGTGACAAAC<br>CGGCAGAAAAACATCCCCCAGTTGACA<br>GCCAACCAGCAGTTCCTTATCGCCAGG<br>CTCATCTGGTACCAGGACGGGTACGAG<br>CAGCCTTCTGATGAAGATTTGAAGAGG<br>ATTACGCAGACGTGGCAGCAAGCGGA<br>CGATGAAAACGAAGAGTCGGACACTC<br>CCTTCCGCCAGATCACAGAGATGACTA<br>TCCTCACGGTCCAACTTATCGTGGAGT<br>TCGCGAAGGGATTGCCAGGGTTCGCCA<br>AGATCTCGCAGCCTGATCAAATTACGC<br>TGCTTAAGGCTTGCTCAAGTGAGGTAA<br>TGATGCTCCGAGTCGCGCGACGATACG<br>ATGCGGCCTCAGACAGTATTCTGTTCG<br>CGAACAACCAAGCGTACACTCGCGACA<br>ACTACCGCAAGGCTGGCATGGCCGAGG<br>TCATCGAGGATCTACTGCACTTCTGCC<br>GGTGCATGTACTCTATGGCGTTGGACA<br>ACATCCATTACGCGCTGCTCACGGCTG<br>TCGTCATCTTTTCTGACCGGCCAGGGTT<br>GGAGCAGCCGCAACTGGTGGAAGAGA<br>TCCAGCGGTACTACCTGAATACGCTCC<br>GCATCTATATCCTGAACCAGCTGAGCG<br>GGTCGGCGCGTTCGTCCGTCATATACG<br>GCAAGATCCTCTCAATCCTCTCTGAGC<br>TACGCACGCTCGGCATGCAAAACTCCA<br>ACATGTGCATCTCCCTCAAGCTCAAGA<br>ACAGAAAGCTGCCGCCTTTCCTCGAGG<br>AGATCTGGGATGTGGCGGACATGTCGC<br>ACACCCAACCGCCGCCTATCCTCGAGT<br>CCCCCACGAATCTCTAG |

| Name | SEQ ID NO | Nucleotide Sequence |
|---|---|---|
| Human EEF1A1<br>promoter variant | 139 | GAGCGTGCGTGAGGCTCCGGTGCCCGTCAGTGGGCAGAGCGC<br>ACATCGCCCACAGTCCCCGAGAAGTTGGGGGGAGGGGTCGG<br>CGATTGAACCGGTGCCTAGAGAAGGTGGCGCGGGGTAAACTG<br>GGAAAGTGATGTCGTGTACTGGCTCCGCCTTTTTCCCGAGGGT<br>GGGGGAGAACCGTATATAAGTGCAGTAGTCGCCGTGAACGTT<br>CTTTTTCGCAACGGGTTTGCCGCCAGAACACAG |
| UBC promoter | 140 | GGCCTCCGCGCCGGGTTTTGGCGCCTCCCGCGGGCGCCCCCCT<br>CCTCACGGCGAGCGCTGCCACGTCAGACGAAGGGCGCAGCGA<br>GCGTCCTGATCCTTCCGCCCGGACGCTCAGGACAGCGGCCCGC<br>TGCTCATAAGACTCGGCCTTAGAACCCCAGTATCAGCAGAAGG |

TABLE 12-continued

| Exemplary Sequences | | |
|---|---|---|
| | | ACATTTTAGGACGGGACTTGGGTGACTCTAGGGCACTGGTTTT CTTTCCAGAGAGCGGAACAGGCGAGGAAAAGTAGTCCCTTCT CGGCGATTCTGCGGAGGGATCTCCGTGGGGCGGTGAACGCCG ATGATTATATAAGGACGCGCCGGGTGTGGCACAGCTAGTTCCG TCGCAGCCGGGATTTGGGTCGCGGTTCTTGTTTGTGGATCGCT GTGATCGTCACTTGGTGAGTAGCGGGCTGCTGGGCTGGGTACG TGCGCTCGGGGTTGGCGAGTGTGTTTTGTGAAGTTTTTTAGGC ACCTTTTGAAATGTAATCATTTGGGTCAATATGTAATTTTCAGT GTTAGACTAGTAAATTGTCCGCTAAATTCTGGCCGTTTTTGGCT TTTTTGTTAGACG |
| 6 site GAL4-inducible proximal factor binding element (PFB) | 141 | ATTGTTCGGAGCAGTGCGGCGCGTTTAGCGGAGTACTGTCCTC CGATATTAATCGGGGCAGACTATTCCGGGGTTTACCGGCGCAC TCTCGCCCGAACTTCACCGGCGGTCTTTCGTCCGTGCTTTATCG GGGCGGATCACTCCGAAC |
| Synthetic minimal promoter 1 [Inducible Promoter] | 142 | AGGTCTATATAAGCAGAGCTCGTTTAGTGAACCCTCATTCTGG AGACGGATCCCGAGCCGAGTGTTTTGACCTCCATAGAA |
| Synthetic 5' UTR based on RPL6 | 143 | CAGCCGCTAAATCCAAGGTAAGGTCAGAAGA |
| SV40e poly A | 144 | AACTTGTTTATTGCAGCTTATAATGGTTACAAATAAAGCAATA GCATCACAAATTTCACAAATAAAGCATTTTTTTCACTGCATTCT AGTTGTGGTTTGTCCAAACTCATCAATGTATCTTATCATGTCTG G |
| Bidirectional aCA poly A [bidirectional poly A] | 145 | ATCGATTAATCTAGCGGCCCTAGACGAGCAGACATGATAAGA TACATTGATGAGTTTGGACAAACCACAACTAGAATGCAGTGA AAAAAATGCTTTATTTGTGAAATTTGTGATGCTATTGCTTTATT TGTAACCATTATAAGCTGCAATAAACAAGTTAACAACAACAAT TGCATTCATTTTATGTTTCAGGTTCAGGGGGAGATGTGGGAGG TTTTTTAAAGCAAGTAAAACCTCTACAAATGTGGTAAAATCCG ATAAGCGTACCTAGAGGC |
| 2xRbm3 IRES | 146 | ACTAGTTTTATAATTTCTTCTTCCAGAATTTCTGACATTTTATA ATTTCTTCTTCCAGAAGACTCACAACCTC |
| EMCV IRES | 147 | CCCCCTCTCCCTCCCCCCCCCCTAACGTTACTGGCCGAAGCCG CTTGGAATAAGGCCGGTGTGCGTTTGTCTATATGTTATTTTCCA CCATATTGCCGTCTTTTGGCAATGTGAGGGCCCGGAAACCTGG CCCTGTCTTCTTGACGAGCATTCCTAGGGGTCTTTCCCCTCTCG CCAAAGGAATGCAAGGTCTGTTGAATGTCGTGAAGGAAGCAG TTCCTCTGGAAGCTTCTTGAAGACAAACAACGTCTGTAGCGAC CCTTTGCAGGCAGCGGAACCCCCCACCTGGCGACAGGTGCCTC TGCGGCCAAAAGCCACGTGTATAAGATACACCTGCAAAGGCG GCACAACCCCAGTGCCACGTTGTGAGTTGGATAGTTGTGGAAA GAGTCAAATGGCTCTCCTCAAGCGTATTCAACAAGGGGCTGAA GGATGCCCAGAAGGTACCCCATTGTATGGGATCTGATCTGGGG CCTCGGTGCACATGCTTTACATGTGTTTAGTCGAGGTTAAAAA ACGTCTAGGCCCCCCGAACCACGGGGACGTGGTTTTCCTTTGA AAAACACGATC |

What is claimed is:

1. A nucleic acid encoding a chimeric antigen receptor (CAR), comprising:

(a) a ROR-1 antigen binding domain comprising: (i) a first polypeptide comprising the an amino acid sequence of SEQ ID NO: 36; and (ii) a second polypeptide comprising the amino acid sequence of SEQ ID NO: 17;

(b) a transmembrane domain; and (c) a CD3 zeta signaling domain.

2. The nucleic acid of claim 1, wherein the CD3 zeta signaling domain comprises a polypeptide having at least 90% identity with the amino acid sequence of SEQ ID NO: 93.

3. The nucleic acid of claim 1, further encoding a polypeptide having at least 90% identity with an amino acid sequence of any one of SEQ ID NOs: 94-108.

4. The nucleic acid of claim 1, further encoding a cell tag.

5. The nucleic acid claim 4, wherein the cell tag is a truncated epidermal growth factor receptor.

6. The nucleic acid of claim 4, wherein the cell tag comprises a polypeptide having at least 90% identity with the amino acid sequence of SEQ ID NO: 109 or SEQ ID NO: 110.

7. The nucleic acid of claim 1, further encoding: (a) a first gene switch polypeptide comprising a DNA binding domain fused to a first nuclear receptor ligand binding domain; (b) a second gene switch polypeptide comprising a transactivation domain fused to a second nuclear receptor ligand binding domain; and (c) a linker connecting the first gene switch polypeptide and the second gene switch polypeptide.

8. A vector comprising the nucleic acid of claim 4 and a nucleic acid sequence encoding a cytokine.

9. The vector of claim 8, wherein the cell tag comprises a polypeptide having at least 90% identity with the amino acid sequence of SEQ ID NO: 110.

10. The vector of claim 8, wherein the cytokine is IL-15.

11. The vector of claim 8, wherein the backbone is Tc1/mariner-type transposon DNA plasmid.

12. An immune effector cell comprising the nucleic acid of claim 1.

13. The immune effector cell of claim 12 further comprising a cell tag and a cytokine.

14. The immune effector cell of claim 13, wherein the cytokine is IL-15.

15. The immune effector cell of claim 13, wherein the cell tag comprises a polypeptide having at least 90% identity with the amino acid sequence of SEQ ID NO: 110.

16. The immune effector cell of claim 13, wherein the CAR comprises a polypeptide having the amino acid sequence of SEQ ID NO: 79.

17. A method for stimulating a T cell-mediated immune response to a target cell population or tissue in a human subject in need thereof, the method comprising administering to the human subject an effective amount of the cell of claim 12 wherein the cell administered to the human subject also comprises a cell tag, and wherein the target cell population or tissue expresses ROR-1.

18. A method of treating cancer in a human subject in need thereof, the method comprising administering to the human subject one or more doses of an effective amount of engineered T-cells, wherein the engineered T-cells comprise a CAR encoded by the nucleic acid of claim 1 and a membrane bound IL-15, and wherein the cancer expresses ROR-1.

19. A vector comprising the nucleic acid of claim 4 and a nucleic acid sequence encoding a fusion protein comprising: IL-15, or a functional fragment or variant thereof; and IL-15RΔ, or a functional fragment or variant thereof.

20. The vector of claim 19, wherein the fusion protein comprises an amino acid sequence having at least 90% identity with the amino acid sequence of SEQ ID NO: 113.

21. The vector of claim 19, wherein the fusion protein comprises the amino acid sequence of SEQ ID NO: 113.

22. The nucleic acid of claim 1, wherein the CAR further comprises a spacer.

23. The nucleic acid of claim 22, wherein the spacer comprises a stalk region and at least one stalk extension region.

24. The nucleic acid of claim 23, wherein each stalk extension region contains at least one fewer dimerization site as compared to the stalk region.

25. The nucleic acid of claim 24, wherein the stalk region is proximal to the transmembrane domain.

26. The nucleic acid of claim 22, wherein the spacer comprises an amino acid sequence having at least 90% identity with the amino acid sequence of SEQ ID NO: 85.

27. The nucleic acid of claim 1, wherein the transmembrane domain comprises an amino acid sequence having at least 90% identity with the amino acid sequence of SEQ ID NO: 87.

28. The nucleic acid of claim 1, wherein the CAR further comprises a 4-11313 co-stimulatory signaling domain and/or a CD28 co-stimulatory domain.

29. The nucleic acid of claim 28, wherein the CAR comprises a CD28 co-stimulatory domain.

30. The nucleic acid of claim 29, wherein the CD28 co-stimulatory domain comprises an amino acid sequence having at least 90% identity with the amino acid sequence of SEQ ID NO: 90.

31. The nucleic acid of claim 1, wherein the CAR comprises:

(a) a spacer comprising a polypeptide comprising an amino acid sequence having at least 90% identity with SEQ ID NO: 85;

(b) a transmembrane domain comprising a polypeptide comprising an amino acid sequence having at least 90% identity with SEQ ID NO: 87;

(c) a CD28 costimulatory signaling domain comprising an amino acid sequence having at least 90% identity with SEQ ID NO: 90; and (d) a CD3 zeta signaling domain comprising an amino acid sequence having at least 90% identity with SEQ ID NO: 93.

32. The nucleic acid of claim 1, wherein the CAR comprises the amino acid sequence of SEQ ID NO: 79.

33. The nucleic acid of claim 1, wherein the CD3 zeta signaling domain comprises a polypeptide having at least 95% identity with the amino acid sequence of SEQ ID NO: 93.

34. The nucleic acid of claim 1, wherein the CD3 zeta signaling domain comprises a polypeptide having at least 98% identity with the amino acid sequence of SEQ ID NO: 93.

35. The nucleic acid of claim 1, wherein the CD3 zeta signaling domain comprises the amino acid sequence of SEQ ID NO: 93.

36. The nucleic acid of claim 22, wherein the spacer comprises an amino acid sequence having at least 95% identity with the amino acid sequence of SEQ ID NO: 85.

37. The nucleic acid of claim 22, wherein the spacer comprises an amino acid sequence having at least 98% identity with the amino acid sequence of SEQ ID NO: 85.

38. The nucleic acid of claim 22, wherein the spacer comprises the amino acid sequence of SEQ ID NO: 85.

39. The nucleic acid of claim 1, wherein the transmembrane domain comprises an amino acid sequence having at least 95% identity with the amino acid sequence of SEQ ID NO: 87.

40. The nucleic acid of claim 1, wherein the transmembrane domain comprises an amino acid sequence having at least 98% identity with the amino acid sequence of SEQ ID NO: 87.

41. The nucleic acid of claim 1, wherein the transmembrane domain comprises the amino acid sequence of SEQ ID NO: 87.

42. The nucleic acid of claim 29, wherein the CD28 co-stimulatory domain comprises an amino acid sequence having at least 95% identity with the amino acid sequence of SEQ ID NO: 90.

43. The nucleic acid of claim 29, wherein the CD28 co-stimulatory domain comprises an amino acid sequence having at least 98% identity with the amino acid sequence of SEQ ID NO: 90.

44. The nucleic acid of claim 29, wherein the CD28 co-stimulatory domain comprises the amino acid sequence of SEQ ID NO: 90.

45. The vector of claim 8, wherein the cell tag comprises a polypeptide having at least 95% identity with the amino acid sequence of SEQ ID NO: 110.

46. The vector of claim 8, wherein the cell tag comprises a polypeptide having at least 98% identity with the amino acid sequence of SEQ ID NO: 110.

47. The vector of claim 8, wherein the cell tag comprises the amino acid sequence of SEQ ID NO: 110.

48. The vector of claim 19, wherein the fusion protein comprises an amino acid sequence having at least 95% identity with the amino acid sequence of SEQ ID NO: 113.

49. The vector of claim 19, wherein the fusion protein comprises an amino acid sequence having at least 98% identity with the amino acid sequence of SEQ ID NO: 113.

50. The nucleic acid of claim 1, wherein the CAR comprises:

(a) a spacer comprising a polypeptide comprising an amino acid sequence having at least 95% identity with SEQ ID NO: 85;

(b) a transmembrane domain comprising a polypeptide comprising an amino acid sequence having at least 95% identity with SEQ ID NO: 87;

(c) a CD28 costimulatory signaling domain comprising an amino acid sequence having at least 95% identity with SEQ ID NO: 90; and (d) a CD3 zeta signaling domain comprising an amino acid sequence having at least 95% identity with SEQ ID NO: 93.

51. The nucleic acid of claim 1, wherein the CAR comprises:

(a) a spacer comprising a polypeptide comprising an amino acid sequence having at least 98% identity with SEQ ID NO: 85;

(b) a transmembrane domain comprising a polypeptide comprising an amino acid sequence having at least 98% identity with SEQ ID NO: 87;

(c) a CD28 costimulatory signaling domain comprising an amino acid sequence having at least 98% identity with SEQ ID NO: 90; and (d) a CD3 zeta signaling domain comprising an amino acid sequence having at least 98% identity with SEQ ID NO: 93.

52. The nucleic acid of claim 1, wherein the CAR comprises:

(a) a spacer comprising the amino acid sequence of SEQ ID NO: 85;

(b) a transmembrane domain comprising the amino acid sequence of SEQ ID NO: 87;

(c) a CD28 costimulatory signaling domain comprising the amino acid sequence of SEQ ID NO: 90; and (d) a CD3 zeta signaling domain comprising the amino acid sequence of SEQ ID NO: 93.

53. The nucleic acid of claim 1, wherein the CAR comprises an amino acid sequence having at least 90% identity with the amino acid sequence of SEQ ID NO: 79.

54. The nucleic acid of claim 1, wherein the CAR comprises an amino acid sequence having at least 95% identity with the amino acid sequence of SEQ ID NO: 79.

55. The nucleic acid of claim 1, wherein the CAR comprises an amino acid sequence having at least 98% identity with the amino acid sequence of SEQ ID NO: 79.

56. The vector of claim 8 encoding: (a) a CAR comprising an amino acid sequence having at least 95% identity with the amino acid sequence of SEQ ID NO: 79; (b) a cell tag comprising an amino acid sequence having at least 95% identity with the amino acid sequence of SEQ ID NO: 110; and (c) a cytokine comprising an amino acid sequence having at least 95% identity with the amino acid sequence of SEQ ID NO: 113.

57. The vector of claim 8 encoding: (a) a CAR comprising an amino acid sequence having at least 98% identity with the amino acid sequence of SEQ ID NO: 79; (b) a cell tag comprising an amino acid sequence having at least 98% identity with the amino acid sequence of SEQ ID NO: 110; and (c) a cytokine comprising an amino acid sequence having at least 98% identity with the amino acid sequence of SEQ ID NO: 113.

58. The vector of claim 8 encoding: (a) a CAR comprising the amino acid sequence of SEQ ID NO: 79; (b) a cell tag comprising the amino acid sequence of SEQ ID NO: 110; and (c) a cytokine comprising the amino acid sequence of SEQ ID NO: 113.

* * * * *